United States Patent
Anderson et al.

(10) Patent No.: US 10,590,085 B2
(45) Date of Patent: Mar. 17, 2020

(54) HETEROCYCLIC AMIDES AS KINASE INHIBITORS

(71) Applicant: GlaxoSmithKline Intellectual Property Development Limited, Brentford, Middlesex (GB)

(72) Inventors: Niall Andrew Anderson, Stevenage (GB); Deepak Bandyopadhyay, King of Prussia, PA (US); Alain Claude-Marie Daugan, Les Ulis (FR); Frederic G. Donche, Les Ulis (FR); Patrick M. Eidam, Stevenage (GB); Nicolas Eric Faucher, Les Ulis (FR); Nicolas S. George, Les Ulis (FR); Philip Anthony Harris, Collegeville, PA (US); Jae U. Jeong, Collegeville, PA (US); Bryan W. King, Collegeville, PA (US); Clark A. Sehon, Collegeville, PA (US); Gemma Victoria White, Stevenage (GB); David Duff Wisnoski, Collegeville, PA (US)

(73) Assignee: GLAXOSMITHKLINE INTELLECTUAL PROPERTY DEVELOPMENT LIMITED, Brentford, Middlesex (GB)

(*) Notice: Subject to any disclaimer, the term of this patent is extended or adjusted under 35 U.S.C. 154(b) by 0 days.

(21) Appl. No.: 15/575,235

(22) PCT Filed: May 19, 2016

(86) PCT No.: PCT/IB2016/052948
§ 371 (c)(1),
(2) Date: Nov. 17, 2017

(87) PCT Pub. No.: WO2016/185423
PCT Pub. Date: Nov. 24, 2016

(65) Prior Publication Data
US 2018/0134665 A1 May 17, 2018

Related U.S. Application Data

(60) Provisional application No. 62/197,602, filed on Jul. 28, 2015, provisional application No. 62/167,359,
(Continued)

(51) Int. Cl.
| | | |
|---|---|---|
| A61K 31/415 | (2006.01) | |
| A61K 31/422 | (2006.01) | |
| A61K 31/454 | (2006.01) | |
| A61K 31/4545 | (2006.01) | |
| A61K 31/506 | (2006.01) | |
| A61K 31/5377 | (2006.01) | |
| C07D 231/06 | (2006.01) | |
| C07D 401/14 | (2006.01) | |

(Continued)

(52) U.S. Cl.
CPC .......... *C07D 231/06* (2013.01); *A61K 31/415* (2013.01); *A61K 31/422* (2013.01); *A61K 31/454* (2013.01); *A61K 31/4545* (2013.01); *A61K 31/506* (2013.01); *A61K 31/5377* (2013.01); *A61P 21/00* (2018.01); *C07D 401/04* (2013.01); *C07D 401/06* (2013.01); *C07D 401/14* (2013.01); *C07D 403/04* (2013.01); *C07D 403/06* (2013.01); *C07D 405/04* (2013.01); *C07D 405/06* (2013.01); *C07D 405/14* (2013.01); *C07D 409/06* (2013.01); *C07D 409/14* (2013.01); *C07D 413/04* (2013.01); *C07D 413/14* (2013.01); *C07D 417/14* (2013.01); *C07D 487/04* (2013.01)

(58) Field of Classification Search
None
See application file for complete search history.

(56) References Cited

U.S. PATENT DOCUMENTS

| 4,839,376 A | 6/1989 | Yamashita et al. |
| 4,990,529 A * | 2/1991 | Yamashita ........... C07D 231/06 424/436 |

FOREIGN PATENT DOCUMENTS

| EP | 0 295 695 A2 | 12/1988 |
| EP | 1 853 600 | 11/2007 |

(Continued)

OTHER PUBLICATIONS

Liu et al., "Design and synthesis of N-phenylacetyl (sulfonyl) 4,5-dihydropyrazole derivatives as potential antitumor agents", *Bioorganic & Medicinal Chemistry Letters*, vol. 21, No. 10, pp. 2916-2920 (2011).

(Continued)

*Primary Examiner* — Samantha L Shterengarts
(74) *Attorney, Agent, or Firm* — Jane F. Djung; Duke M. Fitch; Edward R. Gimmi

(57) ABSTRACT

Disclosed are compounds having the formula (I):

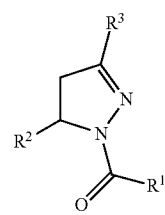

wherein $R^1$, $R^2$, and $R^3$ are as defined herein, and methods of making and using the same.

31 Claims, 5 Drawing Sheets

Related U.S. Application Data filed on May 28, 2015, provisional application No. 62/163,552, filed on May 19, 2015.

(51) Int. Cl.

| | | |
|---|---|---|
| C07D 405/14 | (2006.01) | |
| C07D 413/14 | (2006.01) | |
| C07D 401/04 | (2006.01) | |
| C07D 401/06 | (2006.01) | |
| C07D 405/04 | (2006.01) | |
| C07D 405/06 | (2006.01) | |
| C07D 409/14 | (2006.01) | |
| C07D 417/14 | (2006.01) | |
| C07D 403/04 | (2006.01) | |
| C07D 487/04 | (2006.01) | |
| A61P 21/00 | (2006.01) | |
| C07D 403/06 | (2006.01) | |
| C07D 409/06 | (2006.01) | |
| C07D 413/04 | (2006.01) | |

(56) References Cited

FOREIGN PATENT DOCUMENTS

| EP | 3 061 751 A1 | 8/2016 |
|---|---|---|
| JP | S64-079157 A | 3/1989 |
| WO | WO 2004/075857 A2 | 9/2004 |
| WO | WO 2004/098590 A1 | 11/2004 |
| WO | WO 2010/075561 A1 | 7/2010 |
| WO | WO 2014/125444 A1 | 8/2014 |

OTHER PUBLICATIONS

Liu et al., "Synthesis and biological activity of arylpyrazole derivatives", *Hecheng Huaxue / Chinese Journal of Synthetic Chemistry, Chengdu Yuji Huaxuesuo*, China, vol. 15, No. 2, pp. 212-215 (2007) (Abstract).

Liu et al, "Synthesis and fungicidal activity of novel 5-arylpyrazole derivatives", *Yingyong Huaxue* (*Chinese Journal of Applied Chemistry*), vol. 24, No. 10, pp. 1162-1166 (2007) (Abstract).

Wang et al., "Dihydropyrazole derivatives as telomerase inhibitors: Structure-based design, synthesis, SAR and anticancer evaluation in vitro and in vivo", *European Journal of Medicinal Chemistry*, vol. 112, pp. 231-251 (2016).

Xiao et al., "Identification of human telomerase inhibitors having the core of N-acyl-4,5-dihydropyrazole with anticancer effects", *Bioorganic & Medicinal Chemistry Letters*, vol. 26, No. 6, pp. 1508-1511 (2016).

\* cited by examiner

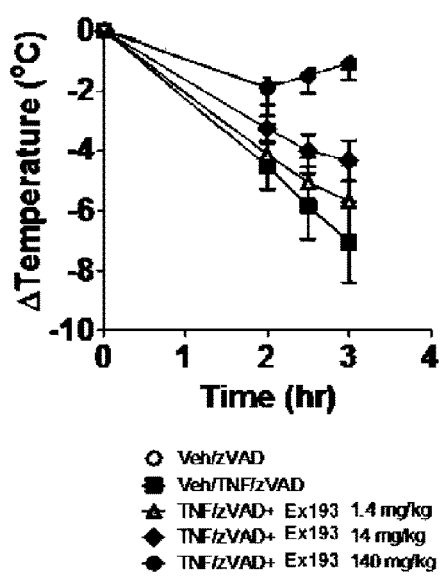
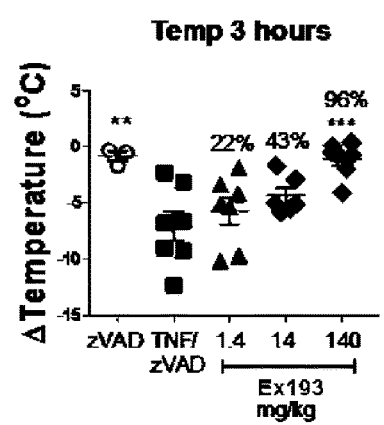
FIG. 2A
FIG. 2B

HETEROCYCLIC AMIDES AS KINASE INHIBITORS

This application is a § 371 of International Application No. PCT/IB2016/052948, filed May 19, 2016, which claims the benefit of U.S. Provisional Application No. 62/163,552, filed May 19, 2015, U.S. Provisional Application No. 62/167,359, filed May 28, 2015 and U.S. Provisional Application No. 62/197,602, filed Jul. 28, 2015, which are incorporated herein in their entireties.

FIELD OF THE INVENTION

The present invention relates to heterocyclic amides that inhibit RIP1 kinase and methods of making and using the same.

BACKGROUND OF THE INVENTION

Receptor-interacting protein-1 (RIP1) kinase, originally referred to as RIP, is a TKL family serine/threonine protein kinase involved in innate immune signaling. RIP1 kinase is a RHIM domain containing protein, with an N-terminal kinase domain and a C-terminal death domain ((2005) Trends Biochem. Sci. 30, 151-159). The death domain of RIP1 mediates interaction with other death domain containing proteins including Fas and TNFR-1 ((1995) Cell 81 513-523), TRAIL-R1 and TRAIL-R2 ((1997) Immunity 7, 821-830) and TRADD ((1996) Immunity 4, 387-396), while the RHIM domain is crucial for binding other RHIM domain containing proteins such as TRIF ((2004) Nat Immunol. 5, 503-507), DAI ((2009) EMBO Rep. 10, 916-922) and RIP3 ((1999) J. Biol. Chem. 274, 16871-16875); (1999) Curr. Biol. 9, 539-542) and exerts many of its effects through these interactions. RIP1 is a central regulator of cell signaling, and is involved in mediating both pro-survival and programmed cell death pathways which will be discussed below.

The role for RIP1 in cell signaling has been assessed under various conditions [including TLR3 ((2004) Nat Immunol. 5, 503-507), TLR4 ((2005) J. Biol. Chem. 280, 36560-36566), TRAIL (Cell Signal. 2015 February; 27(2): 306-14), FAS ((2004) J. Biol. Chem. 279, 7925-7933)], but is best understood in the context of mediating signals downstream of the death receptor TNFR1 ((2003) Cell 114, 181-190). Engagement of the TNFR by TNF leads to its oligomerization, and the recruitment of multiple proteins, including linear K63-linked polyubiquitinated RIP1 ((2006) Mol. Cell 22, 245-257), TRAF2/5 ((2010) J. Mol. Biol. 396, 528-539), TRADD ((2008) Nat. Immunol. 9, 1037-1046) and cIAPs ((2008) Proc. Natl. Acad. Sci. USA. 105, 11778-11783), to the cytoplasmic tail of the receptor. This complex which is dependent on RIP1 as a scaffolding protein (i.e. kinase independent), termed complex I, provides a platform for pro-survival signaling through the activation of the NFκB and MAP kinases pathways ((2010) Sci. Signal. 115, re4). Alternatively, binding of TNF to its receptor under conditions promoting the deubiquitination of RIP1 (by proteins such as A20 and CYLD or inhibition of the cIAPs) results in receptor internalization and the formation of complex II or DISC (death-inducing signaling complex) ((2011) Cell Death Dis. 2, e230). Formation of the DISC, which contains RIP1, TRADD, FADD and caspase 8, results in the activation of caspase 8 and the onset of programmed apoptotic cell death also in a RIP1 kinase independent fashion ((2012) FEBS J 278, 877-887). Apoptosis is largely a quiescent form of cell death, and is involved in routine processes such as development and cellular homeostasis. Under conditions where the DISC forms and RIP3 is expressed, but apoptosis is inhibited (such as FADD/caspase 8 deletion, caspase inhibition or viral infection), a third RIP1 kinase-dependent possibility exists. RIP3 can now enter this complex, become phosphorylated by RIP1 and initiate a caspase-independent programmed necrotic cell death through the activation of MLKL and PGAM5 ((2012) Cell 148, 213-227); ((2012) Cell 148, 228-243); ((2012) Proc. Natl. Acad. Sci. USA. 109, 5322-5327). As opposed to apoptosis, programmed necrosis (not to be confused with passive necrosis which is not programmed) results in the release of danger associated molecular patterns (DAMPs) from the cell. These DAMPs are capable of providing a "danger signal" to surrounding cells and tissues, eliciting proinflammatory responses including inflammasome activation, cytokine production and cellular recruitment ((2008 Nat. Rev. Immunol 8, 279-289).

Dysregulation of RIP1 kinase-mediated programmed cell death has been linked to various inflammatory diseases, as demonstrated by use of the RIP3 knockout mouse (where RIP1-mediated programmed necrosis is completely blocked) and by Necrostatin-1 (a tool inhibitor of RIP1 kinase activity with poor oral bioavailability). The RIP3 knockout mouse has been shown to be protective in inflammatory bowel disease (including Ulcerative colitis and Crohn's disease) ((2011) Nature 477, 330-334), Psoriasis ((2011) Immunity 35, 572-582), retinal-detachment-induced photoreceptor necrosis ((2010) PNAS 107, 21695-21700), retinitis pigmentosa ((2012) Proc. Natl. Acad. Sci., 109:36, 14598-14603), cerulein-induced acute pancreatitis ((2009) Cell 137, 1100-1111) and Sepsis/systemic inflammatory response syndrome (SIRS) ((2011) Immunity 35, 908-918). Necrostatin-1 has been shown to be effective in alleviating ischemic brain injury ((2005) Nat. Chem. Biol. 1, 112-119), retinal ischemia/reperfusion injury ((2010) J. Neurosci. Res. 88, 1569-1576), Huntington's disease ((2011) Cell Death Dis. 2 e115), renal ischemia reperfusion injury ((2012) Kidney Int. 81, 751-761), cisplatin induced kidney injury ((2012) Ren. Fail. 34, 373-377) and traumatic brain injury ((2012) Neurochem. Res. 37, 1849-1858). Other diseases or disorders regulated at least in part by RIP1-dependent apoptosis, necrosis or cytokine production include hematological and solid organ malignancies ((2013) Genes Dev. 27: 1640-1649), bacterial infections and viral infections ((2014) Cell Host & Microbe 15, 23-35) (including, but not limited to, tuberculosis and influenza ((2013) Cell 153, 1-14)) and Lysosomal storage diseases (particularly, Gaucher Disease, Nature Medicine Advance Online Publication, 19 Jan. 2014, doi:10.1038/nm.3449).

A potent, selective, small molecule inhibitor of RIP1 kinase activity would block RIP1-dependent cellular necrosis and thereby provide a therapeutic benefit in diseases or events associated with DAMPs, cell death, and/or inflammation.

SUMMARY OF THE INVENTION

The invention is directed to a compound according to Formula (I):

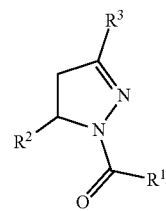

(I)

wherein:
$R^1$ is $(C_1-C_4)$alkoxy-$CH_2$—, phenyl$(C_1-C_4)$alkoxy-$CH_2$—, or a substituted or unsubstituted $(C_2-C_6)$alkyl, $(C_2-C_4)$alkynyl, $(C_3-C_6)$cycloalkyl, $(C_3-C_6)$cycloalkyl-$(C_1-C_4)$alkyl-group, or a substituted or unsubstituted 5-6 membered heterocycloalkyl group further optionally substituted by halogen or $(C_1-C_4)$alkyl, wherein said substituted $(C_2-C_6)$alkyl, $(C_3-C_6)$cycloalkyl, $(C_3-C_6)$cycloalkyl-alkyl-, or 5-6 membered heterocycloalkyl group is substituted by 1, 2 or 3 substituents independently selected from hydroxyl, (benzyloxy)carbonyl)amino, cyano, halogen, $(C_1-C_4)$alkyl, halo$(C_1-C_4)$alkyl, $(C_1-C_4)$alkoxy, $(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkoxy-CO—, $(C_1-C_4)$alkylNHCO—, $((C_1-C_4)$alkyl$)((C_1-C_4)$alkyl$)$NCO—, halo$(C_1-C_4)$alkyl-CO—, optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-$SO_2$—, optionally substituted phenyl$(C_1-C_4)$alkyl-CO—, optionally substituted 5-6 membered heteroaryl-CO—, and optionally substituted 9-10 membered heteroaryl-CO—, wherein said optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-$SO_2$—, optionally substituted phenyl$(C_1-C_4)$alkyl-CO—, optionally substituted 5-6 membered heteroaryl-CO—, or optionally substituted 9-10 membered heteroaryl-CO— is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$cycloalkyl and 5-6 membered heterocycloalkyl; or said substituted $(C_2-C_4)$alkynyl, $(C_3-C_6)$cycloalkyl or 5-6 membered heterocycloalkyl group is substituted by an optionally substituted phenyl, 5-6 membered heteroaryl or 9-membered heteroaryl group, wherein said phenyl, 5-6 membered heteroaryl or 9-membered heteroaryl group is optionally substituted by 1 or 2 substituents independently selected from halogen, $(C_1-C_4)$alkyl, $(C_1-C_4)$alkyl-CO—, halo$(C_1-C_4)$alkyl, and halo$(C_1-C_4)$alkyl-CO—;

$R^2$ is a substituted or unsubstituted phenyl, $(C_3-C_6)$cycloalkyl, 5-6 membered oxygen-containing heterocycloalkyl, 5-6 membered heteroaryl, 9-membered heteroaryl, 9-10 membered carbocyclic-aryl, or 9-10 membered heterocyclic-aryl group, wherein said substituted phenyl, $(C_3-C_6)$cycloalkyl, 5-6 membered heterocycloalkyl, 5-6 membered heteroaryl, 9-membered heteroaryl, 9-10 membered carbocyclic-aryl, or 9-10 membered heterocyclic-aryl group is substituted by 1, 2 or 3 substituents independently selected from halogen, $(C_1-C_4)$alkyl, halo$(C_1-C_4)$alkyl, $(C_1-C_4)$alkoxy, halo$(C_1-C_4)$alkoxy, and cyano; and $R^3$ is H or halogen;

or a salt, particularly a pharmaceutically acceptable salt, thereof, provided the compound is not cyclohexyl(5-phenyl-4,5-dihydro-1H-pyrazol-1-yl)methanone.

The compounds according to Formula (I), or salts, particularly pharmaceutically acceptable salts, thereof, inhibit the activity and/or function of RIP1 kinase. Accordingly, these compounds may be particularly useful for the treatment of RIP1 kinase-mediated diseases or disorders. Such RIP1 kinase-mediated diseases or disorders are diseases or disorders that are mediated by activation of RIP1 kinase, and as such, are diseases or disorders where inhibition of RIP1 kinase would provide benefit.

In particular, the compounds of Formula (I) that inhibit the activity and/or function of RIP1 kinase have the stereochemistry as designated in Formula (II):

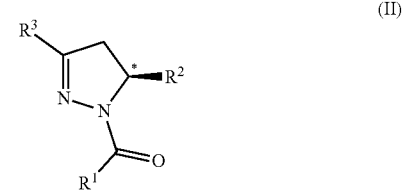

(II)

wherein $R^1$, $R^2$, and $R^3$ are defined in accordance with Formula (I). Generally, based on the definitions of $R^2$ and $R^3$ provided herein, the stereochemistry at the * chiral carbon center is (S).

Compounds of Formula (I) having the (R) stereochemistry at the * chiral carbon center (generally, as based on the definitions of $R^2$ and $R^3$ provided herein) may be useful tool compounds as negative controls to help confirm the on-target effects of the active (S) enantiomer.

The invention is further directed to a compound according to Formula (III):

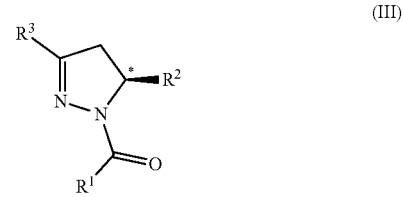

(III)

wherein:

$R^1$ is $(C_1-C_4)$alkoxy-$CH_2$—, phenyl$(C_1-C_4)$alkoxy-$CH_2$—, an unsubstituted indoyl, a substituted or unsubstituted $(C_2-C_6)$alkyl, $(C_2-C_4)$alkynyl, $(C_3-C_6)$cycloalkyl, $(C_3-C_6)$cycloalkyl-alkyl-, phenyl, or 5-6 membered heteroaryl group, or a substituted or unsubstituted 5-6 membered heterocycloalkyl group further optionally substituted by halogen or $(C_1-C_4)$alkyl, wherein said substituted $(C_2-C_6)$alkyl, $(C_3-C_6)$cycloalkyl, $(C_3-C_6)$cycloalkyl-alkyl-, 5-6 membered heterocycloalkyl, phenyl, or 5-6 membered heteroaryl group is substituted by 1, 2 or 3 substituents independently selected from hydroxyl, (benzyloxy)carbonyl)amino, cyano, halogen, $(C_1-C_4)$alkyl, halo$(C_1-C_4)$alkyl, $(C_1-C_4)$alkoxy, $(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkoxy-CO—, $(C_1-C_4)$alkylNHCO—, $((C_1-C_4)$alkyl$)((C_1-C_4)$alkyl$)$NCO—, halo$(C_1-C_4)$alkyl-CO—, optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-$SO_2$—, optionally substituted phenyl$(C_1-C_4)$alkyl-CO—, optionally substituted 5-6 membered heteroaryl-CO—, and optionally substituted 9-10 membered heteroaryl-CO—, wherein said optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-$SO_2$—, optionally substituted phenyl$(C_1-C_4)$alkyl-CO—, optionally substituted 5-6 membered heteroaryl- CO—, or optionally substituted 9-10 membered heteroaryl-CO— is optionally substituted by 1 or 2 substituents independently selected from halogen, cyano, ($C_1$-$C_4$)alkyl, ($C_1$-$C_4$)alkoxy, ($C_1$-$C_4$)alkyl-CO—, halo($C_1$-$C_4$)alkyl, halo($C_1$-$C_4$)alkyl-CO—, ($C_3$-$C_6$)cycloalkyl and 5-6 membered heterocycloalkyl; or said substituted ($C_2$-$C_4$)alkynyl, ($C_3$-$C_6$)cycloalkyl, 5-6 membered heterocycloalkyl, phenyl, or 5-6 membered heteroaryl group is substituted by an optionally substituted phenyl, 5-6 membered heteroaryl or 9-membered heteroaryl group,
wherein said phenyl, 5-6 membered heteroaryl or 9-membered heteroaryl group is optionally substituted by 1 or 2 substituents independently selected from halogen, ($C_1$-$C_4$)alkyl, ($C_1$-$C_4$)alkyl-CO—, halo($C_1$-$C_4$)alkyl, and halo($C_1$-$C_4$)alkyl-CO—;

$R^2$ is a substituted or unsubstituted phenyl, ($C_3$-$C_6$)cycloalkyl, 5-6 membered oxygen-containing heterocycloalkyl, 5-6 membered heteroaryl, 9-membered heteroaryl, 9-10 membered carbocyclic-aryl, or 9-10 membered heterocyclic-aryl group,
wherein said substituted phenyl, ($C_3$-$C_6$)cycloalkyl, 5-6 membered heterocycloalkyl, 5-6 membered heteroaryl, 9-membered heteroaryl, 9-10 membered carbocyclic-aryl, or 9-10 membered heterocyclic-aryl group is substituted by 1, 2 or 3 substituents independently selected from halogen, ($C_1$-$C_4$)alkyl, halo($C_1$-$C_4$)alkyl, ($C_1$-$C_4$)alkoxy, halo($C_1$-$C_4$)alkoxy, and cyano; and $R^3$ is H, halogen, or methyl;

or a salt, particularly a pharmaceutically acceptable salt, thereof, for use in therapy.

BRIEF DESCRIPTION OF THE DRAWINGS

FIG. 2A shows the temperature loss over time in mice after oral pre-dosing with the compound of Example 193 or vehicle followed by simultaneous i.v. administration of mouse TNF and zVAD.

FIG. 2B shows the temperature loss in mice 3 hours after oral pre-dosing with the compound of Example 193 or vehicle followed by simultaneous i.v. administration of mouse TNF and zVAD.

FIG. 3B shows the temperature loss in mice 2.5 hours after oral pre-dosing with the compound of Example 203 or vehicle followed by simultaneous i.v. administration of mouse TNF and zVAD.

DETAILED DESCRIPTION OF THE INVENTION

Figure 1A:
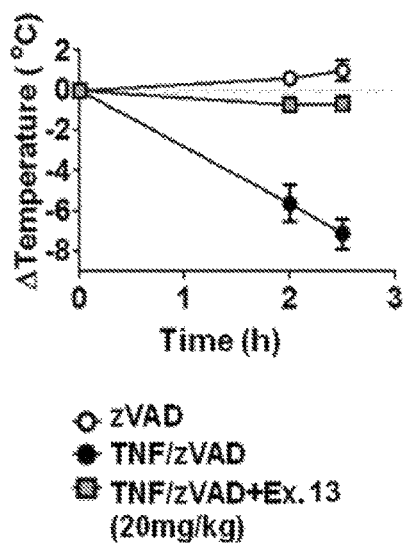
FIG. 1A shows the temperature loss over time in mice after oral pre-dosing with the compound of Example 13 or vehicle followed by simultaneous i.v. administration of mouse TNF and zVAD.
Figure 1B:
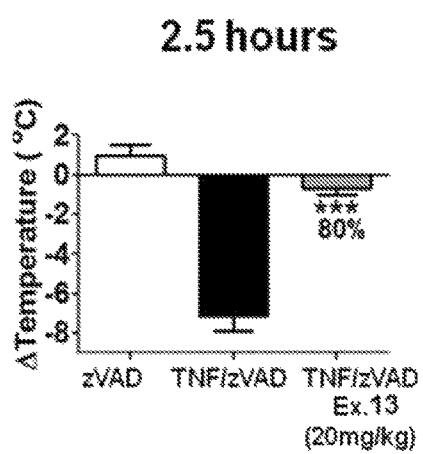
FIG. 1B shows the temperature loss in mice 2.5 hours after oral pre-dosing with the compound of Example 13 or vehicle followed by simultaneous i.v. administration of mouse TNF and zVAD.
Figure 3A:
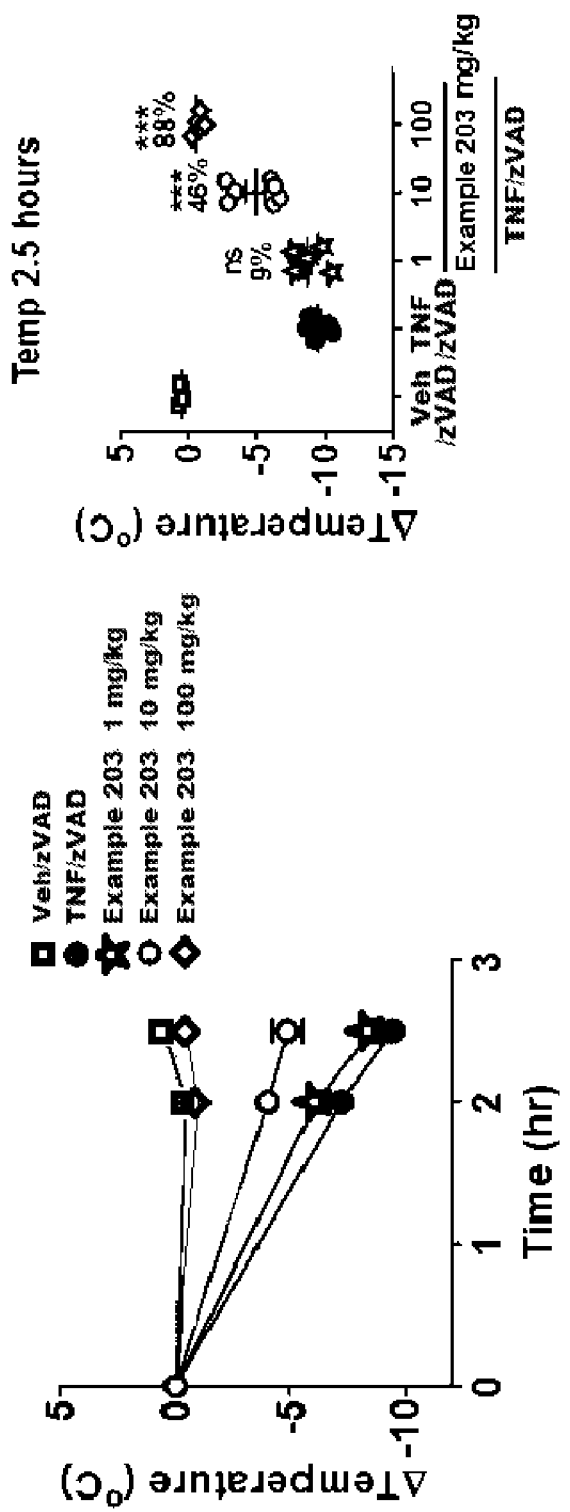
FIG. 3A shows the temperature loss over time in mice after oral pre-dosing with the compound of Example 203 or vehicle followed by simultaneous i.v. administration of mouse TNF and zVAD.

In one embodiment, the invention is also directed to a compound according to Formula (I), wherein:

$R^1$ is a substituted or unsubstituted ($C_2$-$C_6$)alkyl, ($C_4$-$C_6$)cycloalkyl, ($C_4$-$C_6$)cycloalkyl-alkyl-, or 5-6 membered heterocycloalkyl group,
wherein said substituted ($C_2$-$C_6$)alkyl, ($C_4$-$C_6$)cycloalkyl, ($C_4$-$C_6$)cycloalkyl-alkyl-, or 5-6 membered heterocycloalkyl group is substituted by 1, 2 or 3 substituents independently selected from hydroxyl, (benzyloxy)carbonyl)amino, halogen, ($C_1$-$C_4$)alkyl, halo($C_1$-$C_4$)alkyl, ($C_1$-$C_4$)alkyl-CO—, halo($C_1$-$C_4$)alkyl-CO—, and an optionally substituted 5-6 membered heteroaryl-CO—, wherein said optionally substituted 5-6 membered heteroaryl-CO— is optionally substituted by 1 or 2 substituents independently selected from ($C_1$-$C_4$)alkyl, ($C_1$-$C_4$)alkyl-CO—, halo($C_1$-$C_4$)alkyl, and halo($C_1$-$C_4$)alkyl-CO—, or said substituted ($C_4$-$C_6$)cycloalkyl or 5-6 membered heterocycloalkyl group is substituted by an optionally substituted phenyl, 5-6 membered heteroaryl or 9-membered heteroaryl optional substituted by 1 or 2 substituents independently selected from halogen, ($C_1$-$C_4$)alkyl, ($C_1$-$C_4$)alkyl-CO—, halo($C_1$-$C_4$)alkyl, and halo($C_1$-$C_4$)alkyl-CO—;

$R^2$ is a substituted or unsubstituted phenyl, ($C_3$-$C_6$)cycloalkyl, 5-membered oxygen-containing heterocycloalkyl, 5-6 membered heteroaryl or 9-membered heteroaryl group,
wherein said substituted phenyl, ($C_3$-$C_6$)cycloalkyl, 5-membered heterocycloalkyl, 5-6 membered heteroaryl or 9-membered heteroaryl group is substituted by 1, 2 or 3 substituents independently selected from halo, ($C_1$-$C_4$)alkyl, halo($C_1$-$C_4$)alkyl, ($C_1$-$C_4$)alkoxy, and cyano; and $R^3$ is H;

or a salt, particularly a pharmaceutically acceptable salt, thereof, provided the compound is not cyclohexyl(5-phenyl-4,5-dihydro-1H-pyrazol-1-yl)methanone.

In another embodiment, $R^1$ is a substituted or unsubstituted ($C_2$-$C_6$)alkyl, ($C_4$-$C_6$)cycloalkyl, ($C_4$-$C_6$)cycloalkyl-alkyl-, or 5-6 membered heterocycloalkyl group,
wherein said substituted ($C_2$-$C_6$)alkyl, ($C_4$-$C_6$)cycloalkyl, ($C_4$-$C_6$)cycloalkyl-alkyl-, or 5-6 membered heterocycloalkyl group is substituted by 1, 2 or 3 substituents independently selected from hydroxyl, (benzyloxy)carbonyl)amino, halogen, ($C_1$-$C_4$)alkyl, halo($C_1$-$C_4$)alkyl, ($C_1$-$C_4$)alkyl-CO—, halo($C_1$-$C_4$)alkyl-CO—, and an optionally substituted 5-6 membered heteroaryl-CO—, wherein said optionally substituted 5-6 membered heteroaryl-CO— is optionally substituted by 1 or 2 substituents independently selected from ($C_1$-$C_4$)alkyl, ($C_1$-$C_4$)alkyl-CO—, halo($C_1$-$C_4$)alkyl, and halo($C_1$-$C_4$)alkyl-CO—, or said substituted ($C_4$-$C_6$)cycloalkyl or 5-6 membered heterocycloalkyl group is substituted by an optionally substituted phenyl, 5-6 membered heteroaryl or 9-membered heteroaryl optional substituted by 1 or 2 substituents independently selected from halogen, ($C_1$-$C_4$)alkyl, ($C_1$-$C_4$) alkyl-CO—, halo($C_1$-$C_4$)alkyl, and halo($C_1$-$C_4$)alkyl-CO—;

$R^2$ is a substituted or unsubstituted phenyl, 5-6 membered oxygen-containing heterocycloalkyl, wherein said substituted 5-6 membered heterocycloalkyl is substituted by 1, 2 or 3 substituents independently selected from halo, ($C_1$-$C_4$)

alkyl, halo($C_1$-$C_4$)alkyl, ($C_1$-$C_4$)alkoxy, and cyano; and $R^3$ is H; or a salt, particularly a pharmaceutically acceptable salt, thereof.

The invention is further directed to a compound according to Formula (III), wherein:

$R^1$ is an unsubstituted indoyl or a substituted or unsubstituted ($C_2$-$C_6$)alkyl, ($C_4$-$C_6$)cycloalkyl, ($C_4$-$C_6$)cycloalkyl-alkyl-, 5-6 membered heterocycloalkyl, phenyl, or 5-6 membered heteroaryl group, wherein said substituted ($C_2$-$C_6$)alkyl, ($C_4$-$C_6$)cycloalkyl, ($C_4$-$C_6$)cycloalkyl-alkyl-, 5-6 membered heterocycloalkyl, phenyl, or 5-6 membered heteroaryl group is substituted by 1, 2 or 3 substituents independently selected from hydroxyl, (benzyloxy)carbonyl)amino, halogen, ($C_1$-$C_4$)alkyl, halo($C_1$-$C_4$)alkyl, ($C_1$-$C_4$)alkyl-CO—, halo($C_1$-$C_4$)alkyl-CO—, and an optionally substituted 5-6 membered heteroaryl-CO—, wherein said optionally substituted 5-6 membered heteroaryl-CO— is optionally substituted by 1 or 2 substituents independently selected from ($C_1$-$C_4$)alkyl, ($C_1$-$C_4$)alkyl-CO—, halo($C_1$-$C_4$)alkyl, and halo($C_1$-$C_4$)alkyl-CO—, or said substituted ($C_4$-$C_6$)cycloalkyl, 5-6 membered heterocycloalkyl, phenyl, or 5-6 membered heteroaryl group is substituted by an optionally substituted phenyl, 5-6 membered heteroaryl or 9-membered heteroaryl optional substituted by 1 or 2 substituents independently selected from halogen, ($C_1$-$C_4$)alkyl, ($C_1$-$C_4$)alkyl-CO—, halo($C_1$-$C_4$)alkyl, and halo($C_1$-$C_4$)alkyl-CO—;

$R^2$ is a substituted or unsubstituted phenyl, ($C_3$-$C_6$)cycloalkyl, 5-membered oxygen-containing heterocycloalkyl, 5-6 membered heteroaryl or 9-membered heteroaryl group, wherein said substituted phenyl, ($C_3$-$C_6$)cycloalkyl, 5-membered heterocycloalkyl, 5-6 membered heteroaryl or 9-membered heteroaryl group is substituted by 1, 2 or 3 substituents independently selected from halo, ($C_1$-$C_4$)alkyl, halo($C_1$-$C_4$)alkyl, ($C_1$-$C_4$)alkoxy, and cyano; and $R^3$ is H or methyl;

or a salt, particularly a pharmaceutically acceptable salt, thereof.

The invention is further directed to a compound according to Formula (III), wherein:

$R^1$ is an unsubstituted indoyl or a substituted or unsubstituted ($C_2$-$C_6$)alkyl, ($C_4$-$C_6$)cycloalkyl, ($C_4$-$C_6$)cycloalkyl-alkyl-, 5-6 membered heterocycloalkyl, phenyl, or 5-6 membered heteroaryl group, wherein said substituted ($C_2$-$C_6$)alkyl, ($C_4$-$C_6$)cycloalkyl, ($C_4$-$C_6$)cycloalkyl-alkyl-, 5-6 membered heterocycloalkyl, phenyl, or 5-6 membered heteroaryl group is substituted by 1, 2 or 3 substituents independently selected from hydroxyl, (benzyloxy)carbonyl)amino, halogen, ($C_1$-$C_4$)alkyl, halo($C_1$-$C_4$)alkyl, ($C_1$-$C_4$)alkyl-CO—, halo($C_1$-$C_4$)alkyl-CO—, and an optionally substituted 5-6 membered heteroaryl-CO—, wherein said optionally substituted 5-6 membered heteroaryl-CO— is optionally substituted by 1 or 2 substituents independently selected from ($C_1$-$C_4$)alkyl, ($C_1$-$C_4$)alkyl-CO—, halo($C_1$-$C_4$)alkyl, and halo($C_1$-$C_4$)alkyl-CO—, or said substituted ($C_4$-$C_6$)cycloalkyl, 5-6 membered heterocycloalkyl, phenyl, or 5-6 membered heteroaryl group is substituted by an optionally substituted phenyl, 5-6 membered heteroaryl or 9-membered heteroaryl optional substituted by 1 or 2 substituents independently selected from halogen, ($C_1$-$C_4$)alkyl, ($C_1$-$C_4$)alkyl-CO—, halo($C_1$-$C_4$)alkyl, and halo($C_1$-$C_4$)alkyl-CO—;

$R^2$ is a substituted or unsubstituted phenyl, 5-6 membered oxygen-containing heterocycloalkyl, wherein said substituted 5-6 membered heterocycloalkyl is substituted by 1, 2 or 3 substituents independently selected from halo, ($C_1$-$C_4$)alkyl, halo($C_1$-$C_4$)alkyl, ($C_1$-$C_4$)alkoxy, and cyano; and $R^3$ is H or methyl; or a salt, particularly a pharmaceutically acceptable salt, thereof.

The invention is further directed to a compound according to Formula (III), wherein:

$R^1$ is an unsubstituted indoyl or a substituted or unsubstituted ($C_2$-$C_6$)alkyl, ($C_4$-$C_6$)cycloalkyl, ($C_4$-$C_6$)cycloalkyl-alkyl-, 5-6 membered heterocycloalkyl, phenyl, or 5-6 membered heteroaryl group, wherein said substituted ($C_2$-$C_6$)alkyl, ($C_4$-$C_6$)cycloalkyl, ($C_4$-$C_6$)cycloalkyl-alkyl-, 5-6 membered heterocycloalkyl, phenyl, or 5-6 membered heteroaryl group is substituted by 1, 2 or 3 substituents independently selected from hydroxyl, (benzyloxy)carbonyl)amino, halogen, ($C_1$-$C_4$)alkyl, halo($C_1$-$C_4$)alkyl, ($C_1$-$C_4$)alkyl-CO—, halo($C_1$-$C_4$)alkyl-CO—, and an optionally substituted 5-6 membered heteroaryl-CO—, wherein said optionally substituted 5-6 membered heteroaryl-CO— is optionally substituted by 1 or 2 substituents independently selected from ($C_1$-$C_4$)alkyl, ($C_1$-$C_4$)alkyl-CO—, halo($C_1$-$C_4$)alkyl, and halo($C_1$-$C_4$)alkyl-CO—, or said substituted ($C_4$-$C_6$)cycloalkyl, 5-6 membered heterocycloalkyl, phenyl, or 5-6 membered heteroaryl group is substituted by an optionally substituted phenyl, 5-6 membered heteroaryl or 9-membered heteroaryl optional substituted by 1 or 2 substituents independently selected from halogen, ($C_1$-$C_4$)alkyl, ($C_1$-$C_4$)alkyl-CO—, halo($C_1$-$C_4$)alkyl, and halo($C_1$-$C_4$)alkyl-CO—;

$R^2$ is a substituted or unsubstituted phenyl, ($C_3$-$C_6$)cycloalkyl, 5-membered oxygen-containing heterocycloalkyl, 5-6 membered heteroaryl or 9-membered heteroaryl group, wherein said substituted phenyl, ($C_3$-$C_6$)cycloalkyl, 5-membered heterocycloalkyl, 5-6 membered heteroaryl or 9-membered heteroaryl group is substituted by 1, 2 or 3 substituents independently selected from halo, ($C_1$-$C_4$)alkyl, halo($C_1$-$C_4$)alkyl, ($C_1$-$C_4$)alkoxy, and cyano; and $R^3$ is H or methyl; or a salt, particularly a pharmaceutically acceptable salt, thereof.

In one embodiment, a compound of Formula (III) excludes cyclohexyl(5-phenyl-4,5-dihydro-1H-pyrazol-1-yl)methanone, or a salt thereof.

In another embodiment, a compound of Formula (III) excludes the following compounds:
(4,5-dihydro-5-phenyl-1H-pyrazol-1-yl)-3-pyridinyl-methanone,
[4,5-dihydro-5-(2-methoxyphenyl)-1H-pyrazol-1-yl]-3-pyridinyl-methanone,
(4,5-dihydro-5-phenyl-1H-pyrazol-1-yl)-2-furanyl-methanone,
[5-(2-furanyl)-4,5-dihydro-1H-pyrazol-1-yl]-3-pyridinyl-methanone,
(4,5-dihydro-5-phenyl-1H-pyrazol-1-yl)-phenyl-methanone,
(4,5-dihydro-5-phenyl-1H-pyrazol-1-yl)-4-pyridinyl-methanone,
(4,5-dihydro-5-phenyl-1H-pyrazol-1-yl)-2-pyridinyl-methanone,
[4,5-dihydro-5-(3-methoxyphenyl)-1H-pyrazol-1-yl]-3-pyridinyl-methanone,
[4,5-dihydro-5-(4-methoxyphenyl)-1H-pyrazol-1-yl]-3-pyridinyl-methanone,
(4,5-dihydro-5-phenyl-1H-pyrazol-1-yl)-2-pyrazinyl-methanone,
[5-(2-fluorophenyl)-4,5-dihydro-1H-pyrazol-1-yl]-3-pyridinyl-methanone,

[4,5-dihydro-5-(2-methylphenyl)-1H-pyrazol-1-yl]-3-pyridinyl-methanone,
[5-(4-chlorophenyl)-4,5-dihydro-1H-pyrazol-1-yl]-3-pyridinyl-methanone,
[4,5-dihydro-5-(3-methylphenyl)-1H-pyrazol-1-yl]-3-pyridinyl-methanone,
[4,5-dihydro-5-(4-methylphenyl)-1H-pyrazol-1-yl]-3-pyridinyl-methanone,
[5-(2-chlorophenyl)-4,5-dihydro-1H-pyrazol-1-yl]-3-pyridinyl-methanone,
[4,5-dihydro-5-(3-pyridinyl)-1H-pyrazol-1-yl]-3-pyridinyl-methanone,
(4,5-dihydro-5-phenyl-1H-pyrazol-1-yl)[4-(trifluoromethyl)phenyl]-methanone, and
(4,5-dihydro-5-phenyl-1H-pyrazol-1-yl)-2-thienyl-methanone,
or a salt thereof.

In another embodiment, a compound of Formula (III) excludes the following compounds:
[5-(2-chlorophenyl)-4,5-dihydro-3-methyl-1H-pyrazol-1-yl]-3-pyridinyl-methanone,
[5-(2-chlorophenyl)-4,5-dihydro-3-methyl-1H-pyrazol-1-yl](2-fluorophenyl)-methanone,
[5-(2-chlorophenyl)-4,5-dihydro-3-methyl-1H-pyrazol-1-yl][4-(trifluoromethyl)phenyl]-methanone,
1-[5-(2-chlorophenyl)-4,5-dihydro-3-methyl-1H-pyrazol-1-yl]-1-hexanone,
1-[5-(2-chlorophenyl)-4,5-dihydro-3-methyl-1H-pyrazol-1-yl]-1-butanone,
1-[5-(2-chlorophenyl)-4,5-dihydro-3-methyl-1H-pyrazol-1-yl]-1-propanone,
[5-(2,4-dichlorophenyl)-4,5-dihydro-3-methyl-1H-pyrazol-1-yl]-3-pyridinyl-methanone,
[5-(2,4-dichlorophenyl)-4,5-dihydro-3-methyl-1H-pyrazol-1-yl](2-fluorophenyl)-methanone,
[5-(2,4-dichlorophenyl)-4,5-dihydro-3-methyl-1H-pyrazol-1-yl][4-(trifluoromethyl)phenyl]-methanone,
1-[5-(2,4-dichlorophenyl)-4,5-dihydro-3-methyl-1H-pyrazol-1-yl]-1-pentanone,
1-[5-(2,4-dichlorophenyl)-4,5-dihydro-3-methyl-1H-pyrazol-1-yl]-1-butanone,
1-[5-(2,4-dichlorophenyl)-4,5-dihydro-3-methyl-1H-pyrazol-1-yl]-1-propanone,
[4,5-dihydro-3-methyl-5-(4-methylphenyl)-1H-pyrazol-1-yl]phenyl-methanone,
(4,5-dihydro-3-methyl-5-phenyl-1Hpyrazol-1-yl)-4-pyridinyl-methanone, and
[5-(2-furanyl)-4,5-dihydro-3-methyl-1H-pyrazol-1-yl]phenyl-methanone,
or a salt thereof.

In another embodiment, a compound of Formula (III) excludes the following compounds:
(4,5-dihydro-3-methyl-5-phenyl-1Hpyrazol-1-yl)phenyl-methanone,
1-[(5S)-4,5-dihydro-3-methyl-5-phenyl-1H-pyrazol-1-yl]-3-phenyl-1-propanone,
[4,5-dihydro-5-(2-hydroxy-3-methylphenyl)-3-methyl-1H-pyrazol-1-yl]phenyl-methanone,
(2-chlorophenyl)[4,5-dihydro-5-(2-hydroxyphenyl)-3-methyl-1H-pyrazol-1-yl]-methanone,
[4,5-dihydro-5-(2-hydroxyphenyl)-3-methyl-1H-pyrazol-1-yl](2-methylphenyl)-methanone,
[4,5-dihydro-5-(2-hydroxyphenyl)-3-methyl-1H-pyrazol-1-yl](4-methylphenyl)-methanone,
[4,5-dihydro-5-(2-hydroxyphenyl)-3-methyl-1H-pyrazol-1-yl]phenyl-methanone,
[2,5-dihydro-5-(1H-indol-3-yl)-3-methyl-1H-pyrazol-1-yl]-4-pyridinyl-methanone, and
[2,5-dihydro-5-(1H-indol-3-yl)-3-methyl-1H-pyrazol-1-yl]-3-pyridinyl-methanone,
or a salt thereof.

As used herein, the term "alkyl" represents a saturated, straight or branched hydrocarbon group having the specified number of carbon atoms. The term "$(C_2-C_6)$alkyl" refers to an alkyl moiety containing from 2 to 6 carbon atoms. Exemplary alkyls include, but are not limited to methyl, ethyl, n-propyl, isopropyl, n-butyl, isobutyl, s-butyl, and t-butyl.

When a substituent term such as "alkyl" is used in combination with another substituent term, for example as in "$(C_4-C_6)$cycloalkyl-alkyl-", the linking substituent term (e.g., alkyl) is intended to encompass a multi-valent moiety, wherein the point of attachment is through that linking substituent. Generally, the linking substituent is di-valent. An example of a "$(C_3-C_7)$cycloalkyl-alkyl-" group includes, but is not limited to, cyclopentyl-methyl-.

The term "halo($C_1-C_4$)alkyl" represents a group having one or more halogen atoms, which may be the same or different, at one or more carbon atoms of an alkyl moiety containing from 1 to 4 carbon atoms. Examples of "halo($C_1-C_4$)alkyl" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

"Alkenyl" refers to straight or branched hydrocarbon group having at least 1 and up to 3 carbon-carbon double bonds. Examples include ethenyl and propenyl.

"Alkoxy" refers to an "alkyl-oxy-" group, containing an alkyl moiety attached through an oxygen linking atom. For example, the term "$(C_1-C_4)$alkoxy" represents a saturated, straight or branched hydrocarbon moiety having at least 1 and up to 4 carbon atoms attached through an oxygen linking atom. Exemplary "$(C_1-C_4)$alkoxy" groups include, but are not limited to, methoxy, ethoxy, n-propoxy, isopropoxy, n-butoxy, s-butoxy, and t-butoxy.

The term "halo($C_1-C_4$)alkoxy" refers to a "haloalkyl-oxy-" group, containing a "halo($C_1-C_4$)alkyl" moiety attached through an oxygen linking atom, which halo($C_1-C_4$)alkyl refers to a moiety having one or more halogen atoms, which may be the same or different, at one or more carbon atoms of an alkyl moiety containing from 1 to 4 carbon atoms. Exemplary "halo($C_1-C_4$)alkoxy" groups include, but are not limited to, —$OCHF_2$ (difluoromethoxy), —$OCF_3$ (trifluoromethoxy), —$OCH_2CF_3$ (trifluoroethoxy), and —$OCH(CF_3)_2$ (hexafluoroisopropoxy).

A carbocyclic group is a cyclic group in which all of the ring members are carbon atoms, which may be saturated, partially unsaturated (non-aromatic) or fully unsaturated (aromatic). The term "carbocyclic" includes cycloalkyl and aryl groups.

"Cycloalkyl" refers to a non-aromatic, saturated, cyclic hydrocarbon group containing the specified number of carbon atoms. For example, the term "$(C_3-C_6)$cycloalkyl" refers to a non-aromatic cyclic hydrocarbon ring having from three to six ring carbon atoms. Exemplary "$(C_3-C_6)$cycloalkyl" groups include cyclopropyl, cyclobutyl, cyclopentyl, and cyclohexyl.

The terms "cycloalkyloxy" or "cycloalkoxy" refer to a group containing a cycloalkyl moiety, defined hereinabove, attached through an oxygen linking atom. Exemplary "$(C_3-C_6)$cycloalkyloxy" groups include cyclopropyloxy, cyclobutyloxy, cyclopentyloxy, and cyclohexyloxy.

"Aryl" refers to a group or moiety comprising an aromatic, monocyclic or bicyclic hydrocarbon radical containing from 6 to 10 carbon ring atoms and having at least one aromatic ring. Examples of "aryl" groups are phenyl, naphthyl, indenyl, and dihydroindenyl (indanyl). Generally, aryl is phenyl.

The term "9-10 membered carbocyclic-aryl" refers to a bicyclic group or moiety specifically comprising a phenyl moiety fused to a 5-6 membered saturated or partially saturated carbocyclic moiety. Examples of "9-10 membered carbocyclic-aryl" groups include dihydroindenyl (indanyl) and tetrahydronaphthyl.

A heterocyclic group is a cyclic group having, as ring members, atoms of at least two different elements, which cyclic group may be saturated, partially unsaturated (non-aromatic) or fully unsaturated (aromatic).

"Heterocycloalkyl" refers to a non-aromatic, monocyclic or bicyclic group containing 3-10 ring atoms, being saturated and containing one or more (generally one or two) ring heteroatoms independently selected from oxygen, sulfur, and nitrogen. Examples of "heterocycloalkyl" groups include, but are not limited to, aziridinyl, thiiranyl, oxiranyl, azetidinyl, oxetanyl, thietanyl, pyrrolidinyl, tetrahydrofuranyl, tetrahydrothienyl, piperidinyl, piperazinyl, tetrahydropyranyl, tetrahydrothiopyranyl, 1,4-dioxanyl, 1,4-oxathiolanyl, 1,4-oxathianyl, 1,4-dithianyl, morpholinyl, and thiomorpholinyl.

Examples of "4-membered heterocycloalkyl" groups include oxetanyl, thietanyl and azetidinyl.

The term "5-6-membered heterocycloalkyl" represents a non aromatic, monocyclic group, which is fully saturated, containing 5 or 6 ring atoms, which includes one or two heteroatoms selected independently from oxygen, sulfur, and nitrogen. Illustrative examples of 5 to 6-membered heterocycloalkyl groups include, but are not limited to pyrrolidinyl, piperidinyl, piperazinyl, tetrahydrofuranyl, tetrahydrothienyl, tetrahydropyranyl, tetrahydrothiopyranyl, morpholinyl, and thiomorpholinyl.

"Heteroaryl" represents a group or moiety comprising an aromatic monocyclic or bicyclic radical, containing 5 to 10 ring atoms, including 1 to 4 heteroatoms independently selected from nitrogen, oxygen and sulfur. This term also encompasses bicyclic heterocyclic-aryl groups containing either an aryl ring moiety fused to a heterocycloalkyl ring moiety or a heteroaryl ring moiety fused to a cycloalkyl ring moiety.

Illustrative examples of heteroaryls include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl (pyridyl), oxo-pyridyl (pyridyl-N-oxide), pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, indolizinyl, indolyl, isoindolyl, dihydroindolyl, benzimidazolyl, dihydrobenzimidazolyl, benzoxazolyl, dihydrobenzoxazolyl, benzothiazolyl, benzoisothiazolyl, dihydrobenzoisothiazolyl, indazolyl, imidazopyridinyl, pyrazolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

The term "9-10 membered heterocyclic-aryl" refers to a bicyclic group or moiety specifically comprising a phenyl moiety fused to a 5-6 membered saturated or partially saturated heterocyclic moiety. Examples of "9-10 membered heterocyclic-aryl" groups include 2,3-dihydrobenzofuryl (dihydrobenzofuranyl), 2,3-dihydrobenzothienyl, 1,3-benzodioxolyl, dihydrobenzodioxinyl (dihydro-1,4-benzodioxinyl), dihydroindolyl, tetrahydroquinolinyl, and tetrahydroisoquinolinyl.

As used herein, "5-6-membered heteroaryl" represents an aromatic monocyclic group containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Examples of 5-membered heteroaryl groups include furyl (furanyl), thienyl, pyrrolyl, imidazolyl, pyrazolyl, triazolyl, tetrazolyl, thiazolyl, isothiazolyl, thiadiazolyl, oxazolyl, isoxazolyl, oxadiazolyl and oxo-oxadiazolyl. Selected 6-membered heteroaryl groups include pyridinyl, oxo-pyridyl, pyrazinyl, pyrimidinyl, pyridazinyl and triazinyl.

Bicyclic heteroaryl groups include 6,5-fused heteroaryl (9-membered heteroaryl) and 6,6-fused heteroaryl (10-membered heteroaryl) groups. Examples of 6,5-fused heteroaryl (9-membered heteroaryl) groups include benzothienyl, benzofuranyl, indolyl, indolinyl, isoindolyl, isoindolinyl, indazolyl, indolizinyl, isobenzofuryl, 2,3-dihydrobenzofuryl, benzo-1,3-dioxyl, benzoxazolyl, benzothiazolyl, benzimidazolyl, benzoxadiazolyl, benzothiadiazolyl, benzotriazolyl, purinyl and imidazopyridinyl.

Unless otherwise specified, all bicyclic ring systems may be attached at any suitable position on either ring.

The terms "halogen" and "halo" represent chloro, fluoro, bromo, or iodo substituents. "Oxo" represents a double-bonded oxygen moiety; for example, if attached directly to a carbon atom forms a carbonyl moiety (C=O). "Hydroxy" or "hydroxyl" is intended to mean the radical —OH. As used herein, the term "cyano" refers to the group —CN.

As used herein, the term "optionally substituted" indicates that a group (such as an alkyl, cycloalkyl, alkoxy, heterocycloalkyl, aryl, or heteroaryl group) or ring or moiety (such as a carbocyclic or heterocyclic ring or moiety) may be unsubstituted, or the group, ring or moiety may be substituted with one or more substituent(s) as defined. In the case where groups may be selected from a number of alternative groups, the selected groups may be the same or different.

The term "independently" means that where more than one substituent is selected from a number of possible substituents, those substituents may be the same or different.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The compounds of this invention contain one or more asymmetric centers (also referred to as a chiral center), such as a chiral carbon, or a chiral —SO— moiety. The stereochemistry of the chiral carbon center present in compounds of this invention is generally represented in the compound names and/or in the chemical structures illustrated herein. Compounds of this invention containing one or more chiral centers may be present as racemic mixtures, diastereomeric mixtures, enantiomerically enriched mixtures, diastereomerically enriched mixtures, or as enantiomerically or diastereomerically pure individual stereoisomers.

In those instances where the stereochemistry of the chiral carbon center present in compounds of this invention is not represented in the compound name or in the accompanying chemical structure, it will be understood that the compound is present as a mixture of enantiomers or diastereomers. It is understood that one skilled in the art can obtain either the (R) or (S) isomer of any stereoisomeric compound mixture described herein using the resolution techniques described herein or using other conventional resolution techniques.

Individual stereoisomers of a compound described herein may be resolved (or mixtures of stereoisomers may be enriched) using methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The alternative definitions for the various groups and substituent groups of Formulas (I), (II), and/or (III) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

As used herein, the terms "compound(s) of the invention" or "compound(s) of this invention" mean a compound of Formula(s) (I), (II), and/or (III), as defined herein, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, included within the present invention are the compounds of Formulas (I), (II), and (III), as defined herein, in any salt or non-salt form and any physical form thereof, and mixtures of various forms. While such are included within the present invention, it will be understood that the compounds of Formulas (I), (II), and (III), as defined herein, in any salt or non-salt form, and in any physical form thereof, may have varying levels of activity, different bioavailabilities and different handling properties for formulation purposes.

In embodiments of the compounds of Formulas (I), (II), and (III), $R^1$ is $(C_1-C_4)$alkoxy-$CH_2$—, phenyl$(C_1-C_4)$alkoxy-$CH_2$—, or a substituted or unsubstituted $(C_2-C_6)$ alkyl, $(C_2-C_4)$alkynyl, $(C_3-C_6)$cycloalkyl, $(C_3-C_6)$cycloalkyl-$(C_1-C_4)$alkyl-group, or a substituted or unsubstituted 5-6 membered heterocycloalkyl group further optionally substituted by halogen or $(C_1-C_4)$alkyl, wherein said substituted $(C_2-C_6)$alkyl, $(C_3-C_6)$cycloalkyl, $(C_3-C_6)$cycloalkyl-alkyl-, or 5-6 membered heterocycloalkyl group is substituted by 1, 2 or 3 substituents independently selected from hydroxyl, (benzyloxy)carbonyl)amino, cyano, halogen, $(C_1-C_4)$alkyl, halo$(C_1-C_4)$alkyl, $(C_1-C_4)$alkoxy, $(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkoxy-CO—, $(C_1-C_4)$alkylNHCO—, $(((C_1-C_4)$alkyl)$((C_1-C_4)$alkyl)NCO—, halo$(C_1-C_4)$alkyl-CO—, optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-$SO_2$—, optionally substituted phenyl$(C_1-C_4)$alkyl-CO—, optionally substituted 5-6 membered heteroaryl-CO—, and optionally substituted 9-10 membered heteroaryl-CO—, wherein said optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-$SO_2$—, optionally substituted phenyl$(C_1-C_4)$alkyl-CO—, optionally substituted 5-6 membered heteroaryl-CO—, or optionally substituted 9-10 membered heteroaryl-CO—, is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$cycloalkyl and 5-6 membered heterocycloalkyl; or said substituted $(C_2-C_4)$alkynyl, $(C_4-C_6)$cycloalkyl or 5-6 membered heterocycloalkyl group is substituted by an optionally substituted phenyl, 5-6 membered heteroaryl or 9-membered heteroaryl group, wherein said phenyl, 5-6 membered heteroaryl or 9-membered heteroaryl group is optionally substituted by 1 or 2 substituents independently selected from halogen, $(C_1-C_4)$alkyl, $(C_1-C_4)$alkyl-CO—, halo$(C_1-C_4)$alkyl, and halo$(C_1-C_4)$alkyl-CO—.

In embodiments of the compounds of Formulas (I), (II), and (III), $R^1$ is $(C_1-C_4)$alkoxy-$CH_2$—, phenyl$(C_1-C_4)$alkoxy-$CH_2$—, or a substituted or unsubstituted $(C_2-C_6)$ alkyl, $(C_2-C_4)$alkynyl, $(C_3-C_6)$cycloalkyl, $(C_3-C_6)$cycloalkyl-$(C_1-C_4)$alkyl-group, or a substituted or unsubstituted 5-6 membered heterocycloalkyl group further optionally substituted by halogen or $(C_1-C_4)$alkyl, wherein said substituted $(C_2-C_6)$alkyl, $(C_3-C_6)$cycloalkyl, or $(C_3-C_6)$cycloalkyl-alkyl-group is substituted by 1, 2 or 3 substituents independently selected from hydroxyl, (benzyloxy)carbonyl)amino, cyano, halogen, $(C_1-C_4)$alkyl, halo $(C_1-C_4)$alkyl, and $(C_1-C_4)$alkoxy; or wherein said substituted 5-6 membered heterocycloalkyl group is substituted by 1, 2 or 3 substituents independently selected from hydroxyl, (benzyloxy)carbonyl)amino, cyano, halogen, $(C_1-C_4)$alkyl, halo$(C_1-C_4)$alkyl, $(C_1-C_4)$alkoxy, $(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkoxy-CO—, $(C_1-C_4)$alkylNHCO—, $(((C_1-C_4)$alkyl)$((C_1-C_4)$alkyl)NCO—, halo $(C_1-C_4)$alkyl-CO—, optionally substituted $(C_3-C_6)$ cycloalkyl-CO—, optionally substituted $(C_3-C_6)$cycloalkyl-$(C_1-C_4)$alkyl-CO—, optionally substituted phenyl-CO—, optionally substituted phenyl-$SO_2$—, optionally substituted phenyl$(C_1-C_4)$alkyl-CO—, optionally substituted 5-6 membered heteroaryl-CO—, and optionally substituted 9-10 membered heteroaryl-CO—, wherein said optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-$SO_2$—, optionally substituted phenyl$(C_1-C_4)$alkyl-CO—, optionally substituted 5-6 membered heteroaryl-CO—, or optionally substituted 9-10 membered heteroaryl-CO—, is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$cycloalkyl and 5-6 membered heterocycloalkyl, and wherein said substituted 5-6 membered heterocycloalkyl group is further optionally substituted by halogen or $(C_1-C_4)$alkyl; or said substituted $(C_2-C_4)$alkynyl, or 5-6 membered heterocycloalkyl group is substituted by an optionally substituted phenyl, 5-6 membered heteroaryl or 9-membered heteroaryl group, wherein said phenyl, 5-6 membered heteroaryl or 9-membered heteroaryl group is optionally substituted by 1 or 2 substituents independently selected from halogen, $(C_1-C_4)$alkyl, $(C_1-C_4)$alkyl-CO—, halo$(C_1-C_4)$alkyl, and halo$(C_1-C_4)$alkyl-CO—, and wherein said substituted 5-6 membered heterocycloalkyl group is further optionally substituted by halogen or $(C_1-C_4)$alkyl.

In another embodiment, $R^1$ is a substituted or unsubstituted $(C_2-C_6)$alkyl, $(C_4-C_6)$cycloalkyl, $(C_4-C_6)$cycloalkyl-alkyl-, or 5-6 membered heterocycloalkyl group, wherein said substituted $(C_2-C_6)$alkyl, $(C_4-C_6)$cycloalkyl, $(C_4-C_6)$cycloalkyl-alkyl-, or 5-6 membered heterocycloalkyl group is substituted by 1, 2 or 3 substituents independently selected from hydroxyl, (benzyloxy)carbonyl)amino, halogen, $(C_1-C_4)$alkyl, halo$(C_1-C_4)$alkyl, $(C_1-C_4)$alkyl-CO—, halo$(C_1-C_4)$alkyl-CO—, and an optionally substituted 5-6 membered heteroaryl-CO—, wherein said optionally substituted 5-6 membered heteroaryl-CO— is optionally substituted by 1 or 2 substituents independently selected from $(C_1-C_4)$alkyl, $(C_1-C_4)$alkyl-CO—, halo$(C_1-C_4)$alkyl, and halo$(C_1-C_4)$alkyl-CO—, or said substituted $(C_4-C_6)$cycloalkyl or 5-6 membered heterocycloalkyl group is substituted by an optionally substituted phenyl, 5-6 membered heteroaryl or 9-membered heteroaryl optional substituted by 1 or 2 substituents independently selected from halogen, $(C_1-C_4)$alkyl, $(C_1-C_4)$alkyl-CO—, halo$(C_1-C_4)$alkyl, and halo$(C_1-C_4)$alkyl-CO—.

In one embodiment of the compounds of Formulas (I), (II), and (III), $R^1$ is $(C_1-C_4)$alkoxy-CH$_2$—, phenyl$(C_1-C_4)$alkoxy-CH$_2$—. In specific embodiments, $R^1$ is methoxymethyl- or benzyloxymethyl-.

In one embodiment of the compounds of Formulas (I), (II), and (III), $R^1$ is an unsubstituted $(C_3-C_6)$alkyl group. In specific embodiments, $R^1$ is isopropyl, tert-butyl, 2-methyl-butan-1-yl, or 2,3-dimethyl-butan-1-yl. In select embodiments, $R^1$ is tert-butyl.

In other embodiments of the compounds of Formulas (I), (II), and (III), $R^1$ is a substituted $(C_2-C_6)$alkyl group, substituted by a cyano, hydroxyl, $(C_1-C_4)$alkoxy, or a (benzyloxy)carbonyl)amino group. In other embodiments, $R^1$ is a $(C_2-C_5)$alkyl group, substituted by a cyano, hydroxyl, $(C_1-C_4)$alkoxy, or a (benzyloxy)carbonyl)amino group. In specific embodiments, $R^1$ is 1-cyano-1-methylethyl, 1-methoxy-1-methylethyl, ((benzyloxy)carbonyl)amino-ethyl- or 3-hydroxy-2-methyl-propan-2-yl.

In other embodiments of the compounds of Formulas (I), (II), and (III), $R^1$ is a substituted $(C_2-C_6)$alkyl group, substituted by a hydroxyl or a (benzyloxy)carbonyl)amino group. In other embodiments, $R^1$ is a $(C_2-C_5)$alkyl group, substituted by a hydroxyl or a (benzyloxy)carbonyl)amino group. In specific embodiments, $R^1$ is ((benzyloxy)carbonyl)amino-ethyl- or 3-hydroxy-2-methyl-propan-2-yl.

In one embodiment of the compounds of Formulas (I), (II), and (III), $R^1$ is a substituted $(C_2-C_4)$alkynyl, substituted by phenyl. In a specific embodiment, $R^1$ is phenylethynyl-.

In other embodiments, $R^1$ is a substituted or unsubstituted $(C_4-C_6)$cycloalkyl or $(C_4-C_6)$cycloalkyl-alkyl- group. In specific embodiments, $R^1$ is an unsubstituted $(C_4-C_6)$cycloalkyl or $(C_4-C_6)$cycloalkyl-alkyl- group. In more specific embodiments, $R^1$ is cyclobutyl, cyclopentyl, cyclohexyl or cyclopentylmethyl-.

In other embodiments, $R^1$ is a substituted $(C_3-C_6)$cycloalkyl or $(C_3-C_6)$cycloalkyl-alkyl- group substituted by $(C_1-C_4)$alkyl, halo$(C_1-C_4)$alkyl, or cyano. In specific embodiments, $R^1$ is 1-(methyl)cycloprop-1-yl, 1-(trifluoromethyl)cycloprop-1-yl, 1-(cyano)cycloprop-1-yl or 1-(cyano)cyclopent-1-yl.

In still other embodiments, $R^1$ is a substituted or unsubstituted 5-6 membered heterocycloalkyl group. In still other embodiments, $R^1$ is a substituted or unsubstituted 5-6 membered heterocycloalkyl group further optionally substituted by halogen or $(C_1-C_4)$alkyl.

In one embodiment of the compounds of Formulas (I), (II), and (III), $R^1$ is an optionally substituted 5-6 membered heterocycloalkyl group, wherein the heterocycloalkyl group contains one oxygen atom. In a specific embodiment, $R^1$ is unsubstituted tetrahydropyranyl or tetrahydrofuranyl. More specifically, $R^1$ is tetrahydropyran-3-yl (tetrahydro-2H-pyran-3-yl), or tetrahydropyran-4-yl (tetrahydro-2H-pyran-4-yl).

In another embodiment, $R^1$ is a substituted 6-membered heterocycloalkyl group, wherein the heterocycloalkyl group contains one nitrogen atom. In this embodiment, $R^1$ is a substituted piperidinyl group. In another embodiment, $R^1$ is a substituted piperidinyl group further optionally substituted by halogen or $(C_1-C_4)$alkyl.

In another embodiment, when $R^1$ is a substituted 6-membered heterocycloalkyl group containing one nitrogen atom (a substituted piperidinyl group), the heterocycloalkyl group is substituted by a substituent selected from $(C_1-C_4)$alkyl-CO—, halo$(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkylNHCO—, optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-SO$_2$—, optionally substituted phenyl$(C_1-C_4)$alkyl-CO—, optionally substituted 5-6 membered heteroaryl-CO—, and optionally substituted 9-10 membered heteroaryl-CO—, wherein said optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-SO$_2$—, optionally substituted phenyl$(C_1-C_4)$alkyl-CO—, optionally substituted 5-6 membered heteroaryl-CO—, or optionally substituted 9-10 membered heteroaryl-CO—, is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$cycloalkyl and 5-6 membered heterocycloalkyl.

In another embodiment, when $R^1$ is a substituted 6-membered heterocycloalkyl group containing one nitrogen atom (a substituted piperidinyl group) further substituted by halogen or $(C_1-C_4)$alkyl, wherein the heterocycloalkyl group is substituted by a substituent selected from $(C_1-C_4)$alkyl-CO—, halo$(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkylNHCO—, optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-SO$_2$—, optionally substituted phenyl$(C_1-C_4)$alkyl-CO—, optionally substituted 5-6 membered heteroaryl-CO—, and optionally substituted 9-10 membered heteroaryl-CO—, wherein said optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-SO$_2$—, optionally substituted phenyl$(C_1-C_4)$alkyl-CO—, optionally substituted 5-6 membered heteroaryl-CO—, or optionally substituted 9-10 membered heteroaryl-CO— is optionally substituted by 1 or 2 substituents independently selected from halogen, cyano, $(C_1-C_4)$ alkyl, $(C_1-C_4)$alkoxy, $(C_1-C_4)$alkyl-CO—, halo$(C_1-C_4)$ alkyl, halo$(C_1-C_4)$alkyl-CO—, $(C_3-C_6)$cycloalkyl and 5-6 membered heterocycloalkyl.

In another embodiment, when $R^1$ is a substituted 6-membered heterocycloalkyl group containing one nitrogen atom (a substituted piperidinyl group), the heterocycloalkyl group is substituted by a substituent selected from $(C_1-C_4)$alkyl-CO—, halo$(C_1-C_4)$alkyl-CO—, and a substituted 5-membered heteroaryl-CO—, wherein the substituted 5-membered heteroaryl-CO— is substituted by $(C_1-C_4)$alkyl, $(C_1-C_2)$alkyl-CO—, or halo$(C_1-C_2)$alkyl-CO—.

In another embodiment, $R^1$ is a substituted 6-membered heterocycloalkyl group containing one nitrogen atom (a substituted piperidinyl group), wherein the heterocycloalkyl group is substituted by a substituent selected from $(C_1-C_4)$ alkyl-CO—, halo$(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkylNHCO—, $(C_3-C_6)$cycloalkyl-CO—, $(C_3-C_6)$cycloalkyl-$(C_1-C_4)$alkyl-CO—, optionally substituted phenyl-CO—, phenyl-SO$_2$—, phenyl$(C_1-C_4)$alkyl-CO—, optionally substituted 5-6 membered heteroaryl-CO—, and 9-membered heteroaryl-CO—, wherein said optionally substituted phenyl-CO— or optionally substituted 5-6 membered heteroaryl-CO— is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$cycloalkyl and 5-6 membered heterocycloalkyl.

In another embodiment, $R^1$ is a substituted 6-membered heterocycloalkyl group containing one nitrogen atom (a substituted piperidinyl group) further substituted by halogen or $(C_1-C_4)$alkyl, wherein the heterocycloalkyl group is substituted by a substituent selected from $(C_1-C_4)$alkyl-CO—, halo$(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkylNHCO—, $(C_3-C_6)$cycloalkyl-CO—, $(C_3-C_6)$cycloalkyl-$(C_1-C_4)$alkyl-CO—, optionally substituted phenyl-CO—, phenyl-SO$_2$—, phenyl$(C_1-C_4)$alkyl-CO—, optionally substituted 5-6 membered heteroaryl-CO—, and 9-membered heteroaryl-CO—, wherein said optionally substituted phenyl-CO— or optionally substituted 5-6 membered heteroaryl-CO— is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$cycloalkyl and 5-6 membered heterocycloalkyl.

In another embodiment, $R^1$ is a substituted 6-membered heterocycloalkyl group containing one nitrogen atom (a substituted piperidinyl group), wherein the heterocycloalkyl group is substituted by a substituent selected from $(C_1-C_4)$ alkyl-CO—, halo$(C_1-C_4)$alkyl-CO—, and a substituted 5-membered heteroaryl-CO—, and wherein the substituted 5-membered heteroaryl-CO— is substituted by $(C_1-C_4)$ alkyl.

In specific embodiments, $R^1$ is a substituted piperidin-4-yl group. In this embodiment, $R^1$ is a substituted piperidin-4-yl substituted by a substituent selected from $(C_1-C_4)$alkyl-CO—, halo$(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkylNHCO—, $(C_3-C_6)$cycloalkyl-CO—, $(C_3-C_6)$cycloalkyl-$(C_1-C_4)$alkyl-CO—, optionally substituted phenyl-CO—, phenyl-SO$_2$—, phenyl$(C_1-C_4)$alkyl-CO—, optionally substituted 5-6 membered heteroaryl-CO—, and 9-membered heteroaryl-CO—, wherein said optionally substituted phenyl-CO— or optionally substituted 5-6 membered heteroaryl-CO— is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$ cycloalkyl and 5-6 membered heterocycloalkyl.

In specific embodiments, $R^1$ is a substituted piperidin-4-yl group further substituted by halogen or $(C_1-C_4)$alkyl. In this embodiment, $R^1$ is a substituted piperidin-4-yl substituted by a substituent selected from $(C_1-C_4)$alkyl-CO—, halo$(C_1-C_4)$ alkyl-CO—, cyano$(C_1-C_4)$alkyl-CO—, $(C_1-C_4)$alkoxy-$(C_1-C_4)$alkyl-CO—, $(C_1-C_4)$alkylNHCO—, $(C_3-C_6)$cycloalkyl-CO—, $(C_3-C_6)$cycloalkyl-$(C_1-C_4)$alkyl-CO—, optionally substituted phenyl-CO—, phenyl-SO$_2$—, phenyl$(C_1-C_4)$ alkyl-CO—, optionally substituted 5-6 membered heteroaryl-CO—, and 9-membered heteroaryl-CO—, wherein said optionally substituted phenyl-CO— or optionally substituted 5-6 membered heteroaryl-CO— is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$ cycloalkyl and 5-6 membered heterocycloalkyl, wherein the substituted piperidin-4-yl group is further substituted by halogen or $(C_1-C_4)$alkyl.

In specific embodiments, $R^1$ is a substituted piperidin-4-yl group. In this embodiment, $R^1$ is a substituted piperidin-4-yl substituted by a substituent selected from $(C_1-C_4)$alkyl-CO—, halo$(C_1-C_4)$alkyl-CO—, and a substituted 5-membered heteroaryl-CO—, wherein said substituted 5-membered heteroaryl-CO— is substituted by $(C_1-C_4)$alkyl.

In a further embodiment of the compounds of Formulas (I), (II), and (III), $R^1$ is a substituted piperidin-4-yl group substituted by $CH_3CO$—, $CH_3CH_2CO$—, $CH_3CH_2CH_2CO$—, $(CH_3)_2CHCO$—, —$COCH_2CN$, $CH_3OCH_2CO$—, $CF_3CO$—, $CH_3CH_2NHCO$—, cyclopropyl-CO—, cyclobutyl-CO—, cyclopentyl-CO—, cyclohexyl-CO—, cyclohexyl-$CH_2CO$—, pyridin-2-yl-CO—, pyridin-3-yl-CO—, pyridin-4-yl-CO—, 5-chloro-pyridin-2-yl-CO—, 5-fluoro-pyridin-2-yl-CO—, 6-chloro-pyridin-2-yl-CO—, 6-chloro-pyridin-3-yl-CO—, 4-methyl-pyridin-2-yl-CO—, 6-methyl-pyridin-2-yl-CO—, pyrimidin-2-yl, phenyl-CO—, phenyl-SO$_2$—, 4-chlorophenyl-CO—, 4-fluorophenyl-CO—, 4-methoxyphenyl-CO—, 4-cyanophenyl-CO—, 2,4-difluorophenyl-CO—, 3,5-difluorophenyl-CO—, benzyl-CO—, thiazol-2-yl-CO—, thiazol-4-yl-CO—, thiazol-5-yl-CO—, isothiazol-3-yl-CO—, isothiazol-4-yl-CO—, isothiazol-5-yl-CO—, oxazol-2-yl-CO—, oxazol-4-yl-CO—, oxazol-5-yl-CO—, isoxazol-5-yl-CO—, 1-methyl-1H-imidazol-2-yl-CO—, 1-methyl-1H-pyrrol-2-yl-CO—, 1-methyl-1H-pyrazol-3-yl-CO—, 1-methyl-1H-pyrazol-4-yl-CO—, 1-methyl-1H-pyrazol-5-yl-CO—, 3-methyl-1H-pyrazol-5-yl-CO—, 2-methyloxazol-4-yl-CO—, 2-methyloxazol-5-yl-CO—, 5-methyisoxazol-3-yl-CO—, 5-methyisoxazol-4-yl-CO—, 5-methylthien-2-yl-CO-(5-methyl-thiophen-2-yl-CO—), 1-methyl-1H-imidazol-4-yl-CO—, 2-methylthiazol-4-yl-CO—, 2-methylthiazol-5-yl-CO—, 4-methylthiazol-2-yl-CO—, 5-methylthiazol-2-yl-CO—, 2,4-dimethylthiazol-5-yl-CO—, 1H-pyrazol-4-yl-CO—, 1H-pyrazol-3-yl-CO—, 1H-1,2,3-triazol-4-yl-CO—, 1H-1,2,5-thiadiazol-3-yl-CO—, 1H-1,2,3-thiadiazol-5-yl-CO—, benzo[d]thiazol-2-yl-CO—, benzo[d]isoxazol-3-yl-CO—, benzo[d][1,2,3]triazol-6-yl-CO—, 1H-indol-2-yl-CO—, 1H-indol-3-yl-CO—, 1H-indazol-6-yl-CO-1H-indazol-6-yl-CO—, imidazo[1,2-b]pyridazin-2-yl-CO—, 5-cyclopropylisoxazol-3-yl or 4-morpholinophenyl.

Specifically, $R^1$ is piperidin-4-yl, substituted on N by the above-noted substituents.

In a further embodiment of the compounds of Formulas (I), (II), and (III), $R^1$ is a substituted piperidin-4-yl group substituted by CH$_3$CO—, CF$_3$CO—, or 1-methyl-1H-pyrrol-2-yl-CO—. Specifically, R$^1$ is piperidin-4-yl, substituted on N by CH$_3$CO—, CF$_3$CO—, or 1-methyl-1H-pyrrol-2-yl-CO—. In another embodiment of the compounds of Formulas (I), (II), and (III), R$^1$ is a piperidin-4-yl group substituted by CH$_3$CO—. Accordingly, in specific embodiments, R$^1$ is 1-(acetyl)piperidin-4-yl-, 1-(2,2,2-trifluoroacetyl)piperidin-4-yl- or 1-(1-methyl-1H-pyrrolyl-2-carbonyl)piperidin-4-yl-. In other specific embodiments, R$^1$ is 1-(acetyl)piperidin-4-yl-. In another embodiment of the compounds of Formulas (I), (II), and (III), R$^1$ is a piperidin-4-yl group substituted by methyl or fluoro and further substituted by CH$_3$CO— or phenyl-CO—.

In another embodiment of the compounds of Formulas (I), (II), and (III), when R$^1$ is a substituted 6-membered heterocycloalkyl group containing one nitrogen atom (a substituted piperidinyl group), the heterocycloalkyl is optionally substituted by a halogen or (C$_1$-C$_4$)alkyl substituent and is further substituted by an optionally substituted phenyl, 5-6 membered heteroaryl or 9-membered heteroaryl, wherein the optionally substituted phenyl, 6-membered heteroaryl or 9-membered heteroaryl group is optionally substituted by 1 or 2 substituents independently selected from halogen, (C$_1$-C$_4$)alkyl, (C$_1$-C$_4$)alkyl-CO—, halo(C$_1$-C$_3$)alkyl, and halo(C$_1$-C$_3$)alkyl-CO—.

In another embodiment of the compounds of Formulas (I), (II), and (III), when R$^1$ is a substituted 6-membered heterocycloalkyl group containing one nitrogen atom (a substituted piperidinyl group), the heterocycloalkyl (the substituted piperidinyl group) is substituted by an optionally substituted phenyl, 5-6 membered heteroaryl or 9-membered heteroaryl, wherein the optionally substituted phenyl, 6-membered heteroaryl or 9-membered heteroaryl group is optionally substituted by 1 or 2 substituents independently selected from halogen, (C$_1$-C$_4$)alkyl, (C$_1$-C$_4$)alkyl-CO—, halo(C$_1$-C$_3$)alkyl, and halo(C$_1$-C$_3$)alkyl-CO—.

In another embodiment of the compounds of Formulas (I), (II), and (III), R$^1$ is a substituted 6-membered heterocycloalkyl group containing one nitrogen atom (a substituted piperidinyl group), wherein the heterocycloalkyl group is optionally substituted by a halogen or (C$_1$-C$_4$)alkyl substituent and is further substituted by an optionally substituted phenyl, 6-membered heteroaryl or 9-membered heteroaryl group, wherein the optionally substituted phenyl, 6-membered heteroaryl or 9-membered heteroaryl group is optionally substituted by halogen, (C$_1$-C$_4$)alkyl, or halo(C$_1$-C$_4$)alkyl.

In another embodiment of the compounds of Formulas (I), (II), and (III), R$^1$ is a substituted 6-membered heterocycloalkyl group containing one nitrogen atom (a substituted piperidinyl group), wherein the heterocycloalkyl group is substituted by an optionally substituted phenyl, 6-membered heteroaryl or 9-membered heteroaryl group, wherein the optionally substituted phenyl, 6-membered heteroaryl or 9-membered heteroaryl group is optionally substituted by halogen, (C$_1$-C$_4$)alkyl, or halo(C$_1$-C$_4$)alkyl.

In another embodiment of the compounds of Formulas (I), (II), and (III), R$^1$ is a substituted 6-membered heterocycloalkyl group containing one nitrogen atom (a substituted piperidinyl group), wherein the heterocycloalkyl group is optionally substituted by a halogen or (C$_1$-C$_4$)alkyl substituent and is further substituted by an unsubstituted phenyl, a substituted or unsubstituted 6-membered heteroaryl containing one or two nitrogen atoms, or an unsubstituted 9-membered heteroaryl, wherein the substituted 6-membered heteroaryl group is substituted by halogen, (C$_1$-C$_4$)alkyl, or halo(C$_1$-C$_4$)alkyl.

In another embodiment of the compounds of Formulas (I), (II), and (III), R$^1$ is a substituted 6-membered heterocycloalkyl group containing one nitrogen atom (a substituted piperidinyl group), wherein the heterocycloalkyl group is substituted by an unsubstituted phenyl, a substituted or unsubstituted 6-membered heteroaryl containing one or two nitrogen atoms, or an unsubstituted 9-membered heteroaryl, wherein the substituted 6-membered heteroaryl group is substituted by halogen, (C$_1$-C$_4$)alkyl, or halo(C$_1$-C$_4$)alkyl.

In another embodiment of the compounds of Formulas (I), (II), and (III), R$^1$ is a substituted piperidin-4-yl, substituted by a halogen or (C$_1$-C$_4$)alkyl and further substituted by an unsubstituted phenyl, a substituted or unsubstituted 6-membered heteroaryl containing one or two nitrogen atoms, or an unsubstituted 9-membered heteroaryl, wherein the substituted 6-membered heteroaryl group is substituted by halogen, (C$_1$-C$_4$)alkyl, or halo(C$_1$-C$_4$)alkyl.

In another embodiment of the compounds of Formulas (I), (II), and (III), R$^1$ is a substituted piperidin-4-yl, substituted by an unsubstituted phenyl, a substituted or unsubstituted 6-membered heteroaryl containing one or two nitrogen atoms, or an unsubstituted 9-membered heteroaryl, wherein the substituted 6-membered heteroaryl group is substituted by halogen, (C$_1$-C$_4$)alkyl, or halo(C$_1$-C$_4$)alkyl.

In another embodiment, R$^1$ is a substituted piperidin-4-yl, substituted by an unsubstituted phenyl or 9-membered heteroaryl.

In another embodiment, R$^1$ is a substituted piperidin-4-yl, substituted by a halogen or (C$_1$-C$_4$)alkyl and further substituted by a substituted or unsubstituted 6-membered heteroaryl containing one or two nitrogen atoms, wherein said substituted 6-membered heteroaryl is substituted by halogen, (C$_1$-C$_4$)alkyl, or halo(C$_1$-C$_4$)alkyl.

In another embodiment, R$^1$ is a substituted piperidin-4-yl, substituted by a substituted or unsubstituted 6-membered heteroaryl containing one or two nitrogen atoms, wherein said substituted 6-membered heteroaryl is substituted by halogen, (C$_1$-C$_4$)alkyl, or halo(C$_1$-C$_4$)alkyl.

In one embodiment of the compounds of Formulas (I), (II), and (III), R$^1$ is a substituted piperidin-4-yl group substituted by a halogen or (C$_1$-C$_4$)alkyl and further substituted by an unsubstituted phenyl or benzoxazolyl, or an optionally substituted pyridyl or pyrimidinyl, optionally substituted by halogen, (C$_1$-C$_4$)alkyl, or halo(C$_1$-C$_4$)alkyl, particularly fluoro, methyl or trifluoromethyl In one embodiment of the compounds of Formulas (I), (II), and (III), R$^1$ is a substituted piperidin-4-yl group substituted by an unsubstituted phenyl or benzoxazolyl, or an optionally substituted pyridyl or pyrimidinyl, optionally substituted by halogen, (C$_1$-C$_4$)alkyl, or halo(C$_1$-C$_4$)alkyl, particularly fluoro, methyl or trifluoromethyl.

In more specific embodiments, R$^1$ is 1-(5-methylpyrimidin-2-yl)piperidin-4-yl, 1-(5-fluoropyridin-2-yl)piperidin-4-yl, 1-(5-methylpyridin-2-yl)piperidin-4-yl, 1-(5-fluoropyrimidin-2-yl)piperidin-4-yl, 4-fluoro-1-(5-fluoropyrimidin-2-yl)piperidin-4-yl, 4-methyl-1-(5-fluoropyrimidin-2-yl)piperidin-4-yl (or 1-(5-fluoropyrimidin-2-yl)-4-methylpiperidin-4-yl), 1-(pyrimidin-2-yl)piperidin-4-yl, 4-methyl-1-(pyrimidin-2-yl)piperidin-4-yl, 1-(phenyl)piperidin-4-yl, 1-(pyridin-2-yl)piperidin-4-yl, 1-(thiazol-2-yl)piperidin-4-yl, 1-(benzo[d]oxazol-2-yl)piperidin-4-yl, or 5-(trifluoromethyl)pyridin-2-yl)piperidin-4-yl In other more specific embodiments, R$^1$ is 1-(5-methylpyrimidin-2-yl)piperidin-4-yl, 1-(5-fluoropyridin-2-yl)piperidin-4-yl, 1-(5-methylpyridin-2-yl)piperidin-4-yl, 1-(5-fluoropyrimidin-2-yl)piperidin-4-yl, 1-(pyrimidin-2-yl)piperidin-4-yl, 1-(phenyl)piperidin-4-yl, 1-(pyridin-2-yl)

piperidin-4-yl, 1-(benzo[d]oxazol-2-yl)piperidin-4-yl, or 5-(trifluoromethyl)pyridin-2-yl)piperidin-4-yl In one embodiment of the compounds of Formula (III), $R^1$ is an unsubstituted indoyl; particularly, $R^1$ is indoyl-2-yl.

In another embodiment of the compounds of Formula (III), $R^1$ is an unsubstituted phenyl. In other embodiments of the compounds of Formula (III), $R^1$ is a substituted phenyl, wherein in the phenyl is substituted by a $(C_1-C_4)$alkyl group; particularly, $R^1$ is 3-methyl-phenyl (m-tolyl) or a 4-methyl-phenyl (p-tolyl).

In other embodiments of the compounds of Formula (III), $R^1$ is a substituted 5-membered heteroaryl, substituted by a $(C_1-C_4)$alkyl group. In another embodiment of the compounds of Formula (III), $R^1$ is an unsubstituted 5-membered heteroaryl, particularly, $R^1$ is thien-2-yl.

In one embodiment of the compounds of Formulas (I), (II), and (III), $R^2$ is a substituted or unsubstituted phenyl, $(C_3-C_6)$cycloalkyl, 5-6 membered oxygen-containing heterocycloalkyl, 5-6 membered heteroaryl, 9-membered heteroaryl, 9-10 membered carbocyclic-aryl, or 9-10 membered heterocyclic-aryl group, wherein said substituted phenyl, $(C_3-C_6)$cycloalkyl, 5-6 membered heterocycloalkyl, 5-6 membered heteroaryl, 9-membered heteroaryl, 9-10 membered carbocyclic-aryl, or 9-10 membered heterocyclic-aryl group is substituted by 1, 2 or 3 substituents independently selected from halogen, $(C_1-C_4)$alkyl, halo$(C_1-C_4)$alkyl, $(C_1-C_4)$alkoxy, halo$(C_1-C_4)$alkoxy, and cyano.

In another embodiment, $R^2$ is a substituted or unsubstituted phenyl, $(C_3-C_6)$cycloalkyl, 5-6 membered oxygen-containing heterocycloalkyl, 5-6 membered heteroaryl or 9-membered heteroaryl group, wherein said substituted phenyl, $(C_3-C_6)$cycloalkyl, 5-membered heterocycloalkyl, 5-6 membered heteroaryl or 9-membered heteroaryl group is substituted by 1, 2 or 3 substituents independently selected from halo, $(C_1-C_4)$alkyl, halo$(C_1-C_4)$alkyl, $(C_1-C_4)$alkoxy, and cyano.

In another embodiment of the compounds of Formulas (I), (II), and (III), $R^2$ is a substituted or unsubstituted phenyl, $(C_3-C_6)$cycloalkyl, 5-membered oxygen-containing heterocycloalkyl, 5-6 membered heteroaryl or 9-membered heteroaryl group, wherein said substituted phenyl, $(C_3-C_6)$cycloalkyl, 5-membered oxygen-containing heterocycloalkyl, 5-6 membered heteroaryl or 9-membered heteroaryl group is substituted by 1, 2 or 3 substituents independently selected from halo, $(C_1-C_4)$alkyl, halo$(C_1-C_4)$alkyl, $(C_1-C_4)$alkoxy, and cyano.

In another embodiment, $R^2$ is an unsubstituted phenyl, $(C_5-C_6)$cycloalkyl, 5-6 membered oxygen-containing heterocycloalkyl, 5-6 membered heteroaryl, 9-membered heteroaryl, 9-10 membered carbocyclic-aryl, or 9-10 membered heterocyclic-aryl group, or a substituted phenyl or 5-6 membered heteroaryl, where said substituted phenyl, or 5-6 membered heteroaryl is substituted by 1 or 2 substituents independently selected from halo, $(C_1-C_4)$alkyl, halo$(C_1-C_4)$alkyl, $(C_1-C_4)$alkoxy, halo$(C_1-C_4)$alkoxy, and cyano.

In another embodiment, $R^2$ is an unsubstituted phenyl, $(C_5-C_6)$cycloalkyl, 5-membered oxygen-containing heterocycloalkyl, 5-6 membered heteroaryl or 9-membered heteroaryl group; or a substituted phenyl or 5-6 membered heteroaryl, where said substituted phenyl, or 5-6 membered heteroaryl is substituted by 1 or 2 substituents independently selected from halo, $(C_1-C_4)$alkyl, halo$(C_1-C_4)$alkyl, $(C_1-C_4)$alkoxy, and cyano.

In another embodiment, $R^2$ is an unsubstituted phenyl, $(C_5-C_6)$cycloalkyl, 5-6 membered oxygen-containing heterocycloalkyl, 6-membered heteroaryl, 9-membered heteroaryl, 9-10 membered carbocyclic-aryl, or 9-10 membered heterocyclic-aryl group, or a substituted phenyl or 6-membered heteroaryl, wherein the substituted phenyl or 6-membered heteroaryl is substituted by 1 or 2 substituents independently selected from halo, $(C_1-C_4)$alkyl, halo$(C_1-C_4)$alkyl, $(C_1-C_4)$alkoxy, halo$(C_1-C_4)$alkoxy, and cyano.

In another embodiment, $R^2$ is an unsubstituted phenyl, $(C_5-C_6)$cycloalkyl, 5-membered oxygen-containing heterocycloalkyl, 6-membered heteroaryl or 9-membered heteroaryl group, or a substituted phenyl or 6-membered heteroaryl, wherein the substituted phenyl or 6-membered heteroaryl is substituted by 1 or 2 substituents independently selected from halo, $(C_1-C_4)$alkyl, halo$(C_1-C_4)$alkyl, $(C_1-C_4)$alkoxy, and cyano.

In specific embodiments, when $R^2$ is a substituted or unsubstituted 6-membered heteroaryl, the 6-membered heteroaryl contains one or two nitrogen atoms.

In one embodiment of the compounds of Formulas (I), (II), and (III), $R^2$ is unsubstituted phenyl.

In another embodiment, $R^2$ is phenyl substituted by 1 or 2 substituents independently selected from halo, $(C_1-C_4)$alkyl, halo$(C_1-C_4)$alkyl, $(C_1-C_4)$alkoxy, halo$(C_1-C_4)$alkoxy, and cyano. In selected embodiments, $R^2$ is phenyl substituted by 1 or 2 substituents independently selected from chloro, fluoro, methyl, trifluoromethyl, methoxy, difluoromethoxy, and cyano.

In another embodiment, $R^2$ is phenyl substituted by 1 or 2 substituents independently selected from halo, $(C_1-C_4)$alkyl, halo$(C_1-C_4)$alkyl, $(C_1-C_4)$alkoxy, and cyano. In selected embodiments, $R^2$ is phenyl substituted by 1 or 2 substituents independently selected from chloro, fluoro, methyl, trifluoromethyl, methoxy, and cyano. In other selected embodiments $R^2$ is a substituted phenyl, wherein the substituted phenyl is substituted by 1 or 2 halo substituents, specifically 1 or 2 fluoro groups. In specific embodiments $R^2$ is phenyl, substituted 2 fluoro substituents.

In specific embodiments, $R^2$ is 3-chlorophenyl, 4-chlorophenyl, 2-fluorophenyl, 3-fluorophenyl, 4-fluorophenyl, 3,4-dichlorophenyl, 3,5-difluorophenyl, 2-methylphenyl, 4-methylphenyl, 4-trifluoromethylphenyl, 4-methoxyphenyl, 4-difluoromethoxyphenyl, 3-cyanophenyl, 4-cyanophenyl, 2-fluoro-5-methylphenyl, 2-fluoro-4-methylphenyl, 3-fluoro-5-methylphenyl, 3-fluoro-4-methylphenyl, or 4-chloro-3-fluorophenyl.

In specific embodiments, $R^2$ is 3-chlorophenyl, 4-chlorophenyl, 3-fluorophenyl, 3,4-dichlorophenyl, 2-methylphenyl, 4-methylphenyl, 4-trifluoromethylphenyl, 4-methoxyphenyl, 3-cyanophenyl, 4-cyanophenyl, 2-fluoro-5-methylphenyl, 2-fluoro-4-methylphenyl, 3-fluoro-5-methylphenyl, or 3-fluoro-4-methylphenyl. In other specific embodiments, $R^2$ is 3,5-difluorophenyl.

In one embodiment of the compounds of Formulas (I), (II), and (III), $R^2$ is unsubstituted $(C_5-C_6)$cycloalkyl, particularly, cyclopentyl or cyclohexyl.

In one embodiment of the compounds of Formulas (I), (II), and (III), $R^2$ is unsubstituted 5-6 membered oxygen-containing heterocycloalkyl, particularly, $R^2$ is unsubstituted 6-membered oxygen-containing heterocycloalkyl, particularly, tetrahydropyran-2-yl (tetrahydro-2H-pyran-2-yl).

In another embodiment, $R^2$ is an unsubstituted 5-membered heteroaryl. In a specific embodiment, $R^2$ is unsubstituted oxazolyl, particularly, oxazol-4-yl.

In another embodiment of the compounds of Formulas (I), (II), and (III), $R^2$ is an optionally substituted 6-membered heteroaryl containing 1 or 2 nitrogen heteroatoms, wherein the heteroaryl is optionally substituted by 1 or 2 substituents independently selected from halo, $(C_1-C_4)$alkyl, halo$(C_1-C_4)$alkyl, and $(C_1-C_4)$alkoxy.

In another embodiment, $R^2$ is an optionally substituted pyridinyl or pyrazinyl, optionally substituted by 1 or 2 substituents independently selected from halo, $(C_1-C_4)$alkyl, halo$(C_1-C_4)$alkyl, and $(C_1-C_4)$alkoxy. In another embodiment, $R^2$ is an optionally substituted pyridinyl, optionally substituted by 1 or 2 substituents independently selected from halo, $(C_1-C_4)$alkyl, halo$(C_1-C_4)$alkyl, and $(C_1-C_4)$alkoxy.

In another embodiment, $R^2$ is an optionally substituted pyridinyl or pyrazinyl, optionally substituted by 1 or 2 substituents independently selected from chloro, fluoro, methyl, and methoxy. In another embodiment, $R^2$ is an optionally substituted pyridinyl, optionally substituted by 1 or 2 substituents independently selected from chloro, fluoro, methyl and methoxy.

In specific embodiments, $R^2$ is pyridin-2-yl, pyridin-3-yl, 5-methylpyridin-2-yl, 5-fluoro-6-methylpyridin-2-yl, 5-fluoropyridin-3-yl, 5-chloropyridin-3-yl, 5-methylpyridin-3-yl, 6-methylpyridin-3-yl, 6-methoxypyridin-3-yl, or 5-methylpyrazin-2-yl.

In selected embodiments $R^2$ is a substituted or unsubstituted phenyl or a substituted or unsubstituted pyridyl, wherein the substituted phenyl or substituted pyridyl is substituted by 1 or 2 substituents independently selected from halo, $(C_1-C_4)$alkyl, halo$(C_1-C_4)$alkyl, and $(C_1-C_4)$alkoxy, specifically chloro, fluoro, methyl and methoxy.

In another embodiment of the compounds of Formulas (I), (II), and (III), $R^2$ is an optionally substituted 9-membered heteroaryl group, particularly, an unsubstituted indolyl (1Hindolyl). In specific embodiments, $R^2$ is indol-4-yl, indol-5-yl, or indol-6-yl.

In another embodiment of the compounds of Formulas (I), (II), and (III), $R^2$ is an optionally substituted 9-10 membered carbocyclic-aryl group, particularly, an unsubstituted indanyl (2,3-dihydroindenyl). In specific embodiments, $R^2$ is 2,3-dihydro-1H-inden-5-yl.

In another embodiment of the compounds of Formulas (I), (II), and (III), $R^2$ is an optionally substituted 9-10 membered heterocyclic-aryl group, particularly, an unsubstituted dihydrobenzofuranyl, benzo-1,3-dioxolyl or dihydrobenzo[1,4]dioxinyl. In specific embodiments, $R^2$ is 2,3-dihydrobenzofuran-5-yl, benzo[d][1,3]dioxol-5-yl or 2,3-dihydrobenzo[b][1,4]dioxin-6-yl.

In selected embodiments of the compounds of Formula (III), $R^3$ is H. In other embodiments of the compounds of Formula (III), $R^3$ is methyl. In other embodiments of the compounds of Formula (III), $R^3$ is halogen, specifically bromo.

In a further embodiment, the invention is directed to a compound according to Formula (I), (II), or (III), wherein $R^1$ is an unsubstituted $(C_3-C_6)$alkyl group; $R^2$ is a substituted or unsubstituted phenyl or a substituted or unsubstituted pyridyl, wherein the substituted phenyl or a substituted pyridyl is substituted by 1 or 2 substituents independently selected from halo, $(C_1-C_4)$alkyl, halo$(C_1-C_4)$alkyl, and $(C_1-C_4)$alkoxy; $R^3$ is H; or a salt, particularly a pharmaceutically acceptable salt, thereof. In a specific embodiment, the invention is directed to a compound according to Formula (I), (II), or (III), wherein $R^1$ is tert-butyl; $R^2$ is a substituted or unsubstituted phenyl or a substituted or unsubstituted pyridyl, wherein the substituted phenyl or a substituted pyridyl is substituted by 1 or 2 substituents independently selected from halo, $(C_1-C_4)$alkyl, halo$(C_1-C_4)$alkyl, and $(C_1-C_4)$alkoxy; $R^3$ is H; or a salt, particularly a pharmaceutically acceptable salt, thereof.

In a further embodiment, the invention is directed to a compound according to Formula (I), (II), or (III), wherein $R^1$ is a substituted $(C_2-C_5)$alkyl group, wherein said substituted $(C_2-C_5)$alkyl is substituted by a hydroxyl or a (benzyloxy)carbonyl)amino group; $R^2$ is a substituted or unsubstituted phenyl or a substituted or unsubstituted pyridyl, wherein the substituted phenyl or a substituted pyridyl is substituted by 1 or 2 substituents independently selected from halo, $(C_1-C_4)$alkyl, halo$(C_1-C_4)$alkyl, and $(C_1-C_4)$alkoxy; $R^3$ is H; or a salt, particularly a pharmaceutically acceptable salt, thereof.

In a further embodiment, the invention is directed to a compound according to Formula (I), (II), or (III), wherein $R^1$ is unsubstituted tetrahydropyranyl or tetrahydrofuranyl; $R^2$ is a substituted or unsubstituted phenyl or a substituted or unsubstituted pyridyl, wherein the substituted phenyl or a substituted pyridyl is substituted by 1 or 2 substituents independently selected from halo, $(C_1-C_4)$alkyl, halo$(C_1-C_4)$alkyl, and $(C_1-C_4)$alkoxy; $R^3$ is H; or a salt, particularly a pharmaceutically acceptable salt, thereof.

In a further embodiment, the invention is directed to a compound according to Formula (I), (II), or (III), wherein $R^1$ is a substituted piperidin-4-yl substituted by a substituent selected from $(C_1-C_4)$alkyl-CO—, halo$(C_1-C_4)$alkyl-CO—, and a substituted 5-membered heteroaryl-CO—, wherein said substituted 5-membered heteroaryl-CO— is substituted by $(C_1-C_4)$alkyl; $R^2$ is a substituted or unsubstituted phenyl or a substituted or unsubstituted pyridyl, wherein the substituted phenyl or a substituted pyridyl is substituted by 1 or 2 substituents independently selected from halo, $(C_1-C_4)$alkyl, halo$(C_1-C_4)$alkyl, and $(C_1-C_4)$alkoxy; $R^3$ is H; or a salt, particularly a pharmaceutically acceptable salt, thereof.

In a specific embodiment, the invention is directed to a compound according to Formula (I), (II), or (III), wherein $R^1$ is a substituted piperidin-4-yl substituted by $(C_1-C_4)$alkyl-CO—; $R^2$ is a substituted or unsubstituted phenyl, wherein the substituted phenyl is substituted by 1 or 2 substituents independently selected from halo, $(C_1-C_4)$alkyl, halo$(C_1-C_4)$alkyl, and $(C_1-C_4)$alkoxy; $R^3$ is H; or a salt, particularly a pharmaceutically acceptable salt, thereof.

In a further embodiment, the invention is directed to a compound according to Formula (I), (II), or (III), wherein $R^1$ is a substituted piperidin-4-yl group substituted by an unsubstituted phenyl or benzoxazolyl, or an optionally substituted pyridyl or pyrimidinyl, optionally substituted by halogen, $(C_1-C_4)$alkyl, or halo$(C_1-C_4)$alkyl; $R^2$ is a substituted or unsubstituted phenyl or a substituted or unsubstituted pyridyl, wherein the substituted phenyl or a substituted pyridyl is substituted by 1 or 2 substituents independently selected from halo, $(C_1-C_4)$alkyl, halo$(C_1-C_4)$alkyl, and $(C_1-C_4)$alkoxy; $R^3$ is H; or a salt, particularly a pharmaceutically acceptable salt, thereof.

It will be appreciated that the present invention encompasses compounds of Formulas (I), (II), or (III), as the free base and as salts thereof, for example as a pharmaceutically acceptable salt thereof. In one embodiment the invention relates to compounds of Formulas (I), (II), or (III), in the form of a free base. In another embodiment the invention relates to compounds of Formulas (I), (II), or (III), in the form of a salt, particularly, a pharmaceutically acceptable salt. It will be further appreciated that, in one embodiment, the invention relates to compounds of the Examples in the form of a free base. In another embodiment the invention relates to compounds of the Examples in the form of a salt, particularly, a pharmaceutically acceptable salt.

The compounds of this invention include the following compounds described herein:

(5-(5-fluoropyridin-3-yl)-4,5-dihydro-1H-pyrazol-1-yl)(1-(5-methylpyrimidin-2-yl)piperidin-4-yl)methanone,
(1-(5-fluoropyridin-2-yl)piperidin-4-yl)(5-phenyl-4,5-dihydro-1H-pyrazol-1-yl)methanone,
(1-(5-methylpyridin-2-yl)piperidin-4-yl)(5-phenyl-4,5-dihydro-1H-pyrazol-1-yl)methanone,
(1-(5-methylpyrimidin-2-yl)piperidin-4-yl)(5-phenyl-4,5-dihydro-1H-pyrazol-1-yl)methanone,
(1-(5-fluoropyrimidin-2-yl)piperidin-4-yl)(5-phenyl-4,5-dihydro-1H-pyrazol-1-yl)methanone,
(5-(5-fluoropyridin-3-yl)-4,5-dihydro-1H-pyrazol-1-yl)(1-(5-fluoropyrimidin-2-yl)piperidin-4-yl)methanone,
(5-(5-fluoropyridin-3-yl)-4,5-dihydro-1H-pyrazol-1-yl)(1-(pyrimidin-2-yl)piperidin-4-yl)methanone,
(S)-2,2-dimethyl-1-(5-phenyl-4,5-dihydro-1H-pyrazol-1-yl)propan-1-one,
1-(5-(5-fluoropyridin-3-yl)-4,5-dihydro-1H-pyrazol-1-yl)-2,2-dimethylpropan-1-one,
(S)-1-(5-(5-fluoropyridin-3-yl)-4,5-dihydro-1H-pyrazol-1-yl)-2,2-dimethylpropan-1-one,
(5-phenyl-4,5-dihydro-1H-pyrazol-1-yl)(1-phenylpiperidin-4-yl)methanone,
(1-phenylpiperidin-4-yl)(5-(pyridin-3-yl)-4,5-dihydro-1H-pyrazol-1-yl)methanone,
cyclohexyl(5-(pyridin-3-yl)-4,5-dihydro-1H-pyrazol-1-yl)methanone,
cyclopentyl(5-phenyl-4,5-dihydro-1H-pyrazol-1-yl)methanone,
(5-phenyl-4,5-dihydro-1H-pyrazol-1-yl)(tetrahydro-2H-pyran-4-yl)methanone,
2-cyclopentyl-1-(5-(5-fluoropyridin-3-yl)-4,5-dihydro-1H-pyrazol-1-yl)ethanone,
1-(5-(5-fluoropyridin-3-yl)-4,5-dihydro-1H-pyrazol-1-yl)-2-methylpropan-1-one,
cyclohexyl(5-(5-fluoropyridin-3-yl)-4,5-dihydro-1H-pyrazol-1-yl)methanone,
1-(5-(5-fluoropyridin-3-yl)-4,5-dihydro-1H-pyrazol-1-yl)-2,3-dimethylbutan-1-one,
(5-(pyridin-3-yl)-4,5-dihydro-1H-pyrazol-1-yl)(1-(pyrimidin-2-yl)piperidin-4-yl)methanone,
(S)-(5-(pyridin-3-yl)-4,5-dihydro-1H-pyrazol-1-yl)(1-(pyrimidin-2-yl)piperidin-4-yl)methanone,
2-methyl-1-(5-phenyl-4,5-dihydro-1H-pyrazol-1-yl)propan-1-one,
cyclobutyl(5-phenyl-4,5-dihydro-1H-pyrazol-1-yl)methanone,
(5-phenyl-4,5-dihydro-1H-pyrazol-1-yl)(tetrahydro-2H-pyran-3-yl)methanone,
2-methyl-1-(5-phenyl-4,5-dihydro-1H-pyrazol-1-yl)butan-1-one,
2-cyclopentyl-1-(5-phenyl-4,5-dihydro-1H-pyrazol-1-yl)ethanone,
2,3-dimethyl-1-(5-phenyl-4,5-dihydro-1H-pyrazol-1-yl)butan-1-one,
1-(5-(3,4-dichlorophenyl)-4,5-dihydro-1H-pyrazol-1-yl)-2,2-dimethylpropan-1-one,
(S)-1-(5-(3,4-dichlorophenyl)-4,5-dihydro-1H-pyrazol-1-yl)-2,2-dimethylpropan-1-one,
2,2-dimethyl-1-(5-(pyridin-3-yl)-4,5-dihydro-1H-pyrazol-1-yl)propan-1-one,
(S)-2,2-dimethyl-1-(5-(pyridin-3-yl)-4,5-dihydro-1H-pyrazol-1-yl)propan-1-one,
1-(5-(3-chlorophenyl)-4,5-dihydro-1H-pyrazol-1-yl)-2,2-dimethylpropan-1-one,
(S)-1-(5-(3-chlorophenyl)-4,5-dihydro-1H-pyrazol-1-yl)-2,2-dimethylpropan-1-one,
1-(5-(6-methoxypyridin-3-yl)-4,5-dihydro-1H-pyrazol-1-yl)-2,2-dimethylpropan-1-one,
2,2-dimethyl-1-(5-(5-methylpyridin-2-yl)-4,5-dihydro-1H-pyrazol-1-yl)propan-1-one,
2,2-dimethyl-1-(5-(pyridin-2-yl)-4,5-dihydro-1H-pyrazol-1-yl)propan-1-one,
(S)-2,2-dimethyl-1-(5-(pyridin-2-yl)-4,5-dihydro-1H-pyrazol-1-yl)propan-1-one,
2,2-dimethyl-1-(5-(6-methylpyridin-3-yl)-4,5-dihydro-1H-pyrazol-1-yl)propan-1-one,
(S)-2,2-dimethyl-1-(5-(6-methylpyridin-3-yl)-4,5-dihydro-1H-pyrazol-1-yl)propan-1-one,
1-(5-(2-fluoro-4-methylphenyl)-4,5-dihydro-1H-pyrazol-1-yl)-2,2-dimethylpropan-1-one,
1-(5-(3-fluoro-4-methylphenyl)-4,5-dihydro-1H-pyrazol-1-yl)-2,2-dimethylpropan-1-one,
1-(5-cyclohexyl-4,5-dihydro-1H-pyrazol-1-yl)-2,2-dimethylpropan-1-one,
(S)-1-(5-cyclohexyl-4,5-dihydro-1H-pyrazol-1-yl)-2,2-dimethylpropan-1-one,
1-(5-cyclopentyl-4,5-dihydro-1H-pyrazol-1-yl)-2,2-dimethylpropan-1-one,
2,2-dimethyl-1-(5-(p-tolyl)-4,5-dihydro-1H-pyrazol-1-yl)propan-1-one,
2,2-dimethyl-1-(5-(oxazol-4-yl)-4,5-dihydro-1H-pyrazol-1-yl)propan-1-one,
2,2-dimethyl-1-(5-(o-tolyl)-4,5-dihydro-1H-pyrazol-1-yl)propan-1-one,
2,2-dimethyl-1-(5-(4-(trifluoromethyl)phenyl)-4,5-dihydro-1H-pyrazol-1-yl)propan-1-one,
(S)-2,2-dimethyl-1-(5-(4-(trifluoromethyl)phenyl)-4,5-dihydro-1H-pyrazol-1-yl)propan-1-one,
1-(5-(4-methoxyphenyl)-4,5-dihydro-1H-pyrazol-1-yl)-2,2-dimethylpropan-1-one,
1-(5-(4-chlorophenyl)-4,5-dihydro-1H-pyrazol-1-yl)-2,2-dimethylpropan-1-one,
(S)-1-(5-(4-chlorophenyl)-4,5-dihydro-1H-pyrazol-1-yl)-2,2-dimethylpropan-1-one,
1-(5-(3-fluorophenyl)-4,5-dihydro-1H-pyrazol-1-yl)-2,2-dimethylpropan-1-one,
(S)-1-(5-(3-fluorophenyl)-4,5-dihydro-1H-pyrazol-1-yl)-2,2-dimethylpropan-1-one,
(1-(pyridin-2-yl)piperidin-4-yl)(5-(pyridin-3-yl)-4,5-dihydro-1H-pyrazol-1-yl)methanone,
2,2-dimethyl-1-(5-(5-methylpyridin-3-yl)-4,5-dihydro-1H-pyrazol-1-yl)propan-1-one,
2,2-dimethyl-1-(5-(tetrahydro-2H-pyran-2-yl)-4,5-dihydro-1H-pyrazol-1-yl)propan-1-one,
2,2-dimethyl-1-(5-(5-methylpyrazin-2-yl)-4,5-dihydro-1H-pyrazol-1-yl)propan-1-one,
1-(5-(5-fluoro-6-methylpyridin-2-yl)-4,5-dihydro-1H-pyrazol-1-yl)-2,2-dimethylpropan-1-one,
1-(5-(5-chloropyridin-3-yl)-4,5-dihydro-1H-pyrazol-1-yl)-2,2-dimethylpropan-1-one,
1-(5-(3-fluoro-5-methylphenyl)-4,5-dihydro-1H-pyrazol-1-yl)-2,2-dimethylpropan-1-one,
1-(5-(2-fluoro-5-methylphenyl)-4,5-dihydro-1H-pyrazol-1-yl)-2,2-dimethylpropan-1-one,
4-(1-pivaloyl-4,5-dihydro-1H-pyrazol-5-yl)benzonitrile,
3-(1-pivaloyl-4,5-dihydro-1H-pyrazol-5-yl)benzonitrile,
1-(5-(1H-indol-6-yl)-4,5-dihydro-1H-pyrazol-1-yl)-2,2-dimethylpropan-1-one,
1-(5-(1H-indol-5-yl)-4,5-dihydro-1H-pyrazol-1-yl)-2,2-dimethylpropan-1-one, (S)-1-(5-(1H-indol-5-yl)-4,5-dihydro-1H-pyrazol-1-yl)-2,2-dimethylpropan-1-one,
1-(5-(1H-indol-4-yl)-4,5-dihydro-1H-pyrazol-1-yl)-2,2-dimethylpropan-1-one,
(S)-1-(5-(1H-indol-4-yl)-4,5-dihydro-1H-pyrazol-1-yl)-2,2-dimethylpropan-1-one,
(1-(benzo[d]oxazol-2-yl)piperidin-4-yl)(5-(pyridin-3-yl)-4,5-dihydro-1H-pyrazol-1-yl)methanone,
benzyl ((2R)-1-oxo-1-(5-phenyl-4,5-dihydro-1H-pyrazol-1-yl)propan-2-yl)carbamate,
(5-phenyl-4,5-dihydro-1H-pyrazol-1-yl)(1-(pyrimidin-2-yl)piperidin-4-yl)methanone,
(S)-(5-phenyl-4,5-dihydro-1H-pyrazol-1-yl)(1-(pyrimidin-2-yl)piperidin-4-yl)methanone,
3-hydroxy-2,2-dimethyl-1-(5-phenyl-4,5-dihydro-1H-pyrazol-1-yl)propan-1-one,
(1-methyl-1H-pyrrol-2-yl)(4-(5-phenyl-4,5-dihydro-1H-pyrazole-1-carbonyl)piperidin-1-yl)methanone,
(5-phenyl-4,5-dihydro-1H-pyrazol-1-yl)(1-(pyridin-2-yl)piperidin-4-yl)methanone,
2,2,2-trifluoro-1-(4-(5-phenyl-4,5-dihydro-1H-pyrazole-1-carbonyl)piperidin-1-yl)ethanone,
(5-phenyl-4,5-dihydro-1H-pyrazol-1-yl)(1-(5-(trifluoromethyl)pyridin-2-yl)piperidin-4-yl)methanone,
(1-(benzo[d]oxazol-2-yl)piperidin-4-yl)(5-phenyl-4,5-dihydro-1H-pyrazol-1-yl)methanone,
1-(4-(5-phenyl-4,5-dihydro-1H-pyrazole-1-carbonyl)piperidin-1-yl)ethanone, as the free base, or as a salt, particularly a pharmaceutically acceptable salt, thereof.

Representative compounds of this invention further include the following compounds:
(S)-(1-(5-fluoropyridin-2-yl)piperidin-4-yl)(5-phenyl-4,5-dihydro-1H-pyrazol-1-yl)methanone,
(1-(5-fluoropyrimidin-2-yl)piperidin-4-yl)(5-phenyl-3-(trifluoromethyl)-4,5-dihydro-1H-pyrazol-1-yl)methanone,
(S)-(5-(5-fluoropyridin-3-yl)-4,5-dihydro-1H-pyrazol-1-yl)(1-(5-fluoropyrimidin-2-yl)piperidin-4-yl)methanone,
1-(4-(5-(benzo[d][1,3]dioxol-5-yl)-4,5-dihydro-1H-pyrazole-1-carbonyl)piperidin-1-yl)ethanone,
(S)-(5-phenyl-4,5-dihydro-1H-pyrazol-1-yl)(1-phenylpiperidin-4-yl)methanone,
(S)-(5-phenyl-4,5-dihydro-1H-pyrazol-1-yl)(tetrahydro-2H-pyran-4-yl)methanone,
(5-(6-methylpyridin-3-yl)-4,5-dihydro-1H-pyrazol-1-yl)(1-(pyrimidin-2-yl)piperidin-4-yl)methanone,
(5-(6-methylpyridin-3-yl)-4,5-dihydro-1H-pyrazol-1-yl)(1-(pyridin-2-yl)piperidin-4-yl)methanone,
(S)-(1-(pyridin-2-yl)piperidin-4-yl)(5-(pyridin-3-yl)-4,5-dihydro-1H-pyrazol-1-yl)methanone,
(S)-4-(1-pivaloyl-4,5-dihydro-1H-pyrazol-5-yl)benzonitrile,
(5-phenyl-4,5-dihydro-1H-pyrazol-1-yl)(1-(trifluoromethyl)cyclopropyl)methanone,
2,2-dimethyl-3-oxo-3-(5-phenyl-4,5-dihydro-1H-pyrazol-1-yl)propanenitrile,
2-methoxy-2-methyl-1-(5-phenyl-4,5-dihydro-1H-pyrazol-1-yl)propan-1-one,
1-(5-phenyl-4,5-dihydro-1H-pyrazole-1-carbonyl)cyclopentanecarbonitrile,
(3-methyl-5-phenyl-4,5-dihydro-1H-pyrazol-1-yl)(1-(pyridin-2-yl)piperidin-4-yl)methanone,
(1-(5-fluoropyrimidin-2-yl)piperidin-4-yl)(3-methyl-5-phenyl-4,5-dihydro-1H-pyrazol-1-yl)methanone,
(5-(5-methylpyrazin-2-yl)-4,5-dihydro-1H-pyrazol-1-yl)(1-(pyridin-2-yl)piperidin-4-yl)methanone,
(4-methyl-1-(pyrimidin-2-yl)piperidin-4-yl)(5-(5-methylpyrazin-2-yl)-4,5-dihydro-1H-pyrazol-1-yl)methanone,
(1-(cyclohexanecarbonyl)piperidin-4-yl)(5-phenyl-4,5-dihydro-1H-pyrazol-1-yl)methanone,
(1-(cyclobutanecarbonyl)piperidin-4-yl)(5-phenyl-4,5-dihydro-1H-pyrazol-1-yl)methanone,
1-(4-(5-phenyl-4,5-dihydro-1H-pyrazole-1-carbonyl)piperidin-1-yl)propan-1-one,
2-methyl-1-(4-(5-phenyl-4,5-dihydro-1H-pyrazole-1-carbonyl)piperidin-1-yl)propan-1-one,
(5-phenyl-4,5-dihydro-1H-pyrazol-1-yl)(1-picolinoylpiperidin-4-yl)methanone,
(5-phenyl-4,5-dihydro-1H-pyrazol-1-yl)(1-(pyrimidine-2-carbonyl)piperidin-4-yl)methanone,
(1-(4-morpholinobenzoyl)piperidin-4-yl)(5-phenyl-4,5-dihydro-1H-pyrazol-1-yl)methanone,
(1-(5-chloropicolinoyl)piperidin-4-yl)(5-phenyl-4,5-dihydro-1H-pyrazol-1-yl)methanone,
(1-isonicotinoylpiperidin-4-yl)(5-phenyl-4,5-dihydro-1H-pyrazol-1-yl)methanone,
(1-(6-methylpicolinoyl)piperidin-4-yl)(5-phenyl-4,5-dihydro-1H-pyrazol-1-yl)methanone,
(1-(6-chloropicolinoyl)piperidin-4-yl)(5-phenyl-4,5-dihydro-1H-pyrazol-1-yl)methanone,
(1-(6-chloronicotinoyl)piperidin-4-yl)(5-phenyl-4,5-dihydro-1H-pyrazol-1-yl)methanone,
(1-nicotinoylpiperidin-4-yl)(5-phenyl-4,5-dihydro-1H-pyrazol-1-yl)methanone,
(1-(5-fluoropicolinoyl)piperidin-4-yl)(5-phenyl-4,5-dihydro-1H-pyrazol-1-yl)methanone,
(1-(4-chlorobenzoyl)piperidin-4-yl)(5-phenyl-4,5-dihydro-1H-pyrazol-1-yl)methanone,
2-phenyl-1-(4-(5-phenyl-4,5-dihydro-1H-pyrazole-1-carbonyl)piperidin-1-yl)ethanone,
(1-(4-methoxybenzoyl)piperidin-4-yl)(5-phenyl-4,5-dihydro-1H-pyrazol-1-yl)methanone,
(5-phenyl-4,5-dihydro-1H-pyrazol-1-yl)(1-(thiazole-2-carbonyl)piperidin-4-yl)methanone,
(5-cyclopropylisoxazol-3-yl)(4-(5-phenyl-4,5-dihydro-1H-pyrazole-1-carbonyl)piperidin-1-yl)methanone,
oxazol-4-yl(4-(5-phenyl-4,5-dihydro-1H-pyrazole-1-carbonyl)piperidin-1-yl)methanone,
(1-methyl-1H-imidazol-2-yl)(4-(5-phenyl-4,5-dihydro-1H-pyrazole-1-carbonyl)piperidin-1-yl)methanone,
(1-methyl-1H-pyrazol-5-yl)(4-(5-phenyl-4,5-dihydro-1H-pyrazole-1-carbonyl)piperidin-1-yl)methanone,
(1-methyl-1H-pyrazol-3-yl)(4-(5-phenyl-4,5-dihydro-1H-pyrazole-1-carbonyl)piperidin-1-yl)methanone,
(2-methyloxazol-4-yl)(4-(5-phenyl-4,5-dihydro-1H-pyrazole-1-carbonyl)piperidin-1-yl)methanone,
(1-methyl-1H-imidazol-4-yl)(4-(5-phenyl-4,5-dihydro-1H-pyrazole-1-carbonyl)piperidin-1-yl)methanone,
(2-methylthiazol-4-yl)(4-(5-phenyl-4,5-dihydro-1H-pyrazole-1-carbonyl)piperidin-1-yl)methanone,
(1-(4-methylpicolinoyl)piperidin-4-yl)(5-phenyl-4,5-dihydro-1H-pyrazol-1-yl)methanone,
(5-methylthiophen-2-yl)(4-(5-phenyl-4,5-dihydro-1H-pyrazole-1-carbonyl)piperidin-1-yl)methanone,
(1-(1H-pyrazole-4-carbonyl)piperidin-4-yl)(5-phenyl-4,5-dihydro-1H-pyrazol-1-yl)methanone,
(2-methylthiazol-5-yl)(4-(5-phenyl-4,5-dihydro-1H-pyrazole-1-carbonyl)piperidin-1-yl)methanone,
isothiazol-5-yl(4-(5-phenyl-4,5-dihydro-1H-pyrazole-1-carbonyl)piperidin-1-yl)methanone,
(2-methyloxazol-5-yl)(4-(5-phenyl-4,5-dihydro-1H-pyrazole-1-carbonyl)piperidin-1-yl)methanone, (1-methyl-1H-pyrazol-4-yl)(4-(5-phenyl-4,5-dihydro-1H-pyrazole-1-carbonyl)piperidin-1-yl)methanone,
(5-methylisoxazol-3-yl)(4-(5-phenyl-4,5-dihydro-1H-pyrazole-1-carbonyl)piperidin-1-yl)methanone,
2-(benzyloxy)-1-(5-phenyl-4,5-dihydro-1H-pyrazol-1-yl)ethanone,
(1-(4-fluorobenzoyl)piperidin-4-yl)(5-phenyl-4,5-dihydro-1H-pyrazol-1-yl)methanone,
(1-(2,4-difluorobenzoyl)piperidin-4-yl)(5-phenyl-4,5-dihydro-1H-pyrazol-1-yl)methanone,
4-(4-(5-phenyl-4,5-dihydro-1H-pyrazole-1-carbonyl)piperidine-1-carbonyl)benzonitrile,
(1-(1H-pyrazole-3-carbonyl)piperidin-4-yl)(5-phenyl-4,5-dihydro-1H-pyrazol-1-yl)methanone,
3-oxo-3-(4-(5-phenyl-4,5-dihydro-1H-pyrazole-1-carbonyl)piperidin-1-yl)propanenitrile,
(2,4-dimethylthiazol-5-yl)(4-(5-phenyl-4,5-dihydro-1H-pyrazole-1-carbonyl)piperidin-1-yl)methanone,
(1-(3,5-difluorobenzoyl)piperidin-4-yl)(5-phenyl-4,5-dihydro-1H-pyrazol-1-yl)methanone,
(1-(1H-1,2,3-triazole-4-carbonyl)piperidin-4-yl)(5-phenyl-4,5-dihydro-1H-pyrazol-1-yl)methanone,
(1-(1,2,3-thiadiazole-5-carbonyl)piperidin-4-yl)(5-phenyl-4,5-dihydro-1H-pyrazol-1-yl)methanone,
benzo[d]thiazol-2-yl(4-(5-phenyl-4,5-dihydro-1H-pyrazole-1-carbonyl)piperidin-1-yl)methanone,
(1-(1H-indazole-3-carbonyl)piperidin-4-yl)(5-phenyl-4,5-dihydro-1H-pyrazol-1-yl)methanone,
(1-phenyl-1H-imidazol-4-yl)(4-(5-phenyl-4,5-dihydro-1H-pyrazole-1-carbonyl)piperidin-1-yl)methanone,
(1-(1H-benzo[d][1,2,3]triazole-6-carbonyl)piperidin-4-yl)(5-phenyl-4,5-dihydro-1H-pyrazol-1-yl)methanone,
(1-(1H-indazole-6-carbonyl)piperidin-4-yl)(5-phenyl-4,5-dihydro-1H-pyrazol-1-yl)methanone,
imidazo[1,2-b]pyridazin-2-yl(4-(5-phenyl-4,5-dihydro-1H-pyrazole-1-carbonyl)piperidin-1-yl)methanone,
3-phenyl-1-(4-(5-phenyl-4,5-dihydro-1H-pyrazole-1-carbonyl)piperidin-1-yl)prop-2-yn-1-one,
benzo[d]isoxazol-3-yl(4-(5-phenyl-4,5-dihydro-1H-pyrazole-1-carbonyl)piperidin-1-yl)methanone,
oxazol-5-yl(4-(5-phenyl-4,5-dihydro-1H-pyrazole-1-carbonyl)piperidin-1-yl)methanone,
oxazol-2-yl(4-(5-phenyl-4,5-dihydro-1H-pyrazole-1-carbonyl)piperidin-1-yl)methanone,
(3-methyl-1H-pyrazol-5-yl)(4-(5-phenyl-4,5-dihydro-1H-pyrazole-1-carbonyl)piperidin-1-yl)methanone,
(5-methylthiazol-2-yl)(4-(5-phenyl-4,5-dihydro-1H-pyrazole-1-carbonyl)piperidin-1-yl)methanone,
isoxazol-5-yl(4-(5-phenyl-4,5-dihydro-1H-pyrazole-1-carbonyl)piperidin-1-yl)methanone,
(5-phenyl-4,5-dihydro-1H-pyrazol-1-yl)(1-(thiazole-5-carbonyl)piperidin-4-yl)methanone,
isoxazol-3-yl(4-(5-phenyl-4,5-dihydro-1H-pyrazole-1-carbonyl)piperidin-1-yl)methanone,
(5-phenyl-4,5-dihydro-1H-pyrazol-1-yl)(1-(thiazole-4-carbonyl)piperidin-4-yl)methanone,
(1-(1,2,5-thiadiazole-3-carbonyl)piperidin-4-yl)(5-phenyl-4,5-dihydro-1H-pyrazol-1-yl)methanone,
isothiazol-4-yl(4-(5-phenyl-4,5-dihydro-1H-pyrazole-1-carbonyl)piperidin-1-yl)methanone,
(4-methylthiazol-2-yl)(4-(5-phenyl-4,5-dihydro-1H-pyrazole-1-carbonyl)piperidin-1-yl)methanone,
(5-methyloxazol-4-yl)(4-(5-phenyl-4,5-dihydro-1H-pyrazole-1-carbonyl)piperidin-1-yl)methanone,
(1-(cyclopropanecarbonyl)piperidin-4-yl)(5-phenyl-4,5-dihydro-1H-pyrazol-1-yl)methanone,
(5-phenyl-4,5-dihydro-1H-pyrazol-1-yl)(1-(phenylsulfonyl)piperidin-4-yl)methanone,
2-methoxy-1-(4-(5-phenyl-4,5-dihydro-1H-pyrazole-1-carbonyl)piperidin-1-yl)ethanone,
(1-(cyclopentanecarbonyl)piperidin-4-yl)(5-phenyl-4,5-dihydro-1H-pyrazol-1-yl)methanone,
1-(4-(5-phenyl-4,5-dihydro-1H-pyrazole-1-carbonyl)piperidin-1-yl)butan-1-one,
(1-benzoylpiperidin-4-yl)(5-phenyl-4,5-dihydro-1H-pyrazol-1-yl)methanone,
2-cyclohexyl-1-(4-(5-phenyl-4,5-dihydro-1H-pyrazole-1-carbonyl)piperidin-1-yl)ethanone,
(1-benzoyl-4-methylpiperidin-4-yl)(5-phenyl-4,5-dihydro-1H-pyrazol-1-yl)methanone,
1-(4-methyl-4-(5-phenyl-4,5-dihydro-1H-pyrazole-1-carbonyl)piperidin-1-yl)ethanone,
(1-(1H-indole-2-carbonyl)piperidin-4-yl)(5-phenyl-4,5-dihydro-1H-pyrazol-1-yl)methanone,
(1-(1H-indole-3-carbonyl)piperidin-4-yl)(5-phenyl-4,5-dihydro-1H-pyrazol-1-yl)methanone,
1-(4-(5-(2,3-dihydrobenzofuran-5-yl)-4,5-dihydro-1H-pyrazole-1-carbonyl)piperidin-1-yl)ethanone,
1-(4-(5-(2,3-dihydro-1H-inden-5-yl)-4,5-dihydro-1H-pyrazole-1-carbonyl)piperidin-1-yl)ethanone,
(5-(2,3-dihydro-1H-inden-5-yl)-4,5-dihydro-1H-pyrazol-1-yl)(1-(5-fluoropyrimidin-2-yl)piperidin-4-yl)methanone,
(5-(4-(difluoromethoxy)phenyl)-4,5-dihydro-1H-pyrazol-1-yl)(1-(5-fluoropyrimidin-2-yl)piperidin-4-yl)methanone,
(5-(6-methylpyridin-3-yl)-4,5-dihydro-1H-pyrazol-1-yl)(1-(oxazole-5-carbonyl)piperidin-4-yl)methanone,
(1-(5-fluoropyrimidin-2-yl)piperidin-4-yl)(5-(6-methylpyridin-3-yl)-4,5-dihydro-1H-pyrazol-1-yl)methanone,
4-(1-(1-(5-fluoropyrimidin-2-yl)piperidine-4-carbonyl)-4,5-dihydro-1H-pyrazol-5-yl)benzonitrile,
(4-fluoro-1-(5-fluoropyrimidin-2-yl)piperidin-4-yl)(5-phenyl-4,5-dihydro-1H-pyrazol-1-yl)methanone,
(1-(5-fluoropyrimidin-2-yl)-4-methylpiperidin-4-yl)(5-phenyl-4,5-dihydro-1H-pyrazol-1-yl)methanone,
N-ethyl-4-(5-phenyl-4,5-dihydro-1H-pyrazole-1-carbonyl)piperidine-1-carboxamide,
1-(3-bromo-5-phenyl-4,5-dihydro-1H-pyrazol-1-yl)-2,2-dimethylpropan-1-one,
1-(4-(5-phenyl-4,5-dihydro-1H-pyrazole-1-carbonyl)piperidin-1-yl)ethanone,
1-(4-(5-(4-(difluoromethoxy)phenyl)-4,5-dihydro-1H-pyrazole-1-carbonyl)piperidin-1-yl)ethanone,
1-(4-(5-(2,3-dihydrobenzo[b][1,4]dioxin-6-yl)-4,5-dihydro-1H-pyrazole-1-carbonyl)piperidin-1-yl)ethanone,
(S)-1-(4-(5-(3-fluorophenyl)-4,5-dihydro-1H-pyrazole-1-carbonyl)piperidin-1-yl)ethanone,
1-(4-(5-(3,5-difluorophenyl)-4,5-dihydro-1H-pyrazole-1-carbonyl)piperidin-1-yl)ethanone,
(S)-1-(4-(5-(3,5-difluorophenyl)-4,5-dihydro-1H-pyrazole-1-carbonyl)piperidin-1-yl)ethanone,
1-(4-(5-(2-fluorophenyl)-4,5-dihydro-1H-pyrazole-1-carbonyl)piperidin-1-yl)ethanone,
(S)-1-(4-(5-(2-fluorophenyl)-4,5-dihydro-1H-pyrazole-1-carbonyl)piperidin-1-yl)ethanone,
1-(4-(5-(4-fluorophenyl)-4,5-dihydro-1H-pyrazole-1-carbonyl)piperidin-1-yl)ethanone,
(S)-1-(4-(5-(4-fluorophenyl)-4,5-dihydro-1H-pyrazole-1-carbonyl)piperidin-1-yl)ethanone,
((1-methylcyclopropyl)(5-phenyl-4,5-dihydro-1H-pyrazol-1-yl)methanone,
1-(4-(5-(4-chlorophenyl)-4,5-dihydro-1H-pyrazole-1-carbonyl)piperidin-1-yl)ethanone, (1-(4-(5-(4-chloro-3-fluorophenyl)-4,5-dihydro-1H-pyrazole-1-carbonyl)piperidin-1-yl)ethanone,
1-(5-phenyl-4,5-dihydro-1H-pyrazole-1-carbonyl)cyclopropanecarbonitrile,
(5-phenyl-4,5-dihydro-1H-pyrazol-1-yl)(1-(thiazol-2-yl)piperidin-4-yl)methanone, as the free base, or as a salt, particularly a pharmaceutically acceptable salt, thereof.

In one embodiment, this invention is directed to (S)-1-(4-(5-(3,5-difluorophenyl)-4,5-dihydro-1H-pyrazole-1-carbonyl)piperidin-1-yl)ethanone, or a pharmaceutically acceptable salt thereof. In another embodiment, this invention is directed to (S)-1-(4-(5-(3,5-difluorophenyl)-4,5-dihydro-1H-pyrazole-1-carbonyl)piperidin-1-yl)ethanone. In still another embodiment, the compound of the invention is a crystalline form of (S)-1-(4-(5-(3,5-difluorophenyl)-4,5-dihydro-1H-pyrazole-1-carbonyl)piperidin-1-yl)ethanone characterized by the PXRD pattern of FIG. 5.

The invention also includes various deuterated forms of the compounds of Formulas (I), (II), and/or (III). Each available hydrogen atom attached to a carbon atom may be independently replaced with a deuterium atom. A person of ordinary skill in the art will know how to synthesize deuterated forms of the compounds of Formulas (I), (II), and/or (III). For example, commercially available deuterated starting materials may be employed in the preparation of deuterated analogs of the compounds of Formulas (I), (II), and/or (III) or they may be synthesized using conventional techniques employing deuterated reagents (e.g. by reduction using lithium aluminum deuteride or sodium borodeuteride or by metal-halogen exchange followed by quenching with $D_2O$ or methanol-$d_3$).

The skilled artisan will appreciate that solvates (particularly, hydrates) of a compound of Formulas (I), (II), or (III), including solvates of salts of a compound of Formulas (I), (II), or (III), may be formed when solvent molecules are incorporated into the crystalline lattice during crystallization. The present invention includes within its scope all possible stoichiometric and non-stoichiometric salt and/or hydrate forms.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

It is well known and understood to those skilled in the art that the apparatus employed, humidity, temperature, orientation of the powder crystals, and other parameters involved in obtaining a powder X-ray diffraction (PXRD) pattern may cause some variability in the appearance, intensities, and positions of the lines in the diffraction pattern. A person skilled in the art is capable of determining if a sample of a crystalline compound has the same form as, or a different form from, a known form by comparison of their PXRD patterns. For example, one skilled in the art can overlay a PXRD pattern of a test sample of a crystalline form with the PXRD pattern of a known form, and using expertise and knowledge in the art, readily determine whether the PXRD pattern of the sample is substantially in accordance with the PXRD pattern of the known form. If the PXRD pattern is substantially in accordance with the known form, the sample form can be readily and accurately identified as having the same form as the known crystalline form. Similarly, a person skilled in the art is capable of determining if a given diffraction angle (expressed in °2θ) obtained from a PXRD pattern is at about the same position as a recited value.

Figure 5:
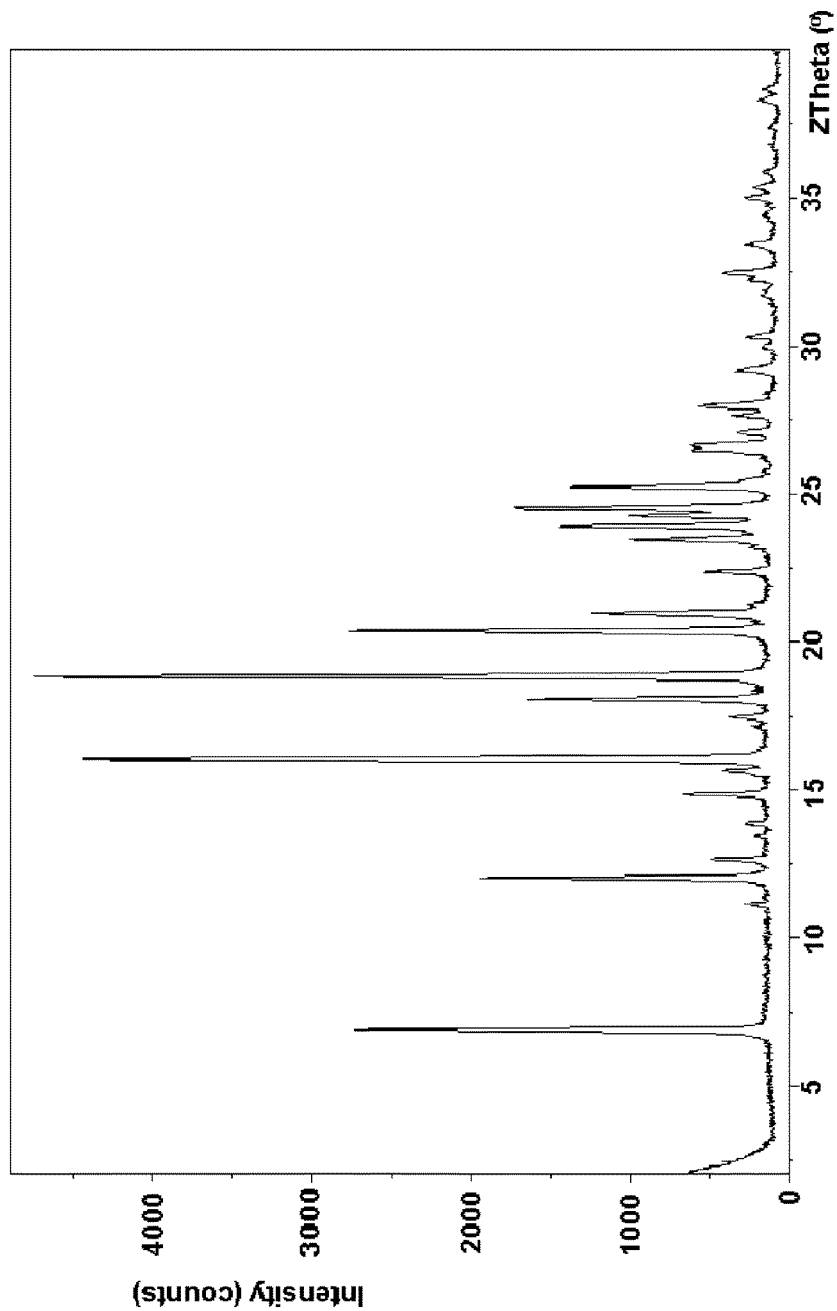
FIG. 5 is a powder x-ray powder diffraction (PXRD) pattern of a crystalline form of (S)-1-(4-(5-(3,5-difluorophenyl)-4,5-dihydro-1H-pyrazole-1-carbonyl)piperidin-1-yl)ethanone.

For example, the PXRD pattern may be identical to that of FIG. 5, or more likely it may be somewhat different. Such a PXRD pattern may not necessarily show each of the lines of the diffraction patterns presented herein, and/or may show a slight change in appearance, intensity, or a shift in position of said lines resulting from differences in the conditions involved in obtaining the data. A person skilled in the art can overlay a PXRD pattern of a sample of a crystalline form of (S)-1-(4-(5-(3,5-difluorophenyl)-4,5-dihydro-1H-pyrazole-1-carbonyl)piperidin-1-yl)ethanone with the PXRD pattern of FIG. 5, and using expertise and knowledge in the art, readily determine whether the PXRD pattern of the sample is substantially in accordance with the PXRD pattern of FIG. 5. If the PXRD pattern is substantially in accordance with FIG. 5, the sample form can be readily and accurately identified as having the same form as the crystalline form of (S)-1-(4-(5-(3,5-difluorophenyl)-4,5-dihydro-1H-pyrazole-1-carbonyl)piperidin-1-yl)ethanone described herein. Similarly, a person skilled in the art is capable of determining if a given diffraction angle (expressed in °2θ) obtained from a PXRD pattern is at about the same position as a recited value.

One embodiment of this invention is directed to a crystalline form of (S)-1-(4-(5-(3,5-difluorophenyl)-4,5-dihydro-1H-pyrazole-1-carbonyl)piperidin-1-yl)ethanone that provides a PXRD pattern substantially in accordance with FIG. 5.

Because of their potential use in medicine, the salts of the compounds of Formulas (I), (II), and (III), are preferably pharmaceutically acceptable. Suitable pharmaceutically acceptable salts can include acid or base addition salts.

As used herein, the term "pharmaceutically acceptable" means a compound which is suitable for pharmaceutical use. Salts and solvates (e.g. hydrates and hydrates of salts) of the compounds of Formulas (I), (II), and (III) which are suitable for use in medicine are those wherein the counterion or associated solvent is pharmaceutically acceptable.

Salts and solvates having non-pharmaceutically acceptable counterions or associated solvents are within the scope of the present invention, for example, for use as intermediates in the preparation of other compounds of Formulas (I), (II), and (III) and their salts and solvates.

Salts may be prepared in situ during the final isolation and purification of a compound of Formulas (I), (II), and (III). If a basic compound of Formulas (I), (II), or (III) is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a disclosed compound containing a carboxylic acid or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound. This invention also provides for the conversion of one salt of a compound of this invention, e.g., a hydrochloride salt, into another salt of a compound of this invention, e.g., a sulfate salt.

Salts of the compounds of Formulas (I), (II), and (III) containing a basic amine or other basic functional group may be prepared by any suitable method known in the art, such as treatment of the free base with an acid. Examples of pharmaceutically acceptable salts so formed include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecylsulfate (estolate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride, hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate, proprionate, pyroglutamate, salicylate, sebacate, stearate, succinate, sulfate, tartrate, thiocyanate, p-toluenesulfonate (tosylate), undecylenate, 1-hydroxy-2-naphthoate, 2-hydroxyethanesulfonate (isethionate), 2-oxoglutarate, 4-acetamidobenzoate, and 4-aminosalicylate.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acids such as lysine and arginine.

It will be understood that if a compound of Formula (I), (II), or (III) contained two or more basic moieties, the stoichiometry of salt formation may include 1, 2 or more equivalents of acid. Such salts would contain 1, 2 or more acid counterions, for example, a diacetate or a dihydrochloride salt.

Because the compounds of Formulas (I), (II), and (III), or a pharmaceutically acceptable salt thereof, are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The compounds of this invention may be particularly useful for the treatment of RIP1 kinase-mediated diseases or disorders. Such RIP1 kinase-mediated diseases or disorders are diseases or disorders that are mediated by activation of RIP1 kinase, and as such, are diseases or disorders where inhibition of RIP1 kinase would provide benefit.

In this invention, RIP1 kinase-mediated diseases or disorders are diseases or disorders that are mediated by activation of RIP1 kinase, and as such, are diseases or disorders where inhibition of RIP1 kinase would provide benefit. Such RIP1 kinase-mediated diseases or disorders are diseases/disorders which are likely to be regulated at least in part by programmed necrosis, apoptosis or the production of inflammatory cytokines, particularly inflammatory bowel disease (including Crohn's disease and ulcerative colitis), psoriasis, retinal detachment (and degeneration), retinitis pigmentosa, macular degeneration, pancreatitis, atopic dermatitis, arthritis (including rheumatoid arthritis, spondylarthritis, gout, juvenile idiopathic arthritis (systemic onset juvenile idiopathic arthritis (SoJIA)), psoriatic arthritis), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)) Celiac disease, autoimmune idiopathic thrombocytopenic purpura (autoimmune ITP), transplant rejection (rejection of transplant organs, tissues and cells), ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), neontal hypoxic brain injury, ischemic brain injury, traumatic brain injury allergic diseases (including asthma and atopic dermatitis), burns, multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), cigarette smoke-induced damage, cystic fibrosis, tumor necrosis factor receptor-associated periodic syndrome (TRAPS), a neoplastic tumor, peridontitis, NEMO-mutations (mutations of NF-kappa-B essential modulator gene (also known as IKK gamma or IKKG)), particularly, NEMO-deficiency syndrome, HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as influenza, *staphylococcus*, and *mycobacterium* (tuberculosis)), and Lysosomal storage diseases (particularly, Gaucher disease, and including GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs, and Wolman disease), Stevens-Johnson syndrome, toxic epidermal necrolysis, glaucoma, spinal cord injury, pancreatic ductal adenocarcinoma, hepatocellular carcinoma, mesothelioma, melanoma, acute liver failure and radiation protection/mitigation, auditory disorders such as noise-induced hearing loss and drugs associated with ototoxicity such as cisplatin, or for the treatment of cells ex vivo to preserve vitality and function.

The compounds of the invention, particularly the compounds of Formula (I), (II), or (III), or a pharmaceutically acceptable salt thereof, may be particularly useful for the treatment of the following RIP1 kinase-mediated diseases or disorders: inflammatory bowel disease (including Crohn's disease and ulcerative colitis), psoriasis, retinal detachment (and degeneration), retinitis pigmentosa, macular degeneration, pancreatitis, atopic dermatitis, arthritis (including rheumatoid arthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)) Celiac disease, autoimmune idiopathic thrombocytopenic purpura (autoimmune ITP), transplant rejection (rejection of transplant organs, tissues and cells), ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), neontal hypoxic brain injury, allergic diseases (including asthma and atopic dermatitis), burns, multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), cigarette smoke-induced damage, cystic fibrosis, tumor necrosis factor receptor-associated periodic syndrome (TRAPS), a neoplastic tumor, peridontitis, NEMO-mutations (mutations of NF-kappa-B essential modulator gene (also known as IKK gamma or IKKG)), particularly, NEMO-deficiency syndrome, HOIL-1 deficiency ((also known as RBCK1) hemeoxidized IRP2 ubiquitin ligase-1 deficiency), linear ubiquitin chain assembly complex (LUBAC) deficiency syndrome, hematological and solid organ malignancies, bacterial infections and viral infections (such as influenza, *staphylococcus*, and *mycobacterium* (tuberculosis)), and Lysosomal storage diseases (particularly, Gaucher disease, and including GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs, and Wolman disease), Stevens-Johnson syndrome, toxic epidermal necrolysis, and/or for the treatment of cells ex vivo to preserve vitality and function.

The compounds of the invention, particularly the compounds of Formula (I), (II), or (III), or a pharmaceutically acceptable salt thereof, may be particularly useful for the treatment of the following RIP1 kinase-mediated diseases or disorders, that is, diseases/disorders which are likely to be regulated at least in part by RIP1 kinase activity, particularly inflammatory bowel disease (including Crohn's disease and ulcerative colitis), rheumatoid arthritis, chronic obstructive pulmonary disease (COPD), asthma, cigarette smoke-induced damage, cystic fibrosis, psoriasis, retinal detachment and degeneration, retinitis pigmentosa, macular degeneration, atopic dermatitis, burn injury, periodontitis, a bacterial or viral infection (an infection with a pathogen including but not limited to influenza, *staphylococcus*, and/or *mycobacterium* (tuberculosis), systemic scleroderma (particularly, topical treatment of hardened and/or tightened skin areas), and/or ischemia reperfusion injury of solid organs/transplant rejection (particularly, topical treatment of donor organ (particularly kidney, liver, and heart and/or lung transplants), infusion of organ recipient), and topical treatment of bowels.

The compounds of the invention, particularly the compounds of Formula (I), (II), or (III), or a pharmaceutically acceptable salt thereof, may be useful for the treatment of glaucoma.

The compounds of the invention, particularly the compounds of Formula (I), (II), or (III), or a pharmaceutically acceptable salt thereof, may be particularly useful for treatment of pancreatic ductal adenocarcinoma, hepatocellular carcinoma, mesothelioma, or melanoma.

The compounds of the invention, particularly the compounds of Formula (I), (II), or (III), or a pharmaceutically acceptable salt thereof, may be particularly useful for the treatment of the following RIP1 kinase-mediated disease or disorder: rheumatoid arthritis, inflammatory bowel disease (including Crohn's disease and ulcerative colitis), and psoriasis.

The treatment of the above-noted diseases/disorders may concern, more specifically, the amelioration of organ injury or damage sustained as a result of the noted diseases/disorders. For example, the compounds of this invention may be particularly useful for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcohol steatohepatitis, alcohol steatohepatitis, autoimmune hepatitis autoimmune hepatobiliary diseases, or primary sclerosing cholangitis, or overdose of acetaminophen.

The compounds of this invention may be particularly useful for the amelioration of organ injury or damage sustained as a result of radiation therapy, or amelioration of spinal tissue injury or damage following spinal cord injury or amelioration of liver tissue injury or damage associated acute liver failure. The compounds of this invention may be particularly useful for amelioration of auditory disorders, such as noise-induced hearing loss or auditory disorders following the administration of ototoxic drugs or substances e.g. cisplatin.

The compounds of this invention may be particularly useful for amelioration of solid organ tissue (particularly kidney, liver, and heart and/or lung) injury or damage following transplant or the administration of nephrotoxic drugs or substances e.g. cisplatin. It will be understood that amelioration of such tissue damage may be achieved where possible, by pre-treatment with a compound of Formula (I), (II), or (III), or a pharmaceutically acceptable salt thereof; for example, by pre-treatment of a patient prior to administration of cisplatin or pre-treatment of an organ or the organ recipient prior to transplant surgery. Amelioration of such tissue damage may be achieved by treatment with a compound of Formula (I), (II), or (III), or a pharmaceutically acceptable salt thereof, during transplant surgery. Amelioration of such tissue damage may also be achieved by short-term treatment of a patient with a compound of Formula (I), (II), or (III), or a pharmaceutically acceptable salt thereof, after transplant surgery.

In one embodiment, the compounds of the invention, particularly the compounds of Formula (I), (II), or (III), or a pharmaceutically acceptable salt thereof, may be useful for the treatment of retinal detachment, macular degeneration, and retinitis pigmentosa.

In another embodiment, the compounds of the invention, particularly the compounds of Formula (I), (II), or (III), or a pharmaceutically acceptable salt thereof, may be useful for the treatment of multiple sclerosis.

In one embodiment, the compounds of the invention, particularly the compounds of Formula (I), (II), or (III), or a pharmaceutically acceptable salt thereof, may be useful for the treatment of traumatic brain injury.

In another embodiment, the compounds of the invention, particularly the compounds of Formula (I), (II), or (III), or a pharmaceutically acceptable salt thereof, may be useful for the treatment of Huntington's Disease, Alzheimer's Disease, amyotrophic lateral sclerosis, and Niemann-Pick disease.

The treatment of retinal detachment, macular degeneration, retinitis pigmentosa, multiple sclerosis, traumatic brain injury, Huntington's Disease, Alzheimer's Disease, amyotrophic lateral sclerosis, and Niemann-Pick disease may concern, more specifically, the amelioration of organ injury or damage sustained as a result of these diseases/disorders. For example, the compounds of this invention may be particularly useful for amelioration of brain tissue injury or damage following traumatic brain injury, or for amelioration of brain tissue injury or damage associated of Huntington's Disease, Alzheimer's Disease, amyotrophic lateral sclerosis, and Niemann-Pick disease.

In another embodiment, the compounds of the invention, particularly the compounds of Formula (I), (II), or (III), or a pharmaceutically acceptable salt thereof, may be useful for the treatment of retinal detachment, macular degeneration, and retinitis pigmentosa, and the amelioration of brain tissue injury or damage as a result of multiple sclerosis, traumatic brain injury, Huntington's Disease, Alzheimer's Disease, amyotrophic lateral sclerosis, and Niemann-Pick disease.

Treatment of RIP1-mediated disease conditions may be achieved using a compound of the invention, particularly a compound of Formula (I) or Formula (II) or a pharmaceutically acceptable salt thereof, of as a monotherapy, or in dual or multiple combination therapy, particularly for the treatment of refractory cases, such as in combination with other anti-inflammatory and/or anti-TNF agents, which may be administered in therapeutically effective amounts as is known in the art.

The compounds of the invention, particularly the compounds of Formula (I), (II), or (III), or a pharmaceutically acceptable salt thereof, may be employed alone or in combination with one or more other therapeutic agents, e.g., pharmaceutically active compounds or biologic products (e.g., monoclonal antibodies). Combination therapies according to the present invention thus comprise the administration of at least one compound of the invention, particularly a compound of Formula (I), (II), or (III), or a pharmaceutically acceptable salt thereof, and at least one other therapeutically active agent. Preferably, combination therapies according to the present invention comprise the administration of at least one compound of the invention, particularly a compound of Formula (I), (II), or (III), or a pharmaceutically acceptable salt thereof, and at least one other therapeutic ally active agent, specifically one or two other therapeutically active agents, more specifically one other therapeutically active agent.

For example, amelioration of tissue damage may be achieved by treatment with a compound of Formula (I), (II), or (III), or a pharmaceutically acceptable salt thereof, and at least one other therapeutic ally active agent during transplant surgery. Amelioration of tissue damage may also be achieved by short-term treatment of a patient with a compound of Formula (I), (II), or (III), or a pharmaceutically acceptable salt thereof, and at least one other therapeutic ally active agent after transplant surgery. Amelioration of tissue damage ex vivo, that is ex vivo preservation of tissues, organs and cells may also be achieved by short-term treatment of tissues, organs and cells with a compound of Formula (I), (II), or (III), or a pharmaceutically acceptable salt thereof, and at least one other therapeutic ally active agent, prior to or during transplant surgery.

The compound(s) of the invention, particularly the compounds of Formula (I), (II), or (III), or pharmaceutically acceptable salts thereof, and the other therapeutic agent(s) may be administered together in a single pharmaceutical composition or separately and, when administered separately this may occur simultaneously or sequentially in any order. The amounts of the compound(s) of the invention, particularly a compound of Formula (I), (II), or (III), or pharmaceutically acceptable salts thereof, and the other therapeutic agent(s) and the relative timings of administration will be selected in order to achieve the desired combined therapeutic effect. Thus in a further aspect, there is provided a combination comprising a compound of the invention, particularly a compound of Formula (I), (II), or (III), or a pharmaceutically acceptable salt thereof, together with one or more other therapeutic agents, specifically one or two other therapeutically active agents, more specifically one other therapeutically active agent. In one aspect, there is provided a combination comprising (S)-1-(4-(5-(3,5-difluorophenyl)-4,5-dihydro-1H-pyrazole-1-carbonyl)piperidin-1-yl)ethanone, or a pharmaceutically acceptable salt thereof, together with one or more other therapeutic agents, specifically one or two other therapeutically active agents, more specifically one other therapeutically active agent.

Thus, in one aspect of this invention, a compound of the invention, particularly a compound of Formula (I), (II), or (III), or a pharmaceutically acceptable salt thereof, or a pharmaceutical composition comprising a compound of the invention, particularly a compound of Formula (I), (II), or (III), or a pharmaceutically acceptable salt thereof, may be used in combination with or include one or more other therapeutic agents, for example an anti-inflammatory agent and/or an anti-TNF agent.

The pharmaceutical compositions of the invention typically contain one compound of the invention. However, in certain embodiments, the pharmaceutical compositions of the invention contain more than one compound of the invention. In other embodiments, the pharmaceutical compositions of the invention may comprise one or more additional therapeutic agents, specifically one or two other therapeutically active agents, more specifically one other therapeutically active agent.

A compound that inhibits RIP1 kinase, particularly a compound of Formula (I) or a pharmaceutically acceptable salt thereof, may be administered in combination with other anti-inflammatory agents for any of the indications above, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologics, anti-IL1 agents, anti-IL17 biologics, anti-CD22, anti-integrin agents, anti-IFNa, anti-CD20 or CD4 biologics and other cytokine inhibitors or biologics to T-cell or B-cell receptors or interleukins.

In the treatment of CVA, a compound that inhibits RIP1 kinase, particularly a compound of Formula (I) or a pharmaceutically acceptable salt thereof, may be administered to in combination with a thrombolytic agent (such as tissue plasminogen activator (TPA®), Activase®, Lanoteplase®, Reteplase®, Staphylokinase®, Streptokinase®, Tenecteplase®, Urokinase®), an anticoagulant (such as heparin, coumadin, clopidrogel (Plavix®)), and a platelet aggregation inhibitor (such as dipyridamole (Persantine®), ticlopidine HCL (Ticlid®), eptifibatide (Integrillin®), and/or aspirin).

In the treatment of SIRS, a compound that inhibits RIP1 kinase, particularly a compound of Formula (I) or a pharmaceutically acceptable salt thereof, may be administered in combination with a broad-spectrum antibiotic (such as vacomycin) or other anti-MRSA therapy (cefeprime (Maxipime®), piperacillin/tazobactam (Zosyn®), carbapenem (imipenem, meropenem, doripenem), quinolones (ciprofloxacin, levofloxacin, ofloxacin, moxifloxacin, etc.), and low dose steroids such as hydrocortisones.

In the treatment of inflammatory bowel disease (particularly, Crohn's disease and/or ulcerative colitis), a compound that inhibits RIP1 kinase, particularly a compound of Formula (I) or a pharmaceutically acceptable salt thereof, may be administered in combination with vedolizumab (Entyvio®), alicaforsen, or remestemcel-L (Prochymal®).

In the treatment of psoriasis, a compound that inhibits RIP1 kinase, particularly a compound of Formula (I) or a pharmaceutically acceptable salt thereof, may be administered in combination with ixekizumab, tildrakizumab (MK-3222), or secukinumab (AIN457).

In the treatment of periodontis, a compound that inhibits RIP1 kinase, particularly a compound of Formula (I) or a pharmaceutically acceptable salt thereof, may be administered in combination with an antimicrobial agent, (such as chlorhexidine (Peridex®, PerioChip®, PerioGard®, etc.)) or an antibiotic (such as doxycycline (Vibrox®, Periostat®, Monodox®, Oracea®, Doryx®, etc.) or minocycline (Dynacin®, Minocin®, Arestin®, Dynacin®, etc.).

In the treatment of asthma, a compound that inhibits RIP1 kinase, particularly a compound of Formula (I) or a pharmaceutically acceptable salt thereof, may be administered in combination with an inhaled corticosteroid (ICS) such as fluticasone proprionate (Flovent®), fluticasone furoate (Veramyst®/Avamys®), beclomethasone dipropionate (QVAR®), budesonide (Pulmicort), trimcinolone acetonide (Azmacort®), flunisolide (Aerobid®), mometasone fuorate (Asmanex® Twisthaler®), or Ciclesonide (Alvesco®), a long acting beta agonist (LABA) such as formoterol fumarate (Foradil®), salmeterol xinafoate (Serevent®), indacaterol (Arcapta® Neohaler®); a combination of an ICS and LABA (such as fluticasone furoate and vilanterol (Breo Ellipta®/Relvar Ellipta®), formoterol/budesonide inhalation (Symbicort®), mometasone furoate/formoterol fumarate dihydrate (Dulera®), beclomethasone dipropionate/formoterol (Inuvair®), fluticasone propionate/eformoterol fumarate dehydrate (Flutiform®), and fluticasone propionate/salmeterol (Advair®), a short acting beta agonist ((SABA) such as salbutamol dry-powder inhalation, albuterol sulfate (ProAir®, Proventil HFA®, Ventolin HFA®, AccuNeb® Inhalation Solution), levalbuterol tartrate (Xopenex® HFA), an antimuscarinic agent such as ipratropium bromide (Atrovent® HFA); an antimuscarinic in combination with a beta-agonist such as ipratropium bromide/albuterol (Combivent® Respimat®); a long-acting muscarinic antagonist ((LAMA) such as umeclidinium bromide (Incruse®) or tiotropium bromide (Spiriva®HandiHaler; a combination of a LAMA and a LABA, such as umeclidinium bromide and vilanterol (Anoro®) a leukotriene modifier (such as montelukast sodium (Singulair®), zafirlukast (Accolate®), or zileuton (Zyflo®), and anti-IgE (such as omalizumab (Xolair®)), a methylxanthine bronchodilator (such as theophylline (Accurbron®, Aerolate®, Aquaphyllin®, Asbron®, Bronkodyl®, Duraphyl®, Elixicon®, Elixomin®, Elixophyllin®, Labid®, Lanophyllin®, Quibron-T®, Slo-Bid®, Slo-Phyllin®, Somophyllin®, Sustaire®, Synophylate®, T-Phyll®, Theo-24®, Theo-Dur®, Theobid®, Theochron®, Theoclear®, Theolair®, Theolixir®, Theophyl®, Theovent®, Uni-Dur®, Uniphyl®), a mast cell inhibitor (such as cromulyn sodium (Nasalcrom®) and nedocromil sodium (Tilade®)).

Other agents that may be suitable for use in combination therapy in the treatment of asthma include a protein tyrosine kinase inhibitor (masitinib), CRTH2/D-prostanoid receptor antangonist (AMG 853), an epinephrine inhalation aerosol (E004), reslizumab, Vectura's VR506, lebrikizumab (RG3637), a combination phosphodiesterase (PDE)-3 and (PDE)-4 inhibitor (RPL554).

In the treatment of COPD, a compound that inhibits RIP1 kinase, particularly a compound of Formula (I) or a pharmaceutically acceptable salt thereof, may be administered in combination with a LABA (such as salmeterol xinafoate (Serevent), aformoterol tartrate (Brovana®), formoterol fumarate inhalation powder (Foradil®), indacterol maleate (Arcapta® Neohaler®), a long-acting inhaled anticholinergic (or muscarinic antagonist, such as umeclidinium (Incruse Ellipta®), tiotropium bromide (Spiriva®), and aclidinium bromide (Tudorza® Pressair®), a phosphodiesterase (PDE-r) inhibitor (such as roflumilast, Daliresp®), a combination ICS/LABA (such as fluticasone furoate and vilanterol (Breo Ellipta®/Relvar Ellipta®), fluticasone propionate/salmeterol (Advair®), budesonide/formoterol (Symbicort®), mometasone/formoterol (Dulera®), or fluticasone propionate/eformoterol fumarate dehydrate (Flutiform®); an antimuscarinic such as such as ipratropium bromide (Atrovent®);); an antimuscarinic in combination with a beta-agonist such as ipratropium bromide/albuterol (Combivent® Respimat®); a long-acting antimuscarinic such as umeclidinium bromide (Incruse®) or tiotropium bromide (Spiriva®); umeclidinium/vilanterol (Anoro Ellipta®); a combination of a LAMA and a LABA, such as umeclidinium bromide and vilanterol (Anoro®).

Other agents that may be suitable for use in combination therapy in the treatment of COPD include SCH527123 (a CXCR2 antagonist), glycoprronium bromide ((NVA237) Seebri® Breezhaler®), glycopyrronium bromide and indacaterol maleate ((QVA149) Ultibro® Breezhaler®), glycopyrrolate and formoterol fumarate (PT003), indacaterol maleate (QVA149), olodaterol (Striverdi® Respimat®), tiotropium (Spiriva®)/olodaterol (Striverdi® Respimat®), and aclidinium/formoterol inhalation.

In the treatment of a *mycobacterium* infection (tuberculosis), a compound that inhibits RIP1 kinase, particularly a compound of Formula (I) or a pharmaceutically acceptable salt thereof, may be administered in combination with an antimycobacterial agent (such as isoniazid (INH), ehambutol (Myambutol®), rifampin (Rifadin®), and pyrazinamide (PZA)) a bactericidal antibiotic (such as rifabutin (Mycobutin®) or rifapentine (Priftin®)), an aminoglycoside (Capreomycin®), a fluorquinolone (levofloxacin, moxifloxicin, ofloxacin), thioamide (ehionamide), cyclosporine (Sandimmune®), para-aminosalicyclic acid (Paser®), cycloserine (Seromycin®), kanamycin (Kantrex®), streptomycin, viomycin, capreomycin (Capastat®)), bedaquiline fumarate (Sirturo®), oxazolidinone (Sutezolid®), or delamanid (OPC-67683).

In the treatment of systemic scleroderma, a compound that inhibits RIP1 kinase, particularly a compound of Formula (I) or a pharmaceutically acceptable salt thereof, may be administered in combination with an oral corticosteroid (such as prednisolone (Delatsone®, Orapred, Millipred, Omnipred, Econopred, Flo-Pred), an immunosuppressive agent (such as methotrexate (Rhuematrex®, Trexall®), cyclosporine (Sandimmune®), anti-thymocyte globulin (Atgam®), mycophenolate mofetil (CellCept®), cyclophosphamide (Cytoxan®), FK506 (tacrolimus), thalidomide (Thalomid®), chlorambucil (Leukeran®), azathioprine (Imuran®, Azasan®)), a calcium channel blocker (such as nifedipine (Procardia®, Adalat®) or nicardipine (Cardene®), a topical emollient (nitroglycerin ointment), an ACE inhibitor (such as lisinopril (Zestril®, Prinivil®), diltaizem (Cardizem®, Cardizem SR®, Cardizem CD®, Cardia®, Dilacor®, Tiazac®)), a serotonin reuptake inhibitor (such as fluoxetine (Prozac®)), an endothelin-1 receptor inhibitor (such as bosentan (Tracleer®) or epoprostenol (Flolan®, Veletri®, Prostacyclin®)) an anti-fibrotic agent (such as colchicines (Colcrys®), para-aminobenzoic acid (PABA), dimethyl sulfoxide (KMSO), and D-penicillamine (Cuprimine®, Depen®), interferon alpha and interferon gamma (INF-g)), a proton-pump Inhibitor (such as omeprazole (Prilosec®), metoclopramide (Reglan®), lansoprazole (Prevacid®), esomeprazole (Nexium®), pantoprazole (Protonix®), rabeprazole (Aciphex®)) or imatinib (Gleevec®) ARG201 (arGentis Pharmaceutical), belimumab (Benlysta®), tocilizumab (Actema®).

In the treatment of cystic fibrosis, a compound that inhibits RIP1 kinase, particularly a compound of Formula (I) or a pharmaceutically acceptable salt thereof, may be administered in combination with a cystic fibrosis transmembrane conductance regulator (CFTR) potentiator (ivacftor (Kalydeco®)) a mucolytic agent (such as dornase alpha (Pulmozyme®)), pancreatic enzymes (such as Pancrelipase (Creon®, Pancreaze®, Ultresa®, Zenpep®)), a bronchodilator (such as albuterol (AccuNeb®, ProAir®, Proventil HFA®, VoSpire ER®, Ventolin HFA®)), an antibiotic (including inhaled, oral or parenteral, such as tobramycin solution for inhalation (TOBI®, Bethkis®, TOBI Podhaler®), aztreonam inhalation (Azactam®, Cayston®), colistimethate sodium (Coly-Mycin®), cephalosporins (cefadroxil monohydrate (Duricef®), cefazolin (Kefzol®), cephalexin (Keflex®), cefazolin (Ancef®, etc.), fluoroquinolones (moxifloxacin, levofloxacin, gemifloxacin, etc), azithromycin (Zithromax®), gentamicin (Garamycin®), piperacillin/tazobacam (Zosyn®), cephalexin (Keflex®), ceftazidime (Fortaz, Tazicef), ciprofloxin (Cipro XR, Proquin XR), trimethoprim/sulfamethoxazole (Bactrim DS, Septra DS), chloramphenicol)), or ivacftor (Kalydeco®)/lumacaftor (VX-809), ataluren (Translarna®), or with tiopropium bromide (Spiriva® Handihaler®) as add on to standard therapy.

In the treatment of retinitis pigmentosa, a compound that inhibits RIP1 kinase, particularly a compound of Formula (I) or a pharmaceutically acceptable salt thereof, may be administered in combination with a ciliary neutrotrophic growth factor (NT-501-CNTF) or gene transfer agent, UshStat®.

In the treatment of macular degeneration, a compound that inhibits RIP1 kinase, particularly a compound of Formula (I) or a pharmaceutically acceptable salt thereof, may be administered in combination with opthalmalic intravitreal injections (afibercept (Eylea®)) or with an anti-vascular endothelial growth factor (VEGF) inhibitor (such as ranibizumab (Lucentis®) or pegaptanib sodium (Macugen®)), a ciliary neurotrophic growth factor agent (NT501), iSONEP®, or bevacizumab (Avastin®).

In the treatment of influenza, a compound that inhibits RIP1 kinase, particularly a compound of Formula (I) or a pharmaceutically acceptable salt thereof, may be administered in combination with a trivalent (IIV3) inactivated influenza vaccine (such as Afluria®, Fluarix®, Flucelvax®, FluLaval®, Fluvirin®, Fluzone®), a quadrivalent (IIV4) inactivated influenza vaccine (such as Fluarix® Quadrivalent, Flulaval® Quadrivalent, Fluzone® Quadrivalent), a trivalent recombinant influenza vaccine (such as FluBlok®), a quadrivalent live attenuated influenza vaccine (such as FluMist® Quadrivalent), an antiviral agent (such as oseltamivir (Tamiflu®), zanamivir (Relenza®), rimantadine (Flumadine®), or amantadine (Symmetrel®)), or Fluad®, Fludase, FluNhance®, Preflucel, or VaxiGrip®

In the treatment of a *staphylococcus* infection, a compound that inhibits RIP1 kinase, particularly a compound of Formula (I) or a pharmaceutically acceptable salt thereof, may be administered in combination with an antibiotic (such as a β-Lactam cephalosporin (Duricef®, Kefzol®, Ancef®, Biocef®, etc), nafcillin (Unipen®), a sulfonamide (sulfamethoxazole and trimethoprim (Bacrim®, Septra®) sulfasalazine (Azulfidine®), acetyl sulfisoxazole (Gantrisin®), etc), or vancomycin (Vancocin®)).

In the treatment of transplant rejection, a compound that inhibits RIP1 kinase, particularly a compound of Formula (I) or a pharmaceutically acceptable salt thereof, may be administered in combination with a high-dose corticosteroid (such as prednisone (Deltasone®), methylprednisolone (SoluMedrol®) etc.) a calcineurin inhibitor (such as cyclosporine (Sandimmune®, Neoral®, Gengraf®), tacrolimus (Prograf®, Astragraf XL®)), an mTor inhibitor (such as sirolimus (Rapamune®) or everolimus (Afinitor®)), an anti-proliferative agent (such as azathioprine (Imuran®, Azasan®), mycophenolate mofetil (CellCept®), or mycophenolate sodium (Myfortic®)), a monoclonal antibody (such as muromonab-CD3 (Orthoclone OKT3®)), an interleukine-2 receptor antagonist ((Basiliximab®, Simulect®), daclizumab (Zenapax®), or rituximab (Rituxan®)), a polyclonal anti-T-cell antibody (such as anti-thymocyte gamma globulin-equine (Atgam®), or antithymocyte globulin-rabbit (Thymoglobulin®)) an anti-CD40 antagonist (ASKP-1240), a JAK inhibitor (ASP015K), or an anti-TCR murine mAb (TOL101).

In the treatment of atopic dermatitis, a compound that inhibits RIP1 kinase, particularly a compound of Formula (I) or a pharmaceutically acceptable salt thereof, may be administered in combination with a topical immunomodulator or calcineurin inhibitor (such as pimecrolimus (Elidel®) or tacrolimus ointment (Protopic®)), a topical corticosteroid (such as hydrocortizone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methylprednisolone (Medrol®), or prednisolone (Pediapred®, Prelone®), an immunosuppressant (such as cyclosporine (Neoral®) or interferon gamma (Alferon N®, Infergen®, Intron A, Roferon-A®)), an antihistamine (for itching such as Atarax®, Vistaril®, Benadryl®), an antibiotic (such as penicillin derivatives flucloxacillin (Floxapen®) or dicloxacillin (Dynapen®), erythromycin (Eryc®, T-Stat®, ErythraDerm®, etc.)), anon-steroidal immunosuppressive agent (such as azathioprine (Imuran®, Azasan®), methotrexate (Rhuematrex®, Trexall®), cyclosporin (Sandimmune®), or mycophenolate mofetil (CellCept®)).

In one embodiment of this invention, the at least one other therapeutically active agent is selected from a thrombolytic agent, a tissue plasminogen activator, an anticoagulant, and a platelet aggregation inhibitor. In another embodiment, the at least one other therapeutically active agent is selected from heparin, coumadin, clopidrogel, dipyridamole, ticlopidine HCL, eptifibatide, and aspirin. In one embodiment, the RIP1 kinase-mediated disease or disorder treated with these agents is a cerebrovascular accident.

In one embodiment of this invention, the at least one other therapeutically active agent is selected from broad-spectrum antibiotic, anti-MRSA therapy and a low dose steroid. In another embodiment, the at least one other therapeutically active agent is selected from vacomycin, cefeprime, a combination of piperacillin and tazobactam, imipenem, meropenem, doripenem, ciprofloxacin, levofloxacin, ofloxacin, moxifloxacin, and hydrocortisone. In one embodiment, the RIP1 kinase-mediated disease or disorder treated with these agents is systemic inflammatory response syndrome.

In one embodiment of this invention, the at least one other therapeutically active agent is alicaforse or remestemcel-L. In one embodiment, the RIP1 kinase-mediated disease or disorder treated with these agents is Crohn's disease or ulcerative colitis.

In one embodiment of this invention, the at least one other therapeutically active agent is ixekizumab, or tildrakizumab. In one embodiment, the RIP1 kinase-mediated disease or disorder treated with these agents is psoriasis.

In one embodiment of this invention, the at least one other therapeutically active agent is an antimicrobial agent or an antibiotic. In another embodiment, the at least one other therapeutically active agent is selected from chlorhexidine, doxycycline and minocycline. In one embodiment, the RIP1 kinase-mediated disease or disorder treated with these agents is periodontitis.

In one embodiment of this invention, the at least one other therapeutically active agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. In another embodiment, the at least one other therapeutically active agent is selected from fluticasone proprionate, beclomethasone dipropionate, budesonide, trimcinolone acetonide, flunisolide, mometasone fuorate, or ciclesonide, formoterol fumarate, salmeterol xinafoate, a combination of fluticasone furoate and vilanterol, a combination of formoterol and budesonide inhalation, a combination of beclomethasone dipropionate and formoterol, a combination of fluticasone propionate and salmeterol, albuterol sulfate, levalbuterol tartrate, a combination of ipratropium bromide and albuterol, ipratropium bromide, montelukast sodium, zafirlukast, zileuton, omalizumab theophylline, cromulyn sodium, nedocromil sodium, and a combination of mometasone furoate and formoterol fumarate dihydrate. In another embodiment, the at least one other therapeutically active agent is selected from protein tyrosine kinase inhibitor, a CRTH2/D-prostanoid receptor antagonist, an epinephrine inhalation aerosol, and a combination of a phosphodiesterase-3 inhibitor and a phosphodiesterase-4 inhibitor. In another embodiment, the at least one other therapeutically active agent is selected from masitinib, AMG 853, indacaterol, E004, a combination of fluticasone furoate and fluticasone proprionate, a combination of vinanterol fluticasone furoate, a combination of fluticasone propionate and eformoterol fumarate dehydrate, reslizumab, salbutamol, tiotropium bromide, a combination of formoterol and budesonide, fluticasone furoate, VR506, lebrikizumab, and RPL554. In one embodiment, the RIP1 kinase-mediated disease or disorder treated with these agents is asthma.

In one embodiment of this invention, the at least one other therapeutically active agent is selected from a long acting beta agonist, a long-acting inhaled anticholinergic or muscarinic antagonist, a phosphodiesterase inhibitor, a combination an inhaled corticosteroid long acting beta agonist, a short acting beta agonist, and an inhaled corticosteroid. In another embodiment, the at least one other therapeutically active agent is selected from salmeterol xinafoate, a combination of umeclidinium and vilanterol, umeclidinium, aformoterol tartrate, formoterol fumarate, indacterol maleate, a combination of fluticasone propionate and eformoterol fumarate dehydrate, tiotropium bromide, aclidinium bromide, roflumilast, a combination of fluticasone furoate and vilanterol, a combination of fluticasone propionate and salmeterol, a combination of budesonide and formoterol, a combination of mometasone and formoterol, a combination of ipratropium bromide and albuterol sulfate, a combination of albuterol and ipratropium, ipratropium bromide, albuterol sulfate, budesonide, fluticasone propionate, and beclometasone dipropionate. In another embodiment, the at least one other therapeutically active agent is selected from SCH527123, glycoprronium bromide, a combination of glycopyrronium bromide and indacaterol maleate, a combination of glycopyrrolate and formoterol fumarate, indacaterol maleate, olodaterol, tiotropium, olodaterol, and a combination of aclidinium and formoterol. In one embodiment, the RIP1 kinase-mediated disease or disorder treated with these agents is COPD.

In one embodiment of this invention, the at least one other therapeutically active agent is an antimycobacterial agent or a bactericidal antibiotic. In another embodiment, the at least one other therapeutically active agent is selected from isoniazid, ehambutol, rifampin, pyrazinamide, rifabutin, rifapentine, capreomycin, levofloxacin, moxifloxicin, ofloxacin, ehionamide, cycloserine, kanamycin, streptomycin, viomycin, bedaquiline fumarate, PNU-100480, and delamanid. In one embodiment, the RIP1 kinase-mediated disease or disorder treated with these agents is a *mycobacterium* infection.

In one embodiment of this invention, the at least one other therapeutically active agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab. In another embodiment, the at least one other therapeutically active agent is selected from prednisolone, anti-thymocyte globulin, FK506 (tacrolimus), thalidomide, chlorambucil, nifedipine, nicardipine, nitroglycerin ointment, lisinopril, diltaizem, fluoxetine, bosentan, epoprostenol, colchicines, para-aminobenzoic acid, dimethyl sulfoxide, D-penicillamine, interferon alpha, interferon gamma (INF-g)), omeprazole, metoclopramide, lansoprazole, esomeprazole, pantoprazole, rabeprazole, imatinib, ARG201, and tocilizumab. In one embodiment, the RIP1 kinase-mediated disease or disorder treated with these agents is systemic scleroderma.

In one embodiment of this invention, the at least one other therapeutically active agent is selected from a cystic fibrosis transmembrane conductance regulator potentiator, a mucolytic agent, pancreatic enzymes, a bronchodilator, an antibiotic, or ivacftor/lumacaftor, ataluren, and tiopropium bromide. In another embodiment, the at least one other therapeutically active agent is selected from ivacftor, dornase alpha, pancrelipase, albuterol, tobramycin, aztreonam, colistimethate sodium, cefadroxil monohydrate, cefazolin, cephalexin, cefazolin, moxifloxacin, levofloxacin, gemifloxacin, azithromycin, gentamicin, piperacillin/tazobacam, ceftazidime, ciprofloxin, trimethoprim/sulfamethoxazole, chloramphenicol, or ivacftor/lumacaftor, ataluren, and tiopropium bromide. In one embodiment, the RIP1 kinase-mediated disease or disorder treated with these agents is cystic fibrosis.

In one embodiment of this invention, the at least one other therapeutically active agent is a ciliary neutrotrophic growth factor or a gene transfer agent. In another embodiment, the at least one other therapeutically active agent is NT-501-CNTF or a gene transfer agent encoding myosin VIIA (MY07A). In one embodiment, the RIP1 kinase-mediated disease or disorder treated with these agents is retinitis pigmentosa.

In one embodiment of this invention, the at least one other therapeutically active agent is selected from opthalmalic intravitreal injections, an anti-vascular endothelial growth factor inhibitor, and a ciliary neurotrophic growth factor agent. In another embodiment, the at least one other therapeutically active agent is selected from afibercept, ranibizumab, pegaptanib sodium, NT501, humanized sphingomab, and bevacizumab. In one embodiment, the RIP1 kinase-mediated disease or disorder treated with these agents is macular degeneration.

In one embodiment of this invention, the at least one other therapeutically active agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, or inactivated influenza vaccine. In another embodiment, the at least one other therapeutically active agent is selected from oseltamivir, zanamivir, rimantadine, or amantadine. In one embodiment, the RIP1 kinase-mediated disease or disorder treated with these agents is influenza.

In one embodiment of this invention, the at least one other therapeutically active agent is selected from a β-Lactam, nafcillin, sulfamethoxazolem, trimethoprim, sulfasalazine, acetyl sulfisoxazole, and vancomycin. In one embodiment, the RIP1 kinase-mediated disease or disorder treated with these agents is a *staphylococcus* infection.

In one embodiment of this invention, the at least one other therapeutically active agent is selected from a monoclonal antibody, a polyclonal anti-T-cell antibody, an anti-thymocyte gamma globulin-equine antibody, an antithymocyte globulin-rabbit antibody, an anti-CD40 antagonist, a JAK inhibitor, and an anti-TCR murine mAb. In another embodiment, the at least one other therapeutically active agent is selected from muromonab-CD3, ASKP-1240, ASP015K, and TOL101. In one embodiment, the RIP1 kinase-mediated disease or disorder treated with these agents is transplant rejection.

In one embodiment of this invention, the at least one other therapeutically active agent is selected from a topical immunomodulator or calcineurin inhibitor, a topical corticosteroid, an oral corticosteroid, an interferon gamma, an antihistamine, or an antibiotic. In another embodiment, the at least one other therapeutically active agent is selected from pimecrolimus, tacrolimus, hydrocortizone, betamethasone, flurandrenolide, fluticasone, triamcinolone, fluocinonide, clobetasol, hydrocortisone, methylprednisolone, prednisolone, an interferon alpha protein, a recombinant synthetic type I interferon, interferon alpha-2a, interferon alpha-2b, hydroxyzine, diphenhydramine, flucloxacillin, dicloxacillin, and erythromycin. In one embodiment, the RIP1 kinase-mediated disease or disorder treated with these agents is atopic dermatitis.

Accordingly, one embodiment of this invention is directed to a method of inhibiting RIP1 kinase comprising contacting a cell with a compound of the invention. Another embodiment of this invention is a method of inhibiting RIP1 kinase comprising contacting a cell with a compound of Formula (II) or Formula (III) or a salt, particularly a pharmaceutically acceptable salt, thereof. A particular embodiment of this invention is to a method of inhibiting RIP1 kinase comprising contacting a cell with a compound of Formula (II) or (III), or a salt, particularly a pharmaceutically acceptable salt, thereof.

In another embodiment, the invention is directed to a method of treating a RIP1 kinase-mediated disease or disorder (for example, a disease or disorder recited herein) comprising administering a therapeutically effective amount of a compound of Formula (I), (II), or (III), or a salt, particularly a pharmaceutically acceptable salt thereof, to a human in need thereof. In a particular embodiment, the invention is directed to a method of treating a RIP1 kinase-mediated disease or disorder (for example, a disease or disorder recited herein) comprising administering a therapeutically effective amount of a compound disclosed herein, or a salt, particularly a pharmaceutically acceptable salt thereof, to a human in need thereof. In one specific embodiment, the invention is directed to a method of treating a RIP1 kinase-mediated disease or disorder (specifically, a disease or disorder recited herein) comprising administering a therapeutically effective amount of (S)-1-(4-(5-(3,5-difluorophenyl)-4,5-dihydro-1H-pyrazole-1-carbonyl)piperidin-1-yl) ethanone, or a pharmaceutically salt thereof, to a human in need thereof. In another specific embodiment, the invention is directed to a method of treating a RIP1 kinase-mediated disease or disorder (specifically, a disease or disorder recited herein) comprising administering a therapeutically effective amount of (S)-1-(4-(5-(3,5-difluorophenyl)-4,5-dihydro-1H-pyrazole-1-carbonyl)piperidin-1-yl)ethanone to a human in need thereof.

This invention also provides a compound of Formula (I), (II), or (III), or a pharmaceutically acceptable salt thereof, for use in therapy. This invention provides a compound of Formula (I), (II), or (III), or a pharmaceutically acceptable salt thereof, for use in the treatment of a RIP1 kinase-mediated disease or disorder (for example, a disease or disorder recited herein). Specifically, this invention provides a compound described herein, or a pharmaceutically acceptable salt thereof, for use in therapy. More specifically, this invention provides (S)-1-(4-(5-(3,5-difluorophenyl)-4,5-dihydro-1H-pyrazole-1-carbonyl)piperidin-1-yl)ethanone, or a pharmaceutically salt thereof, for use in therapy. More specifically, this invention provides (S)-1-(4-(5-(3,5-difluorophenyl)-4,5-dihydro-1H-pyrazole-1-carbonyl)piperidin-1-yl)ethanone for use in therapy.

In another embodiment, this invention provides a compound of the invention for use in the treatment of a RIP1 kinase-mediated disease or disorder, specifically, a disease or disorder recited herein. This invention provides a compound described herein, or a pharmaceutically acceptable salt thereof, for use in the treatment of a RIP1 kinase-mediated disease or disorder, specifically, a disease or disorder recited herein. In another specific embodiment, this invention provides (S)-1-(4-(5-(3,5-difluorophenyl)-4,5-dihydro-1H-pyrazole-1-carbonyl)piperidin-1-yl)ethanone, or a pharmaceutically acceptable salt thereof, for use in the treatment of a RIP1 kinase-mediated disease or disorder, specifically, a disease or disorder recited herein. In another specific embodiment, this invention provides (S)-1-(4-(5-(3,5-difluorophenyl)-4,5-dihydro-1H-pyrazole-1-carbonyl)piperidin-1-yl)ethanone for use in the treatment of a RIP1 kinase-mediated disease or disorder, specifically, a disease or disorder recited herein.

This invention specifically provides for the use of a compound of Formula (I), (II) or (III), or a pharmaceutically acceptable salt thereof, as an active therapeutic substance. More specifically, this invention provides for the use of the compounds described herein for the treatment of a RIP1 kinase-mediated disease or disorder, specifically, a disease or disorder recited herein. Accordingly, the invention provides for the use of a compound of Formula (I), (II) or (III), as an active therapeutic substance in the treatment of a human in need thereof with a RIP1 kinase-mediated disease or disorder, specifically, a disease or disorder recited herein. In one embodiment, this invention provides for the use of (S)-1-(4-(5-(3,5-difluorophenyl)-4,5-dihydro-1H-pyrazole-1-carbonyl)piperidin-1-yl)ethanone, or a pharmaceutically acceptable salt thereof, as an active therapeutic substance for the treatment of a RIP1 kinase-mediated disease or disorder, specifically, a disease or disorder recited herein. In a more specific embodiment, this invention provides for the use of (S)-1-(4-(5-(3,5-difluorophenyl)-4,5-dihydro-1H-pyrazole-1-carbonyl)piperidin-1-yl)ethanone as an active therapeutic substance for the treatment of a RIP1 kinase-mediated disease or disorder, specifically, a disease or disorder recited herein.

The invention further provides for the use of a compound of Formula (I), (II) or (III), or a salt thereof, particularly a pharmaceutically acceptable salt thereof, in the manufacture of a medicament for use in the treatment of a RIP1 kinase-mediated disease or disorder, for example the diseases and disorders recited herein. Specifically, the invention also provides for the use of a compound described herein, or a pharmaceutically acceptable salt thereof, in the manufacture of a medicament for use in the treatment of a RIP1 kinase-mediated disease or disorder, for example the diseases and disorders recited herein. In one embodiment, the invention provides for the use of (S)-1-(4-(5-(3,5-difluorophenyl)-4,5-dihydro-1H-pyrazole-1-carbonyl)piperidin-1-yl)ethanone, or a pharmaceutically acceptable salt thereof, in the manufacture of a medicament for use in the treatment of a RIP1 kinase-mediated disease or disorder, for example the diseases and disorders recited herein. In another embodiment, the invention provides for the use of (S)-1-(4-(5-(3,5-difluorophenyl)-4,5-dihydro-1H-pyrazole-1-carbonyl)piperidin-1-yl)ethanone in the manufacture of a medicament for use in the treatment of a RIP1 kinase-mediated disease or disorder, for example the diseases and disorders recited herein.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), (II), or (III), or a pharmaceutically acceptable salt thereof, is a quantity of an inventive agent that, when administered to a human in need thereof, is sufficient to modulate and/or inhibit the activity of RIP1 kinase such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of a RIP1 kinase mediated disease or disorder, as described hereinabove.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg.

For use in therapy, the compounds of the invention will be normally, but not necessarily, formulated into a pharmaceutical composition prior to administration to a patient. Accordingly, the invention also is directed to pharmaceutical compositions comprising a compound of the invention and one or more pharmaceutically acceptable excipients. The invention is directed to a pharmaceutical composition comprising a compound of Formula (I), (II), or (III), or a pharmaceutically acceptable salt thereof, and one or more pharmaceutically acceptable excipients. In one embodiment, there is provided a pharmaceutical composition comprising (S)-1-(4-(5-(3,5-difluorophenyl)-4,5-dihydro-1H-pyrazole-1-carbonyl)piperidin-1-yl)ethanone, or a pharmaceutically acceptable salt thereof, and one or more pharmaceutically acceptable excipients. In another embodiment, there is provided a pharmaceutical composition comprising (S)-1-(4-(5-(3,5-difluorophenyl)-4,5-dihydro-1H-pyrazole-1-carbonyl)piperidin-1-yl)ethanone, and one or more pharmaceutically acceptable excipients. In another embodiment, there is provided a pharmaceutical composition comprising crystalline (S)-1-(4-(5-(3,5-difluorophenyl)-4,5-dihydro-1H-pyrazole-1-carbonyl)piperidin-1-yl)ethanone having the PXRD pattern of FIG. 5 and one or more pharmaceutically acceptable excipients.

The invention is further directed to a pharmaceutical composition comprising a compound of Formula (I), (II), or (III), or a pharmaceutically acceptable salt thereof, and one or more pharmaceutically acceptable excipients and at least one other therapeutically active agent, specifically one or two other therapeutically active agents, more specifically one other therapeutically active agent. In one embodiment, there is provided a pharmaceutical composition comprising (S)-1-(4-(5-(3,5-difluorophenyl)-4,5-dihydro-1H-pyrazole-1-carbonyl)piperidin-1-yl)ethanone, or a pharmaceutically acceptable salt thereof, one or more pharmaceutically acceptable excipients, and at least one other therapeutically active agent, specifically one or two other therapeutically active agents, more specifically one other therapeutically active agent. In another embodiment, there is provided a pharmaceutical composition comprising (S)-1-(4-(5-(3,5-difluorophenyl)-4,5-dihydro-1H-pyrazole-1-carbonyl)piperidin-1-yl)ethanone, one or more pharmaceutically acceptable excipients, and at least one other therapeutically active agent, specifically one or two other therapeutically active agents, more specifically one other therapeutically active agent. In a further embodiment, there is provided a pharmaceutical composition comprising comprising crystalline (S)-1-(4-(5-(3,5-difluorophenyl)-4,5-dihydro-1H-pyrazole-1-carbonyl)piperidin-1-yl)ethanone having the PXRD pattern of FIG. 5, one or more pharmaceutically acceptable excipients, and at least one other therapeutically active agent, specifically one or two other therapeutically active agents, more specifically one other therapeutically active agent.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. A dose of the pharmaceutical composition contains at least a therapeutically effective amount of a compound of this invention (i.e., a compound of Formula (I), (II), or (III), or a pharmaceutically acceptable salt, thereof). When prepared in unit dosage form, the pharmaceutical compositions may contain from 1 mg to 1000 mg of a compound of this invention.

As provided herein, unit dosage forms (pharmaceutical compositions) containing from 1 mg to 1000 mg of a compound of the invention may be administered one, two, three, or four times per day, preferably one, two, or three times per day, and more preferably, one or two times per day, to effect treatment of a RIP1 kinase-mediated disease or disorder.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms suitable for use with the compounds of this invention include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company). Accordingly, another embodiment of this invention is a method of preparing a pharmaceutical composition comprising the step of admixing a compound of Formula (I), (II), or (III), or a pharmaceutically acceptable salt, thereof, with one or more pharmaceutically acceptable excipients. Another embodiment of this invention is a method of preparing a pharmaceutical composition comprising the step of admixing crystalline (S)-1-(4-(5-(3,5-difluorophenyl)-4,5-dihydro-1H-pyrazole-1-carbonyl)piperidin-1-yl)ethanone having the PXRD pattern of FIG. 5 with one or more pharmaceutically acceptable excipients.

In one aspect, the invention is directed to a topical dosage form such as a cream, ointment, lotion, paste, or gel comprising an effective amount of a compound of the invention and one or more pharmaceutically acceptable excipients. Lipophilic formulations, such as anhydrous creams and ointments, generally will have a base derived from fatty alcohols, and polyethylene glycols. Additional additives include alcohols, non-ionic surfactants, and antioxidants. For ointments, the base normally will be an oil or mixture of oil and wax, e.g., petrolatum. Also, an antioxidant normally will be included in minor amounts. Because the compositions are applied topically and the effective dosage can be controlled by the total composition applied, the percentage of active ingredient in the composition can vary widely. Convenient concentrations range from 0.5% to 20%.

Topically applied gels can also be a foamable suspension gel comprising a compound of the invention, as an active agent, one or more thickening agents, and optionally, a dispersing/wetting agent, a pH-adjusting agent, a surfactant, a propellant, an antioxidant, an additional foaming agent, a chelating/sequestering agent, a solvent, a fragrance, a coloring agent, a preservative, wherein the gel is aqueous and forms a homogenous foam.

In one aspect, the invention is directed to a topical dosage form that can be administered by inhalation, that is, by intranasal and oral inhalation administration. Appropriate dosage forms for such administration, such as an aerosol formulation or a metered dose inhaler, may be prepared by conventional techniques. Intranasal sprays may be formulated with aqueous or non-aqueous vehicles with the addition of agents such as thickening agents, buffer salts or acid or alkali to adjust the pH, isotonicity adjusting agents or anti-oxidants. Solutions for inhalation by nebulization may be formulated with an aqueous vehicle with the addition of agents such as acid or alkali, buffer salts, isotonicity adjusting agents or antimicrobials.

Formulations for administration by inhalation or foamable gel often require the use of a suitable propellant. Capsules and cartridges of e.g. gelatin for use in an inhaler or insufflator may be formulated using a suitable powder base such as lactose or starch.

In another aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The reactions described herein are applicable for producing compounds of Formulas (I), (II), and (III) having a variety of different substituent groups (e.g., $R^1$, $R^2$, etc.), as defined herein. The skilled artisan will appreciate that if a particular substituent is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999).

Names for the intermediate and final compounds described herein were generated using the software naming program ACD/Name Pro V6.02 available from Advanced Chemistry Development, Inc., 110 Yonge Street, 14$^{th}$ Floor, Toronto, Ontario, Canada, M5C 1T4 (http://www.acdlabs.com/) or the naming program in ChemDraw, Struct=Name Pro 12.0, as part of ChemBioDraw Ultra, available from CambridgeSoft. 100 CambridgePark Drive, Cambridge, Mass. 02140 USA (www.cambridgesoft.com).

It will be appreciated by those skilled in the art that in certain instances these programs may name a structurally depicted compound as a tautomer of that compound. It is to be understood that any reference to a named compound or a structurally depicted compound is intended to encompass all tautomers of such compounds and any mixtures of tautomers thereof.

$^1$H NMR spectra were recorded in either CDCl$_3$ or DMSO-d$_6$ on either a Bruker DPX 400, Bruker Avance DRX, Varian Unity 400 spectrometer or JEOL Delta all working at 400 MHz. The internal standard used was either tetramethylsilane or the residual protonated solvent at 7.25 ppm for CDCl$_3$ or 2.50 ppm for DMSO-d$_6$.

Mass spectrum was recorded on a Waters ZQ mass spectrometer using alternative-scan positive and negative mode electrospray ionisation. Cone voltage: 20 or 5V.

LC/MS Method 1: HPLC was conducted on a X-Select CSH C18 XP column (2.5 μm 30×4.6 mm id) eluting with 0.1% formic acid in water (solvent A) and 0.1% formic acid in acetonitrile (solvent B), using the following elution gradient 0-3 min.: 5% to 100% B, 3-4 min. 100% B, at a flow rate of 1.8 ml/min. at 40° C.

LC/MS Method 2: The UPLC analysis was conducted on an Acquity UPLC CSH C18 column (50 mm×2.1 mm, i.d. 1.7 μm packing diameter) at 40° C. eluting with 0.1% formic acid in water (solvent A) and 0.1% formic acid in acetonitrile (solvent B), using the following elution gradient: 0 min: 97%/3% (A/B), 1.5 min. 5%/95% (A/B), 1.9 min. 5%/95% (A/B), 2 min. 97%/3% (A/B), with a flow rate of 1 mL/min. with UV detection a summed signal from wavelength of 210 nm to 350 nm.

LC/MS Method 3: UPLC was conducted on a Acquity UPLC BEH C$_{18}$ column (50 mm×2.1 mm ID, 1.7 mm) eluting with 0.1% formic acid in water (solvent A) and 0.1% formic acid in acetonitrile (solvent B), using the following elution gradient 0-3.8 minutes: 3% to 98% B, 3.8-4.5 minutes 97% B with a flow rate of between 0.6 to 1 mL/minute. at a temperature of 35 or 40° C. with UV detection range: 210 to 350 nm.

LC/MS Method 4: HPLC was conducted on a X-Bridge C-18 (150×4.6 mm, 3.5 μm) eluting with Mobile Phase: A: 10 mM Ammonium Acetate, and B: 100% acetonitrile, using the following elution gradient-time/% B: 0/5, 1.5/5, 3/15, 7/55, 10/95, 15/95, 17/5, 20/5, at a flow rate of 1.0 mL/minute at 40° C. Diluent 70:30 (acetonitrile:H$_2$O).

LC/MS Method 5: Analytical HPLC was conducted on a X-Select CSH C18 XP column (2.5 μm 30×4.6 mm id) eluting with 0.1% formic acid in water (solvent A) and 0.1% formic acid in acetonitrile (solvent B), using the following elution gradient 0-4 minutes: 0% to 50% B at a flow rate of 1.8 ml/minute at 40° C.

Analytical chiral SFC was conducted on a Chiralpak IC (4.6×250 mm) 5μ CO$_2$ eluting with 40% modifier of 0.5% DEA in methanol, at a flow rate of 3 mL/minute at 30° C. and pressure of 100 bar.

Analytical chiral HPLC Method 1: on AD-H was using 4.6×150 mm column, 50:50 EtOH:Heptane with 0.1% isopropylamine at 254 nm, at a flow rate of 1 mL/min. Analytical chiral HPLC Method 2: CHIRALPAK IE 250× 4.6 5 μm, C7/EtOH 70/30+0.1% TFA+0.3% TEA, 1.5 mL/min, 40° C.

In the following experimental descriptions, the following abbreviations may be used:

| Abbreviation | Meaning |
|---|---|
| 2-MeTHF | 2-methyltetrahydrofuran |
| aq | aqueous |
| BINAP | 2,2'-bis(diphenylphosphino)-1,1'-binaphthalene |
| BOC, tBOC, Boc | tert-butoxycarbonyl |
| br | broad |
| brine | saturated aqueous sodium chloride |
| CH$_2$Cl$_2$ or DCM | methylene chloride or 1,2-dichloromethane |
| CH$_3$CN or MeCN | acetonitrile |
| CPME | cyclo-pentyl methyl ether |
| CH$_3$NH$_2$ | methylamine |
| Cs$_2$CO$_3$ | cesium carbonate |
| Cy or CyH | cyclohexane |
| d | day |
| DCE | 1,2-dichloroethane |
| DIBAL or DIBAL-H | diisobutylaluminium hydride |
| DIEA or DIPEA | diisopropyl ethylamine |
| DMAP | 4-dimethylaminopyidine |
| DMF | N,N-dimethylformamide |
| DMSO | dimethylsulfoxide |
| EDC | 1-ethyl-3-(3-dimethylaminopropyl) carbodiimide |
| equiv | equivalents |
| Et | ethyl |
| Et$_3$N or TEA | triethylamine |
| Et$_2$O | diethyl ether |
| EtOH | ethanol |
| EtOAc | ethyl acetate |
| h, hr | hour(s) |
| HATU | O-(7-Azabenzotriazol-1yl)-N,N,N',N'-tetramethylyronium hexafluorophosphate |
| HCl | hydrochloric acid |
| i-Pr$_2$NEt | N',N'-diisopropylethylamine |
| KOH | potassium hyudroxide |
| KOt-Bu | potassium tert-butoxide |
| LCMS | liquid chromatography-mass spectroscopy |
| LiHDMS | lithium hexamethyldisilazide |
| LiOH | lithium hydroxide |
| Me | methyl |
| MeOH or CH$_3$OH | methanol |
| MgSO$_4$ | magnesium sulfate |
| min | minute(s) |
| MnO$_2$ | manganese dioxide |
| MS | mass spectrum |
| μw | microwave |
| NaBH$_4$ | sodium borohydride |
| Na$_2$CO$_3$ | sodium carbonate |
| NaH | sodium hydride |
| NaHCO$_3$ | sodium bicarbonate |
| NaOH | sodium hydroxide |
| Na$_2$SO$_4$ | sodium sulfate |
| N$_2$H$_2$ | hydrazine |
| NH$_4$Cl | ammonium chloride |
| NH$_4$OH | ammonium hydroxide |
| NiCl$_2$•6H$_2$O | nickel (II) chloride hexahydrate |
| NMP | N-methyl-2-pyrrolidone |
| o.n. | overnight |
| PCC | pyridinium chlorochromate |
| PdOAc$_2$ | lead acetate |
| Ph | phenyl |
| PPh$_3$ | triphenyl phospine |
| POCl$_3$ | phosphoryl chloride |
| Pr | propyl |
| PyBROP | Bromotripyrrolidinophosphonium hexafluorophosphate |
| rbf | round bottom flask |
| rm or rxn mixture | reaction mixture |
| rt | room temperature |
| satd. | saturated |
| sm or SM | starting material |
| SOCl$_2$ | thionyl chloride |
| T3P | propylphosphonic anhydride |
| TBAF | tetra n-butyl ammonium flouride |
| t-BuOH | tert-butanol |
| TEA | triethylamine |
| TFA | trifluoroacetic acid |
| THF | tetrahydrofuran |
| TLC | thin layer chromatography |
| t$_R$ or Rf | retention time |
| UPLC | ultra performance liquid chromatography |
| UV | ultraviolet |

Preparation 1

5-methylnicotinaldehyde

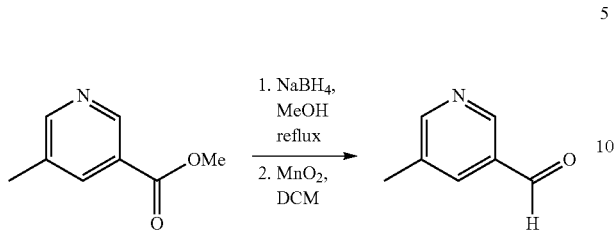

Step 1: NaBH$_4$ (3.31 g, 87.5 mmol) was added at rt to a solution of methyl 5-methylnicotinate (2.37 g, 15.7 mmol) in MeOH (50 mL). The mixture was stirred at rt for 6 h then heated overnight at reflux. The reaction was allowed to cool to rt then it was quenched by cautious addition of Na$_2$SO$_4$.10H$_2$O. The suspension was stirred for 2 h at rt, then volatiles were removed under reduced pressure. The residue was taken up in CH$_2$Cl$_2$, filtered and concentrated under reduced pressure to yield 1.85 g (97%) of crude (5-methylpyridin-3-yl)methanol which was used in next step without further purification. MS (m/z) 124 (M+H$^+$).

Step 2: MnO$_2$ (46.2 g, 531 mmol) was added to a stirred solution of (5-methylpyridin-3-yl)methanol in dry DCM (75 mL). The suspension was stirred at rt for 4 h. The mixture was filtered and the solvent was removed under reduced pressure to give 1.91 g (60%) of 5-methylpyridine-3-carbaldehyde. Crude product was used without further purification. MS (m/z) 122 (M+H$^+$).

Preparation 2 tetrahydro-2H-pyran-2-carbaldehyde

DMSO (690 µL, 9.71 mmol) was added to a cold (−78° C.) solution of oxalyl chloride (410 µL, 4.85 mmol) in dry CH$_2$Cl$_2$ (22 mL), under inert atmosphere. After 5 min stirring, tetrahydropyran-2-methanol (500 µL, 4.42 mmol) was added and the reaction was stirred for 30 minutes at −78° C. Et$_3$N (3.1 mL, 22.3 mmol) was added dropwise and the reaction was allowed to warm up to room temperature. After complete consumption of the alcohol as observed by TLC, the reaction was quenched with saturated NH$_4$Cl (aq), stirred for 5 minutes and extracted with CH$_2$Cl$_2$. Combined organic extracts were dried over Na$_2$SO$_4$ and filtered. The solution of crude oxane-2-carbaldehyde was not concentrated under reduced pressure in order to avoid losses due to the suspected volatility of the product and was used as a solution in the next step.

Preparation 3

(E)-3-(5-methylpyrazin-2-yl)prop-2-en-1-ol

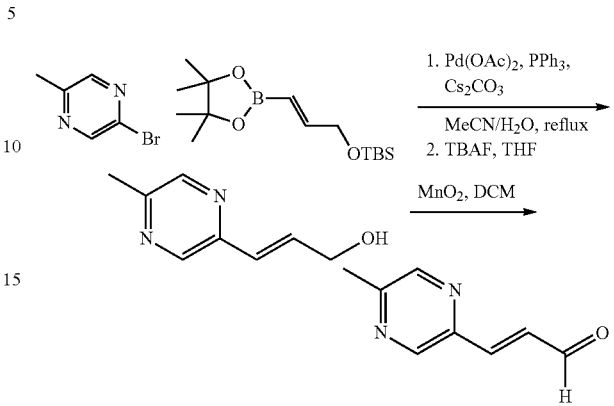

Step 1: To 2-bromo-5-methylpyrazine (2 g, 11.6 mmol) in MeCN/H$_2$O 4/1 (40 ml), tert-butyldimethyl {[(2E)-3-(tetramethyl-1,3,2-dioxaborolan-2-yl)prop-2-en-1-yl]oxy}silane (3.98 ml, 12.1 mmol), Cs$_2$CO$_3$ (7.53 g, 23.1 mmol), PPh$_3$ (0.76 g, 2.9 mmol and Pd(OAc)$_2$ (0.13 g, 0.58 mmol) were added and the reaction heated at reflux (~100° C. external temperature) for 1.5 h. The organic solvent was removed in vacuo and the organic mixture partitioned between water and EtOAc. The aqueous phase was back-extracted with EtOAc and the combined organic phases were washed with brine, dried over anhydrous Na$_2$SO$_4$ and the solvent removed in vacuo. The obtained crude brown oil was purified by flash chromatography (Silica, 340 Snap cartridge, from 100% Cy to Cy/EtOAc 60/40) affording the title compound (2.57 g, 84%). MS (m/z) 265 (M+H$^+$).

Step 2: TBAF 1.0 M in THF (12 mL, 12 mmol) was added at 0° C. to a solution of 2-[(1E)-3-[(tert-butyldimethylsilyl)oxy]prop-1-en-1-yl]-5-methylpyrazine (2.57 g, 9.72 mmol) in dry THF (24 mL). After 1 h stirring at 0° C. the reaction was quenched by the addition of 2.63 g solid NaHCO$_3$ and the suspension was stirred at rt for 1.5 h. The suspension was filtered and concentrated under reduced pressure to give 7.99 g of crude product. Crude product was purified by silica gel chromatography (Biotage SP, 100 g cartridge, EtOAc/MeOH 100:0 to 90:10) to give 1.40 g (96%) of (2E)-3-(5-methylpyrazin-2-yl)prop-2-en-1-ol. MS (m/z) 151 (M+H$^+$).

Step 3: MnO$_2$ (20.5 g, 236 mmol) was added to a stirred solution of (2E)-3-(5-methylpyrazin-2-yl)prop-2-en-1-ol in dry DCM (35 mL). The suspension was stirred at rt for 4 h. The mixture was filtered and the solvent was removed under reduced pressure to give 740 mg (54%) of (2E)-3-(5-methylpyrazin-2-yl)prop-2-enal. Crude product was used without further purification. MS (m/z) 149 (M+H$^+$).

The following intermediate used for the preparation of titled example compounds was synthesized using methods analogous to the ones described above.

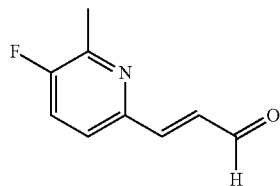

Preparation 4

5-chloronicotinaldehyde

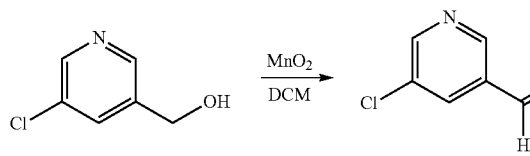

To a solution of (5-chloropyridin-3-yl)methanol (292 mg, 2.03 mmol) in dry DCM (10 ml) MnO$_2$ (3.54 g, 40.6 mmol) was added. The mixture was stirred at rt o.n. The solid was filtered (washing with DCM) and the solution was evaporated to dryness to give the title compound (128 mg, 0.9 mmol, purity: 85% by NMR, recovery: 44%). MS (m/z) 142, 144 (M+H$^+$).

Preparation 5

(E)-3-(pyridin-3-yl)acrylaldehyde

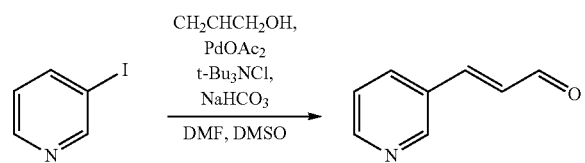

To a stirred solution of 3-iodopyridine (5 g, 24.39 mmol) in DMF (25 mL) and DMSO (25 mL) was added allyl alcohol (1.91 mL, 29.3 mmol), PdOAc$_2$ (1.095 g, 4.88 mmol), tetrabutylammonium chloride (7.22 g, 24.39 mmol) and NaHCO$_3$ (5.12 g, 61.0 mmol). The reaction mixture was stirred at 60° C. for 16 hr under oxygen atmosphere. TLC indicated completion of the reaction, and it the mixture was cooled to the rt. The reaction mixture was filtered through Celite rinsing with EtOAc (100 mL). The filtrate was diluted with water (150 mL) and EtOAc (100 mL) and the layers separated. The aqueous layer was extracted with EtOAc (100 mL). The combined organic layers were dried over anhydrous Na$_2$SO$_4$, filtered and concentrated in vacuo to provide the title compound (1 g, 73% purity, 22% yield). MS (m/z) 134 (M+H$^+$).

Preparation 6

(E)-3-(5-fluoropyridin-3-yl)acrylaldehyde

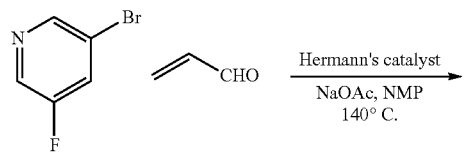

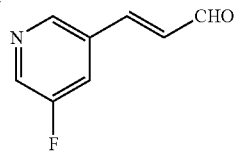

To a solution of 3-bromo-5-fluoropyridine (5.0 g, 28.4 mmol), Herrmann's catalyst (0.533 g, 0.568 mmol) and sodium acetate (2.56 g, 31.3 mmol) in NMP (60 mL) stirred under nitrogen at room temp in sealed tube, after degassing with nitrogen for 10 mins was added acrylaldehyde (1.752 g, 31.3 mmol). The reaction mixture was stirred at 140° C. for 2 hr. TLC indicated, SM was completed, then it was cooled to rt, added water (200 mL), extracted with DCM (100 mL) and organic layer was concentrated to get crude. The crude compound was purified by silicagel column using 10-30% EtOAc in hexane to afford (E)-3-(5-fluoropyridin-3-yl)acrylaldehyde (2.0 g, 12.67 mmol, 44.6% yield) as pale yellow solid which was confirmed by spectral analysis. MS (m/z) 152 (M+H$^+$).

Preparation 7

Methyl 1-(5-fluoropyridin-2-yl)piperidine-4-carboxylate

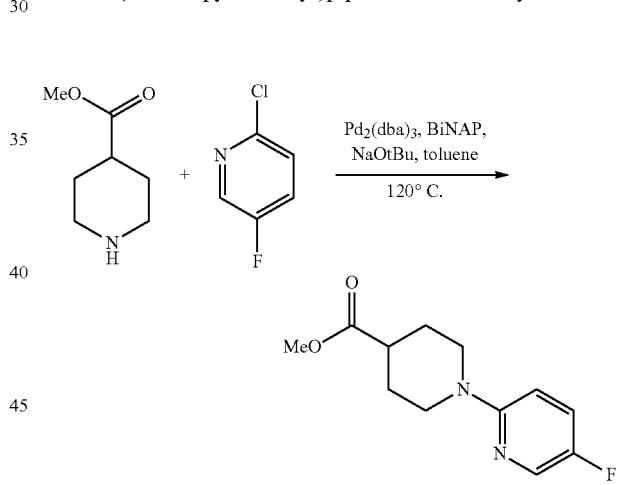

To a solution of methyl piperidine-4-carboxylate (4.6 ml, 34.22 mmol) and 2-chloro-5-fluoropyridine (1.5 g, 11.4 mmol) in dry toluene (25 ml) sodium tert-butoxide (1.37 g, 14.25 mmol), BINAP (212 mg, 0.34 mmol), and tris(dibenzylideneacetone)dipalladium(0) (104 mg, 0.114 mmol) were added. The mixture was heated to 120° C. and stirred at this temperature for 2 hr then cooled to rt Water (30 ml) and EtOAc (20 ml) were added. Phases were separated, and the aqueous layer was extracted (2×) with EtOAc. The combined organic phases were dried over Na$_2$SO$_4$ and evaporated. Crude product was purified by flash chromatography (Silica, Cy/EtOAc from 1/0 to 8/2) to give the title compound (1.8 g, 7.6 mmol, purity: 97% by UV a/a, recovery: 66%). MS (m/z) 239 (M+H$^+$).

The following intermediates used for the preparation of titled example compounds were synthesized using methods analogous to the ones described above.

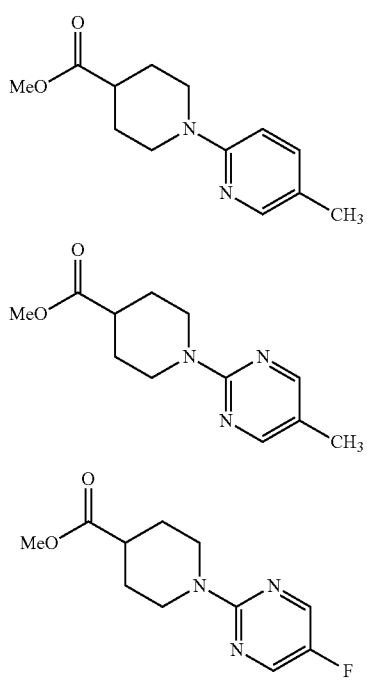

Preparation 8

Methyl 1-(oxazole-5-carbonyl)piperidine-4-carboxylate

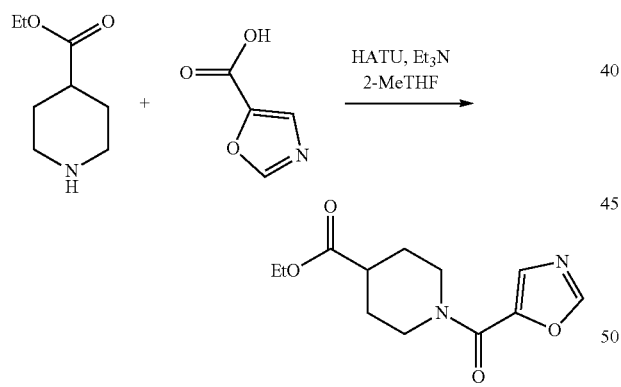

To a solution of ethyl piperidine-4-carboxylate (15.3 g, 97 mmol) on 2-MeTHF (300 mL) at rt, oxazole-5-carboxylic acid (11.00 g, 97 mmol), HATU (38.9 g, 102 mmol) and Et$_3$N (14.92 mL, 107 mmol) were added. The reaction mixture was stirred at rt for 18 hours. Water (500 mL) was added and extracted with EtOAc (2×300 mL). The combined organic phases were dried over Na$_2$SO$_4$, filtered off and evaporated to dryness. The residue was purified by chromatography [silica, CyH/(EtOAc-EtOH 3:1) 100/0 to 75/25] to afford the title compound (23.6 g, purity: >95% by LCMS, recovery: 96%) as a yellow oil. LCMS (m/z) 253 (M+H)$^+$, retention time: 1.68 min, method 1 20V.

Preparation 9

1-(5-fluoropyridin-2-yl)piperidine-4-carboxylic Acid

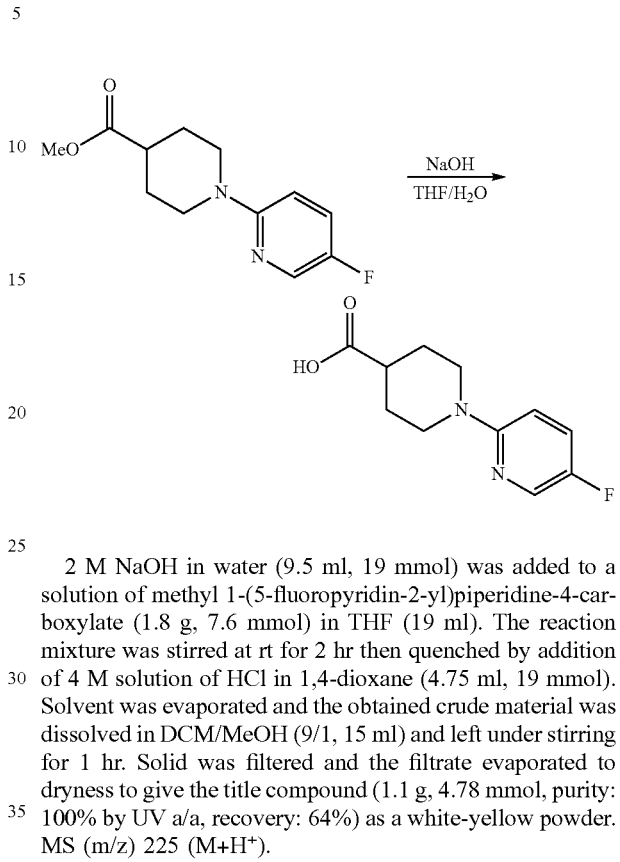

2 M NaOH in water (9.5 ml, 19 mmol) was added to a solution of methyl 1-(5-fluoropyridin-2-yl)piperidine-4-carboxylate (1.8 g, 7.6 mmol) in THF (19 ml). The reaction mixture was stirred at rt for 2 hr then quenched by addition of 4 M solution of HCl in 1,4-dioxane (4.75 ml, 19 mmol). Solvent was evaporated and the obtained crude material was dissolved in DCM/MeOH (9/1, 15 ml) and left under stirring for 1 hr. Solid was filtered and the filtrate evaporated to dryness to give the title compound (1.1 g, 4.78 mmol, purity: 100% by UV a/a, recovery: 64%) as a white-yellow powder. MS (m/z) 225 (M+H$^+$).

The following intermediates used for the preparation of titled example compounds were synthesized using methods analogous to the ones described above.

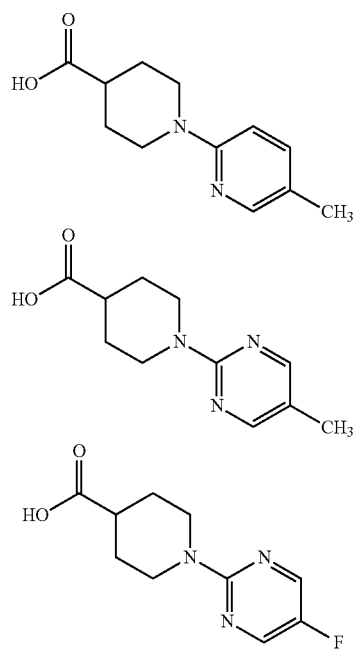

-continued

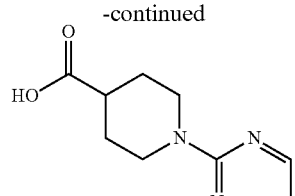

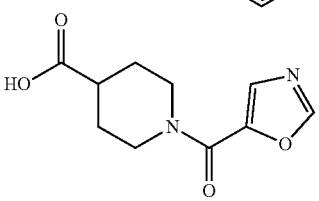

Preparation 10

Methyl 1-(pyrimidin-2-yl)piperidine-4-carboxylate

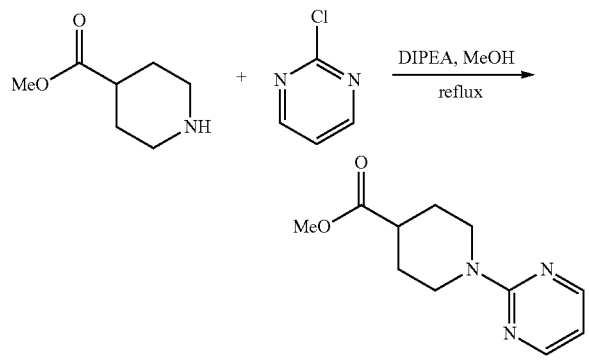

To a solution of methyl piperidine-4-carboxylate (0.8 g, 5.59 mmol) in dry MeOH (20 ml) 2-chloropyrimidine (0.7 g, 6.14 mmol) and DIPEA (2 ml, 11.18 mmol) were added. The mixture was heated to reflux and stirred at this temperature overnight. Solvents were evaporated and the crude mixture purified by flash chromatography (Silica, Cy/EtOAC from 1/0 to 0/1) to give the title compound (0.25 g, 1.13 mmol, purity >97% by UV a/a, recovery: 20%). MS (m/z) 222 (M+H$^+$).

Preparation 11

1-phenylpiperidine-4-carbonyl Chloride

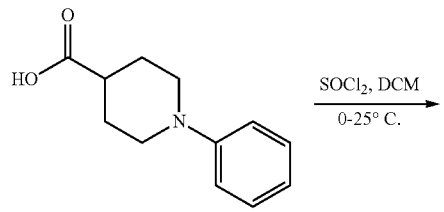

-continued

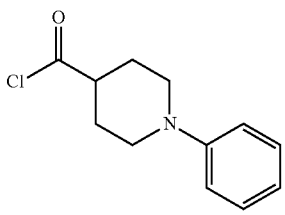

To a solution of 1-phenylpiperidine-4-carboxylic acid (500 mg, 2.436 mmol) in DCM (10 mL) stirred under nitrogen at 0° C. was added SOCl$_2$ (0.889 mL, 12.18 mmol) dropwise over 5 min. The reaction mixture was stirred at 0-25° C. for 16 hr. TLC indicated the starting material was consumed, and the mixture was concentrated under vacuum (under nitrogen atmosphere) to provide 1-phenylpiperidine-4-carbonyl chloride (520 mg, 2.325 mmol, 95% yield), which was confirmed by TLC and used in the next step.

The following intermediate used for the preparation of titled example compounds was synthesized using methods analogous to the ones described above. Thionyl chloride may be substituted for the oxalyl chloride or for the Ghosez's reagent.

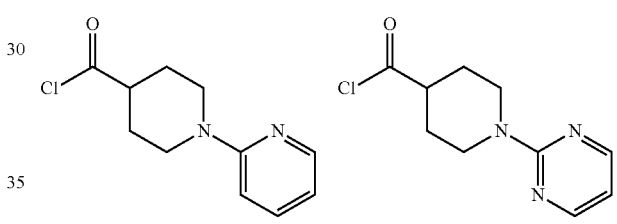

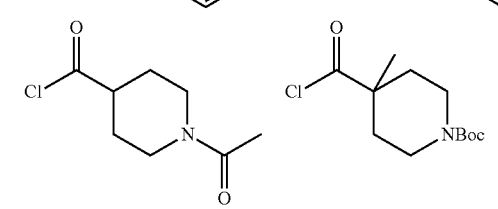

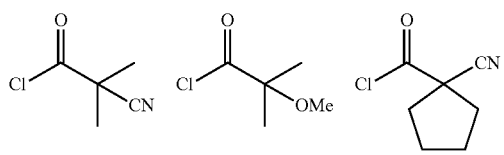

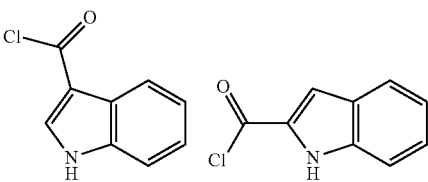

Preparation 12

(E)-3-(6-methoxypyridin-3-yl)acrylaldehyde

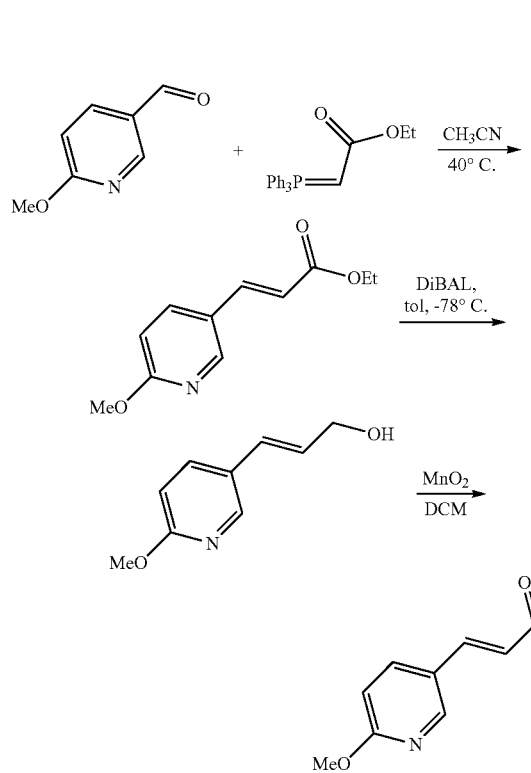

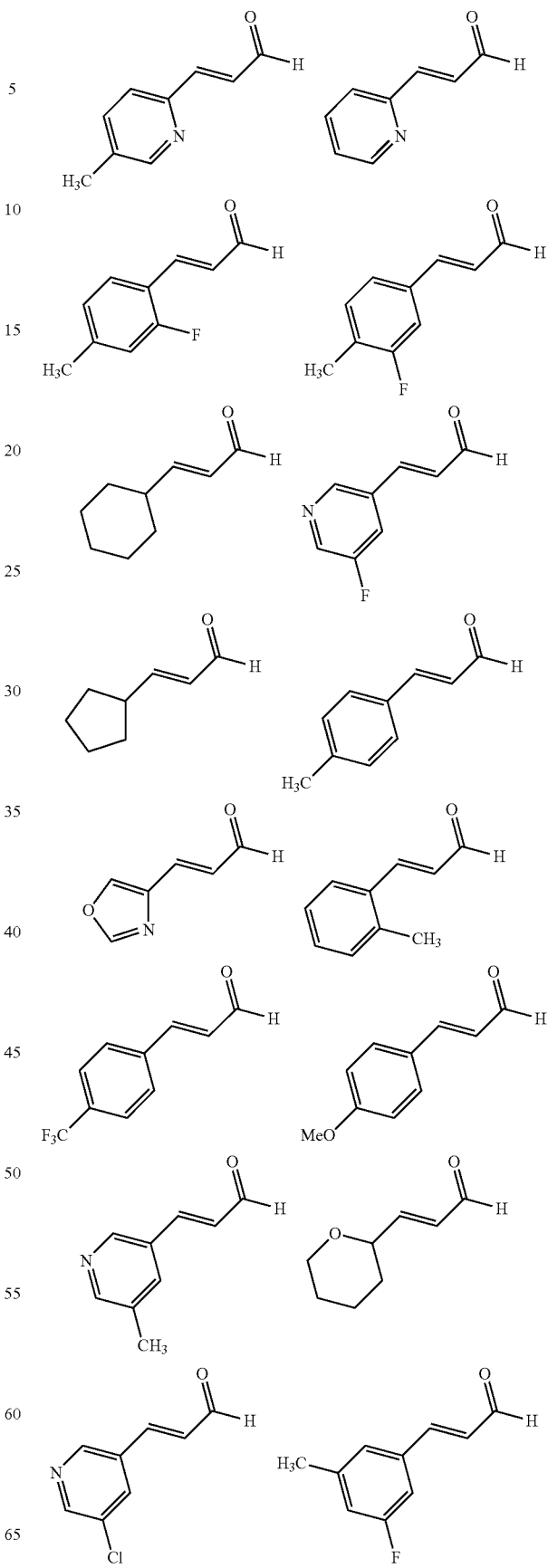

Step 1: To a solution of 6-methoxypyridine-3-carbaldehyde (2 g, 14.6 mmol) in dry $CH_3CN$ (20 ml) (carbethoxymethylene)triphenylphosphoran (5.59 g, 16.06 mmol) was added and the reaction was stirred at 40° C. o.n. The solvent was evaporated and the obtained crude was purified by flash chromatography (Silica Cy/EtOAc from 9/1 to 0/1) to give the desired compound (3.01 g, 14.5 mmol, purity: 100% by UV a/a, recovery: 99%). MS (m/z) 208 (M+H$^+$).

Step 2: To a solution of (E)-ethyl 3-(6-methoxypyridin-3-yl)acrylate (3.01 g, 14.5 mmol) in dry toluene (30 ml) at −78° C., 1M DIBAL solution in toluene (31.9 ml) was added dropwise, and the reaction was stirred at this temperature for 3 hours. $Na_2SO_4 \times 10H_2O$ was added portionwise at −78° C., and the mixture was stirred at this temperature for 30 minutes then it was left to reach rt The mixture was stirred at rt for 1 h. The solid was filtered (washing with DCM) and the solution was concentrated. The obtained crude was purified by flash chromatography (Silica, Cy/EtOAc from 8/2 to 4/6) to give (E)-3-(6-methoxypyridin-3-yl)prop-2-en-1-ol (2.09 g, 12.65 mmol, purity >99% by UV a/a, recovery: 87%). MS (m/z) 166 (M+H$^+$).

Step 3: To a solution of (E)-3-(6-methoxypyridin-3-yl)prop-2-en-1-ol (2.09 g, 12.7 mmol) in dry DCM (25 ml), $MnO_2$ (16.55 g, 190.5 mmol) was added, and the reaction was stirred at rt for 3 h. The solid was removed by filtration (washing with DCM), and the filtrate was evaporated to dryness to give (E)-3-(6-methoxypyridin-3-yl)acrylaldehyde (1.9 g, 11.64 mmol, purity: >99% by UV a/a, recovery: 92%). MS (m/z) 164 (M+H$^+$).

The following intermediates used for the preparation of titled example compounds were synthesized using methods analogous to the ones described above.

-continued

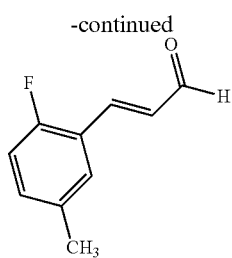

Preparation 13

(E)-4-(3-oxoprop-1-en-1-yl)benzonitrile

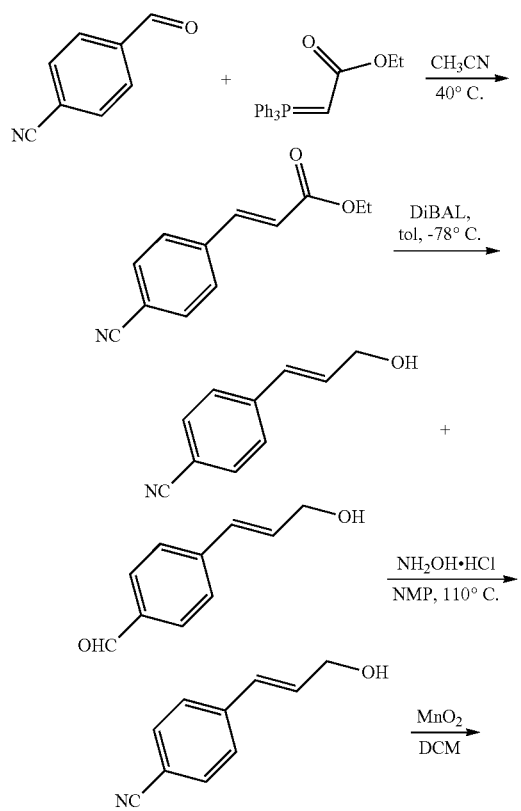

Step 1: To 4-formylbenzonitrile (1 g, 7.63 mmol) in dry CH₃CN (8 ml) (carbethoxymethylene)triphenylphosphorane (2.9 g, 8.39 mmol) was added and the reaction was stirred at 40° C. overnight. The reaction was diluted with EtOAc and washed with a solution of NaHCO₃ 5%, the organic solvent was removed under vacuum to afford 3.9 g of crude material. The crude was purified by Biotage System Flash (SNAP100, from Cy 100% to Cy/EtOAc 7/3), fractions were collected to give 1.64 g (107%) of the desired compound. MS (m/z) 202 (M+H⁺).

Step 2: Ethyl (2E)-3-(4-cyanophenyl)prop-2-enoate (1.6 g, 7.95 mmol) was dissolved in 15 ml of dry toluene, and the solution was cooled to −78° C. DIBAL solution (1M in toluene, 22.3 ml, 22.26 mmol) was added dropwise over 40 minutes, and the reaction was stirred at this temperature for 1.5 h. The reaction was warmed to −30/20° C. and quenched with EtOAc (5 ml) and satured aqueous sodium potassium tartrate (Rochelle salt) (30 ml), followed by vigorous stirring for 30 minutes. The aqueous was extracted with EtOAc and the combined organics layer were washed with brine, dried and concentrated under vacuum to give 612 mg as a mixture of alcohol and the corresponding aldehyde. The mixture was purified by flash chromatography (Silica, Cy/EtOAc from 9/1 to 0/1) to give product as a mixture (419 mg, 2.63 mmol, 33%). MS (m/z) 163 (aldehyde) and 160 (nitrile) (M+H⁺).

Step 3: To a solution of the above mixture (419 mg, 2.6 mmol) in NMP (6 ml) hydroxylamine hydrochloride (269 mg, 3.9 mmol) was added. The mixture was stirred at 100° C. for 1 h then at 110° C. for 5 h. The mixture was diluted with EtOAc and washed with water and brine. The organic layer was dried (Na₂SO₄) and evaporated. The crude material was purified by flash chromatography (Silica, Cy/EtOAc from 8/2 to 2/8) to give the desired alcohol (238 mg, 1.5 mmol, purity: 73% by UV a/a, recovery: 57%). MS (m/z) 160 (M+H⁺).

Step 4: To a solution of alcohol (238 mg, 1.5 mmol) in dry DCM (10 mL), MnO₂ (1.95 g, 22.5 mmol) was added, and the reaction was stirred at room temperature for 5 h. The solid was removed by filtration (washing with DCM), and the filtrate was evaporated to dryness to give the title compound (193 mg, purity: 92% by UV a/a, recovery 82%).

The following intermediate used for the preparation of titled example compounds was synthesized using methods analogous to the ones described above.

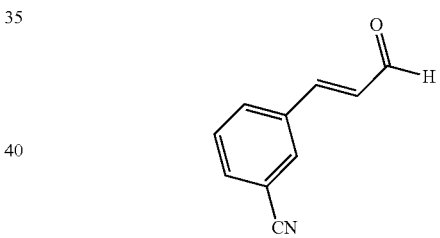

Preparation 14

(E)-3-(4-chlorophenyl)acrylaldehyde

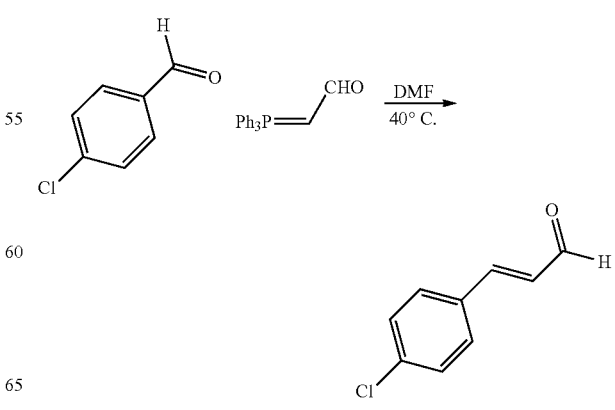

Triphenylphosphornylidene acetaldehyde (1.08 g, 3.55 mmol) were dissolved in 2.5 ml of DMF dry and 4-chlorobenzaldehyde (0.5 g, 3.55 mmol) was added and the reaction was stirred at rt overnight. UPLC showed incomplete reaction, and the reaction mixture was heated at 40° C. for 8 h and then left at rt overnight. Although still incomplete by UPLC, the reaction was diluted with EtOAc and washed into a cold solution of NaHCO$_3$ at 5% (25 ml×4). The organic phase was dried over Na$_2$SO$_4$, filtered and concentrated under reduced pressure. The crude material (1.2 g) was used in the next step without other further purification. MS (m/z) 167 (M+H$^+$).

The following intermediates used for the preparation of titled example compounds were synthesized using methods analogous to the ones described above. THF, 2-MeTHF and toluene may be used instead of DMF. Temperature may be increased until 80° C.

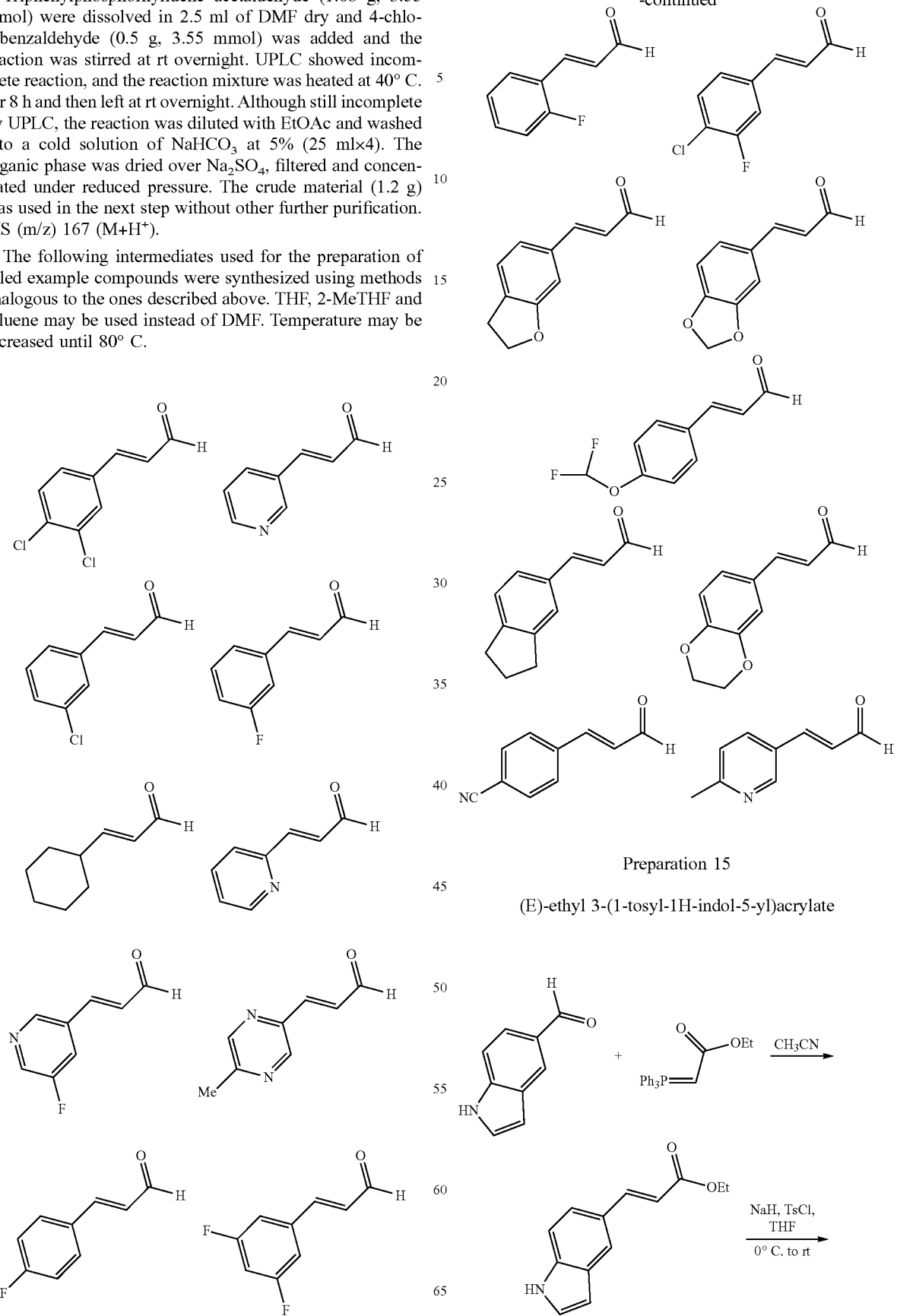

Preparation 15

(E)-ethyl 3-(1-tosyl-1H-indol-5-yl)acrylate

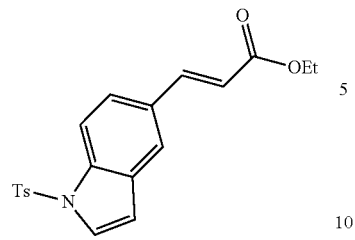

Step 1: To a solution of 1H-indole-5-carbaldehyde (1.5 g, 8.96 mmol) in dry CH₃CN (15 ml) (carbethoxymethylene)triphenylphosphorane (3.43 g, 9.85 mmol) was added, and the reaction was stirred at 40° C. o.n. The reaction was diluted with EtOAc and washed with a solution of NaHCO₃ (5%). The phases were separated, the organic layer was concentrated under vacuum. The crude material was purified by flash chromatography (Silica, Cy/EtOAc from 95/5 to 7/3) to give the desired ester (2.16 g, 10.03 mmol, purity: 95% mixture of isomers, recovery: 97%) as a white solid. MS (m/z) 216 (M+H$^+$).

Step 2: To a suspension of NaH (481 mg, 12.04 mmol) in THF (30 ml), ester (2.16 g, 10.03 mmol) was added at 0° C. After being stirred at 0° C. for 30 min, 4-methylbenzene-1-sulfonylchloride (2.87 g, 15.05 mmol) was added portion wise to the mixture and it was stirred at rt for 5 h. UPLC showed the presence of product and starting material. The reaction mixture was cooled to 0° C. and further NaH (80 mg) was added. The reaction mixture was stirred for 30 min then 4-methylbenzene-1-sulfonylchloride (382 mg) was added. The reaction mixture was stirred at rt o.n. The day after UPLC check still showed presence of starting material. The reaction was cooled to 0° C. and NaH (80 mg) was added then it was stirred at rt for 2 h. NH₄Cl sat. solution and brine was added to the mixture and the aqueous phase was extracted with EtOAc. The combined organic layers were dried over Na₂SO₄ and concentrated in vacuo. The obtained crude was purified by flash chromatography (Silica, Cy/EtOAc from 1/0 to 8/2) to give the title compound (3.279 g, 8.88 mmol, purity 97% by UV a/a, recovery: 88%) as a pink foam. MS (m/z) 370 (M+H$^+$).

The following intermediates used for the preparation of titled example compounds were synthesized using methods analogous to the ones described above.

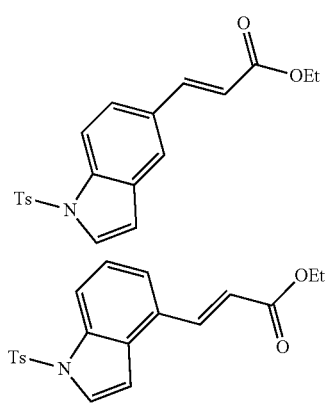

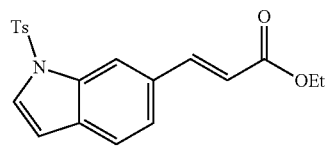

Preparation 16

(E)-ethyl 3-(1-tosyl-1H-indol-6-yl)acrylate

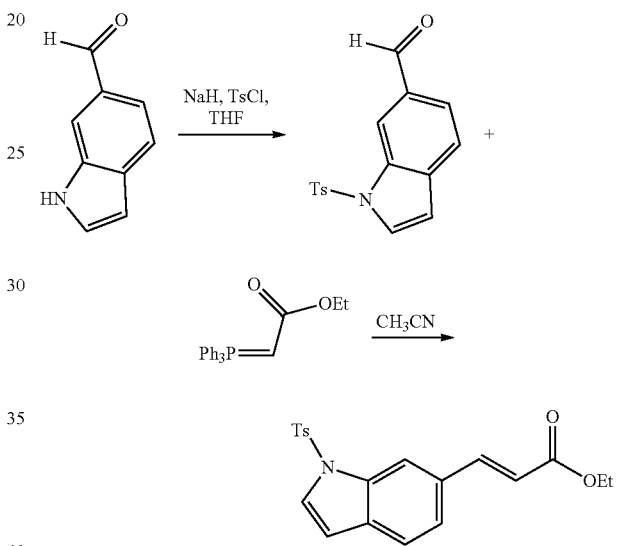

Step 1: To a suspension of NaH (620 mg, 15.5 mmol) in THF (25 ml) was added 1H-indole-6-carbaldehyde (1.5 g, 10.33 mmol) at rt. After being stirred at rt for 20 min, 4-methylbenzene-1-sulfonylchloride (2.95 g, 15.5 mmol) was added to the mixture and left stirring at rt overnight. UPLC showed the presence of product and starting material. NH₄Cl sat solution was added to the mixture and the aqueous phase was extracted with EtOAc. The combined organic layers were dried over sodium sulphate and concentrated in vacuo to give 5.47 g of crude product which was purified by Biotage Sp1 System (SNAP340, from Cy 100% to Cy/EtOAc 8/2), to give 1.48 g (48%) of tosylated aldehyde. MS (m/z) 300 (M+H$^+$).

Step 2: To 1-[(4-methylbenzene)sulfonyl]-1H-indole-6-carbaldehyde (1.46 g, 4.91 mmol) in dry CH₃CN (16 ml) (carbethoxymethylene)triphenylphosphorane (1.88 g, 5.4 mmol) was added and the reaction was stirred at 40° C. for 2 hours. The reaction was diluted with EtOAc and washed with a solution of NaHCO₃ (5%), the organic solvent was removed under vacuum to afford 2.8 g of crude material which was purified by Biotage Sp4 system (SNAP100, from Cy 100% to Cy/EtOAc 8/2), to give 1.26 (69%) of the title compound. MS (m/z) 370 (M+H$^+$).

Preparation 17

(E)-3-(3-fluorophenyl)acrylaldehyde

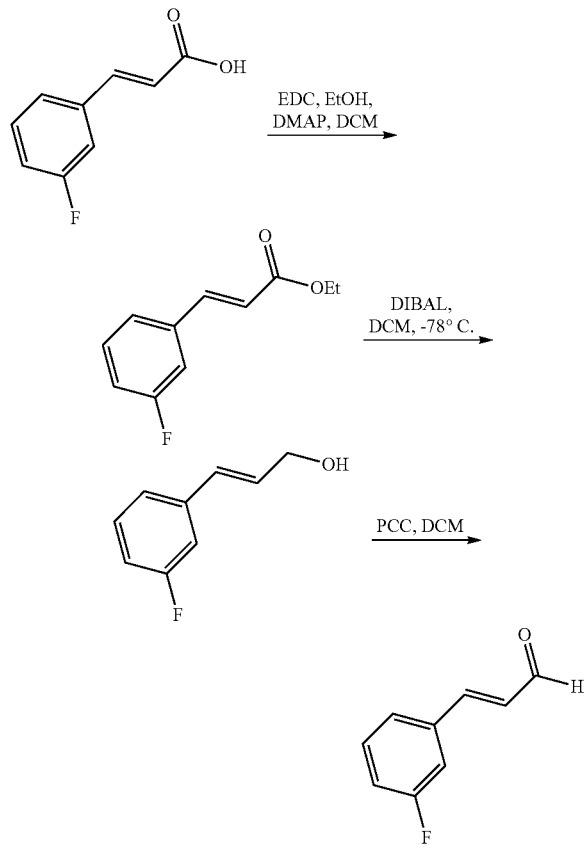

Step 1: To a solution of (E)-3-(3-fluorophenyl)acrylic acid (2.88 g, 17.33 mmol) in DCM (1 mL) was added EDC (3.49 g, 18.20 mmol) and DMAP (0.212 g, 1.733 mmol). The reaction was stirred for 15 minutes and then ethanol (10.12 mL, 173 mmol) was added and the reaction was stirred overnight. The reaction was then concentrated and taken up in DCM and washed with 1N HCl, water, saturated sodium bicarbonate and then brine. The organic layer was dried over Na$_2$SO$_4$, filtered and then concentrated to give 3.06 g of crude material. The sample is used for the next reaction without further purification. $^1$H NMR (DMSO-d$_6$) δ ppm: 7.60-7.71 (m, 1H), 7.55 (d, J=7.8 Hz, 1H), 7.45 (td, J=8.0, 6.1 Hz, 1H), 7.19-7.31 (m, 1H), 6.71 (d, J=16.2 Hz, 1H), 4.20 (q, J=7.1 Hz, 2H), 1.26 (t, J=7.1 Hz, 3H)

Step 2: A solution of (E)-ethyl 3-(3-fluorophenyl)acrylate (3.06 g, 15.76 mmol) in DCM (2 mL DCM/mmol ester) was treated slowly by dropwise addition of DIBAL-H (33.1 mL, 33.1 mmol) in DCM at −78° C. The resulting mixture was stirred for 2 hours at −78° C. and then quenched with 10% NaOH and allowed to warm up to ambient temperature over time. The reaction was stirred overnight to allow the NaOH to break up the residual DIBAL. The organic layer was washed with water, 1N HCl, and brine. The organic layer was then dried over MgSO$_4$, filtered, and then concentrated to give 1.81 g of crude material. The residue was used directly in the next reaction without further purification. $^1$H NMR (DMSO-d$_6$) δ: 7.36 (td, J=7.8, 6.3 Hz, 1H), 7.22-7.31 (m, 2H), 7.00-7.07 (m, 1H), 6.53-6.61 (m, 1H), 6.42-6.51 (m, 1H), 4.94 (t, J=5.6 Hz, 1H), 4.10-4.17 (m, 2H)

Step 3: To a solution of (E)-3-(3-fluorophenyl)prop-2-en-1-ol (1.81 g, 11.89 mmol) in DCM (24 mL) was added 8 grams of Celite followed by PCC (3.85 g, 17.84 mmol). The reaction was monitored by LC/Ms. After reaction was complete the mixture was filtered and concentrated. The brown oil was purified by Normal Phase purification 10% EtOAc and Hexanes to 60%. Pure fractions were collected and concentrated to provide 1.12 g of the title compound (63%). NMR is consistant with structure. 1H NMR (400 MHz, DMSO-d$_6$) δ ppm 9.69 (d, J=7.83 Hz, 1H) 7.74 (d, J=15.92 Hz, 1H) 7.67 (dt, J=10.23, 1.96 Hz, 1H) 7.55-7.64 (m, 1H) 7.51 (td, J=7.89, 5.94 Hz, 1H) 7.23-7.40 (m, 1H) 6.94 (dd, J=16.04, 7.71 Hz, 1H).

Preparation 18

5-phenyl-4,5-dihydro-1H-pyrazole

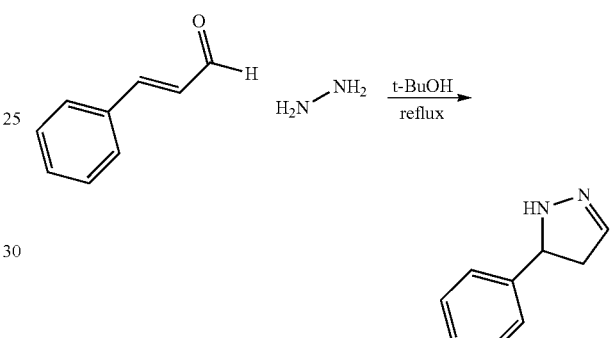

Hydrazine (6.84 mL, 190 mmol) was heated to reflux. A solution of cinnamaldehyde (10 g, 76 mmol) in tert-butanol (20 mL) was added dropwise and the mixture was refluxed overnight. The reaction mixture was concentrated under reduced pressure. The crude material was then diluted with DCM and washed with water. The combined organic layers were washed with water and then dried over Na$_2$SO$_4$, filtered and concentrated under reduced pressure to provide 5-phenyl-4,5-dihydro-1H-pyrazole (9.4 g, 64.3 mmol, 85% yield) of a yellow oil. The product was carried onto the next reaction without further purification. MS (m/z) 147 (M+H$^+$).

Preparation 19

5-phenyl-4,5-dihydro-1H-pyrazole

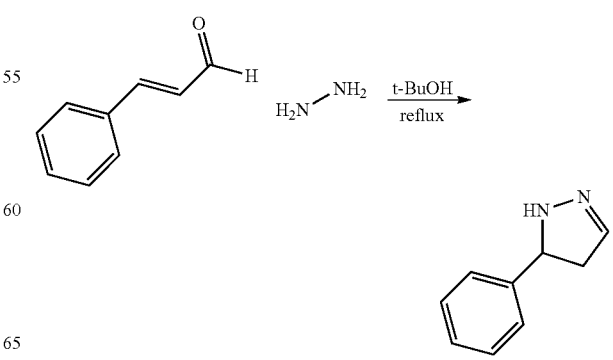

Hydrazine (6.84 mL, 190 mmol) was heated to reflux. A solution of cinnamaldehyde (10 g, 76 mmol) in tert-butanol (20 mL) was added dropwise and the mixture was refluxed overnight. The reaction mixture was concentrated under reduced pressure. The crude material was then diluted with DCM and washed with water. The combined organic layers were washed with water and then dried over $Na_2SO_4$, filtered and concentrated under reduced pressure to provide 5-phenyl-4,5-dihydro-1H-pyrazole (9.4 g, 64.3 mmol, 85% yield) of a yellow oil. The product was carried onto the next reaction without further purification. MS (m/z) 147 (M+H$^+$).

The following intermediates used for the preparation of titled example compounds were synthesized using methods analogous to the ones described above.

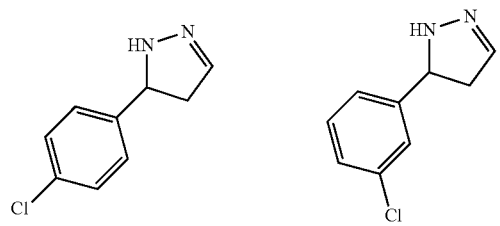 [SMILES: Clc1ccc(C2CC=NN2)cc1 ; Clc1cccc(C2CC=NN2)c1]

Preparation 20

3-(4,5-dihydro-1H-pyrazol-5-yl)-5-fluoropyridine

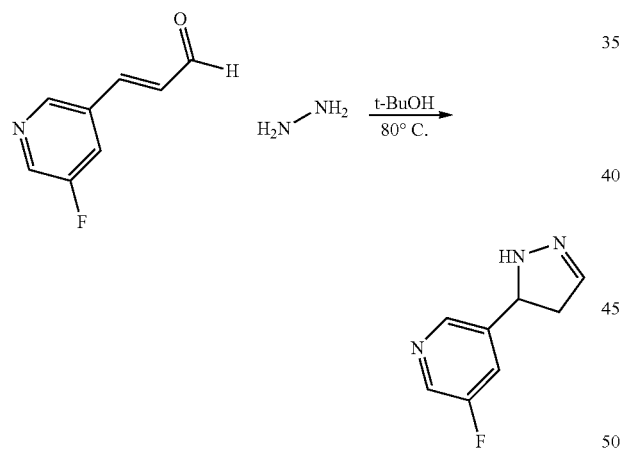

Hydrazine monohydrate (65% w/w in water, 2.46 mL, 33.1 mmol) was added to a solution of 3-(5-fluoropyridin-3-yl)prop-2-enal (1 g, 6.62 mmol) in tert-butanol (25 ml). The reaction solution was heated at 800 overnight then the solvent was removed under vacuum. The crude material was purified by flash chromatography (Silica gel; AcOEt 100% to AcOEt/MeOH 97/3) as eluant) to afford 3-(4,5-dihydro-1H-pyrazol-5-yl)-5-fluoropyridine as an orange oil (0.800 g, 73.2% recovery) as an orange oil. MS (m/z) 156 (M+H$^+$).

The following intermediates used for the preparation of titled example compounds were synthesized using methods analogous to the ones described above with reaction temperatures between 80-95° C. In some cases ethanol was substituted for tert-butanol. In some cases the crude reaction mixture was partitioned between an organic solvent, such as DCM, and water; the organic phase dried and concentrated and the isolated crude product used in the next step without any further purification.

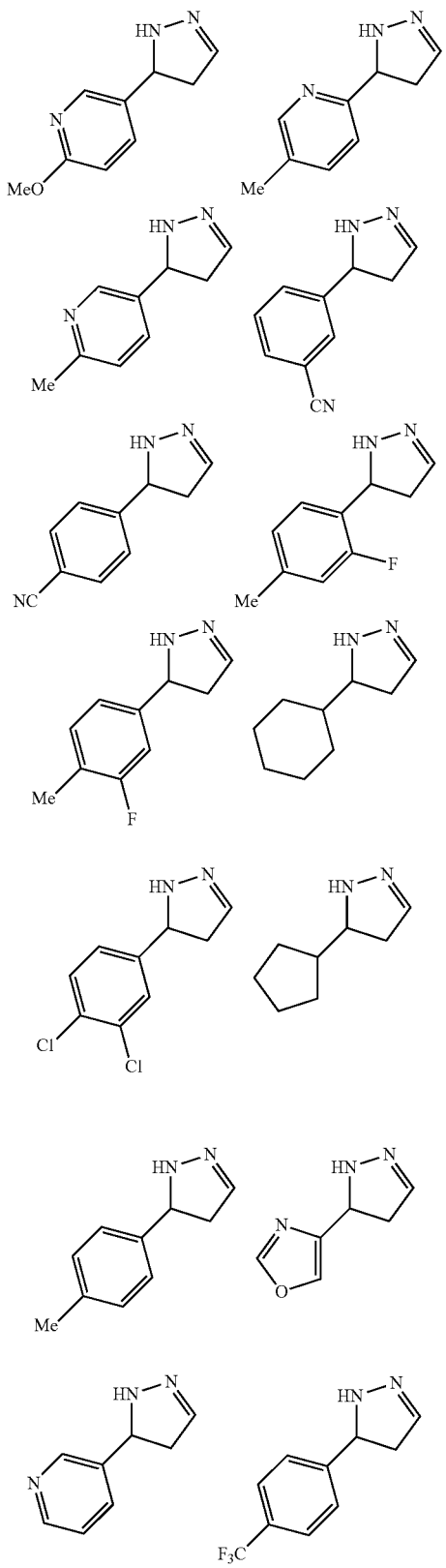

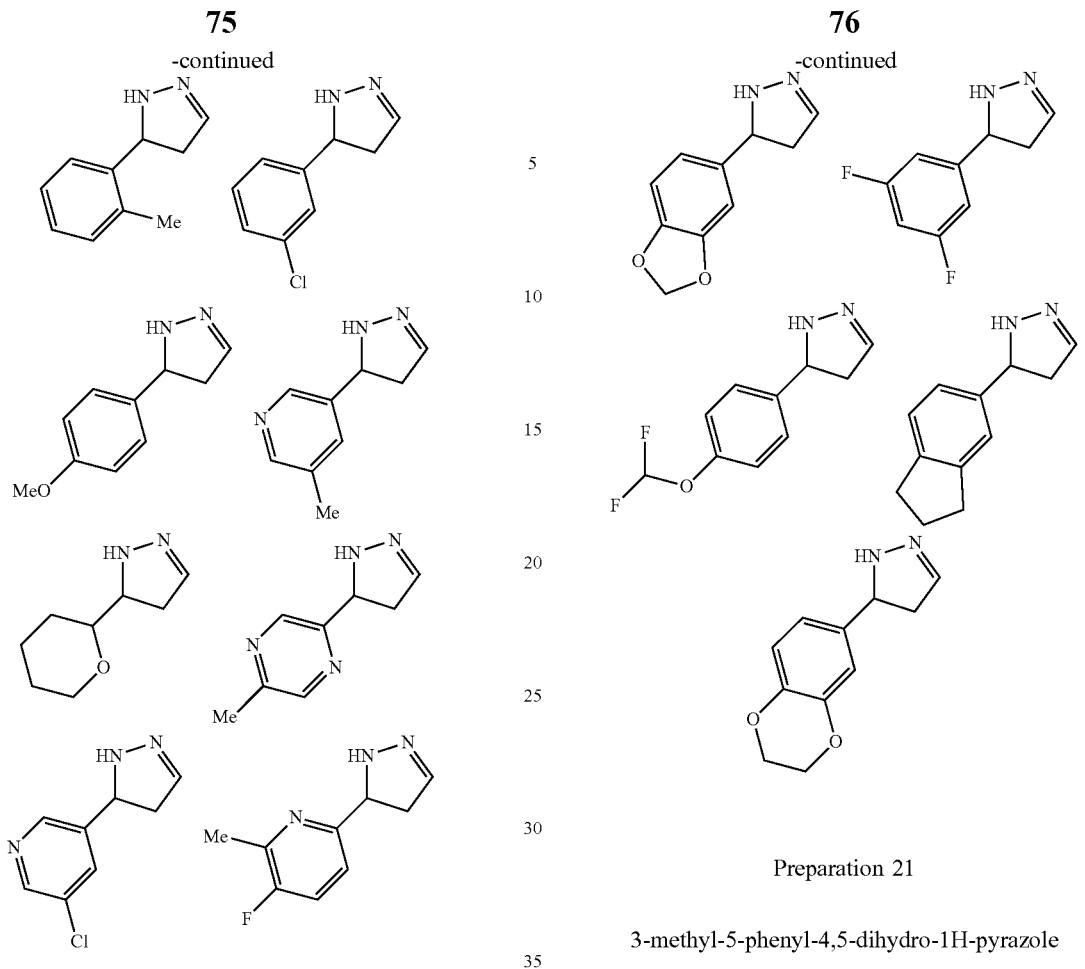

Preparation 21

3-methyl-5-phenyl-4,5-dihydro-1H-pyrazole

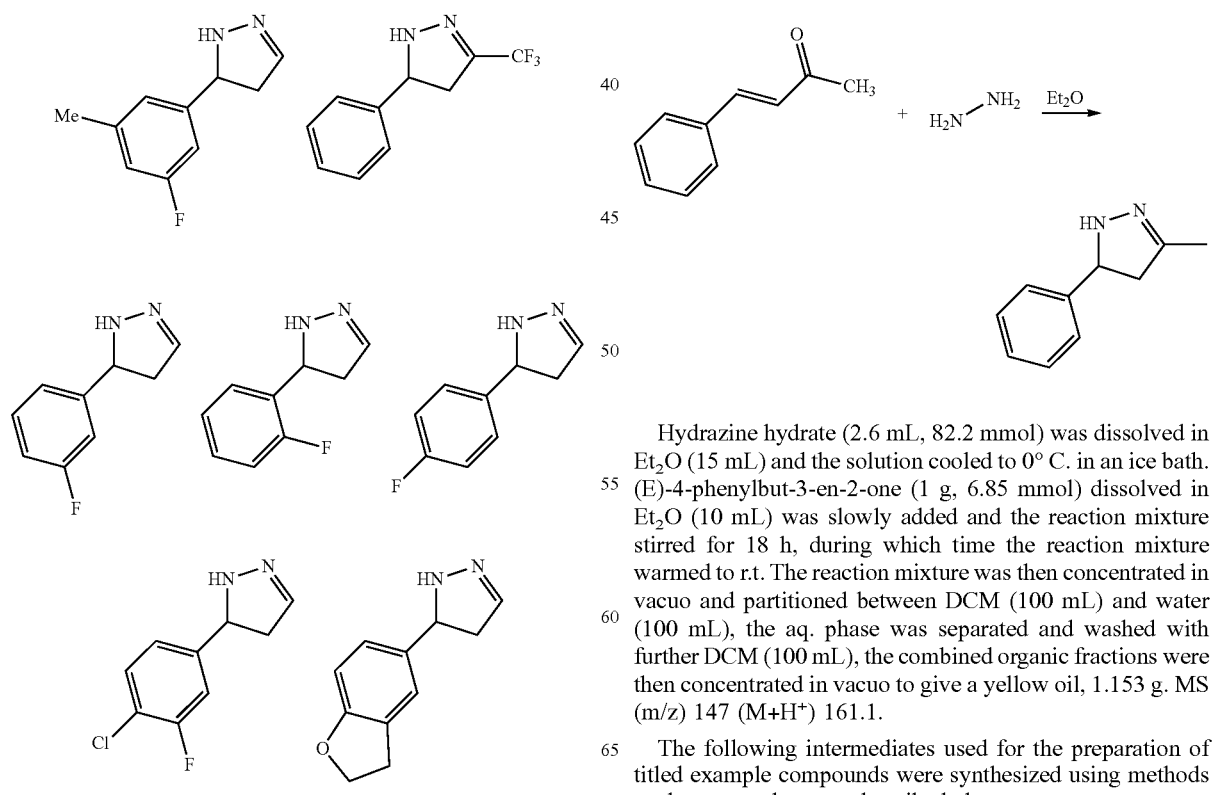

Hydrazine hydrate (2.6 mL, 82.2 mmol) was dissolved in Et$_2$O (15 mL) and the solution cooled to 0° C. in an ice bath. (E)-4-phenylbut-3-en-2-one (1 g, 6.85 mmol) dissolved in Et$_2$O (10 mL) was slowly added and the reaction mixture stirred for 18 h, during which time the reaction mixture warmed to r.t. The reaction mixture was then concentrated in vacuo and partitioned between DCM (100 mL) and water (100 mL), the aq. phase was separated and washed with further DCM (100 mL), the combined organic fractions were then concentrated in vacuo to give a yellow oil, 1.153 g. MS (m/z) 147 (M+H$^+$) 161.1.

The following intermediates used for the preparation of titled example compounds were synthesized using methods analogous to the ones described above.

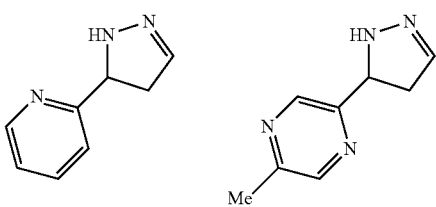 [SMILES: C1=NNC(c2ccccn2)C1 ; Cc1cnc(C2CC=NN2)cn1]

Example 1

(5-(5-fluoropyridin-3-yl)-4,5-dihydro-1H-pyrazol-1-yl)(1-(5-methylpyrimidin-2-yl)piperidin-4-yl)methanone

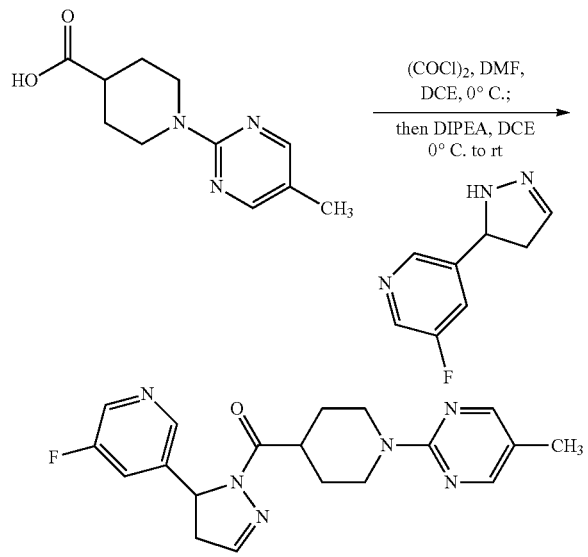

To a solution of oxalyl chloride in dry DCE (1 ml), one drop of DMF was added at 0° C. The mixture was stirred for 10 minutes, and a solution of 1-(5-methylpyrimidin-2-yl)piperidine-4-carboxylic acid (135 mg, 0.52 mmol) in dry DCE (2 ml) was added at 0° C. The mixture was stirred for 45 minutes then a solution of 3-(4,5-dihydro-1H-pyrazol-5-yl)-5-fluoropyridine (86 mg, 0.52 mmol) and DIPEA (0.27 ml, 1.56 mmol) in dry DCE (2 ml) were added dropwise at 0° C. The mixture was left to reach rt and stirred at this temperature for 30 minutes. The solution was concentrated and submitted to for reverse phase purification (2×) to give the title compound (21 mg, 0.057 mmol, purity: 99% by UV a/a, recovery: 11%). $^1$H NMR (DMSO-$d_6$) δ ppm 8.47 (d, J=2.8 Hz, 1H), 8.28 (t, J=1.6 Hz, 1H), 8.20 (d, J=0.8 Hz, 2H), 7.46 (dt, J=9.6, 2.4 Hz, 1H), 7.28 (t, J=1.6 Hz, 1H), 5.40 (dd, J=12.0, 5.2 Hz, 1H), 4.59 (dd, J=13.1, 2.8 Hz, 2H), 3.52 (ddd, J=19.0, 12.1, 1.5 Hz, 1H), 3.29-3.39 (m, 1H), 2.88-2.98 (m, 2H), 2.84 (ddd, J=18.9, 5.3, 1.8 Hz, 1H), 2.07 (s, 3H), 1.69-1.88 (m, 2H), 1.31-1.52 (m, 2H). MS (m/z) 369 (M+H$^+$).

The following intermediate was synthetized in an analogous manner:

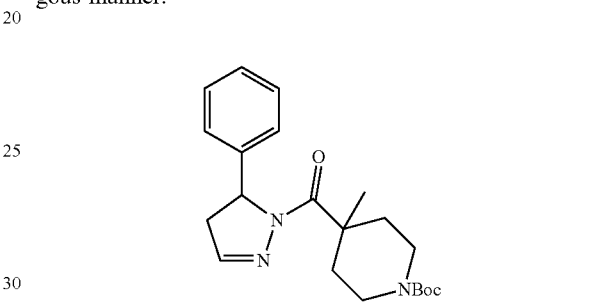

The following compounds were synthesized in an analogous manner. Compounds were isolated as racemates. Chiral HPLC separation to isolate the single active enantiomer was carried out on selected examples, as indicated by the structure. The absolute configuration of the active enantiomer was assigned as (S) in each case, based on the assignment of (S)-2,2-dimethyl-1-(5-phenyl-4,5-dihydro-1H-pyrazol-1-yl) propan-1-one as the active enantiomer as described in Example 13. Prep Method: Chiralcel OD-H column 30 mm×25 cm; 30% EtOH/Heptane, flow=30 mL/min, wavelength 215 nm.

| Ex | Name | Structure | $^1$H NMR | LC retention time (min) | MS (M + H)$^+$ |
|---|---|---|---|---|---|
| 2 | (1-(5-fluoropyridin-2-yl)-piperidin-4-yl)(5-phenyl-4,5-dihydro-1H-pyrazol-1-yl)methanone | 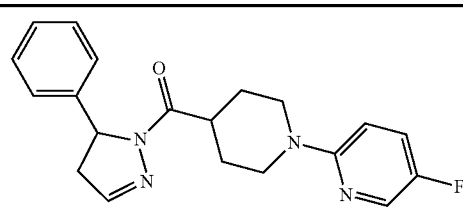 | $^1$H NMR (400 MHz, DMSO-d6) δ ppm 8.07 (d, J = 3.3 Hz, 1H), 7.47 (ddd, J = 9.2, 8.3, 3.2 Hz, 1H), 7.28-7.36 (m, 2H), 7.19-7.27 (m, 2H), 7.07-7.14 (m, 2H), 6.87 (dd, J = 9.3, 3.3 Hz, 1H), 5.31 (dd, J = 11.9, 4.8 Hz, 1H), 4.22 (d, J = 12.9 Hz, 2H), 3.49 (ddd, J = 18.8, 11.9, 1.6 Hz, 1H), 3.26-3.36 (m, 1H), 2.81-2.94 (m, 2H, 2.67 (ddd, J = 18.8, 4.7, 1.8 Hz, 1H, 1.68-1.90 (m, 2H), 1.41-1.62 (m, 2H) | | 353 |
| 3 | (S)-(1-(5-fluoropyridin-2-yl)piperidin-4-yl)(5-phenyl-4,5-dihydro-1H-pyrazol-1-yl)methanone | 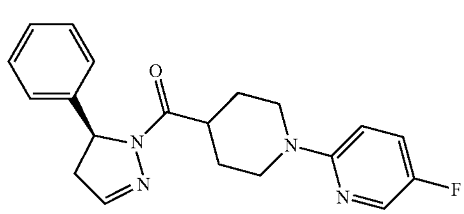 [SMILES: O=C(C1CCN(c2ccc(F)cn2)CC1)N1N=CC[C@H]1c1ccccc1] | $^1$H NMR (400 MHz, DMSO-d6) d ppm 8.07 (d, J = 3.2 Hz, 1H), 7.47 (ddd, J = 9.3, 8.3, 3.2 Hz, 1H), 7.32 (m, 2H), 7.23 (m, 2H), 7.11 (m, 2H), 6.87 (dd, J = 9.3, 3.4 Hz, 1H), 5.31 (dd, J = 12.0, 4.6 Hz, 1H), 4.22 (m, 2H), 3.49 (m, 1H), 3.32 (m, 1H), 2.88 (m, 2H), 2.67 (ddd, J = 18.8, 4.6, 1.7 Hz, 1H), 1.87 (m, 1H), 1.74 (m, 1H), 1.53 | | 353 |

-continued

| Ex | Name | Structure | ¹H NMR | LC retention time (min) | MS (M + H)⁺ |
|---|---|---|---|---|---|
| | | | (m, 2H). LC Method 3: 1.00 min | | |
| 4 | (1-(5-methylpyridin-2-yl)piperidin-4-yl)(5-phenyl-4,5-dihydro-1H-pyrazol-1-yl)methanone | 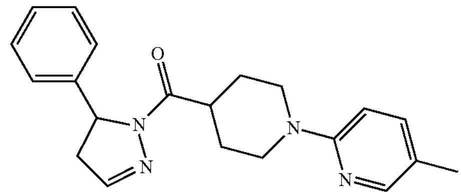 [SMILES: Cc1ccc(N2CCC(C(=O)N3N=CCC3c3ccccc3)CC2)nc1] | ¹H NMR (400 MHz, DMSO-d6) δ ppm 7.90-7.94 (m, 1H), 7.28-7.37 (m, 3H), 7.20-7.26 (m, 2H), 7.07-7.13 (m, 2H), 6.75 (d, J = 8.8 Hz, 1H), 5.30 (dd, J = 12.0, 4.7 Hz, 1H), 4.24 (d, J = 12.9 Hz, 2H), 3.49 (ddd, J = 18.8, 11.9, 1.6 Hz, 1H), 3.26-3.36 (m, 1H), 2.76-2.89 (m, 2H), 2.67 (ddd, J = 18.9, 4.5, 1.8 Hz, 1H), 2.12 (s, 3H), 1.63-1.88 (m, 2H), 1.41-1.60 (m, 2H) | | 349 |
| 5 | (1-5-methylpyrimidin-2-yl)piperidin-4-yl)(5-phenyl-4,5-dihydro-1H-pyrazol-1-yl)methanone | 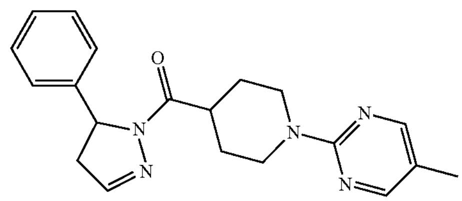 [SMILES: Cc1cnc(N2CCC(C(=O)N3N=CCC3c3ccccc3)CC2)nc1] | ¹H NMR (400 MHz, DMSO-d6) δ ppm 8.20 (d, J = 0.8 Hz, 2H), 7.28-7.35 (m, 2H), 7.20-7.26 (m, 2H), 7.07-7.13 (m, 2H), 5.30 (dd, J = 11.9, 4.5 Hz, 1H), 4.60 (d, J = 12.4 Hz, 2H), 3.49 (ddd, J = 18.9, 11.9, 1.5 Hz, 1H), 3.30-3.41 (m, 1H), 2.94 (tdd, J = 12.7, 7.6, 2.7 Hz, 2H), 2.67 (ddd, J = 18.9, 4.5, 1.8 Hz, 1H), 2.06 (s, 3H), 1.67-1.89 (m, 2H), 1.34-1.54 (m, 2H) | | 350 |
| 6 | (1-(5-fluoropyrimidin-2-yl)piperidin-4-yl)(5-phenyl-4,5-dihydro-1H-pyrazol-1-yl)methanone | 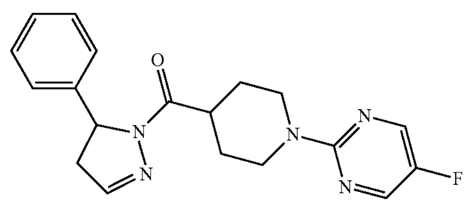 [SMILES: O=C(C1CCN(c2ncc(F)cn2)CC1)N1N=CCC1c1ccccc1] | ¹H NMR (400 MHz, DMSO-d6) δ ppm 8.43 (d, J = 0.8 Hz, 2H), 7.27-7.36 (m, 2H), 7.19-7.26 (m, 2H), 7.06-7.14 (m, 2H), 5.31 (dd, J = 11.7, 4.7 Hz, 1H), 4.56 (d, J = 12.6 Hz, 2H), 3.49 (ddd, J = 18.9, 11.9, 1.5 Hz, 1H), 3.29-3.42 (m, 1H), 3.00 (tdd, J = 12.7, 7.7, 2.8 Hz, 2H), 2.67 (ddd, J = 18.8, 4.7, 1.8 Hz, 1H), 1.88 (d, J = 11.1 Hz, 1H), 1.74 (d, J = 11.4 Hz, 1H), 1.35-1.56 (m, 2H) | | 354 |
| 7 | (S)-(1-(5-fluoropyrimidin-2-yl)piperidin-4-yl)(5-phenyl-4,5-dihydro-1H-pyrazol-1-yl)methanone | 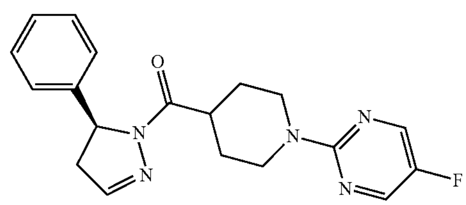 [SMILES: O=C(C1CCN(c2ncc(F)cn2)CC1)N1N=CC[C@H]1c1ccccc1] | ¹H NMR (400 MHz, DMSO-d₆) δ = 8.42 (d, J = 1.0 Hz, 1H), 7.34-7.28 (m, 2H), 7.25-7.20 (m, 2H), 7.12-7.08 (m, 2H), 5.30 (dd, J = 12.0, 4.6 Hz, 1H), 4.59-4.52 (m, 2H), 3.49 (ddd, J = 18.9, 11.9, 1.5 Hz, 1H), 3.36 (tt, J = 11.5, 3.8 Hz, 1H), 3.05-2.95 (m, 2H), 2.67 (ddd, J = 19.0, 4.6, 1.8 Hz, 1H), 1.91-1.70 (m, 2H), 1.56-1.37 (m, 2H). LC Method 3: 1.15 min | | 354 |
| 8 | (1-(5-fluoropyrimidin-2-yl)piperidin-4-yl)(5-phenyl-3-(trifluoromethyl)-4,5-dihydro-1H-pyrazol-1-yl)methanone | 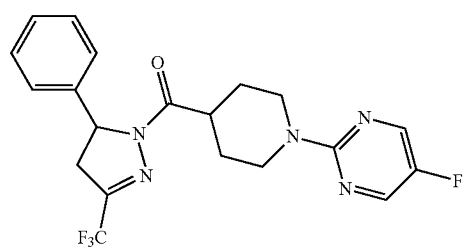 [SMILES: O=C(C1CCN(c2ncc(F)cn2)CC1)N1N=C(C(F)(F)F)CC1c1ccccc1] | 1H NMR (400 MHz, DMSO-d6) d ppm 8.34-8.50 (m, 2H) 7.33-7.43 (m, 2H) 7.24-7.32 (m, 1H) 7.12-7.24 (m, 2H) 5.63 (dd, J = 12.3, 5.3 Hz, 1H) 4.45-4.63 (m, 2H) 3.82 (ddd, J = 18.7, 12.5, 1.8 Hz, 1H) 3.32-3.45 (m, 1H) 3.01-3.12 (m, 2H) 2.85-2.99 (m, 1H) 1.87 d, J = 11.1 Hz, 1H) 1.77 (d, J = 11.3 Hz, 1H), 1.31-1.61 (m, 2H) LC Method 2: 1.34 min | | 422 |
| 9 | (5-(5-fluoropyridin-3-yl)-4,5-dihydro-1H-pyrazol-1-yl)(1-(5-fluoropyrimidin-2-yl)(piperidin-4-yl)-methanone | 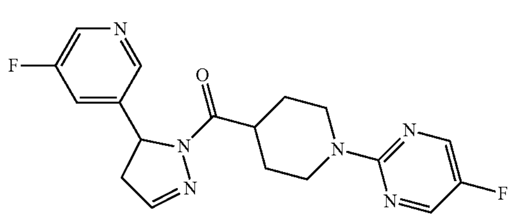 [SMILES: O=C(C1CCN(c2ncc(F)cn2)CC1)N1N=CCC1c1cncc(F)c1] | ¹H NMR (400 MHz, DMSO-d6) δ ppm 8.47 (d, J = 2.5 Hz, 1H), 8.43 (d, J = 0.8 Hz, 2H), 8.28 (t, J = 1.8 Hz, 1H), 7.47 (dt, J = 9.9, 2.3 Hz, 1H), 7.28 (t, J = 1.6 Hz, 1H), 5.40 (dd, J = 12.1, 5.3 Hz, 1H), 4.56 (d, J = 10.6 Hz, 2H), 3.52 (ddd, J = 18.9, 12.1, 1.5 Hz, 1H), 3.29-3.40 (m, 1H), 2.93-3.05 (m, 2H), 2.84 (ddd, J = 19.1, 5.2, 1.8 Hz, 1H), 1.71-1.91 (m, 2H), | | 373 |

| Ex | Name | Structure | $^1$H NMR LC retention time (min) | MS (M + H)$^+$ |
|---|---|---|---|---|
| | | | 1.34-1.54 (m, 2H) | |
| 10 | (S)-(5-(5-fluoropyridin-3-yl)-4,5-dihydro-1H-pyrazol-1-yl)(1-(5-fluoro-pyrimidin-2-yl)piperidin-4-yl)methanone | 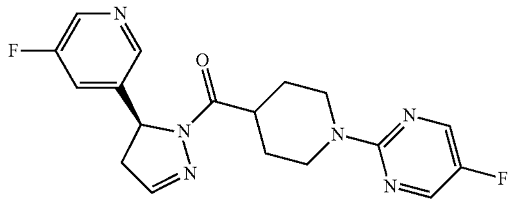 [SMILES: O=C(C1CCN(c2ncc(F)cn2)CC1)N1N=CC[C@H]1c1cncc(F)c1] | $^1$H NMR (400 MHz, DMSO-d6) δ ppm 8.47 (d, J = 2.5 Hz, 1H), 8.43 (s, 2H), 8.29 (s, 1H), 7.47 (d, J = 9.7 Hz, 1H), 7.29 (s, 1H), 5.41 (dd, J = 11.9, 5.0 Hz, 1H), 4.56 (d, J = 12.1 Hz, 2H), 3.52 (dd, J = 18.8, 12.1 Hz, 1H), 3.35 (m, 1H), 2.99 (m, 2H), 2.84 (dd, J = 19.0, 4.2 Hz, 1H), 1.87 (d, J = 12.1 Hz, 1H), 1.76 (d, J = 12.1 Hz, 1H), 1.45 (m, 2H) LC Method 3: 0.94 min | 373 |
| 11 | (5-(5-fluoropyridin-3-yl)-4,5-dihydro-1H-pyrazol-1-yl)(1-(pyrimidin-2-yl)-piperidin-4-yl)methanone | 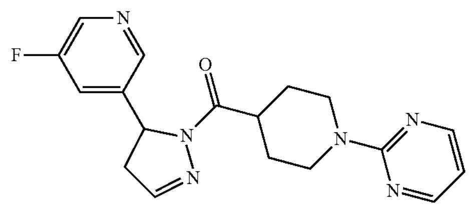 [SMILES: O=C(C1CCN(c2ncccn2)CC1)N1N=CCC1c1cncc(F)c1] | $^1$H NMR (400 MHz, DMSO-d6) δ ppm 8.47 (d, J = 2.5 Hz, 1H), 8.33 (d, J = 4.8 Hz, 2H), 8.28 (s, 1H), 7.46 (dt, J = 9.7, 2.2 Hz, 1H), 7.28 (s, 1H), 6.59 (t, J = 4.8 Hz, 1H), 5.40 (dd, J = 12.0, 5.3 Hz, 1H), 4.65 (d, J = 12.0 Hz, 2H), 3.51 (ddd, J = 19.1, 12.0, 1.5 Hz, 1H), 3.28-3.42 (m, 1H), 2.91-3.03 (m, 2H), 2.83 (ddd, J = 19.0, 5.2, 1.6 Hz, 1H), 1.70-1.92 (m, 2H), 1.31-1.55 (m, 2H) | 355 |
| 12 | 1-(4-(5-(benzo[d][1,3]-dioxol-5-yl)-4,5-dihydro-1H-pyrazole-1-carbonyl)-piperidin-1-yl)ethanone | 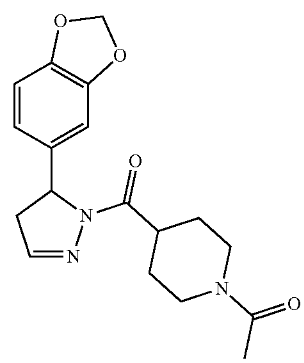 [SMILES: CC(=O)N1CCC(C(=O)N2N=CCC2c2ccc3c(c2)OCO3)CC1] | $^1$H NMR (400 MHz, DMSO-d6) δ ppm 7.21 (s, 1H), 6.84 (d, J = 8 Hz, 1H), 6.63 (m, 1H), 6.59 (m, 1H), 5.98 (s, 2H), 5.22 (dd, J = 12, 4.6 Hz, 1H), 4.35 (m, 1H), 3.82 (d, J = 13.5 Hz, 1H), 3.43 (dd, J = 18.5, 11.9 Hz, 1H), 3.27 (m, 1H), 3.09 (m, 1H), 2.63 (m, 2H), 1.98 (s, 3H), 1.80 (m, 1H), 1.69 (m, 1H), 1.55-1.25 (m, 2H) LC Method 1: 1.85 min | 344 |

Example 13

(S)-2,2-dimethyl-1-(5-phenyl-4,5-dihydro-1H-pyrazol-1-yl)propan-1-one

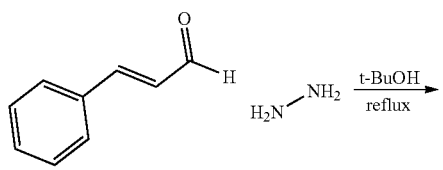

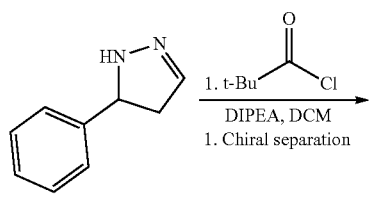

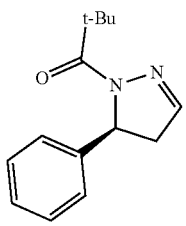

Step 1: Hydrazine (6.84 mL, 190 mmol) was heated to reflux. A solution of cinnamaldehyde (10 g, 76 mmol) in t-BuOH (20 mL) was added dropwise and the mixture was refluxed overnight. The reaction mixture was concentrated under reduced pressure. The crude material was then diluted with DCM and washed with water. The combined organic layers were washed with water and then dried over Na$_2$SO$_4$, filtered and concentrated under reduced pressure to provide 5-phenyl-4,5-dihydro-1H-pyrazole (9.4 g, 64.3 mmol, 85% yield) of a yellow oil. The product was carried onto the next reaction without further purification. MS (m/z) 147 (M+H$^+$).

Step 2: To a solution of 5-phenyl-4,5-dihydro-1H-pyrazole (150 mg, 1.026 mmol) in DCM (3 mL) was added DIPEA (0.376 mL, 2.155 mmol) followed by pivaloyl chloride (0.153 mL, 1.129 mmol). The reaction was very exothermic. After 15 minutes LC/MS was taken and showed it was complete. Reaction was concentrated and then taken up in DMSO and purified by prep HPLC to provide pure racemate. ¹H NMR (400 MHz, DMSO-d₆) δ ppm 1.25 (s, 9H), 2.55 (ddd, J=18.7, 4.6, 1.8 Hz, 1H), 3.37 (ddd, J=18.8, 11.9, 1.6 Hz, 1H), 5.31 (dd, J=11.9, 4.6 Hz, 1H), 7.05-7.12 (m, 2H), 7.18 (t, J=1.6 Hz, 1H), 7.20-7.25 (m, 1H), 7.28-7.34 (m, 2H). MS (m/z) 231 (M+H⁺).

The enantiomers were separated via chiral chromatography on reverse phase HPLC (IC column, 10:90 EtOH:Heptane) to provide 75 mg (30%) of (S)-2,2-dimethyl-1-(5-phenyl-4,5-dihydro-1H-pyrazol-1-yl)propan-1-one. The absolute configurations of the (R) and (S) enantiomers were determined by ab initio VCD analysis. MS (m/z) 231 (M+H⁺). ¹H NMR (DMSO-d₆) δ ppm: 7.28-7.36 (m, 1H), 7.16-7.27 (m, 1H), 7.04-7.12 (m, 1H), 5.32 (dd, J=11.9, 4.5 Hz, 1H), 3.38 (ddd, J=18.9, 11.9, 1.5 Hz, 1H), 2.56 (ddd, J=18.8, 4.5, 1.8 Hz, 1H), 1.26 (s, 9H).

The following compounds were synthesized in an analogous manner using t-BuOH or EtOH as solvent in step 1 and DCM or DMSO as solvent in step 2 along with a DIPEA or TEA as the amine base. Compounds were isolated as racemates. Chiral HPLC separation, as in the above example, to isolate the single active enantiomer was carried out on selected examples, as indicated by the structure. The absolute configuration of the active enantiomer was assigned as (S) in each case, based on the assignment of (S)-2,2-dimethyl-1-(5-phenyl-4,5-dihydro-1H-pyrazol-1-yl)propan-1-one as the active enantiomer as described easier. Polymer bound DIPEA was used in example 68 (see table).

| Ex | Name | Structure | ¹H NMR LC retention time (min) | MS (M + H)⁺ |
|---|---|---|---|---|
| 14 | 1-(5-(5-fluoro-pyridin-3-yl)-4,5-dihydro-1H-pyrazol-1-yl)-2,2-dimethyl-propan-1-one | 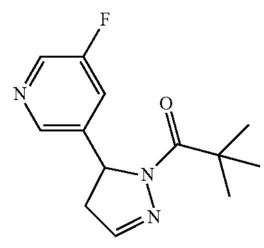 [SMILES: CC(C)(C)C(=O)N1N=CCC1c1cncc(F)c1] | ¹H NMR (400 MHz, DMSO-d6) δ ppm 8.47 (d, J = 2.8 Hz, 1H), 8.25 (t, J = 1.6 Hz, 1H), 7.40 (dt, J = 9.7, 2.2 Hz, 1H), 7.24 (t, J = 1.6 Hz, 1H), 5.41 (dd, J = 12.1, 5.1 Hz, 1H), 3.26-3.47 (m, 1H), 2.73 (ddd, J = 18.9, 5.1, 1.8 Hz, 1H), 1.25 (s, 9H) | 250 |
| 15 | (S)-1-(5-(5-fluoro-pyridin-3-yl)-4,5-dihydro-1H-pyrazol-1-yl)-2,2-dimethyl-propan-1-one | 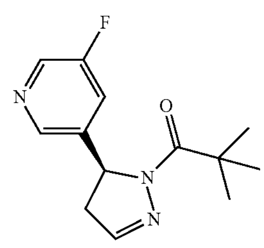 [SMILES: CC(C)(C)C(=O)N1N=CC[C@H]1c1cncc(F)c1] | ¹H NMR (400 MHz, DMSO-d6) δ ppm 8.48 (br. s., 1H), 8.26 (br. s., 1H), 7.41 (d, J = 9.6 Hz, 1H), 7.24 (s, 1H), 5.41 (dd, J = 11.9, 5.1 Hz, 1H), 3.41 (dd, J = 18.6, 12.5 Hz, 1H), 2.73 (dd, J = 18.9, 3.5 Hz, 1H), 1.25 (s, 9H) | 250 |
| 16 | cyclohexyl(5-phenyl-4,5-dihydro-1H-pyrazol-1-yl)methanone | 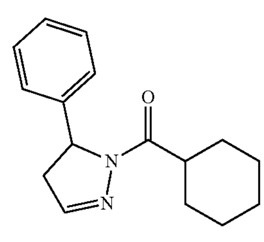 [SMILES: O=C(C1CCCCC1)N1N=CCC1c1ccccc1] | ¹H NMR (400 MHz, DMSO-d6) δ ppm 7.29-7.38 (m, 2H), 7.22-7.28 (m, 1H), 7.19 (t, J = 1.5 Hz, 1H), 7.08-7.14 (m, 2H), 5.31 (dd, J = 11.8, 4.6 Hz, 1H), 3.48 (ddd, J = 18.9, 12.1, 1.5 Hz, 1H), 3.08 (ddd, J = 11.0, 7.6, 3.5 Hz, 1H), 2.66 (ddd, J = 18.8, 4.7, 1.8 Hz, 1H), 1.57-1.89 (m, 5H), 1.07-1.44 (m, 5H) | 257 |
| 17 | (5-phenyl-4,5-dihydro-1H-pyrazol-1-yl)(p-tolyl)-methanone | 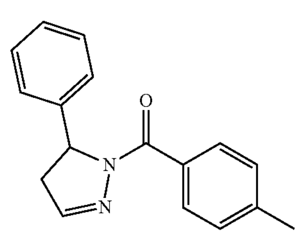 [SMILES: Cc1ccc(C(=O)N2N=CCC2c2ccccc2)cc1] | ¹H NMR (400 MHz, DMSO-d6) δ ppm 7.70 (d, J = 8.3 Hz, 2H), 7.34-7.41 (m, 2H), 7.21-7.33 (m, 6H), 5.55 (dd, J = 11.8, 5.3 Hz, 1H), 3.55 (ddd, J = 18.9, 11.8, 1.5 Hz, 1H), 2.76 (ddd, J = 18.9, 5.0, 1.8 Hz, 1H), 2.38 (s, 3H) | 265 |

| Ex | Name | Structure | ¹H NMR | LC retention time (min) | MS (M + H)⁺ |
|---|---|---|---|---|---|
| 18 | (5-phenyl-4,5-dihydro-1H-pyrazol-1-yl)(1-phenylpiperidin-4-yl)-methanone | 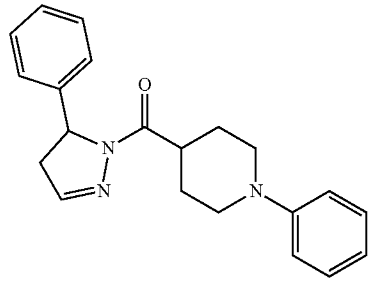 [SMILES: O=C(C1CCN(c2ccccc2)CC1)N1N=CCC1c1ccccc1] | ¹H NMR (400 MHz, DMSO-d6) δ ppm 7.32-7.38 (m, 2H), 7.18-7.29 (m, 4H), 7.14 (d, J = 7.2 Hz, 2H), 6.95 (d, J = 8.1 Hz, 2H), 6.77 (t, J = 7.2 Hz, 1H), 5.34 (dd, J = 11.8, 4.6 Hz, 1H), 3.75 (d, J = 12.5 Hz, 2H), 3.52 (ddd, J = 18.9, 11.9, 1.4 Hz, 1H), 3.20-3.29 (m, 1H), 2.66-2.82 (m, 3H), 1.76-1.96 (m, 2H), 1.58-1.75 (m, 2H) | | 334 |
| 19 | (S)-(5-phenyl-4,5-dihydro-1H-pyrazol-1-yl)(1-phenyl-piperidin-4-yl)-methanone | 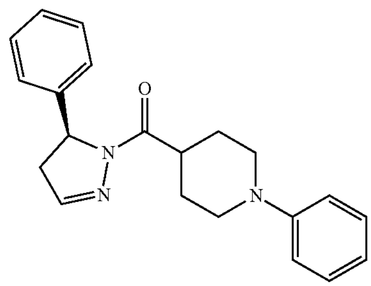 [SMILES: O=C(C1CCN(c2ccccc2)CC1)N1N=CC[C@H]1c1ccccc1] | ¹H NMR (400 MHz, DMSO-d6) d ppm 7.33 (m, 2H), 7.21 (m, 4H), 7.12 (m, 2H), 6.93 (d, J = 7.8 Hz, 2H), 6.75 (t, J = 7.2 Hz, 1H), 5.32(dd, J = 12.0, 4.6 Hz, 1H), 3.73 (m, 2H), 3.49 (ddd, J = 18.9, 11.9, 1.5 Hz, 1H), 3.23 (m, 1H), 2.73 (m, 3H), 1.90 (d, J = 12.0 Hz), 1.77 (m, 1H), 1.65 (m, 2H). LC Method 3: 1.23 min | | 334 |
| 20 | (1-phenylpiperidin-4-yl)(5-(pyridin-3-yl)-4,5-dihydro-1H-pyrazol-1-yl)-methanone | 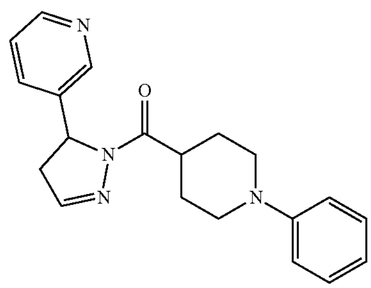 [SMILES: O=C(C1CCN(c2ccccc2)CC1)N1N=CCC1c1cccnc1] | ¹H NMR (400 MHz, DMSO-d6) δ ppm 8.38-8.51 (m, 2H), 7.53 (dt, J = 7.9, 2.0 Hz, 1H), 7.38 (dd, J = 7.6, 4.9 Hz, 1H), 7.29 (t, J = 1.6 Hz, 1H), 7.18-7.25 (m, 2H), 6.95 (d, J = 7.9 Hz, 2H), 6.76 (t, J = 7.2 Hz, 1H), 5.39 (dd, J = 11.9, 4.9 Hz, 1H), 3.74 (d, J = 12.3 Hz, 2H), 3.54 (ddd, J = 18.9, 12.1, 1.5 Hz, 1H), 3.24 (ddt, J = 11.6, 7.8, 3.8 Hz, 1H), 2.67-2.85 (m, 3H), 1.53-1.96 (m, 4H) | | 335 |
| 21 | cyclohexyl(5-(pyridin-3-yl)-4,5-dihydro-1H-pyrazol-1-yl)methanone | 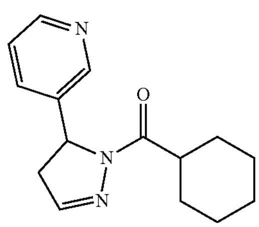 [SMILES: O=C(C1CCCCC1)N1N=CCC1c1cccnc1] | ¹H NMR (400 MHz, DMSO-d6) δ ppm 8.36-8.50 (m, 2H), 7.50 (dt, J = 7.9, 2.0 Hz, 1H), 7.37 (dd, J = 7.5, 4.8 Hz, 1H), 7.24 (t, J = 1.6 Hz, 1H), 5.36 (dd, J = 11.9, 4.9 Hz, 1H), 3.51 (ddd, J = 18.9, 12.0, 1.5 Hz, 1H), 3.06 (ddd, J = 11.1, 7.9, 3.4 Hz, 1H), 2.77 (ddd, J = 19.0, 4.9, 1.8 Hz, 1H), 1.59-1.85 (m, 5H), 1.09-1.42 (m, 5H) | | 258 |
| 22 | cyclopentyl(5-phenyl-4,5-dihydro-1H-pyrazol-1-yl)methanone | 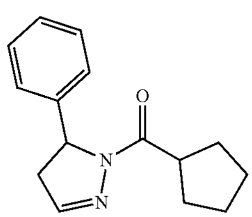 [SMILES: O=C(C1CCCC1)N1N=CCC1c1ccccc1] | ¹H NMR (400 MHz, DMSO-d6) δ ppm pm 7.30-7.38 (m, 2H), 7.23-7.29 (m, 1H), 7.19 (t, J = 1.5 Hz, 1H), 7.10-7.16 (m, 2H), 5.32 (dd, J = 11.8, 4.6 Hz, 1H), 3.41-3.55 (m, 2H), 2.68 (ddd, J = 18.8, 4.7, 1.8 Hz, 1H), 1.49-1.96 (m, 8H) | | 243 |
| 23 | (5-phenyl-4,5-dihydro-1H-pyrazol-1-yl)(m-tolyl)methanone | 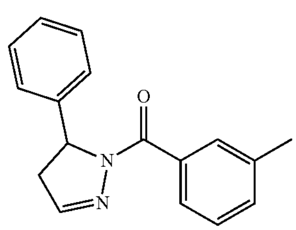 [SMILES: Cc1cccc(C(=O)N2N=CCC2c2ccccc2)c1] | ¹H NMR (400 MHz, DMSO-d6) δ ppm 7.52-7.58 (m, 2H), 7.22-7.42 (m, 8H), 5.55 (dd, J = 11.7, 5.2 Hz, 1H), 3.56 (ddd, J = 18.9, 11.8, 1.5 Hz, 1H), 2.76 (ddd, J = 18.9, 5.0, 1.8 Hz, 1H), 2.37 (s, 3H) | | 265 |

-continued

| Ex | Name | Structure | ¹H NMR LC retention time (min) | MS (M + H)⁺ |
|---|---|---|---|---|
| 24 | (1H-indol-2-yl)(5-phenyl-4,5-dihydro-1H-pyrazol-1-yl)-methanone | 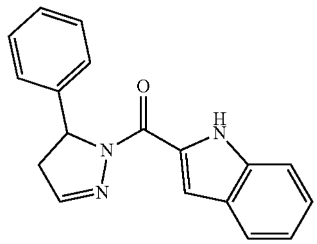 [SMILES: O=C(c1cc2ccccc2[nH]1)N1N=CCC1c1ccccc1] | ¹H NMR (400 MHz, DMSO-d6) δ ppm 11.49 (br. s., 1H), 7.69 (d, J = 7.9 Hz, 1H), 7.43-7.52 (m, 3H), 7.32-7.40 (m, 3H), 7.20-7.31 (m, 4H), 7.07 (t, J = 7.3 Hz, 1H), 5.63 (dd, J = 11.7, 4.5 Hz, 1H), 3.60 (ddd, J = 18.8, 11.8, 1.2 Hz, 1H), 2.81 (ddd, J = 18.8, 4.5, 1.6 Hz, 1H) | 290 |
| 25 | (5-phenyl-4,5-dihydro-1H-pyrazol-1-yl)(tetrahydro-2H-pyran-4-yl)methanone | 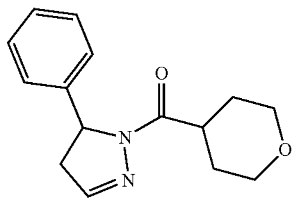 [SMILES: O=C(C1CCOCC1)N1N=CCC1c1ccccc1] | ¹H NMR (400 MHz, DMSO-d6) δ ppm 7.31-7.37 (m, 2H), 7.21-7.29 (m, 2H), 7.08-7.16 (m, 2H), 5.33 (dd, J = 11.8, 4.6 Hz, 1H), 3.89 (dt, J = 11.2, 3.3 Hz, 2H), 3.26-3.56 (m, 4H), 2.69 (ddd, J = 19.0, 4.7, 1.8 Hz, 1H), 1.48-1.78 (m, 4H) | 259 |
| 26 | (S)-(5-phenyl-4,5-dihydro-1H-pyrazol-1-yl)(tetrahydro-2H-pyran-4-yl)-methanone | 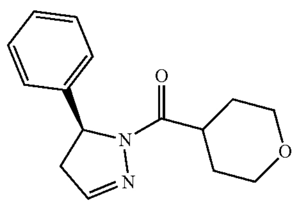 [SMILES: O=C(C1CCOCC1)N1N=CC[C@H]1c1ccccc1] | ¹H NMR (400 MHz, DMSO-d₆) δ = 7.35-7.29 (m, 2H), 7.26-7.20 (m, 2H), 7.12-7.08 (m, 2H), 5.30 (dd, J = 11.7, 4.6 Hz, 1H), 3.86 (td, J = 11.0, 3.4 Hz, 2H), 3.47 (ddd, J = 18.9, 11.9, 1.5 Hz, 1H), 3.41-3.24 (m, 3H), 2.66 (ddd, J = 18.8, 4.6, 1.7 Hz, 1H), 1.75-1.68 (m, 1H), 1.62-1.46 (m, 3H). LC Method 3: 0.82 min | 259 |
| 27 | 2-cyclopentyl-1-(5-(5-fluoropyridin-3-yl)-4,5-dihydro-1H-pyrazol-1-yl)ethanone | 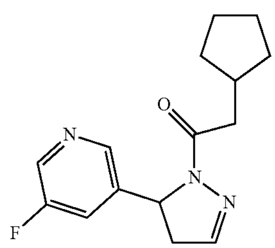 [SMILES: O=C(CC1CCCC1)N1N=CCC1c1cncc(F)c1] | ¹H NMR (CDCl₃) δ ppm 8.30-8.49 (m, 2H), 7.24 (dt, J = 9.0, 2.2 Hz, 1H), 6.99-7.03 (m, 1H), 5.47 (dd, J = 12.1, 5.3 Hz, 1H), 3.52 (ddd, J = 18.7, 12.2, 1.5 Hz, 1H), 2.78-2.92 (m, 2H), 2.63-2.76 (m, 1H), 2.34 (dt, J = 15.5, 7.8 Hz, 1H), 1.78-1.91 (m, 2H), 1.50-1.74 (m, 4H), 1.14-1.35 (m, 2H) | 276 |
| 28 | 1-(5-(5-fluoro-pyridin-3-yl)-4,5-dihydro-1H-pyrazol-1-yl)-2-methyl-propan-1-one | 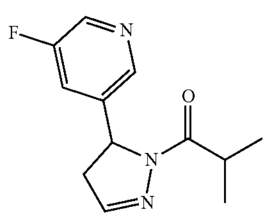 [SMILES: CC(C)C(=O)N1N=CCC1c1cncc(F)c1] | ¹H NMR (400 MHz, DMSO-d6) δ ppm 8.49 (d, J = 2.6 Hz, 1H), 8.31 (s, 1H), 7.47 (dt, J = 9.6, 2.1 Hz, 1H), 7.26 (s, 1H), 5.41 (dd, J = 12.1, 5.3 Hz, 1H), 3.53 (ddd, J = 19.0, 12.1, 1.4 Hz, 1H), 3.24-3.37 (m, 1H), 2.85 (ddd, J = 19.0, 5.3, 1.6 Hz, 1H), 1.06 (dd, J = 10.5, 6.8 Hz, 6H) | 236 |
| 29 | cyclohexyl(5-(5-fluoropyridin-3-yl)-4,5-dihydro-1H-pyrazol-1-yl)-methanone | 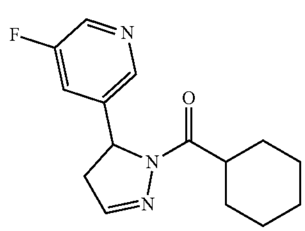 [SMILES: O=C(C1CCCCC1)N1N=CCC1c1cncc(F)c1] | ¹H NMR (400 MHz, DMSO-d6) δ ppm 8.49 (d, J = 2.6 Hz, 1H), 8.29 (s, 1H), 7.45 (dt, J = 9.7, 2.2 Hz, 1H), 7.24 (s, 1H), 5.41 (dd, J = 12.1, 5.3 Hz, 1H), 3.52 (ddd, J = 19.0, 12.1, 1.4 Hz, 1H), 2.99-3.12 (m, 1H), 2.83 (ddd, J = 19.0, 5.3, 1.6 Hz, 1H), 1.57-1.87 (m, 5H), 1.10-1.42 (m, 5H) | 276 |

-continued

| Ex | Name | Structure | ¹H NMR LC retention time (min) | MS (M + H)⁺ |
|---|---|---|---|---|
| 30 | 1-(5-(5-fluoro-pyridin-3-yl)-4,5-dihydro-1H-pyrazol-1-yl)-2,3-dimethyl-butan-1-one | 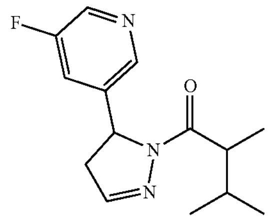 [SMILES: CC(C)C(C)C(=O)N1N=CCC1c1cncc(F)c1] | ¹H NMR (400 MHz, DMSO-d6) δ ppm 8.50 (d, J = 2.9 Hz, 1H), 8.29-8.37 (m, 1H), 7.43-7.53 (m, 1H), 7.23-7.30 (m, 1H), 5.37-5.50 (m, 1H), 3.48-3.61 (m, 1H), 3.02-3.16 (m, 1H), 2.79-2.94 (m, 1H), 1.76-1.94 (m, 1H), 0.96-1.06 (m, 3H), 0.89 (dd, J = 9.9, 6.8 Hz, 4H), 0.81 (t, J = 6.4 Hz, 2H) | 264 |
| 31 | (5-(pyridin-3-yl)-4,5-dihydro-1H-pyrazol-1-yl)(1-(pyrimidin-2-yl)-piperidin-4-yl)-methanone | 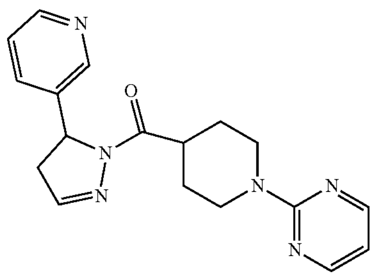 [SMILES: O=C(C1CCN(c2ncccn2)CC1)N1N=CCC1c1cccnc1] | ¹H NMR (400 MHz, DMSO-d6) δ ppm 8.48 (dd, J = 4.7, 1.6 Hz, 1H), 8.42 (d, J = 2.0 Hz, 1H), 8.36 (d, J = 4.8 Hz, 2H), 7.52 (dt, J = 7.9, 2.0 Hz, 1H), 7.37 (dd, J = 7.6, 4.5 Hz, 1H), 7.30 (t, J = 1.6 Hz, 1H), 6.61 (t, J = 4.7 Hz, 1H), 5.39 (dd, J = 11.9, 4.9 Hz, 1H), 4.61-4.73 (m, 2H), 3.54 (ddd, J = 19.0, 12.0, 1.6 Hz, 1H), 3.34-3.45 (m, 1H), 2.93-3.06 (m, 2H), 2.80 (ddd, J = 19.0, 4.9, 1.8 Hz, 1H), 1.73-1.92 (m, 2H), 1.36-1.57 (m, 2H) | 337 |
| 32 | (S)-(5-(pyridin-3-yl)-4,5-dihydro-1H-pyrazol-1-yl)(1-(pyrimidin-2-yl)-piperidin-4-yl)-methanone | 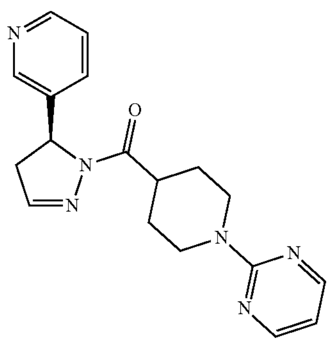 [SMILES: O=C(C1CCN(c2ncccn2)CC1)N1N=CC[C@H]1c1cccnc1] | ¹H NMR (400 MHz, DMSO-d6) δ ppm 8.37-8.49 (m, 2H), 8.33 (d, J = 4.5 Hz, 2H), 7.50 (dt, J = 7.9, 1.9 Hz, 1H), 7.35 (dd, J = 7.7, 4.7 Hz, 1H), 7.28 (t, J = 1.5 Hz, 1H), 6.59 (t, J = 4.7 Hz, 1H), 5.36 (dd, J = 12.0, 4.9 Hz, 1H), 4.57-4.69 (m, 2H), 3.52 (ddd, J = 19.0, 11.9, 1.6 Hz, 1H), 3.26-3.42 (m, 1H), 2.90-3.03 (m, 2H), 2.78 (ddd, J = 19.0, 5.0, 1.8 Hz, 1H), 1.68-1.92 (m, 2H), 1.32-1.55 (m, 2H) | 337 |
| 33 | 2-methyl-1-(5-phenyl-4,5-dihydro-1H-pyrazol-1-yl)-propan-1-one | 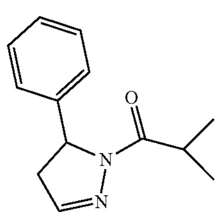 [SMILES: CC(C)C(=O)N1N=CCC1c1ccccc1] | ¹H NMR (400 MHz, DMSO-d6) δ ppm 7.30-7.38 (m, 2H), 7.17-7.29 (m, 2H), 7.10-7.16 (m, 2H), 5.32 (dd, J = 11.9, 4.7 Hz, 1H), 3.50 (ddd, J = 18.8, 11.9, 1.5 Hz, 1H), 3.26-3.39 (m, 1H), 2.68 (ddd, J = 18.9, 4.6, 1.8 Hz, 1H), 1.06 (dd, J = 15.3, 7.0 Hz, 6H) | 217 |
| 34 | cyclobutyl(5-phenyl-4,5-dihydro-1H-pyrazol-1-yl)methanone | 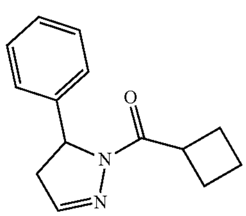 [SMILES: O=C(C1CCC1)N1N=CCC1c1ccccc1] | ¹H NMR (400 MHz, DMSO-d6) δ ppm 7.30-7.39 (m, 2H), 7.22-7.29 (m, 1H), 7.07-7.19 (m, 3H), 5.31 (dd, J = 11.8, 4.8 Hz, 1H), 3.76 (quin, J = 8.5 Hz, 1H), 3.47 (ddd, J = 18.9, 11.8, 1.5 Hz, 1H), 2.67 (ddd, J = 18.9, 4.8, 1.8 Hz, 1H), 2.04-2.22 (m, 4H), 1.87-2.02 (m, 1H), 1.70-1.83 (m, 1H) | 229 |
| 35 | (5-phenyl-4,5-dihydro-1H-pyrazol-1-yl)(tetrahydro-2H-pyran-3-yl)methanone | 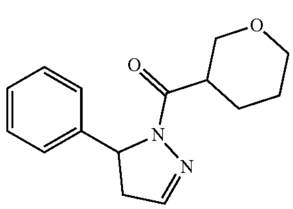 [SMILES: O=C(C1CCCOC1)N1N=CCC1c1ccccc1] | ¹H NMR (400 MHz, DMSO-d6) δ ppm 7.30-7.37 (m, 2H), 7.22-7.29 (m, 2H), 7.12 (ddd, J = 6.9, 3.0, 2.0 Hz, 2H), 5.27-5.35 (m, 1H), 3.86-4.01 (m, 1H), 3.77-3.85 (m, 1H), 3.50 (ddt, J = 18.9, 11.9, 1.6 Hz, 1H), 3.23-3.39 (m, 3H), 2.69 (ddd, J = 18.8, 4.7, 1.1 Hz, 1H), 1.82-2.03 (m, 1H), 1.51-1.71 (m, 3H) | 259 |

-continued

| Ex | Name | Structure | ¹H NMR | LC retention time (min) | MS (M + H)⁺ |
|---|---|---|---|---|---|
| 36 | 2-methyl-1-(5-phenyl-4,5-dihydro-1H-pyrazol-1-yl)butan-1-one | 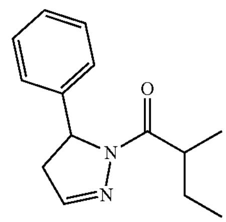 [SMILES: CCC(C)C(=O)N1N=CCC1c1ccccc1] | ¹H NMR (400 MHz, DMSO-d6) δ ppm 7.31-738 (m, 2H), 7.24-7.31 (m, 1H), 7.16-7.23 (m, 2H), 6.97 (s, 1H), 5.37-5.45 (m, 1H), 3.44 (ddd, J = 18.7, 12.0, 1.5 Hz, 1H), 3.30 (dq, J = 10.9, 7.0 Hz, 1H), 2.78-2.88 (m, 1H), 1.76 (dtd, J = 13.5, 7.4, 3.6 Hz, 1H), 1.48 (td, J = 14.5, 7.2 Hz, 1H), 1.12-1.21 (m, 3H), 0.85-0.98 (m, 3H) | | |
| 37 | 2-cyclopentyl-1-(5-phenyl-4,5-dihydro-1H-pyrazol-1-yl)-ethanone | 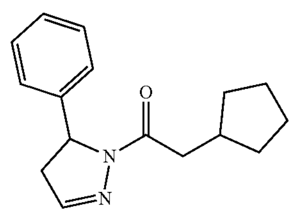 [SMILES: O=C(CC1CCCC1)N1N=CCC1c1ccccc1] | ¹H NMR (400 MHz, DMSO-d6) δ ppm 7.30-7.38 (m, 2H), 7.23-7.29 (m, 1H), 7.11-7.20 (m, 3H), 5.33 (dd, J = 11.8, 4.8 Hz, 1H), 3.50 (ddd, J = 18.9, 12.1, 1.5 Hz, 1H), 2.63-2.77 (m, 2H), 2.49-2.62 (m, 1H), 2.22 (dt, J = 15.3, 7.7 Hz, 1H), 1.39-1.79 (m, 6H), 1.09-1.24 (m, 2H) | | 257 |
| 38 | 2,3-dimethyl-1-(5-phenyl-4,5-dihydro-1H-pyrazol-1-yl)-butan-1-one | 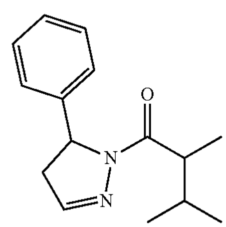 [SMILES: CC(C)C(C)C(=O)N1N=CCC1c1ccccc1] | ¹H NMR (400 MHz, DMSO-d6) δ ppm 7.30-7.37 (m, 2H), 7.22-7.28 (m, 1H), 7.09-7.21 (m, 3H), 5.35 (dd, J = 11.7, 4.5 Hz, 1H), 3.43-3.57 (m, 1H), 3.04-3.17 (m, 1H), 2.67 (ddd, J = 18.9, 4.7, 1.6 Hz, 1H), 1.75-1.92 (m, 1H), 0.95-1.03 (m, 3H), 0.77-0.94 (m, 6H) | | 245 |
| 39 | 1-(5-(3,4-dichlorophenyl)-4,5-dihydro-1H-pyrazol-1-yl)-2,2-dimethyl propan-1-one | 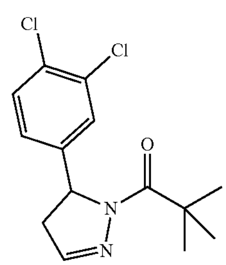 [SMILES: CC(C)(C)C(=O)N1N=CCC1c1ccc(Cl)c(Cl)c1] | ¹H NMR (400 MHz, DMSO-d6) δ ppm 7.60 (d, J = 8.3 Hz, 1H), 7.35 (d, J = 2.3 Hz, 1H), 7.21 (t, J = 1.6 Hz, 1H), 7.07 (dd, J = 8.3, 2.0 Hz, 1H), 5.33 (dd, J = 12.1, 4.8 Hz, 1H), 3.37 (ddd, J = 18.9, 11.9, 1.5 Hz, 1H), 2.63 (ddd, J = 18.9, 4.8, 1.8 Hz, 1H), 1.25 (s, 9H) | | 299/ 301/ 303 |
| 40 | (S)-1-(5-(3,4-dichlorophenyl)-4,5-dihydro-1H-pyrazol-1-yl)-2,2-dimethyl-propan-1-one | 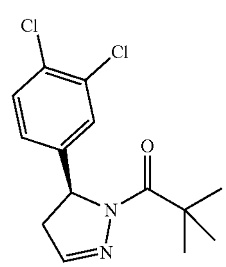 [SMILES: CC(C)(C)C(=O)N1N=CC[C@H]1c1ccc(Cl)c(Cl)c1] | ¹H NMR (400 MHz, DMSO-d6) δ ppm 7.60 (d, J = 8.3 Hz, 1H), 7.35 (d, J = 1.8 Hz, 1H), 7.21 (s, 1H), 7.07 (dd, J = 8.3, 1.8 Hz, 1H), 5.33 (dd, J = 12.0, 4.7 Hz, 1H), 3.34-3.43 (m, 1H), 2.63 (ddd, J = 18.9, 4.7, 1.6 Hz, 1H), 1.25 (s, 9H) | | 299/ 301/ 303 |
| 41 | 2,2-dimethyl-1-(5-(pyridin-3-yl)-4,5-dihydro-1H-pyrazol-1-yl)propan-1-one | 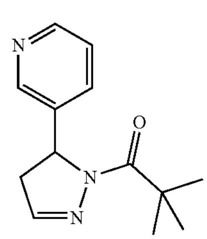 [SMILES: CC(C)(C)C(=O)N1N=CCC1c1cccnc1] | ¹H NMR (400 MHz, DMSO-d6) δ ppm 8.52 (dd, J = 4.7, 1.4 Hz, 1H), 8.48 (d, J = 1.8 Hz, 1H), 7.47 (dt, J = 8.0, 1.8 Hz, 1H), 7.28 (dd, J = 8.0, 4.7 Hz, 1H), 6.97 (t, J = 1.6 Hz, 1H), 5.43 (dd, J = 12.0, 4.9 Hz, 1H), 3.39 (ddd, J = 18.8, 12.0, 1.5 Hz, 1H), 2.73 (ddd, J = 18.9, 4.9, 1.8 Hz, 1H), 1.35 (s, 9H) | | 232 |

| Ex | Name | Structure | ¹H NMR LC retention time (min) | MS (M + H)⁺ |
|---|---|---|---|---|
| 42 | (S)-2,2-dimethyl-1-(5-(pyridin-3-yl)-4,5-dihydro-1H-pyrazol-1-yl)-propan-1-one | 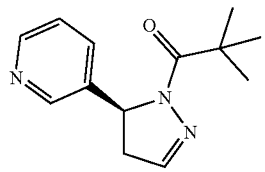 [SMILES: CC(C)(C)C(=O)N1N=CC[C@H]1c1cccnc1] | ¹H NMR (400 MHz, DMSO-d6) δ ppm 8.45 (dd, J = 4.7, 1.4 Hz, 1H), 8.37 (d, J = 1.8 Hz, 1H), 7.47 (dt, J = 8.0, 1.8 Hz, 1H), 7.36 (dd, J = 8.0, 4.7 Hz, 1H), 7.23 (t, J = 1.6 Hz, 1H), 5.37 (dd, J = 12.0, 4.9 Hz, 1H), 3.41 (ddd, J = 18.8, 12.0, 1.5 Hz, 1H), 2.66 (ddd, J = 18.9, 4.9, 1.8 Hz, 1H), 1.25 (s, 9H) | 232 |
| 43 | 1-(5-(3-chlorophenyl)-4,5-dihydro-1H-pyrazol-1-yl)-2,2-dimethyl propan-1-one | 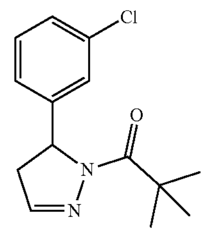 [SMILES: CC(C)(C)C(=O)N1N=CCC1c1cccc(Cl)c1] | LC Method 2: 1.16 min | 265/ 267 |
| 44 | (S)-1-(5-(3-chlorophenyl)-4,5-dihydro-1H-pyrazol-1-yl)-2,2-dimethyl propan-1-one | 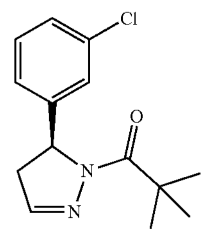 [SMILES: CC(C)(C)C(=O)N1N=CC[C@H]1c1cccc(Cl)c1] | ¹H NMR (400 MHz, DMSO-d6) δ ppm 7.36 (m, 1H), 7.30 (m, 1H), 7.20 (m, 1H), 7.13 (m, 1H), 7.05 (d, J = 7.6 Hz, 1H), 5.33 (dd, J = 11.9, 4.5 Hz, 1H), 3.37 (ddd, J = 18.9, 12.1, 1.6 Hz, 1H), 2.60 (ddd, J = 18.9, 4.7, 1.9 Hz, 1H), 1.26 (s, 9H) | 265/ 267 |
| 45 | 1-(5-(6-methoxy-pyridin-3-yl)-4,5-dihydro-1H-pyrazol-1-yl)-2,2-dimethyl-propan-1-one | 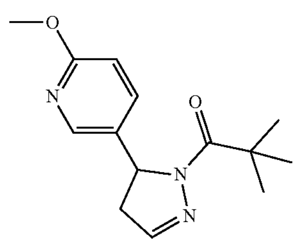 [SMILES: COc1ccc(C2CC=NN2C(=O)C(C)(C)C)cn1] | ¹H NMR (400 MHz, DMSO-d6) δ ppm 7.94 (d, J = 2.5 Hz, 1H), 7.40 (dd, J = 8.6, 2.5 Hz, 1H), 7.22 (t, J = 1.6 Hz, 1H), 6.78 (d, J = 8.6 Hz, 1H), 5.30 (dd, J = 12.0, 4.7 Hz, 1H), 3.82 (s, 3H), 3.31-3.42 (m, 1H), 2.64 (ddd, J = 18.9, 4.8, 1.8 Hz, 1H), 1.23 (s, 9H) | 262 |
| 46 | 2,2-dimethyl-1-(5-(5-methylpyridin-2-yl)-4,5-dihydro-1H-pyrazol-1-yl)-propan-1-one | 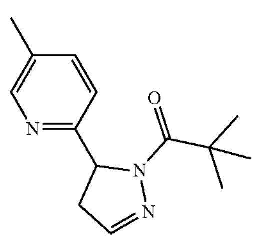 [SMILES: Cc1ccc(C2CC=NN2C(=O)C(C)(C)C)nc1] | ¹H NMR (400 MHz, DMSO-d6) δ ppm 8.29-8.34 (m, 1H), 7.50-7.57 (m, 1H), 7.17 (t, J = 1.6 Hz, 1H), 7.05 (d, J = 8.1 Hz, 1H), 5.31 (dd, J = 12.0, 4.9 Hz, 1H), 3.25-3.37 (m, 1H), 2.72 (ddd, J = 18.6, 4.9, 1.8 Hz, 1H), 2.26 (s, 3H), 1.23 (s, 9H) | 246 |
| 47 | 2,2-dimethyl-1-(5-(pyridin-2-yl)-4,5-dihydro-1H-pyrazol-1-yl)propan-1-one | 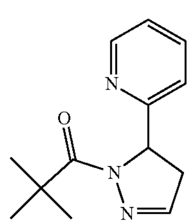 [SMILES: CC(C)(C)C(=O)N1N=CCC1c1ccccn1] | ¹H NMR (400 MHz, DMSO-d6) δ ppm 8.60 (d, J = 4.3 Hz, 1H), 7.96 (t, J = 7.5 Hz, 1H), 7.41-7.49 (m, 1H), 7.29 (d, J = 7.8 Hz, 1H), 7.22 (t, J = 1.5 Hz, 1H), 5.43 (dd, J = 12.0, 5.4 Hz, 1H), 3.39 (ddd, J = 18.8, 12.1, 1.6 Hz, 1H), 2.81 (ddd, J = 18.7, 5.3, 1.8 Hz, 1H), 1.25 (s, 9H) | 232 |

| Ex | Name | Structure | ¹H NMR LC retention time (min) | MS (M + H)⁺ |
|---|---|---|---|---|
| 48 | (S)-2,2-dimethyl-1-(5-(pyridin-2-yl)-4,5-dihydro-1H-pyrazol-1-yl)-propan-1-one | 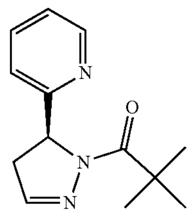 [SMILES: CC(C)(C)C(=O)N1N=CC[C@H]1c1ccccn1] | ¹H NMR (400 MHz, DMSO-d6) δ ppm 8.49 (m, 1H), 7.74 (td, J = 7.6, 1.9 Hz, 1H), 7.25 (ddd, J = 7.6, 4.8, 1.0 Hz, 1H), 7.12-7.19 (m, 2H), 5.35 (dd, J = 12.1, 5.1 Hz, 1H), 3.33-3.39 (m, 1H), 2.74 (ddd, J = 18.7, 5.1, 1.8 Hz, 1H), 1.25 (s, 9H) | 232 |
| 49 | 2,2-dimethyl-1-(5-(6-methylpyridin-3-yl)-4,5-dihydro-1H-pyrazol-1-yl)-propan-1-one | 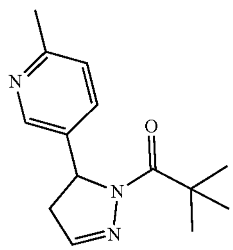 [SMILES: Cc1ccc(C2CC=NN2C(=O)C(C)(C)C)cn1] | LC Method 2: 0.54 min | 246 |
| 50 | (S)-2,2-dimethyl-1-(5-(6-methylpyridin-3-yl)-4,5-dihydro-1H-pyrazol-1-yl)propan-1-one | 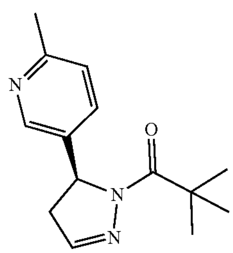 [SMILES: Cc1ccc([C@@H]2CC=NN2C(=O)C(C)(C)C)cn1] | ¹H NMR (400 MHz, DMSO-d6) δ ppm 8.22 (m, 1H), 7.32-7.37 (m, 1H), 7.16-7.24 (m, 2H), 5.32 (dd, J = 12.0, 4.7 Hz, 1H), 3.34-3.44 (m, 1H), 2.63 (ddd, J = 18.9, 4.6, 1.8 Hz, 1H), 2.43 (s, 3H), 1.24 (s, 9H) | 246 |
| 51 | (5-(6-methylpyridin-3-yl)-4,5-dihydro-1H-pyrazol-1-yl)(1-(pyrimidin-2-yl)piperidin-4-yl)methanone | 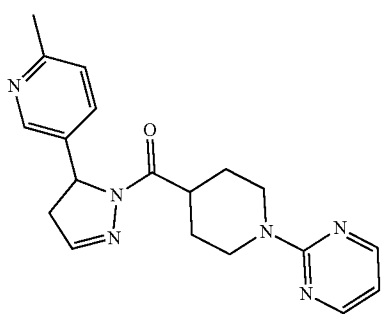 [SMILES: Cc1ccc(C2CC=NN2C(=O)C2CCN(c3ncccn3)CC2)cn1] | ¹H NMR (500 MHz, DMSO-d6) δ ppm 8.34 (d, J = 4.1 Hz, 3H), 8.25 (s, 1H), 7.38 (d, J = 8.0 Hz, 1H), 7.27 (s, 1H), 7.20 (d, J = 8.0 Hz, 1H), 6.59 (br. s., 1H), 5.76 (s, 1H), 5.32 (dd, J = 11.5, 4.1 Hz, 1H), 4.61-4.72 (m, 2H), 3.50 (dd, J = 18.8, 11.9 Hz, 1H), 2.89-3.11 (m, 2H), 2.75 (dd, J = 18.9, 3.8 Hz, 1H), 2.43 (s, 3H), 1.83 (d, J = 13.2 Hz, 1H), 1.75 (d, J = 13.4 Hz, 1H), 1.33-1.57 (m, 2H) LC Method 2: 0.39 min | 351 |
| 52 | (5-(6-methyl-pyridin-3-yl)-4,5-dihydro-1H-pyrazol-1-yl)(1-(pyridin-2-yl)-piperidin-4-yl)-methanone | 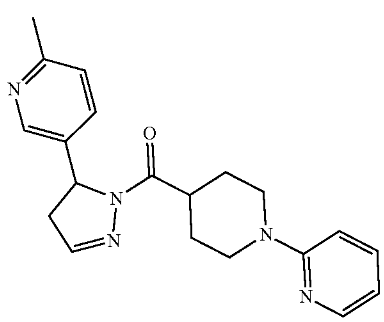 [SMILES: Cc1ccc(C2CC=NN2C(=O)C2CCN(c3ccccn3)CC2)cn1] | ¹H NMR (500 MHz, DMSO-d6) δ ppm 8.25 (s, 1H) 8.09 (d, J = 4.7 Hz, 1H), 7.50 (t, J = 7.7 Hz, 1H), 7.38 (d, J = 8.0 Hz, 1H), 7.27 (s, 1H), 7.20 (d, J = 8.0 Hz, 1H), 6.82 (d, J = 8.5 Hz, 1H), 6.59 (t, J = 5.8 Hz, 1H), 5.76 (s, 1H), 5.32 (dd, J = 11.8, 4.4 Hz, 1H), 4.30 (d, J = 12.1 Hz, 2H), 3.50 (dd, J = 18.8, 11.9 Hz, 1H), 2.80-2.98 (m, 2H), 2.75 (dd, J = 18.9, 4.7 Hz, 1H), 2.43 (s, 3H), 1.82 (d, J = 12.6 Hz, 1H), 1.78-1.28 (m, 2H) LC Method 2: 0.17 min | 350 |

-continued

| Ex | Name | Structure | ¹H NMR LC retention time (min) | MS (M + H)⁺ |
|---|---|---|---|---|
| 53 | 1-(5-(2-fluoro-4-methylphenyl)-4,5-dihydro-1H-pyrazol-1-yl)-2,2-dimethyl-propan-1-one | 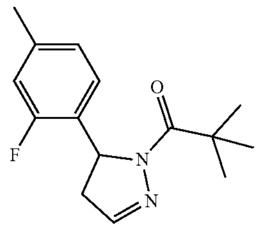 [SMILES: Cc1ccc(C2CC=NN2C(=O)C(C)(C)C)c(F)c1] | ¹H NMR (400 MHz, DMSO-d6) δ ppm 7.20 (t, J = 1.6 Hz, 1H), 6.92-7.03 (m, 2H), 6.83-6.91 (m, 1H), 5.42 (dd, J = 12.1, 5.1 Hz, 1H), 3.38 (ddd, J = 18.8, 12.1, 1.6 Hz, 1H), 2.57 (ddd, J = 18.7, 4.8, 1.5 Hz, 1H), 2.28 (s, 3H), 1.24 (s, 9H) | 263 |
| 54 | 1-(5-(3-fluoro-4-methylphenyl)-4,5-dihydro-1H-pyrazol-1-yl)-2,2-dimethyl-propan-1-one | 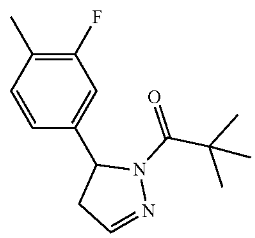 [SMILES: Cc1ccc(C2CC=NN2C(=O)C(C)(C)C)cc1F] | ¹H NMR (400 MHz, DMSO-d6) δ ppm 7.15-7.26 (m, 1H), 6.77-6.85 (m, 1H), 5.29 (dd, J = 11.9, 4.5 Hz, 1H), 3.28-3.41 (m, 1H), 2.57 (ddd, J = 18.8, 4.7, 1.8 Hz, 1H), 2.19 (d, J = 1.5 Hz, 3H), 1.25 (s, 9H) | 263 |
| 55 | 1-(5-cyclohexyl-4,5-dihydro-1H-pyrazol-1-yl)-2,2-dimethyl-propan-1-one | 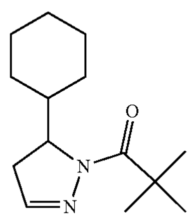 [SMILES: CC(C)(C)C(=O)N1N=CCC1C1CCCCC1] | LC Method 2: 1.26 min | 237 |
| 56 | (S)-1-(5-cyclohexyl-4,5-dihydro-1H-pyrazol-1-yl)-2,2-dimethylpropan-1-one | 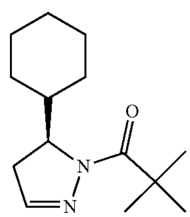 [SMILES: CC(C)(C)C(=O)N1N=CC[C@H]1C1CCCCC1] | ¹H NMR (400 MHz, DMSO-d6) δ ppm 7.05 (s, 1H), 4.25 (m, 1H), 2.72-2.83 (m, 1H), 2.57-2.67 (m, 1H), 1.92-2.03 (m, 1H), 1.64-1.73 (m, 2H), 1.55-1.64 (m, 1H), 1.45 (d, J = 12.6 Hz, 1H), 1.23 (s, 9H), 1.03-1.21 (m, 4H), 0.89-1.02 (m, 1H), 0.75-0.87 (m, 1H) | 237 |
| 57 | 1-(5-cyclopentyl-4,5-dihydro-1H-pyrazol-1-yl)-2,2-dimethylpropan-1-one | 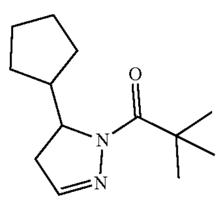 [SMILES: CC(C)(C)C(=O)N1N=CCC1C1CCCC1] | ¹H NMR (400 MHz, DMSO-d6) δ ppm 7.07 (s, 1H), 4.47 (dt, J = 11.4, 4.5 Hz, 1H), 2.88 (ddd, J = 18.8, 11.2, 1.5 Hz, 1H), 2.43-2.60 (m, 1H), 1.31-1.65 (m, 6H), 1.20-1.27 (m, 9H), 0.96-1.19 (m, 3H) | 223 |
| 58 | 2,2-dimethyl-1-(5-(p-tolyl)-4,5-dihydro-1H-pyrazol-1-yl)propan-1-one | 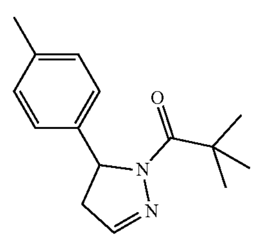 [SMILES: Cc1ccc(C2CC=NN2C(=O)C(C)(C)C)cc1] | ¹H NMR (400 MHz, DMSO-d6) δ ppm 7.17 (t, J = 1.6 Hz, 1H), 7.11 (d, J = 7.8 Hz, 2H), 6.97 (d, J = 8.1 Hz, 2H), 5.27 (dd, J = 11.9, 4.5 Hz, 1H), 3.29-3.40 (m, 1H), 2.47-2.58 (m, 1H), 2.26 (s, 3H), 1.25 (s, 9H) | 245 |
| 59 | 2,2-dimethyl-1-(5-(oxazol-4-yl)-4,5-dihydro-1H-pyrazol-1-yl)propan-1-one | 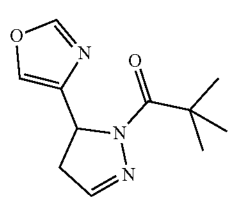 [SMILES: CC(C)(C)C(=O)N1N=CCC1c1cocn1] | ¹H NMR (400 MHz, DMSO-d6) δ ppm 8.28 (s, 1H), 7.85 (s, 1H), 7.19 (t, J = 1.8 Hz, 1H), 5.36 (dd, J = 11.7, 4.7 Hz, 1H), 3.23 (ddd, J = 18.5, 11.8, 1.5 Hz, 1H), 2.84 (ddd, J = 18.5, 4.6, 1.9 Hz, 1H), 1.22 (s, 9H) | 222 |

| Ex | Name | Structure | $^1$H NMR | LC retention time (min) | MS (M + H)$^+$ |
|---|---|---|---|---|---|
| 60 | 2,2-dimethyl-1-(5-(o-tolyl)-4,5-dihydro-1H-pyrazol-1-yl)propan-1-one | 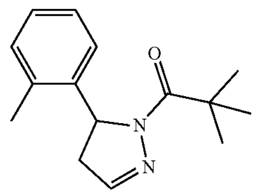 [SMILES: Cc1ccccc1C1CC=NN1C(=O)C(C)(C)C] | $^1$H NMR (400 MHz, DMSO-d6) δ ppm 7.07-7.20 (m, 1H), 6.79 (dd, J = 5.3, 3.8 Hz, 1H), 5.43 (dd, J = 11.9, 4.8 Hz, 1H), 3.43 (ddd, J = 18.7, 12.0, 1.6 Hz, 1H), 2.44 (ddd, J = 18.7, 4.8, 2.0 Hz, 1H), 2.32 (s, 3H), 1.27 (s, 9H) | | 245 |
| 61 | 2,2-dimethyl-1-(5-(4-(trifluoromethyl)-phenyl)-4,5-dihydro-1H-pyrazol-1-yl)-propan-1-one | 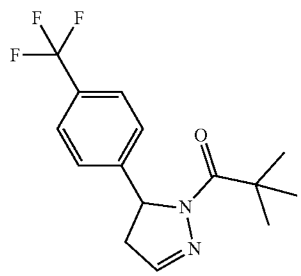 [SMILES: CC(C)(C)C(=O)N1N=CCC1c1ccc(C(F)(F)F)cc1] | $^1$H NMR (CDCl$_3$) δ ppm 7.61 (d, J = 7.8 Hz, 2H), 7.28 (d, J = 8.1 Hz, 2H), 6.96 (t, J = 1.6 Hz, 1H), 5.45 (dd, J = 11.9, 4.5 Hz, 1H), 3.34-3.43 (m, 1H), 2.65-2.72 (m, 1H), 1.3 (s, 9H) | | 299 |
| 62 | (S)-2,2-dimethyl-1-(5-(4-(trifluoromethyl)-phenyl)-4,5-dihydro-1H-pyrazol-1-yl)propan-1-one | 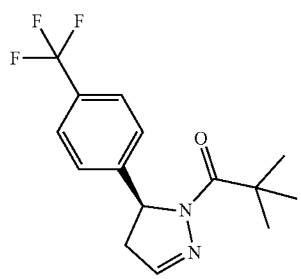 [SMILES: CC(C)(C)C(=O)N1N=CC[C@H]1c1ccc(C(F)(F)F)cc1] | $^1$H NMR (CDCl$_3$) δ ppm 7.59 (d, J = 7.8 Hz, 2H), 7.27 (m, 2H), 6.94 (s, 1H), 5.44 (dd, J = 12.1, 4.8 Hz, 1H), 3.36 (dd, J = 18.6, 12.0 Hz, 1H), 2.67 (m, 1H), 1.35 (s, 9H) | | 299 |
| 63 | 1-(5-(4-methoxy-phenyl)-4,5-dihydro-1H-pyrazol-1-yl)-2,2-dimethyl-propan-1-one | 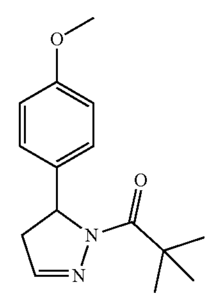 [SMILES: COc1ccc(C2CC=NN2C(=O)C(C)(C)C)cc1] | $^1$H NMR (400 MHz, DMSO-d6) δ ppm 7.17 (t, J = 1.6 Hz, 1H), 6.98-7.05 (m, 2H), 6.82-6.90 (m, 2H), 5.26 (dd, J = 11.7, 4.4 Hz, 1H), 3.72 (s, 3H), 3.27-3.41 (m, 1H), 2.46-2.59 (m, 1H), 1.24 (s, 9H) | | 261 |
| 64 | phenyl(5-phenyl-4,5-dihydro-1H-pyrazol-1-yl)-methanone 2,2,2-trifluoroacetate | 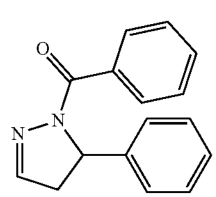 [SMILES: O=C(c1ccccc1)N1N=CCC1c1ccccc1] | $^1$H NMR (400 MHz, DMSO-d6) δ ppm 2.69-2.83 (m, 1H), 3.47-3.62 (m, 1H), 5.54 (dd, J = 11.9, 5.1 Hz, 1H), 7.20-7.55 (m, 9H), 7.71-7.83 (m, 2H) | | 251 |
| 65 | 1-(5-(4-chloro-phenyl)-4,5-dihydro-1H-pyrazol-1-yl)-2,2-dimethyl-propan-1-one | 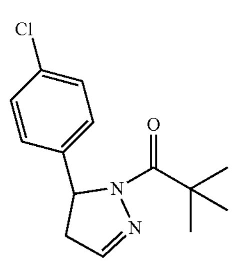 [SMILES: CC(C)(C)C(=O)N1N=CCC1c1ccc(Cl)cc1] | $^1$H NMR (400 MHz, DMSO-d6) δ ppm 1.24 (s, 9H), 2.56 (ddd, J = 19.0, 4.8, 1.8 Hz, 1H), 3.37 (ddd, J = 18.9, 11.9, 1.5 Hz, 1H), 5.31 (dd, J = 11.9, 4.6 Hz, 1H), 7.08-7.14 (m, 2H), 7.19 (t, J = 1.5 Hz, 1H), 7.35-7.41 (m, 2H) | | 265/267 |

| Ex | Name | Structure | $^1$H NMR LC retention time (min) | MS (M + H)$^+$ |
|---|---|---|---|---|
| 66 | (S)-1-(5-(4-chlorophenyl)-4,5-dihydro-1H-pyrazol-1-yl)-2,2-dimethyl-propan-1-one | 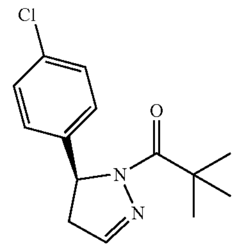 [SMILES: CC(C)(C)C(=O)N1N=CC[C@H]1c1ccc(Cl)cc1] | $^1$H NMR (400 MHz, DMSO-d6) δ ppm 1.24 (s, 9H), 2.56 (ddd, J = 18.9, 4.6, 1.8 Hz, 1H), 3.32-3.42 (m, 1H), 5.31 (dd, J = 11.9, 4.6 Hz, 1H), 7.08-7.14 (m, 2H), 7.19 (t, J = 1.5 Hz, 1H), 7.35-7.41 (m, 2H) | 265/ 267 |
| 67 | 1-(5-(3-fluoro-phenyl)-4,5-dihydro-1H-pyrazol-1-yl)-2,2-dimethylpropan-1-one 2,2,2-trifluoroacetate | 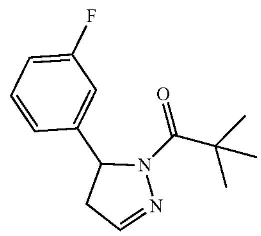 [SMILES: CC(C)(C)C(=O)N1N=CCC1c1cccc(F)c1] | $^1$H NMR (400 MHz, DMSO-d6) δ ppm 1.26 (s, 9H), 2.59 (ddd, J = 18.9, 4.7, 1.9 Hz, 1H), 3.38 (ddd, J = 18.8, 12.0, 1.5 Hz, 1H), 5.34 (dd, J = 12.0, 4.7 Hz, 1H), 6.85-6.96 (m, 2H), 7.03-7.11 (m, 1H), 7.20 (t, J = 1.6 Hz, 1H), 7.33-7.41 (m, 1H) | 249 |
| 68 | (S)-1-(5-(3-fluorophenyl)-4,5-dihydro-1H-pyrazol-1-yl)-2,2-dimethyl-propan-1-one 2,2,2-trifluoroacetate | 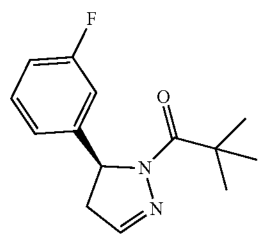 [SMILES: CC(C)(C)C(=O)N1N=CC[C@H]1c1cccc(F)c1] | $^1$H NMR (400 MHz, DMSO-d6) δ ppm 1.26 (s, 9H), 2.59 (ddd, J = 18.9, 4.7, 1.9 Hz, 1H), 3.38 (ddd, J = 18.8, 12.0, 1.5 Hz, 1H), 5.34 (dd, J = 12.0, 4.7 Hz, 1H), 6.85-6.96 (m, 2H), 7.03-7.11 (m, 1H), 7.20 (t, J = 1.6 Hz, 1H), 7.33-7.41 (m, 1H) | 249 |
| 69 | (1-(pyridin-2-yl)-piperidin-4-yl)(5-(pyridin-3-yl)-4,5-dihydro-1H-pyrazol-1-yl)methanone | 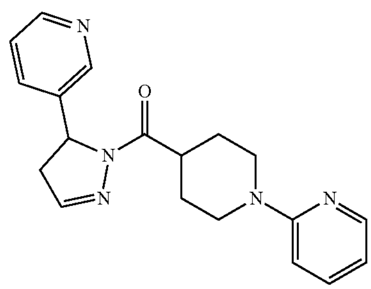 [SMILES: O=C(C1CCN(c2ccccn2)CC1)N1N=CCC1c1cccnc1] | $^1$H NMR (400 MHz, DMSO-d6) δ ppm 8.37-8.53 (m, 2H), 8.07-8.14 (m, 1H), 7.46-7.56 (m, 2H), 7.37 (dd, J = 7.7, 4.8 Hz, 1H), 7.29 (t, J = 1.6 Hz, 1H), 6.83 (d, J = 8.8 Hz, 1H), 6.55-6.65 (m, 1H), 5.38 (dd, J = 12.1, 5.0 Hz, 1H), 4.31 (d, J = 12.9 Hz, 2H), 3.54 (ddd, J = 18.9, 12.1, 1.5 Hz, 1H), 3.26-3.40 (m, 1H), 2.90 (tdd, J = 12.7, 5.7, 2.9 Hz, 2H), 2.80 (ddd, J = 19.0, 4.9, 1.8 Hz, 1H), 1.70-1.90 (m, 2H), 1.39-1.65 (m, 2H) | 336 |
| 70 | (S)-(1-(pyridin-2-yl)piperidin-4-yl)(5-(pyridin-3-yl)-4,5-dihydro-1H-pyrazol-1-yl)-methanone | 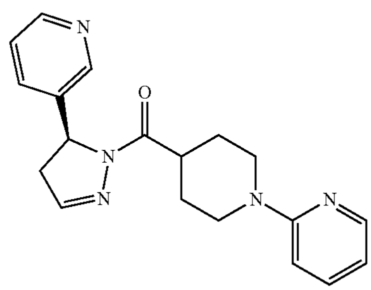 [SMILES: O=C(C1CCN(c2ccccn2)CC1)N1N=CC[C@H]1c1cccnc1] | $^1$H NMR (400 MHz, DMSO-d$_6$) δ = 8.45 (dd, J = 4.8, 1.6 Hz, 1H), 8.39 (d, J = 2.2 Hz, 1H), 8.09-8.06 (m, 1H), 7.52-7.46 (m, 2H), 7.37-7.32 (m, 1H), 7.28-7.26 (m, 1H), 6.81 (d, J = 8.6 Hz, 1H), 6.58 (m, 1H), 5.35 (dd, J = 12.0, 4.9 Hz, 1H), 4.33-4.26 (m, 2H), 3.51 (ddd, J = 19.0, 12.0, 1.6 Hz, 1H), 3.36-3.28 (m, 1H), 2.92-2.83 (m, 2H), 2.77 (ddd, J = 19.0, 5.0, 1.7 Hz, 1H), 1.87-1.69 (m, 2H), 1.59-1.39 (m, 2H) LC Method 3: 0.85 min | 336 |
| 71 | 2,2-dimethyl-1-(5-(5-methylpyridin-3-yl)-4,5-dihydro-1H-pyrazol-1-yl)-propan-1-one | 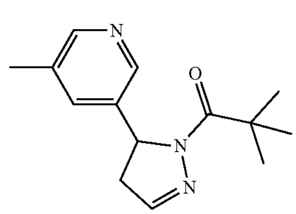 [SMILES: Cc1cncc(C2CC=NN2C(=O)C(C)(C)C)c1] | $^1$H NMR (400 MHz, DMSO-d6) δ ppm 8.29 (d, J = 1.3 Hz, 1H), 8.15 (d, J = 2.0 Hz, 1H), 7.27 (s, 1H), 7.22 (t, J = 1.6 Hz, 1H), 5.32 (dd, J = 11.9, 4.8 Hz, 1H), 3.39 (ddd, J = 18.9, 12.0, 1.6 Hz, 1H), 2.64 (ddd, J = 18.8, 4.8, 1.9 Hz, 1H), 2.27 (s, 3H), 1.25 (s, 9H) | 246 |

-continued

| Ex | Name | Structure | ¹H NMR | LC retention time (min) | MS (M + H)⁺ |
|---|---|---|---|---|---|
| 72 | 2,2-dimethyl-1-(5-(tetrahydro-2H-pyran-2-yl)-4,5-dihydro-1H-pyrazol-1-yl)propan-1-one | 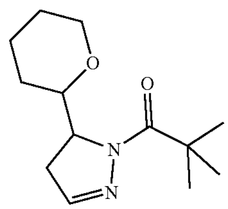 [SMILES: CC(C)(C)C(=O)N1N=CCC1C1CCCCO1] | ¹H NMR (400 MHz, DMSO-d6) δ ppm 7.10 (t, J = 1.6 Hz, 0.25H), 7.03 (t, J = 1.6 Hz, 0.75H), 4.44 (ddd, J = 9.1, 7.1, 4.5 Hz, 0.25H), 4.21 (ddd, J = 9.7, 7.0, 2.3 Hz, 0.75H), 3.68-3.90 (m, 2H), 3.17-3.38 (m, 1H), 2.75-2.86 (m, 2H), 1.71-1.83 (m, 1H), 1.30-1.51 (m, 4H), 0.95-1.28 (m, 10H) | | 239 |
| 73 | 2,2-dimethyl-1-(5-(5-methylpyrazin-2-yl)-4,5-dihydro-1H-pyrazol-1-yl)-propan-1-one | 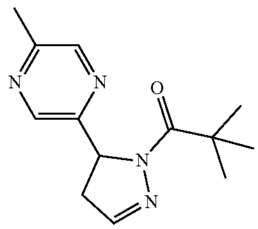 [SMILES: Cc1cnc(C2CC=NN2C(=O)C(C)(C)C)cn1] | ¹H NMR (400 MHz, DMSO-d6) δ ppm 8.45 (d, J = 1.0 Hz, 1H), 8.38 (d, J = 1.5 Hz, 1H), 7.21 (t, J = 1.6 Hz, 1H), 5.40 (dd, J = 12.1, 5.3 Hz, 1H), 3.25-3.39 (m, 1H), 2.80 (ddd, J = 18.7, 5.4, 1.9 Hz, 1H), 2.47 (s, 3H), 1.21 (s, 9H) | | 247 |
| 74 | 1-(5-(5-fluoro-6-methylpyridin-2-yl)-4,5-dihydro-1H-pyrazol-1-yl)-2,2-dimethylpropan-1-one | 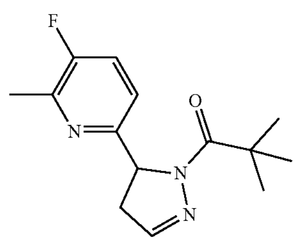 [SMILES: Cc1nc(C2CC=NN2C(=O)C(C)(C)C)ccc1F] | ¹H NMR (400 MHz, DMSO-d6) δ ppm 7.56 (dd, J = 9.3, 8.6 Hz, 1H), 7.17 (t, J = 1.6 Hz, 1H), 7.00 (dd, J = 8.3, 3.8 Hz, 1H), 5.34 (dd, J = 12.0, 4.9 Hz, 1H), 3.26-3.38 (m, 1H), 2.70 (ddd, J = 18.7, 4.8, 1.8 Hz, 1H), 2.39 (d, J = 3.0 Hz, 3H), 1.25 (s, 9H) | | 264 |
| 75 | 1-(5-(5-chloro-pyridin-3-yl)-4,5-dihydro-1H-pyrazol-1-yl)-2,2-dimethylpropan-1-one | 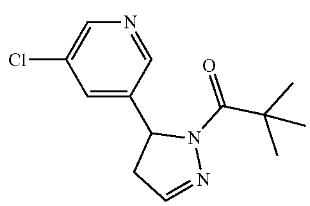 [SMILES: CC(C)(C)C(=O)N1N=CCC1c1cncc(Cl)c1] | ¹H NMR (400 MHz, DMSO-d6) δ ppm 8.52 (d, J = 2.5 Hz, 1H), 8.32 (d, J = 2.0 Hz, 1H), 7.61 (t, J = 2.1 Hz, 1H), 7.24 (t, J = 1.6 Hz, 1H), 5.38 (dd, J = 12.1, 5.1 Hz, 1H), 3.40 (ddd, J = 18.9, 12.1, 1.5 Hz, 1H), 2.74 (ddd, J = 18.9, 5.1, 1.8 Hz, 1H), 1.24 (s, 9H) | | 266/ 268 |
| 76 | 1-(5-(3-fluoro-5-methylphenyl)-4,5-dihydro-1H-pyrazol-1-yl)-2,2-dimethyl-propan-1-one | 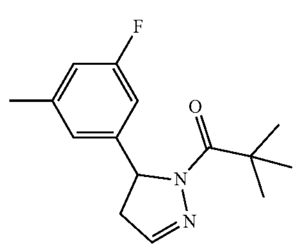 [SMILES: Cc1cc(F)cc(C2CC=NN2C(=O)C(C)(C)C)c1] | ¹H NMR (400 MHz, DMSO-d6) δ ppm 7.18 (t, J = 1.6 Hz, 1H), 6.90 (d, J = 9.9 Hz, 1H), 6.75 (s, 1H), 6.64 (d, J = 9.9 Hz, 1H), 5.29 (dd, J = 11.9, 4.5 Hz, 1H), 3.31-3.41 (m, 1H), 2.57 (ddd, J = 18.8, 4.7, 1.8 Hz, 1H), 2.28 (s, 3H), 1.26 (s, 9H) | | 263 |
| 77 | 1-(5-(2-fluoro-5-methylphenyl)-4,5-dihydro-1H-pyrazol-1-yl)-2,2-dimethyl-propan-1-one | 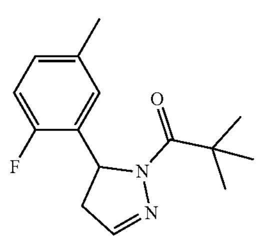 [SMILES: Cc1ccc(F)c(C2CC=NN2C(=O)C(C)(C)C)c1] | ¹H NMR (400 MHz, DMSO-d6) δ ppm 7.21 (t, J = 1.6 Hz, 1H), 7.01-7.11 (m, 2H), 6.78 (dd, J = 73, 1.5 Hz, 1H), 5.42 (dd, J = 12.1, 4.8 Hz, 1H), 3.39 (ddd, J = 18.7, 12.1, 1.5 Hz, 1H), 2.58 (ddd, J = 18.8, 5.0, 1.3 Hz, 1H), 2.23 (s, 3H), 1.26 (s, 9H) | | 263 |

-continued

| Ex | Name | Structure | ¹H NMR LC retention time (min) | MS (M + H)⁺ |
|---|---|---|---|---|
| 78 | 4-(1-pivaloyl-4,5-dihydro-1H-pyrazol-5-yl)benzonitrile | 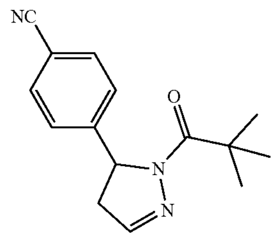 [SMILES: CC(C)(C)C(=O)N1N=CCC1c1ccc(C#N)cc1] | ¹H NMR (400 MHz, DMSO-d6) δ ppm 7.75-7.84 (m, 2H) 7.25-7.33 (m, 2H) 7.21 (t, J = 1.64 Hz, 1H) 5.39 (dd, J = 12.13, 5.05 Hz, 1H) 3.41 (ddd, J = 18.95, 12.13, 1.52 Hz, 1H) 2.59 (ddd, J = 18.88, 4.99, 1.89 Hz, 1H) 1.26 (s, 9H) | 256 |
| 79 | (S)-4-(1-pivaloyl-4,5-dihydro-1H-pyrazol-5-yl)-benzonitrile | 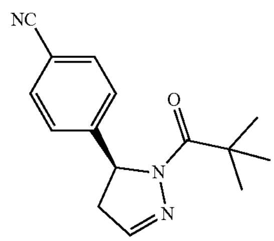 [SMILES: CC(C)(C)C(=O)N1N=CC[C@H]1c1ccc(C#N)cc1] | ¹H NMR (400 MHz, DMSO-d₆) δ = 7.82-7.77 (m, 2H), 7.30-7.25 (m, 2H), 7.20 (t, J = 1.6 Hz, 1H), 5.39 (dd, J = 12.1, 5.0 Hz, 1H), 3.45-3.35 (m, 1H), 2.63-2.54 (m, 1H), 1.25 (s, 9H). LC Method 3: 1.06 min | 256 |
| 80 | 3-(1-pivaloyl-4,5-dihydro-1H-pyrazol-5-yl)benzonitrile | 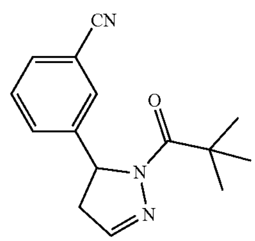 [SMILES: CC(C)(C)C(=O)N1N=CCC1c1cccc(C#N)c1] | ¹H NMR (400 MHz, DMSO-d6) δ ppm 7.68-7.77 (m, 1H) 7.51-7.61 (m, 2H) 7.42 (dt, J = 8.27, 1.29 Hz, 1H) 7.22 (t, J = 1.64 Hz, 1H) 5.37 (dd, J = 12.00, 4.93 Hz, 1H) 3.40 (ddd, J = 18.95, 12.00, 1.64 Hz, 1H) 2.64 (ddd, J = 18.95, 4.93, 1.89 Hz, 1H) 1.25 (s, 9H) | 256 |
| 81 | 2,2-dimethyl-1-(3-methyl-5-phenyl-4,5-dihydro-1H-pyrazol-1-yl)-propan-1-one | 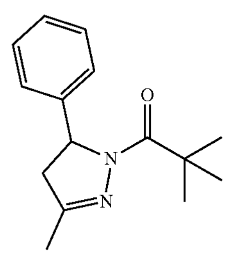 [SMILES: CC1=NN(C(=O)C(C)(C)C)C(c2ccccc2)C1] | ¹H NMR (400 MHz, CDCl₃) δ ppm 1.33 (s, 9H), 2.05 (s, 3H), 2.49-2.58 (m, 1H), 3.17-3.28 (m, 1H), 5.43 (dd, J = 11.8, 4.6 Hz, 1H), 7.09-7.17 (m, 2H), 7.18-7.33 (m, 3H) | 245 |
| 82 | (5-phenyl-4,5-dihydro-1H-pyrazol-1-yl)(1-(trifluoromethyl)cyclopropyl)-methanone | 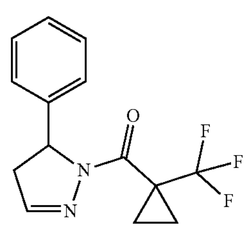 [SMILES: O=C(N1N=CCC1c1ccccc1)C1(C(F)(F)F)CC1] | ¹H NMR (400 MHz, DMSO-d6) δ ppm 7.33 (m, 3H) 7.26 (m, 1H), 7.12 (m, 2H), 5.35 (dd, J = 11., 4.7 Hz, 1H), 3.48 (ddd, J = 18.8, 11.6, 1.5 Hz, 1H), 2.67 (ddd, J = 18.9, 4.7, 1.7 Hz, 1H), 1.31 (m, 4H) LC Method 1: 2.47 min | 283 |
| 83 | 2,2-dimethyl-3-oxo-3-(5-phenyl-4,5-dihydro-1H-pyrazol-1-yl)propanenitrile | 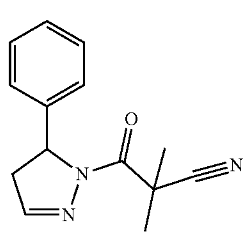 [SMILES: CC(C)(C#N)C(=O)N1N=CCC1c1ccccc1] | ¹H NMR (400 MHz, DMSO-d6) δ ppm 7.42 (s, 1H), 7.35 (m, 2H), 7.27 (m, 1H), 7.14 (d, J = 7.2 Hz, 2H), 5.38 (dd, J = 11.7, 4.5 Hz, 1H), 3.53 (m, 1H), 2.73 (m, 1H), 1.59 (s, 3H), 1.56 (s, 3H) LC Method 1: 2.24 min | 242 |

| Ex | Name | Structure | ¹H NMR | LC retention time (min) | MS (M + H)⁺ |
|---|---|---|---|---|---|
| 84 | 2-methoxy-2-methyl-1-(5-phenyl-4,5-dihydro-1H-pyrazol-1-yl)-propan-1-one | | ¹H NMR (400 MHz, DMSO-d6) δ ppm 7.33 (m, 2H), 7.24 (m, 2H), 7.12 (d, J = 7.2 Hz, 2H), 5.35 (dd, J = 11.8, 4.6 Hz, 1H), 3.41 (dd, 18.7, 11.9 Hz, 1H), 3.08 (s, 3H), 2.6 (m, 1H), 1.44 (s, 3H), 1.42 (s, 3H) LC Method 1: 2.05 min | 247 |
| 85 | 1-(5-phenyl-4,5-dihydro-1H-pyrazole-1-carbonyl)cyclopentanecarbonitrile | | ¹H NMR (400 MHz, DMSO-d6) δ ppm 7.40 (s, 1H), 7.35 (m, 2H), 7.27 (m, 1H), 7.14 (d, J = 7.2 Hz, 2H), 5.37 (dd, J = 11.8, 4.5 Hz, 1H), 3.54 (dd, J = 18.9, 11.8 Hz, 1H), 2.74 (dd, J = 19.1, 1.3 Hz, 1H), 2.28 (m, 4H), 1.71 (m, 4H) LC Method 1: 2.46 min | 268 |
| 86 | (3-methyl-5-phenyl-4,5-dihydro-1H-pyrazol-1-yl)(1-(pyridin-2-yl)-piperidin-4-yl)-methanone | | ¹H NMR (400 MHz, CDCl₃) δ ppm 8.19 (d, J = 4.2 Hz, 2H), 7.51 (t, J = 7.6 Hz, 1H), 7.20-7.41 (m, 3H), 7.15 (d, J = 7.3 Hz, 2H), 6.72 (d, J = 8.8 Hz, 1H), 6.52-6.67 (m, 1H), 5.43 (dd, J = 11.6, 4.5 Hz, 1H), 4.30 (d, J = 13.0 Hz, 2H), 3.21-3.47 (m, 2H), 2.95-3.17 (m, 2H), 2.70 (dd, J = 18.1, 4.4 Hz, 1H), 2.11 (s, 3H), 1.96-2.06 (m, 1H), 1.68-1.96 (m, 3H). LC Method 3: 0.57 min | 349 |
| 87 | (1-(5-fluoro-pyrimidin-2-yl)-piperidin-4-yl)(3-methyl-5-phenyl-4,5-dihydro-1H-pyrazol-1-yl)-methanone | | ¹H NMR (500 MHz, DMSO-d6) δ ppm 8.42 (s, 2H), 7.28-7.44 (m, 2H), 7.20-7.28 (m, 1H), 7.11 (d, J = 7.4 Hz, 2H), 5.35 (dd, J = 11.8, 4.4 Hz, 1H), 4.56 (d, J = 12.9 Hz, 2H), 3.47 (dd, J = 18.4, 11.8 Hz, 1H), 3.18 (br. s., 1H), 2.89-3.12 (m, 2H), 2.62 (dd, J = 18.4, 4.4 Hz, 1H), 2.04 (s, 3H), 1.87 (d, J = 12.4 Hz, 1H), 1.73 (d, J = 12.1 Hz, 1H), 1.35-1.57 (m, 2H). LC Method 2: 1.15 min | 368 |
| 88 | (5-(5-methyl-pyrazin-2-yl)-4,5-dihydro-1H-pyrazol-1-yl)(1-(pyridin-2-yl)-piperidin-4-yl)-methanone | | 1H NMR (400 MHz, DMSO-d6) δ ppm 8.33-8.52 (m, 2H), 7.98-8.13 (m, 1H), 7.49 (ddd, J = 8.7, 6.9, 2.0 Hz, 1H), 6.80 (d, J = 8.6 Hz, 1H), 6.51-6.64 (m, 1H), 5.41 (dd, J = 12.0, 5.4 Hz, 1H), 4.27 (t, J = 13.6 Hz, 2H), 3.44 (ddd, J = 18.8, 12.0, 1.5 Hz, 1H), 3.28 (tt, J = 11.5, 3.9 Hz, 1H), 2.77-3.03 (m, 3H), 2.47 (s, 3H), 1.75 (d, J = 11.1 Hz, 2H), 1.32-1.61 (m, 2H). LC Method 2: 0.39 min | 351 |

| Ex | Name | Structure | $^1$H NMR | LC retention time (min) | MS (M + H)$^+$ |
|---|---|---|---|---|---|
| 89 | (4-methyl-1-(pyrimidin-2-yl)-piperidin-4-yl)(5-(5-methylpyrazin-2-yl)-4,5-dihydro-1H-pyrazol-1-yl)-methanone | 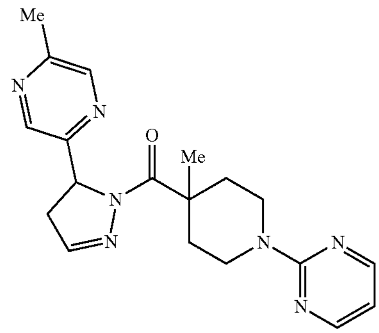 [SMILES: Cc1cnc(C2CC=NN2C(=O)C2(C)CCN(c3ncccn3)CC2)cn1] | 1H NMR (500 MHz, DMSO-d6) δ ppm 8.45 (d, J = 3.6 Hz, 2H), 8.31 (d, J = 4.7 Hz, 2H), 6.56 (t, J = 4.67 Hz, 1H), 5.48 (dd, J = 11.9, 5.4 Hz, 1H), 4.08 (td, J = 9.1, 4.9 Hz, 2H), 3.13-3.28 (m, 1H), 2.82 (dd, J = 18.7, 5.2 Hz, 1H), 2.46 (s, 3H), 2.32 (d, J = 13.2 Hz, 1H), 2.20 (d, J = 13.7 Hz, 1H), 1.35-1.53 (m, 2H), 1.31 (s, 3H), 1.24 (s, 2H). LC Method 2: 0.76 min | | 366 |

Example 90

1-(5-(1H-indol-6-yl)-4,5-dihydro-1H-pyrazol-1-yl)-2,2-dimethylpropan-1-one

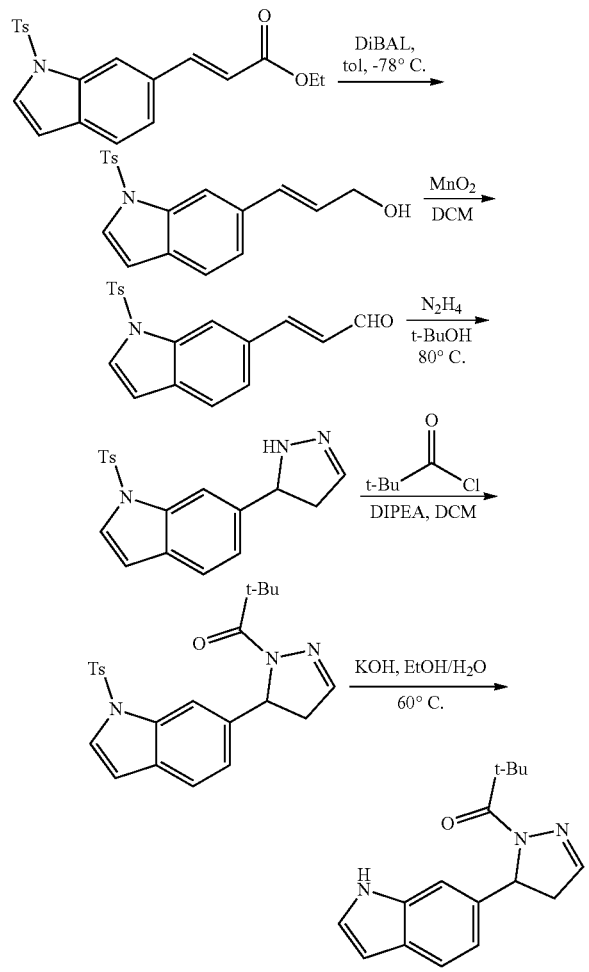

Step 1: Ethyl (2E)-3-{1-[(4-methylbenzene)sulfonyl]-1H-indol-6-yl}prop-2-enoate (3.08 g, 8.34 mmol) was dissolved in 20 ml of toluene dry and cooled to −78° C. To the solution was added DIBAL solution 1M in toluene (23.4 ml, 23.35 mmol) dropwise over 40 minutes, and the reaction was stirred at this temperature for 1 h. The reaction was warmed to −30/20° C. and quenched with EtOAc (6 ml) and saturated aqueous sodium potassium tartrate (Rochelle salts) (50 ml), followed by vigorous stirring for 30 minutes. The aqueous was extracted with EtOAc and the combined organics layer were washed with brine, dried and concentrated under vacuum to give 2.6 g (95%) of the desired alcohol. MS (m/z) 310 (M−OH)$^+$.

Step 2: To a solution of (2E)-3-{1-[(4-methylbenzene)sulfonyl]-1H-indol-6-yl}prop-2-en-1-ol (2.6 g, 7.94 mmol) in 25 ml of DCM dry, MnO$_2$ (13.8 g, 158.83 mmol) was added and the reaction left stirring at rt for 5 hours. The mixture was filtered and the solvent removed under vacuum to give 2.36 g (91%) of the desired aldehyde. MS (m/z) 326 (M+H$^+$).

Step 3: To a stirred solution of (2E)-3-{1-[(4-methylbenzene)sulfonyl]-1H-indol-6-yl}prop-2-enal (2.36 g, 7.25 mmol) in t-BuOH (20 mL), hydrazine (65% in water, 2.7 mL, 36.26 mmol) was added. The reaction was allowed to stir at 80° C. for 4 hours. The solvent was removed in vacuo and the crude was diluted with DCM and washed with NaHCO$_3$ (5% solution). The organic layers were evaporated and purified by Biotage Sp1 System (SNAP340, from Cy/EtOAc 8/2 to 1/1) to give 1.89 g (77%) of the desired product. MS (m/z) 340 (M+H$^+$).

Step 4: To 6-(4,5-dihydro-1H-pyrazol-5-yl)-1-[(4-methylbenzene)sulfonyl]-1H-indole (0.67 g, 1.86 mmol) in dry DCM (5 mL) at 0° C., DIPEA (0.454 mL, 2.6 mmol) was added followed by dropwise addition of 2,2-dimethylpropanoyl chloride (0.251 mL, 2.04 mmol). The reaction was stirred for 4 hours at rt and then washed with 1N HCl, aq. saturated NaHCO$_3$ solution, brine and concentrated. The crude material was purified by Biotage Sp1 System (SNAP50, from Cy 100% to Cy/EtOAc 70/30) to give 540 mg (69%) of the desired compound. MS (m/z) 424 (M+H$^+$).

Step 5: To 2,2-dimethyl-1-(5-{1-[(4-methylbenzene)sulfonyl]-1H-indol-6-yl}-4,5-dihydro-1H-pyrazol-1-yl)propan-1-one (0.303 g, 0.72 mmol), in dry EtOH (4 mL) and water (2 mL), KOH (0.803 mL, 14.31 mmol) was added. The reaction was stirred at 60° C. overnight. After cooling, ice-water and 1N HCl were added to the reaction mixture, and then it was extracted with DCM. The organic layer was concentrated to give 309 mg of 1-(5-(1H-indol-6-yl)-4,5-dihydro-1H-pyrazol-1-yl)-2,2-dimethylpropan-1-one, which was submitted to preparative LC/MS to afford the title compound 58.4 mg (30%) of the title compound. MS (m/z) 270 (M+H$^+$). $^1$H NMR (400 MHz, DMSO-d$_6$) δ ppm 11.02 (br. s., 1H) 7.46 (d, J=8.08 Hz, 1H) 7.25-7.35 (m, 1H) 7.20 (t, J=1.52 Hz, 1H) 7.09 (s, 1H) 6.75 (dd, J=8.08, 1.52 Hz, 1H) 6.31-6.41 (m, 1H) 5.39 (dd, J=11.87, 4.29 Hz, 1H) 3.40 (ddd, J=18.82, 11.87, 1.64 Hz, 1H) 2.60 (ddd, J=18.76, 4.36, 1.89 Hz, 1H) 1.15-1.35 (m, 9H).

The following compounds were synthesized in an analogous manner. LiOH was substituted for KOH in Example 92.

| Ex | Name | Structure | ¹H NMR | MS (M + H)⁺ |
|----|------|-----------|--------|-------------|
| 91 | (S)-1-(5-(1H-indol-5-yl)-4,5-dihydro-1H-pyrazol-1-yl)-2,2-dimethylpropan-1-one | 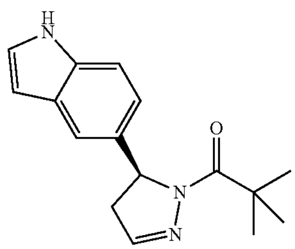 [SMILES: CC(C)(C)C(=O)N1N=CC[C@H]1c1ccc2[nH]ccc2c1] | ¹H NMR (400 MHz, DMSO-d6) δ ppm 11.04 (br. s., 1H), 7.32 (m, 2H), 7.25 (s, 1H), 7.19 (s, 1H), 6.83 (dd, J = 8.3, 1.5 Hz, 1H), 6.37 (br. s., 1H), 5.37 (dd, J = 11.7, 4.2 Hz, 1H), 3.34-3.44 (m, 1H), 2.60 (dt, J = 18.7, 2.1 Hz, 1H), 1.26 (s, 9H) | 270 |
| 92 | 1-(5-(1H-indol-4-yl)-4,5-dihydro-1H-pyrazol-1-yl)-2,2-dimethylpropan-1-one | 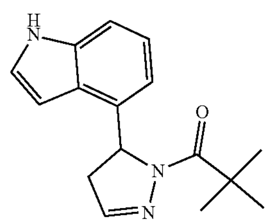 [SMILES: CC(C)(C)C(=O)N1N=CCC1c1cccc2[nH]ccc12] | ¹H NMR (400 MHz, DMSO-d6) δ ppm 11.16 (br. s., 1H), 7.34 (t, J = 2.8 Hz, 1H), 7.21-7.30 (m, 2H), 6.95-7.02 (m, 1H), 6.65 (d, J = 7.1 Hz, 1H), 6.36 (dt, J = 2.0, 1.0 Hz, 1H), 5.61 (dd, J = 12.0, 5.2 Hz, 1H), 3.46 (ddd, J = 18.8, 12.1, 1.6 Hz, 1H), 2.56 (ddd, J = 18.8, 5.2, 1.8 Hz, 1H), 1.27 (s, 9H) | 270 |
| 93 | (S)-1-(5-(1H-indol-4-yl)-4,5-dihydro-1H-pyrazol-1-yl)-2,2-dimethylpropan-1-one | 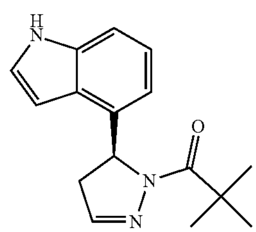 [SMILES: CC(C)(C)C(=O)N1N=CC[C@H]1c1cccc2[nH]ccc12] | ¹H NMR (400 MHz, DMSO-d6) δ ppm 11.16 (br. s., 1H), 7.34 (t, J = 2.7 Hz, 1H), 7.27 (d, J = 8.1 Hz, 1H), 7.23 (s, 1H), 6.99 (t, J = 7.7 Hz, 1H), 6.65 (d, J = 7.3 Hz, 1H), 6.36 (br. s., 1H), 5.61 (dd, J = 12.1, 5.1 Hz, 1H), 3.46 (dd, J = 18.7, 12.1 Hz, 1H), 2.52-2.60 (m, 1H), 1.27 (s, 9H) | 270 |

Example 94

(1-(benzo[d]oxazol-2-yl)piperidin-4-yl)(5-(pyridin-3-yl)-4,5-dihydro-1H-pyrazol-1-yl)methanone

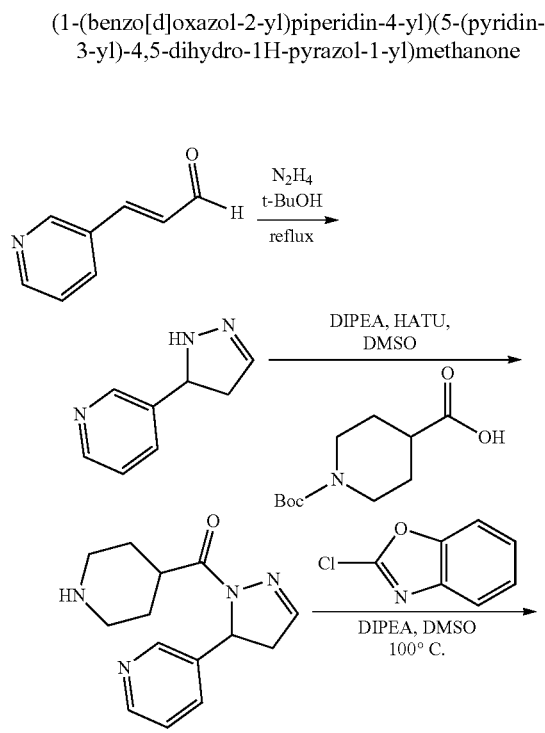

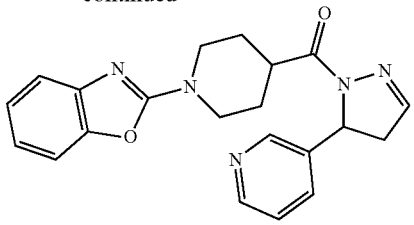

-continued

Step 1: Hydrazine was heated to reflux in a rbf under a nitrogen atmosphere. To the refluxing solution was added dropwise (E)-3-(pyridin-3-yl)acrylaldehyde (2 g, 15.02 mmol) in tert-butanol (20 mL). The mixture was heated overnight. The next day the reaction was concentrated and purified by normal phase HPLC. Conditions used 10% MeOH in DCM/DCM with a gradient from 20% to 80% over 10 minutes. Pure fractions were concentrated to provide 1.08 g (49%) of the desired product. MS (m/z) 148 (M+H⁺).

Step 2: To a solution of 3-(4,5-dihydro-1H-pyrazol-5-yl)pyridine (0.3 g, 2.038 mmol) in DMSO (20 mL) was added DIPEA (0.712 mL, 4.08 mmol) followed by 1-(tert-butoxycarbonyl)piperidine-4-carboxylic acid (0.467 g, 2.04 mmol). The mixture was stirred and then HATU (1.163 g, 3.06 mmol) was added. The reaction turned yellow and then was stirred overnight at 25° C. LCMS the next day showed product. This reaction mixture was immediately injected onto a prep HPLC system and purified under acidic conditions. Pure fractions were concentrated down under slight heat and a nitrogen stream. The Boc group was cleaved under these conditions and carried onto the next reaction. MS (m/z) 259 (M+H⁺).

Step 3: To a solution of piperidin-4-yl(5-(pyridin-3-yl)-4,5-dihydro-1H-pyrazol-1-yl)methanone (500 mg, 1.936 mmol) in DMSO (1 mL) was added 2-chlorobenzo[d]oxazole (297 mg, 1.94 mmol). The reaction was heated at 100° C. for 20 minutes. LCMS indicates product. The crude material was purified under acidic conditions where pure fractions were collected and concentrated to provide 75 mg (8%) of the title compound. MS (m/z) 376 (M+H⁺). ¹H NMR (DMSO-d₆) δppm 1.52-1.69 (m, 2H), 1.79-1.98 (m, 2H), 2.83-2.94 (m, 1H), 3.18-3.41 (m, 3H), 3.55 (ddd, J=19.1, 12.1, 1.6 Hz, 1H), 4.09-4.19 (m, 2H), 5.42-5.54 (m, 1H), 6.97-7.19 (m, 3H), 7.24-7.44 (m, 4H), 7.65-7.80 (m, 1H), 7.91-8.05 (m, 1H).

Example 95

(1-(cyclobutanecarbonyl)piperidin-4-yl)(5-phenyl-4,5-dihydro-1H-pyrazol-1-yl)methanone

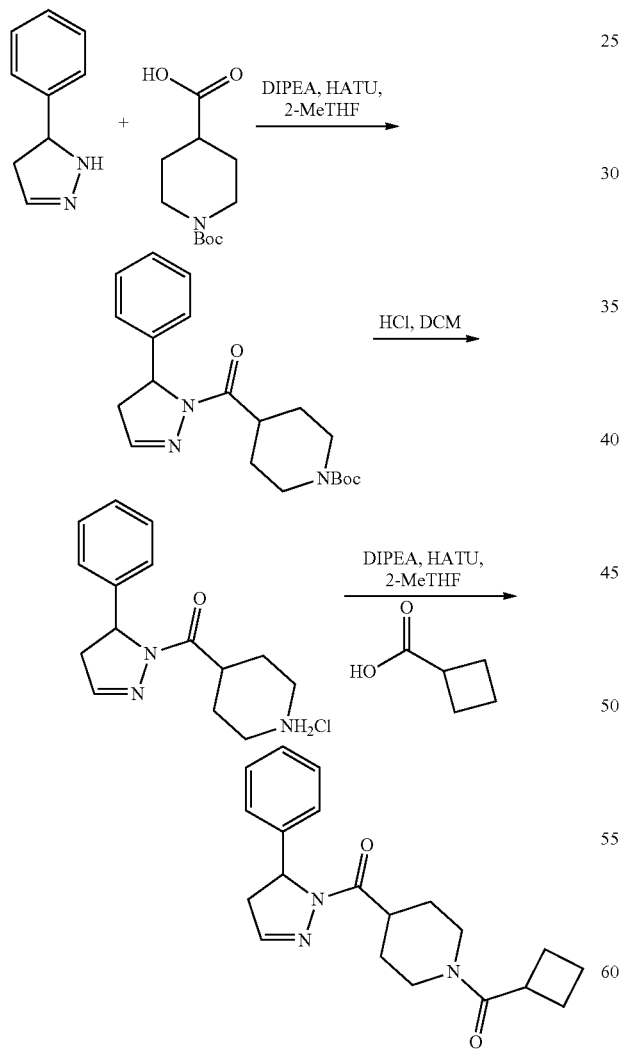

Step 1: To a solution of Boc-Inp-OH (5.18 g, 22.57 mmol) in 2-MeTHF (50 mL) was added DIPEA (7.17 mL, 41.0 mmol), HATU (10.92 g, 28.7 mmol) then 5-phenyl-4,5-dihydro-1H-pyrazole (3 g, 20.52 mmol). The reaction mixture was stirred overnight at rt. The reaction mixture was taken in EtOAc and washed with H₂O and saturated NaHCO₃. The organic layer was dried over anhydrous Na₂SO₄, filtered and concentrated in vacuo. The product was purified by chromatography [silica, CyH/(EtOAc-EtOH 3/1) 100/0 to 30/70]. The residue was triturated in diethyl ether to afford tert-butyl 4-(5-phenyl-4,5-dihydro-1H-pyrazole-1-carbonyl)piperidine-1-carboxylate (4.5 g, 12.59 mmol, purity: >95% by LCMS recovery: 61%) as a white powder. LCMS (m/z) 302 (M+H⁺), retention time: 2.68 min, method 1 20V.

Step 2: To a solution of tert-butyl 4-(5-phenyl-4,5-dihydro-1H-pyrazole-1-carbonyl)piperidine-1-carboxylate (16.7 g, 46.7 mmol) in dichloromethane (200 mL) was added HCl 3M in CPME (62.3 mL, 187 mmol). The reaction mixture was stirred for 72 h at rt. The precipitate was filtered off and washed with diisopropyl ether. The solid was dried under high vacuum at 45° C. to afford (5-phenyl-4,5-dihydro-1H-pyrazol-1-yl)(piperidin-4-yl)methanone, Hydrochloride (13 g, 44.2 mmol, purity: >95% by LCMS, recovery: 95%) as a cream powder. LCMS (m/z) 258 (M+H⁺) corresponding to the free amine, retention time: 1.00 min, method 1 20V.

Step 3: To a solution of cyclobutanecarboxylic acid (0.096 mL, 1.021 mmol) in 2-MeTHF (5 mL) was added DIPEA (0.357 mL, 2.042 mmol), HATU (388 mg, 1.021 mmol) then (5-phenyl-4,5-dihydro-1H-pyrazol-1-yl)(piperidin-4-yl)methanone, Hydrochloride (200 mg, 0.681 mmol). The reaction mixture was stirred overnight at rt. The reaction mixture was taken in EtOAc and washed with H₂O, HCl 0.5 M and saturated NaHCO₃. The organic layer was dried over anhydrous Na₂SO4, filtered and concentrated in vacuo. The residue was purified by chromatography [silica, CyH/(EtOAc-EtOH 3/1) 100/0 to 50/50 to give the pure expected product as a gum. Trituration into diisopropyl ether afforded (1-(cyclobutanecarbonyl)piperidin-4-yl)(5-phenyl-4,5-dihydro-1H-pyrazol-1-yl)methanone (95 mg, 0.280 mmol, purity: >95% by LCMS, recovery: 41% yield) as a white powder. LCMS (m/z) 340 (M+H⁺), retention time: 2.26 min, method 1 20V. ¹H NMR (400 MHz, CHCl₃) δ ppm 7.34 (m, 2H), 7.28 (s, 1H), 7.16 (m, 2H), 6.99 (t, J=1.6 Hz, 1H), 5.37 (dd, J=11.9, 4.8 Hz, 1H), 4.2 (br s, 1H), 3.44 (ddd, J=18.8, 12.0, 1.5 Hz, 1H), 3.33 (tt, J=11.2, 3.8 Hz, 1H), 3.25 (m, 1H), 2.91 (br s, 2H), 2.84 (m, 1H), 2.35 (m, 2H), 2.14 (m, 2H), 1.91 (m, 5H), 1.65 (m, 2H).

The following intermediate was synthesis in analogous manner:

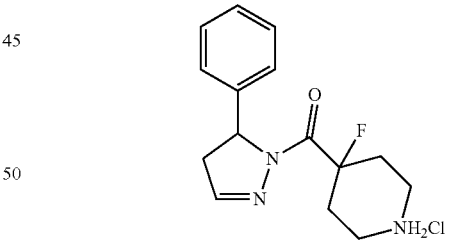

The second step was applied for the synthesis of this intermediate:

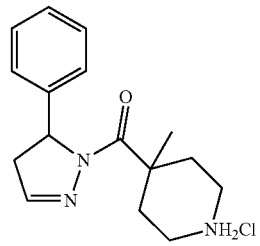

The following compounds were synthesized in an analogous manner. 2-MeTHF may be substituted for DCM, THF and DMF. HATU may be substituted for T3P.

| Ex | Name | Structure | ¹H NMR LC: retention time (min) | MS (M + H)⁺ |
|---|---|---|---|---|
| 96 | (1-(cyclohexane carbonyl) piperidin-4-yl) (5-phenyl-4,5-dihydro-1H-pyrazol-1-yl)-methanone | 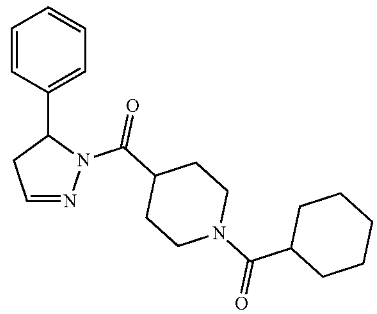 [SMILES: O=C(C1CCCCC1)N1CCC(C(=O)N2N=CCC2c2ccccc2)CC1] | ¹H NMR (400 MHz, DMSO-d6) δ ppm, 7.32 (dd, J = 7.6, 7.2 Hz, 2H), 7.23 (m, 2H), 7.1 (d, J = 7.6 Hz, 2H), 5.30 (dd, J = 11.9, 4.6 Hz, 1H), 4.38 (m, 1H), 3.95 (d, J = 13.3 Hz, 1H), 3.46 (m, 2H), 3.30 (m, 1H), 3.09 (br s, 1H), 2.67 (ddd, J = 18.8, 4.6, 1.7 Hz, 1H), 2.57 (m, 2H), 1.85 (m, 1H), 1.65 (m, 6H), 1.1-1.5 (m, 6H) LC Method: 2.52 min | 368 |
| 97 | 1-(4-(5-phenyl-4,5-dihydro-1H-pyrazole-1-carbonyl)piperidin-1-yl)propan-1-one | 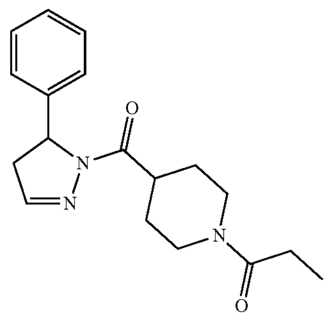 [SMILES: CCC(=O)N1CCC(C(=O)N2N=CCC2c2ccccc2)CC1] | ¹H NMR (400 MHz, DMSO-d6) δ ppm 7.32 (dd, J = 7.6, 7.2 Hz, 2H), 7.24 (m, 2H), 7.1 (d, J = 7.6 Hz, 2H), 5.32 (dd, J = 12.0, 4.6 Hz, 1H), 4.37 (br s, 1H), 3.86 (d, J = 12.9 Hz, 1H), 3.49 (dd, J = 18.4, 12.5 Hz, 1H), 3.29 (m, 1H), 3.08 (t, J = 11.5 Hz, 1H), 2.66 (m, 2H), 2.30 (q, J = 7.4 Hz, 2H), 1.83 (d, J = 12.3 Hz, 1H), 1.71 (m, 1H), 1.39 (m, 2H), 0.97 (t, J = 7.4 Hz, 3H) LC Method: 2.02 min | 314 |
| 98 | 2-methyl-1-(4-(5-phenyl-4,5-dihydro-1H-pyrazole-1-carbonyl)piperidin-1-yl)propan-1-one | 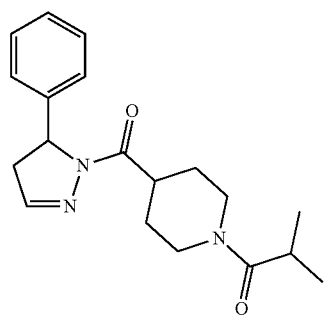 [SMILES: CC(C)C(=O)N1CCC(C(=O)N2N=CCC2c2ccccc2)CC1] | ¹H NMR (400 MHz, CHCl3-d6) δ ppm, 7.3 (m, 3H), 7.6 (m, 2H), 7 (s, 1H), 5.38 (dd, J = 12.0, 4.9 Hz, 1H), 4.61 (m, 1H), 3.99 (m, 1H), 3.47 (dd, 18.8, 12.3 Hz, 1H), 3.36 (m, 1H), 3.15 (t, J = 11.9 Hz, 1H), 2.82 (m, 3H), 1.75 (m, 4H), 1.13 (d, J = 6.6 Hz, 6H) LC Method 1: 2.16 min | 328 |
| 99 | (5-phenyl-4,5-dihydro-1H-pyrazol-1-yl)(1-picolinoylpiperidin-4-yl)methanone | 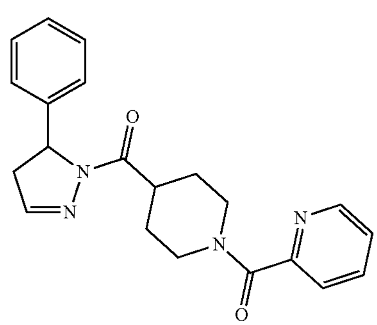 [SMILES: O=C(c1ccccn1)N1CCC(C(=O)N2N=CCC2c2ccccc2)CC1] | ¹H NMR (400 MHz, DMSO-d6) δ ppm, 8.58 (d, J = 4.6 Hz, 1H), 7.91 (t, J = 7.6 Hz, 1H), 7.53 (d, J = 7.8 Hz, 1H), 7.46 (dd, J = 7.1, 5.2 Hz, 1H), 7.32 (m, 2H), 7.25 (m, 2H), 7.11 (t, J = 7.8 Hz, 2H), 5.32 (m, 1H), 4.49 (m, 1H), 3.62 (m, 1H), 3.49 (m, 1H), 3.38 (m, 1H), 3.13 (m, 1H), 2.93 (m, 1H), 2.67 (d, J = 18.8 Hz, 1H), 1.5-2 (m, 4H) LC Method 1: 1.97 min | 363 |

| Ex | Name | Structure | ¹H NMR LC: retention time (min) | MS (M + H)⁺ |
|---|---|---|---|---|
| 100 | (5-phenyl-4,5-dihydro-1H-pyrazol-1-yl)(1-(pyrimidine-2-carbonyl)piperidin-4-yl)methanone | 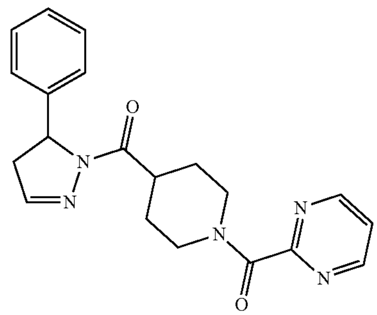 [SMILES: O=C(c1ncccn1)N1CCC(C(=O)N2N=CCC2c2ccccc2)CC1] | ¹H NMR (400 MHz, DMSO-d6) δ ppm, 8.88 (d, J = 4.7 Hz, 1H), 7.58 (t, J = 4.9 Hz, 1H), 7.32 (m, 2H), 7.25 (m, 2H), 7.1 (t, J = 8.4 Hz, 2H), 5.31 (dd, J = 11.7, 4.1 Hz, 1H), 4.46 (m, 1H), 3.62 (m, 1H), 3.46 (m, 2H), 3.23 (m, 2H), 3.13 (m, 1H), 2.96 (m, 1H), 2.67 (d, J = 19.0 Hz, 1H), 1.7-2 (m, 2H), 1.52 (m, 2H) LC Method 1: 1.83 min | 364 |
| 101 | (1-(4-morpholinobenzoyl)piperidin-4-yl)(5-phenyl-4,5-dihydro-1H-pyrazol-1-yl)methanone | 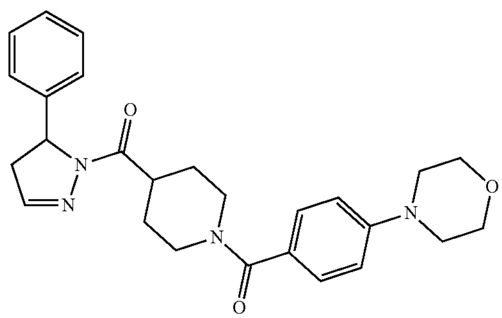 [SMILES: O=C(c1ccc(N2CCOCC2)cc1)N1CCC(C(=O)N2N=CCC2c2ccccc2)CC1] | ¹H NMR (400 MHz, DMSO-d6) δ ppm, 7.32 (m, 2H), 7.26 (dd, 10.1, 8.7 Hz, 4H), 7.11 (d, J = 7.4 Hz, 2H), 6.95 (d, J = 8.7 Hz, 2H), 5.31 (dd, J = 11.9, 4.6 Hz, 1H), 4.2 (br s, 2H), 3.73 (t, J = 4.7 Hz, 4H), 3.49 (dd, J = 18.8, 12 Hz, 1H), 3.36 (m, 1H), 3.17 (t, J = 4.7 Hz, 4H), 3.0 (br s, 2H), 2.65 (m, 1H), 1.85 (d, J = 12.0 Hz, 1H), 1.72 (d, J = 12.0 Hz, 1H), 1.48 (m, 2H) LC Method 1: 2.26 min | 447 |
| 102 | (1-(5-chloropicolinoyl)piperidin-4-yl)(5-phenyl-4,5-dihydro-1H-pyrazol-1-yl)methanone | 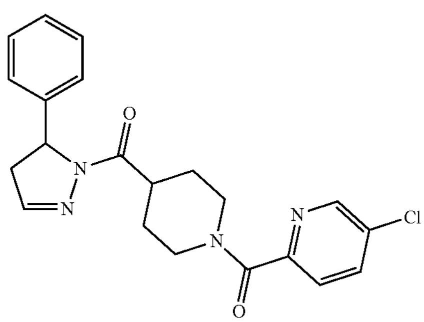 [SMILES: O=C(c1ccc(Cl)cn1)N1CCC(C(=O)N2N=CCC2c2ccccc2)CC1] | ¹H NMR (400 MHz, DMSO-d6) δ ppm, 8.64 (d, J = 2.5 Hz, 1H), 8.05 (m, 1H), 7.6 (d, J = 8.4 Hz, 1H), 7.32 (m, 2H), 7.24 (m, 2H), 7.10 (t, J = 7.5 Hz, 2H), 5.31 (m, 1H), 4.46 (m, 1H), 3.66 (m, 1H), 3.49 (m, 1H), 3.39 (tt, J = 11.3, 3.8 Hz, 1H), 3.14 (m, 1H), 2.93 (m, 1H), 2.67 (m, 1H), 1.4-2 (m, 4H) LC Method 1: 2.29 min | 397 |
| 103 | (1-isonicotinoylpiperidin-4-yl)(5-phenyl-4,5-dihydro-1H-pyrazol-1-yl)methanone | 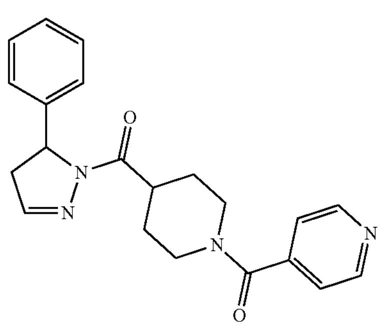 [SMILES: O=C(c1ccncc1)N1CCC(C(=O)N2N=CCC2c2ccccc2)CC1] | ¹H NMR (400 MHz, DMSO-d6) δ ppm, 8.65 (d, J = 5.3 Hz, 2H), 7.37 (d, J = 5.5 Hz, 2H), 7.31 (m, 2H), 7.24 (s, 2H), 7.11 (t, J = 7.0 Hz, 2H), 5.32 (dd, J = 11.7, 3.9 Hz, 1H), 4.45 (m, 1H), 3.63 (m, 1H), 3.49 (m, 1H), 3.38 (m, 1H), 3.15 (m, 1H), 2.93 (m, 1H), 2.68 (d, J = 18.7 Hz, 1H), 1.97 (m, 1H), 1.81 (m, 1H), 1.56 (m, 2H) LC Method 1: 1.65 min | 363 |

-continued

| Ex | Name | Structure | ¹H NMR LC: retention time (min) | MS (M + H)⁺ |
|---|---|---|---|---|
| 104 | (1-(6-methyl-picolinoyl)piperidin-4-yl)(5-phenyl-4,5-dihydro-1H-pyrazol-1-yl)methanone | 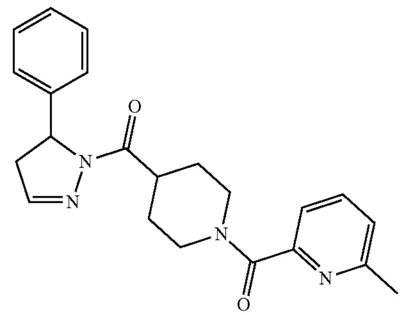 [SMILES: Cc1cccc(C(=O)N2CCC(C(=O)N3N=CCC3c3ccccc3)CC2)n1] | ¹H NMR (400 MHz, DMSO-d6) δ ppm, 7.78 (t, J = 7.7 Hz, 1H), 7.29 (m, 6H), 7.11 (t, J = 7.5 Hz, 2H), 5.31 (m, 1H), 4.47 (m, 1H), 3.64 (m, 1H), 3.49 (m, 1H), 3.38 (m, 1H), 3.12 (m, 1H), 2.91 (m, 1H), 2.67 (m, 1H), 2.48 (s, 3H), 1.45-2 (m, 4H) LC Method 1: 2.01 min | 377 |
| 105 | (1-(6-chloro-picolinoyl)piperidin-4-yl)(5-phenyl-4,5-dihydro-1H-pyrazol-1-yl)methanone | 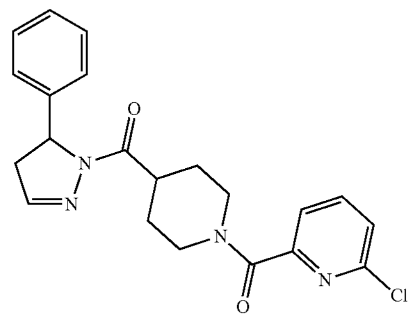 [SMILES: O=C(c1cccc(Cl)n1)N1CCC(C(=O)N2N=CCC2c2ccccc2)CC1] | ¹H NMR (400 MHz, DMSO-d6) δ ppm, 7.98 (m, 1H), 7.61 (d, J = 8.2 Hz, 1H), 7.56 (d, J = 7.6 Hz, 1H), 7.28 (m, 4H), 7.11 (t, J = 7.1 Hz, 2H), 5.32 (dd, J = 11.9, 2.9 Hz, 1H), 4.45 (d, J = 9.3 Hz, 1H), 3.58 (m, 1H), 3.49 (m, 1H), 3.39 (m, 1H), 3.16 (m, 1H), 2.95 (m, 1H), 2.68 (m, 1H), 1.45-2 (m, 4H) LC Method 1: 2.27 min | 397 |
| 106 | (1-(6-chloro-nicotinoyl)piperidin-4-yl)(5-phenyl-4,5-dihydro-1H-pyrazol-1-yl)methanone | 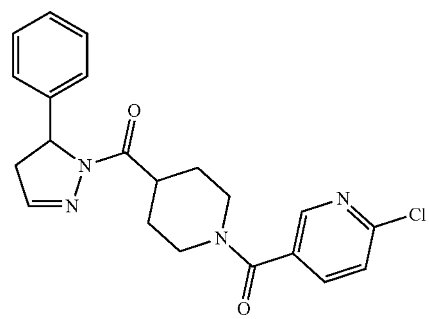 [SMILES: O=C(c1ccc(Cl)nc1)N1CCC(C(=O)N2N=CCC2c2ccccc2)CC1] | ¹H NMR (400 MHz, DMSO-d6) δ ppm, 8.45 (d, J = 1.7 Hz, 1H), 7.9 (dd, J = 8.2, 2.3 Hz, 1H), 7.6 (d, J = 8.2 Hz, 1H), 7.32 (br s, 2H), 7.24 (s, 2H), 7.11 (m, 2H), 5.32 (dd, J = 11.8, 4.4 Hz, 1H), 4.44 (m, 1H), 3.48 (m, 2H), 3.36 (m, 1H), 3.19 (m, 1H), 2.94 (m, 1H), 2.68 (dd, J = 18.8, 3.2 Hz, 1H), 1.5-2 (m, 4H) LC Method 1: 2.21 min | 397 |
| 107 | (1-nicotinoyl-piperidin-4-yl)(5-phenyl-4,5-dihydro-1H-pyrazol-1-yl)-methanone | 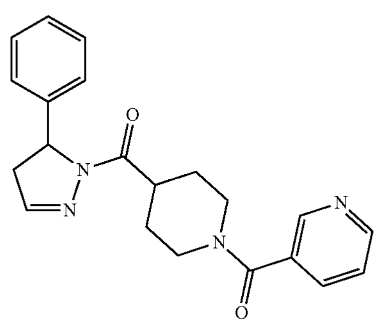 [SMILES: O=C(c1cccnc1)N1CCC(C(=O)N2N=CCC2c2ccccc2)CC1] | ¹H NMR (400 MHz, DMSO-d6) δ ppm, 8.64 (dd, J = 4.7, 1.7 Hz, 1H), 8.58 (d, J = 1.3 Hz, 1H), 7.82 (dt, 7.8, 1.9 Hz, 1H), 7.47 (dd, J = 7.8, 4.9 Hz, 1H), 7.32 (m, 2H), 7.25 (m, 2H), 7.11 (d, J = 7.0 Hz, 2H), 5.32 (dd, J = 11.8, 4.6 Hz, 1H), 4.46 (m, 1H), 3.49 (m, 2H), 3.38 (m, 1H), 3.20 (m, 1H), 2.94 (d, J = 10.2 Hz, 1H), 2.68 (ddd, J = 8.8, 4.5, 1.5 Hz, 1H), 1.5-2 (m, 4H) LC Method 1: 1.77 min | 363 |
| 108 | (1-(5-fluoro-picolinoyl)piperidin-4-yl)(5-phenyl-4,5-dihydro-1H-pyrazol-1-yl)methanone | 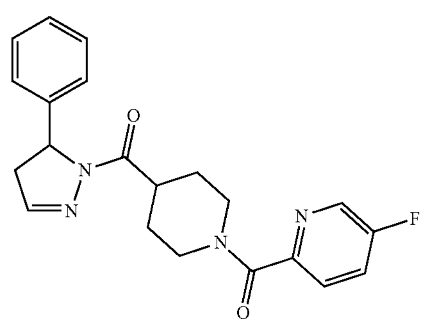 [SMILES: O=C(c1ccc(F)cn1)N1CCC(C(=O)N2N=CCC2c2ccccc2)CC1] | ¹H NMR (400 MHz, DMSO-d6) δ ppm, 8.59 (d, J = 2.8 Hz, 1H), 7.85 (td, J = 8.7, 2.8 Hz, 1H), 7.67 (dd, J = 8.6, 4.6 Hz, 1H), 7.28 (m, 4H), 7.11 (t, J = 7.3 Hz, 2H), 5.32 (m, 1H), 4.47 (d, J = 9.3 Hz, 1H), 3.68 (d, J = 12.5 Hz, 1H), 3.49 (m, 1H), 3.39 (tt, J = 11.3, 3.8 Hz, 1H), 3.15 (m, 1H), 2.93 (m, 1H), 2.67 (m, 1H), 1.6-2 (m, 2H), 1.53 (m, 2H) LC Method 1: 2.12 min | 381 |

-continued

| Ex | Name | Structure | ¹H NMR LC: retention time (min) | MS (M + H)⁺ |
|---|---|---|---|---|
| 109 | (1-(4-chloro-benzoyl)piperidin-4-yl)(5-phenyl-4,5-dihydro-1H-pyrazol-1-yl)-methanone | 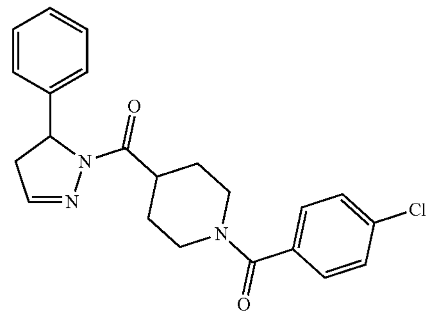 [SMILES: O=C(c1ccc(Cl)cc1)N1CCC(C(=O)N2N=CCC2c2ccccc2)CC1] | ¹H NMR (400 MHz, DMSO-d6) δ ppm, 7.50 (d, J = 7.5 Hz, 2H), 7.41 (d, J = 7.4 Hz, 2H), 7.31 (t, J = 7.0 Hz, 2H), 7.25 (m, 2H), 7.11 (d, J = 7.2 Hz, 2H), 5.31 (dd, J = 11.9, 4.5 Hz, 1H), 4.44 (m, 1H), 3.58 (m, 1H), 3.49 (dd, J = 18.8, 12.1 Hz, 1H), 3.37 (m, 1H), 3.14 (m, 1H), 2.92 (m, 1H), 2.65 (dd, J = 18.8, 3.2 Hz, 1H), 1.7 (m, 2H), 1.5 (m, 2H) LC Method 1: 2.54 min | 396 |
| 110 | 2-phenyl-1-(4-(5-phenyl-4,5-dihydro-1H-pyrazole-1-carbonyl)piperidin-1-yl)ethanone | 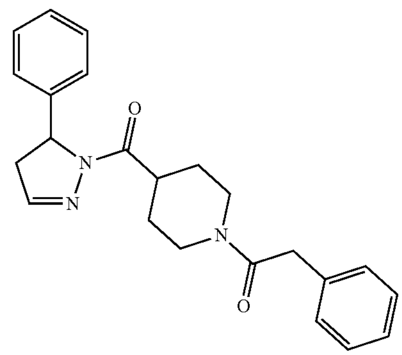 [SMILES: O=C(Cc1ccccc1)N1CCC(C(=O)N2N=CCC2c2ccccc2)CC1] | ¹H NMR (400 MHz, DMSO-d6) δ ppm, 7.31 (m, 4H), 7.22 (m, 5H), 7.09 (d, J = 7.4 Hz, 2H), 5.29 (dd, J = 11.9, 3.5 Hz, 1H), 4.38 (d, J = 9.5 Hz, 1H), 3.97 (d, J = 12.9 Hz, 1H), 3.72 (s, 2H), 3.48 (dd, J = 18.2, 12.5 Hz, 1H), 3.28 (ddt, J = 11.4, 7.7, 3.7 Hz, 1H), 3.08 (m, 1H), 2.67 (m, 2H), 1.75 (m, 2H), 1.31 (m, 2H) LC Method 1: 2.39 min | 376 |
| 111 | 1-(4-methoxy-benzoyl)piperidin-4-yl)(5-phenyl-4,5-dihydro-1H-pyrazol-1-yl)methanone | 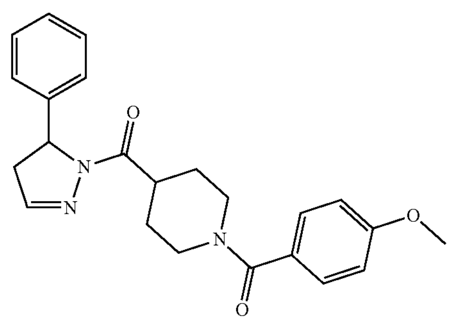 [SMILES: COc1ccc(C(=O)N2CCC(C(=O)N3N=CCC3c3ccccc3)CC2)cc1] | ¹H NMR (400 MHz, DMSO-d6) δ ppm, 7.33 (m, 4H), 7.24 (m, 2H), 7.11 (d, J = 7.2 Hz, 2H), 6.97 (d, J = 8.5 Hz, 2H), 5.31 (dd, J = 11.8, 4.6 Hz, 1H), 4.40 (br s, 1H), 3.79 (s, 3H), 3.8 (br s, 1H), 3.49 (ddd, J = 18.9, 12.1, 1.2 Hz, 1H), 3.37 (m, 1H), 3.02 (br s, 2H), 2.67 (ddd, J = 18.9, 4.6, 1.5 Hz, 1H), 1.85 (br s, 1H), 1.75 (br s, 1H), 1.49 (2H) LC Method 1: 2.34 min | 392 |
| 112 | (5-phenyl-4,5-dihydro-1H-pyrazol-1-yl)(1-(thiazole-2-carbonyl)piperidin-4-yl)methanone | 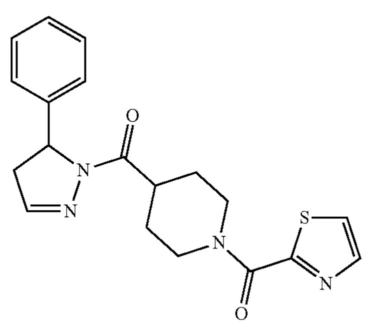 [SMILES: O=C(c1nccs1)N1CCC(C(=O)N2N=CCC2c2ccccc2)CC1] | ¹H NMR (400 MHz, DMSO-d6) δ ppm, 8.02 (d, J = 3.2 Hz, 1H), 8.00 (d, J = 3.2 Hz, 1H), 7.32 (t, J = 7.4 Hz, 2H), 7.24 (m, 2H), 7.11 (d, J = 7.4 Hz, 2H), 5.32 (dd, J = 12.0, 4.6 Hz, 1H), 5.19 (d, J = 10.6 Hz, 1H), 4.44 (d, J = 11.2 Hz, 1H), 3.50 (ddd, J = 18.8, 12.0, 1.3 Hz, 1H), 3.41 (m, 2H), 3.01 (m, 1H), 2.68 (ddd, J = 18.8, 4.6, 1.6 Hz, 1H), 1.95 (m, 1H), 1.82 (m, 1H), 1.55 (m, 2H) LC Method 1: 2.23 min | 369 |

-continued

| Ex | Name | Structure | ¹H NMR LC: retention time (min) | MS (M + H)⁺ |
|---|---|---|---|---|
| 113 | (5-cyclopropyl isoxazol-3-yl)(4-(5-phenyl-4,5-dihydro-1H-pyrazole-1-carbonyl)piperidin-1-yl)methanone | 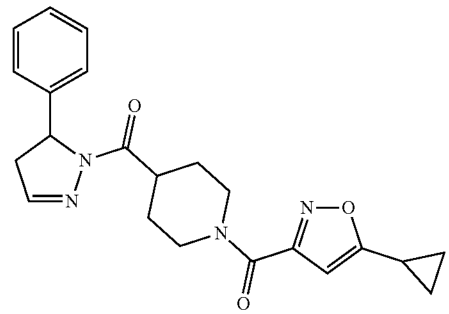 [SMILES: O=C(c1cc(C2CC2)on1)N1CCC(C(=O)N2N=CCC2c2ccccc2)CC1] | ¹H NMR (400 MHz, DMSO-d6) δ ppm, 7.32 (m, 2H), 7.24 (m, 2H), 7.11 (m, 2H), 6.41 (s, 1H), 5.31 (dd, J = 11.8, 4.2 Hz, 1H), 4.43 (d, J = 9.5 Hz, 1H), 3.89 (d, J = 12 Hz, 1H), 3.49 (dd, 18.8, 12.0 Hz, 1H), 3.4 (ddd, J = 11.2, 7.6, 4.0 Hz, 1H), 3.21 (m, 1H), 2.94 (m, 1H), 2.65 (m, 1H), 2.18 (m, 1H), 1.85 (m, 1H), 1.45 (m, 2H), 0.99 (m, 5H) LC Method 1: 2.43 min | 393 |
| 114 | oxazol-4-yl(4-(5-phenyl-4,5-dihydro-1H-pyrazole-1-carbonyl)piperidin-1-yl)methanone | 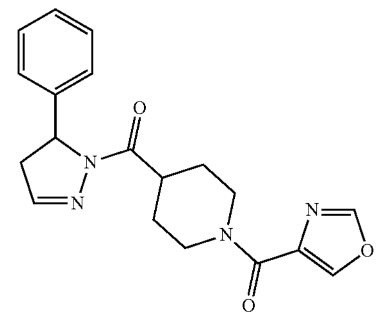 [SMILES: O=C(c1cocn1)N1CCC(C(=O)N2N=CCC2c2ccccc2)CC1] | ¹H NMR (400 MHz, DMSO-d6) δ ppm, 8.55 (d, J = 0.9 Hz, 1H), 8.49 (d, J = 0.9 Hz, 1H) 7.31 (dd, J = 7.6, 7.2 Hz, 2H), 7.24 (m, 2H), 7.11 (d, J = 7.2 Hz, 2H), 5.32 (dd, J = 11.9, 4.6 Hz, 1H), 4.46 (br s, 2H), 3.49 (ddd, J = 18.9, 12.0, 1.4 Hz, 1H), 3.41 (tt, J = 11.4, 3.8 Hz, 1H), 3.23 (br s, 1H), 2.88 (br s, 1H), 2.68 (ddd, J = 18.9, 4.6, 1.7 Hz, 1H), 1.89 (br s, 1H), 1.77 (br s, 1H), 1.5 (br s, 2H) LC Method 1: 1.95 min | 353 |
| 115 | (1-methyl-1H-imidazol-2-yl)(4-(5-phenyl-4,5-dihydro-1H-pyrazole-1-carbonyl)piperidin-1-yl)methanone | 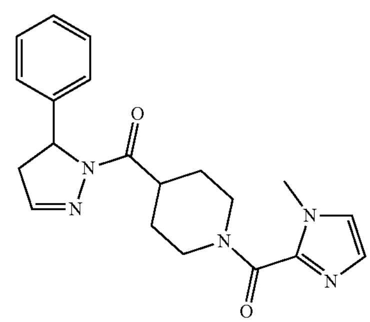 [SMILES: Cn1ccnc1C(=O)N1CCC(C(=O)N2N=CCC2c2ccccc2)CC1] | ¹H NMR (400 MHz, DMSO-d6) δ ppm, 7.29 (m, 5H), 7.11 (d, J = 6.1 Hz, 2H), 6.96 (s, 1H), 5.32 (dd, J = 12.0, 4.6 Hz, 1H), 4.49 (dd, J = 18.6, 14.4 Hz, 2H), 3.97 (s, 3H), 3.5 (dd, J = 18.6, 12.3 Hz, 1H), 3.4 (m, 1H), 3.2 (d, J = 8.7 Hz, 1H), 2.9 (d, J = 12.0, 1H), 2.68 (dd, J = 18.8, 4.4 Hz, 1H), 1.81 (m, 2H), 1.53 (m, 2H) LC Method 1: 1.59 min | 366 |
| 116 | (1-methyl-1H-pyrazol-5-yl)(4-(5-phenyl-4,5-dihydro-1H-pyrazole-1-carbonyl)piperidin-1-yl)methanone | 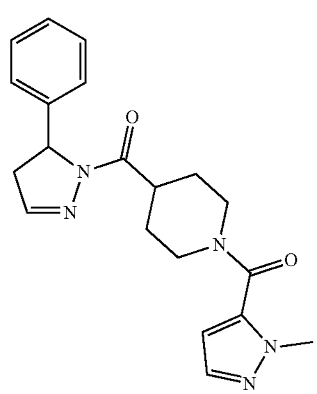 [SMILES: Cn1nccc1C(=O)N1CCC(C(=O)N2N=CCC2c2ccccc2)CC1] | ¹H NMR (400 MHz, DMSO-d6) δ ppm, 7.46 (d, J = 1.9 Hz, 1H), 7.32 (dd, J = 7.4, 7.2 Hz, 2H), 7.24 (m, 2H), 7.11 (d, J = 7.4 Hz, 2H), 6.43 (d, J = 1.9 Hz, 1H), 5.32 (dd, J = 12.0, 4.6 Hz, 1H), 4.44 (br s, 1H), 3.8 (m, 1H), 3.81 (s, 3H), 3.5 (ddd, J = 18.9, 11.9, 1.2 Hz, 1H), 3.37 (m, 1H), 3.22 (br s, 1H), 2.94 (br s, 1H), 2.68 (ddd, J = 18.8, 4.6, 1.6 Hz, 1H), 1.80 (m, 2H), 1.51 (m, 2H) LC Method 1: 2.01 min | 366 |

-continued

| Ex | Name | Structure | ¹H NMR LC: retention time (min) | MS (M + H)⁺ |
|---|---|---|---|---|
| 117 | (1-methyl-1H-pyrazol-3-yl)(4-(5-phenyl-4,5-dihydro-1H-pyrazole-1-carbonyl)piperidin-1-yl)methanone | 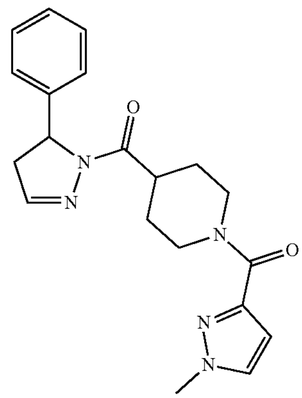 [SMILES: Cn1ccc(C(=O)N2CCC(C(=O)N3N=CCC3c3ccccc3)CC2)n1] | ¹H NMR (400 MHz, DMSO-d6) δ ppm, 7.74 (d, J = 2.1 Hz, 1H), 7.32 (t, J = 7.4 Hz, 2H), 7.24 (m, 2H), 7.11 (d, J = 7.2 Hz, 2H), 6.5 (d, J = 2.3 Hz, 1H), 5.31 (dd, J = 11.9, 4.6 Hz, 1H), 4.60 (br s, 1H), 4.46 (d, J = 10.2 Hz, 1H), 3.87 (s, 3H), 3.49 (dd, J = 18.3, 12.4 Hz, 1H), 3.38 (tt, J = 11.5, 3.8 Hz, 1H), 3.2 (br s, 1H), 2.85 (m, 1H), 2.67 (ddd, J = 18.9, 4.6, 1.7 Hz, 1H), 1.81 (m, 2H), 1.47 (m, 2H) LC Method 1: 1.96 min | 366 |
| 118 | (2-methyloxazol-4-yl)(4-(5-phenyl-4,5-dihydro-1H-pyrazole-1-carbonyl)piperidin-1-yl)methanone | 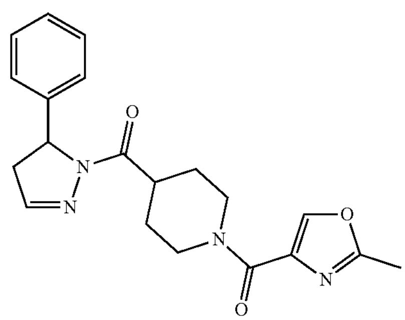 [SMILES: Cc1nc(C(=O)N2CCC(C(=O)N3N=CCC3c3ccccc3)CC2)co1] | ¹H NMR (400 MHz, DMSO-d6) δ ppm 8.37 (s, 1H), 7.32 (dd, J = 7.4, 7.2 Hz, 2H), 7.24 (m, 2H), 7.11 (d, J = 7.2 Hz, 2H), 5.31 (dd, J = 11.9, 4.5 Hz, 1H), 4.56 (br s, 1H), 4.43 (br s, 1H), 3.49 (dd, J = 18.8, 12.0 Hz, 1H), 3.39 (m, 1H), 3.21 (br s, 1H), 2.86 (br s, 1H), 2.67 (m, 1H), 2.44 (s, 3H), 1.88 (br s, 1H), 1.75 (br s, 1H), 1.47 (m, 2H) LC Method 1: 2.02 min | 367 |
| 119 | (1-methyl-1H-imidazol-4-yl)(4-(5-phenyl-4,5-dihydro-1H-pyrazole-1-carbonyl)piperidin-1-yl)methanone | 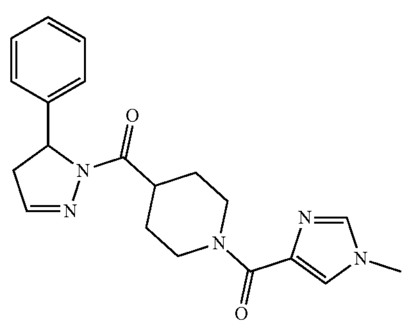 [SMILES: Cn1cnc(C(=O)N2CCC(C(=O)N3N=CCC3c3ccccc3)CC2)c1] | ¹H NMR (400 MHz, DMSO-d6) δ ppm 7.63 (s, 1H), 7.59 (s, 1H), 7.32 (dd, J = 7.6, 7.2 Hz, 2H), 7.24 (m, 2H), 7.1 (d, J = 7.2 Hz, 2H), 5.31 (dd, J = 11.8, 4.4 Hz, 1H), 5.2 (br s, 1H), 4.46 (br s, 1H), 3.67 (s, 3H), 3.49 (dd, J = 18.7, 12.1 Hz, 1H), 3.39 (m, 1H), 3.15 (br s, 1H), 2.83 (br s, 1H), 2.67 (dd, J = 18.8, 3.2 Hz, 1H), 1.85 (d, J = 11.2 Hz, 1H), 1.73 (d, J = 11.2 Hz, 1H), 1.46 (m, 2H) LC Method 1: 1.49 min | 366 |
| 120 | (2-methylthiazol-4-yl)(4-(5-phenyl-4,5-dihydro-1H-pyrazole-1-carbonyl)piperidin-1-yl)methanone | 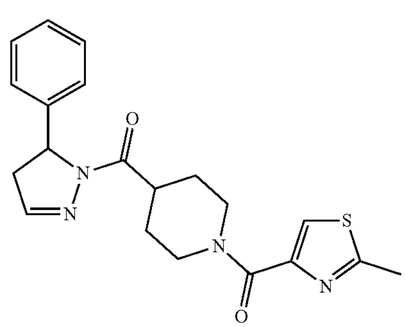 | ¹H NMR (400 MHz, DMSO-d6) δ ppm 7.87 (s, 1H), 7.32 (t, J = 7.4 Hz, 2H), 7.24 (m, 2H), 7.11 (d, J = 7.2 Hz, 2H), 5.31 (dd, J = 11.9, 4.6 Hz, 1H), 4.43 (br s, 1H), 4.41 (br s, 1H), 3.49 (dd, J = 18.3, 12.6 Hz, 1H), 3.38 (m, 1H), 3.18 (br s, 1H), 2.9 (br s, 1H), 2.68 (s, 3H), 2.66 (m, 1H), 1.80 (m, 2H), 1.5 (m, 2H) LC Method 1: 2.10 min | 383 |

| Ex | Name | Structure | ¹H NMR LC: retention time (min) | MS (M + H)⁺ |
|---|---|---|---|---|
| 121 | (1-(4-methyl-picolinoyl)piperidin-4-yl)(5-phenyl-4,5-dihydro-1H-pyrazol-1-yl)methanone | 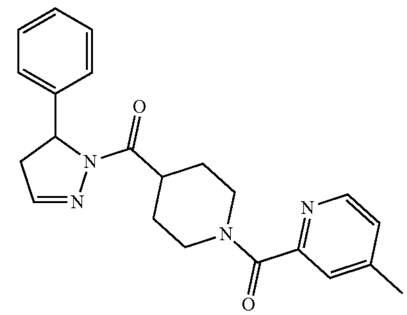 [SMILES: Cc1ccnc(C(=O)N2CCC(C(=O)N3N=CCC3c3ccccc3)CC2)c1] | ¹H NMR (400 MHz, DMSO-d6) δ ppm 8.42 (d, J = 4.9 Hz, 1H), 7.31 (m, 4H), 7.24 (m, 2H), 7.11 (t, J = 7.8 Hz, 2H), 5.31 (dd, J = 11.6, 3.8 Hz, 1H), 4.48 (d, J = 9.3 Hz, 1H), 3.67 (d, J = 11.6 Hz, 1H), 3.38 (m, 1H), 3.12 (m, 1H), 2.91 (m, 1H), 2.67 (dt, J = 18.8, 3.2 Hz, 1H), 2.36 (s, 3H), 1.75 (m, 2H), 1.51 (m, 2H) LC Method 1: 2.03 min | 377 |
| 122 | (5-methylthiophen-2-yl)(4-(5-phenyl-4,5-dihydro-1H-pyrazole-1-carbonyl)piperidin-1-yl)methanone | 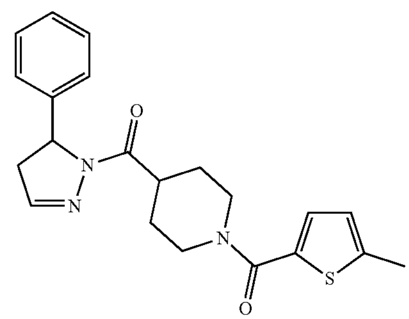 [SMILES: Cc1ccc(C(=O)N2CCC(C(=O)N3N=CCC3c3ccccc3)CC2)s1] | ¹H NMR (400 MHz, DMSO-d6) δ ppm 7.32 (t, J = 7.4 Hz, 2H), 7.24 (m, 2H), 7.18 (d, J = 3.6 Hz, 1H), 7.11 (d, J = 7.2 Hz, 2H), 6.81 (d, J = 2.7 Hz, 1H), 5.32 (dd, J = 18.3, 12.4 Hz, 1H), 4.26 (d, J = 10.1, 2H), 3.50 (dd, J = 18.3, 12.4 Hz, 1H), 3.38 (m, 2H), 3.10 (br s, 1H), 2.68 (m, 1H), 2.46 (s, 3H), 1.89 (d, J = 11.4 Hz, 1H), 1.77 (d, J = 12.7 Hz, 1H), 1.52 (m, 2H) LC Method 1: 2.43 min | 382 |
| 123 | (1-(1H-pyrazole-4-carbonyl)piperidin-4-yl)(5-phenyl-4,5-dihydro-1H-pyrazol-1-yl)methanone | 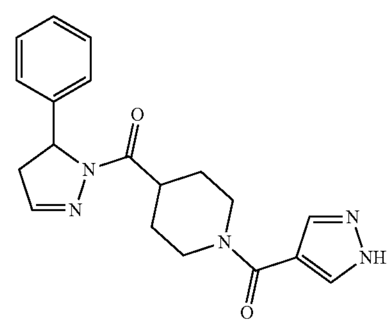 [SMILES: O=C(c1cn[nH]c1)N1CCC(C(=O)N2N=CCC2c2ccccc2)CC1] | ¹H NMR (400 MHz, DMSO-d6) δ ppm 13.15 (s, 1H), 8.04 (s, 1H), 7.68 (s, 1H), 7.32 (dd, J = 7.8, 7.0 Hz, 2H), 7.24 (m, 2H), 7.11 (d, J = 7.2 Hz, 2H), 5.32 (dd, J = 12.0, 4.6 Hz, 1H), 4.25 (br s, 2H), 3.49 (ddd, J = 18.9, 11.9, 1.5 Hz, 1H), 3.36 (m, 1H), 2.90 (br s, 2H), 2.68 (ddd, J = 18.9, 4.6, 1.7 Hz, 1H), 1.87 (d, J = 12.1 Hz, 1H), 1.75 (d, J = 11.4 Hz, 1H), 1.49 (m, 2H) LC Method 1: 3.16 min | 352 |
| 124 | (2-methylthiazol-5-yl)(4-(5-phenyl-4,5-dihydro-1H-pyrazole-1-carbonyl)piperidin-1-yl)methanone | 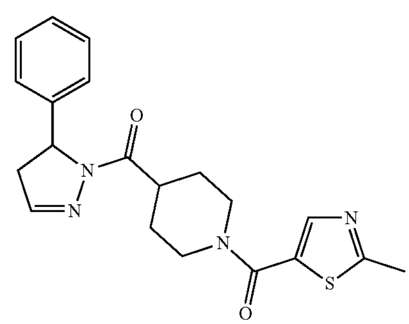 [SMILES: Cc1ncc(C(=O)N2CCC(C(=O)N3N=CCC3c3ccccc3)CC2)s1] | ¹H NMR (400 MHz, DMSO-d6) δ ppm 7.88 (s, 1H), 7.32 (dd, J = 7.6, 7.0 Hz, 2H), 7.24 (m, 2H), 7.11 (d, J = 7.2 Hz, 2H), 5.32 (dd, J = 12.0, 4.6 Hz, 1H), 4.2 (br s, 2H), 3.49 (ddd, J = 18.8, 11.9, 1.5 Hz, 1H), 3.38 (m, 1H), 3.12 (br s, 2H), 2.68 (ddd, J = 18.8, 4.6, 1.6 Hz, 1H), 2.67 (s, 3H), 1.9 (d, J = 11.6 Hz, 1H), 1.78 (d, J = 11.4 Hz, 1H), 1.52 (m, 2H) LC Method 1: 2.07 min | 383 |

| Ex | Name | Structure | ¹H NMR LC: retention time (min) | MS (M + H)⁺ |
|---|---|---|---|---|
| 125 | isothiazol-5-yl(4-(5-phenyl-4,5-dihydro-1H-pyrazole-1-carbonyl)piperidin-1-yl)methanone | 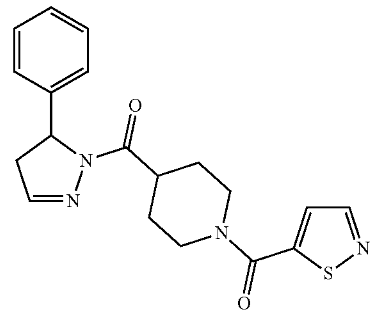 [SMILES: O=C(c1ccns1)N1CCC(C(=O)N2N=CCC2c2ccccc2)CC1] | ¹H NMR (400 MHz, DMSO-d6) δ ppm 8.6 (d, J = 1.74 Hz, 1H), 7.62 (d, J = 1.7 Hz, 1H), 7.32 (dd, J = 7.6, 7.0 Hz, 2H), 7.24 (m, 2H), 7.11 (d, J = 7.2 Hz, 2H), 5.32 (dd, J = 11.8, 4.6 Hz, 1H), 4.41 (br s, 1H), 3.8 (br s, 1H), 3.49 (ddd, J = 18.9, 11.9, 1.4 Hz, 1H), 3.39 (tt, J = 11.3, 3.8 Hz, 1H), 3.28 (m, 1H), 2.99 (m, 1H), 2.68 (ddd, J = 18.9, 4.6, 1.4 Hz, 1H), 1.84 (m, 2H) 1.55 (m, 2H) LC Method 1: 2.11 min | 369 |
| 126 | (2-methyloxazol-5-yl)(4-(5-phenyl-4,5-dihydro-1H-pyrazole-1-carbonyl)piperidin-1-yl)methanone | 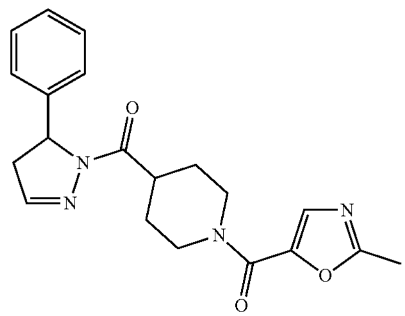 [SMILES: Cc1ncc(C(=O)N2CCC(C(=O)N3N=CCC3c3ccccc3)CC2)o1] | ¹H NMR (400 MHz, DMSO-d6) δ ppm 7.52 (s, 1H), 7.32 (dd, J = 7.6, 7.2 Hz, 2H), 7.24 (m, 2H), 7.11 (d, J = 7.0 Hz, 2H), 5.32 (dd, J = 11.9, 4.6 Hz, 1H), 4.26 (br s, 2H), 3.52 (ddd, J = 18.8, 12.0, 1.5 Hz, 1H), 3.39 (tt, J = 11.9, 3.9 Hz, 1H), 3-3.25 (br s, 2H), 2.68 (ddd, J = 18.8, 4.6, 1.5 Hz, 1H), 2.46 (s, 3H), 1.91 (d, J = 11.3 Hz, 1H), 1.79 (d, J = 11.3 Hz, 1H), 1.52 (m, 2H) LC Method 1: 1.98 min | 367 |
| 127 | (1-methyl-1H-pyrazol-4-yl)(4-(5-phenyl-4,5-dihydro-1H-pyrazole-1-carbonyl)piperidin-1-yl)methanone | 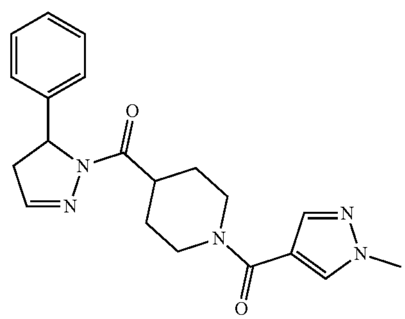 [SMILES: Cn1cc(C(=O)N2CCC(C(=O)N3N=CCC3c3ccccc3)CC2)cn1] | ¹H NMR (400 MHz, DMSO-d6) δ ppm 8.03 (s, 1H), 7.62 (s, 1H), 7.32 (dd, J = 7.6, 7.2 Hz, 2H), 7.24 (m, 2H), 7.11 (d, J = 7.2 Hz, 2H), 5.32 (dd, J = 11.8, 4.6 Hz, 1H), 4.24 (br s, 2H), 3.84 (s, 3H), 3.49 (ddd, J = 18.8, 12.0, 1.5 Hz, 1H), 3.37 (m, 1H), 3.02 (br s, 2H), 2.67 (ddd, J = 18.8, 4.9, 1.5 Hz, 1H), 1.87 (d, J = 11.8 Hz, 1H), 1.75 (d, J = 11.4 Hz, 1H), 1.48 (m, 2H) LC Method 1: 1.90 min | 366 |
| 128 | (5-methylisoxazol-3-yl)(4-(5-phenyl-4,5-dihydro-1H-pyrazole-1-carbonyl)piperidin-1-yl)methanone | 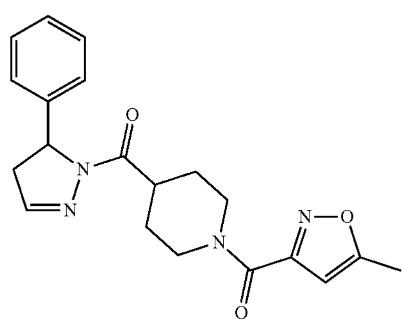 | ¹H NMR (400 MHz, DMSO-d6) δ ppm 7.32 (m, 2H), 7.25 (m, 2H), 7.11 (m, 2H), 6.44 (s, 1H), 5.31 (dd, J = 12.0, 4.5 Hz, 1H), 4.44 (m, 1H), 3.90 (m, 1H), 3.50 (m, 1H), 3.41 (m, 1H), 3.22 (m, 1H), 2.95 (m, 1H), 2.68 (m, 1H), 2.45 (s, 3H), 1.84 (m, 2H), 1.50 (m, 2H) LC Method 1: 2.20 min | 412 (M + HCO₂H⁺) |
| 129 | 2-(benzyloxy)-1-(5-phenyl-4,5-dihydro-1H-pyrazol-1-yl)ethanone | 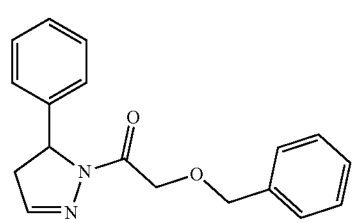 [SMILES: O=C(COCc1ccccc1)N1N=CCC1c1ccccc1] | ¹H NMR (400 MHz, DMSO-d6) δ ppm 7.35 (m, 6H), 7.28 (m, 2H), 7.22 (t, J = 1.5 Hz, 1H), 7.16 (m, 2H), 5.34 (dd, J = 11.9, 4.8 Hz, 1H), 4.54 (d, J = 3.6 Hz, 2H), 4.48 (syst AB, 2H), 3.47 (ddd, J = 18.9, 12.0, 1.7 Hz, 1H), 2.69 (ddd, J = 18.9, 4.9, 1.9 Hz, 1H) LC Method 1: 2.50 min | 295 |

-continued

| Ex | Name | Structure | ¹H NMR LC: retention time (min) | MS (M + H)⁺ |
|---|---|---|---|---|
| 130 | (1-(4-fluoro-benzoyl)piperidin-4-yl)(5-phenyl-4,5-dihydro-1H-pyrazol-1-yl)methanone | 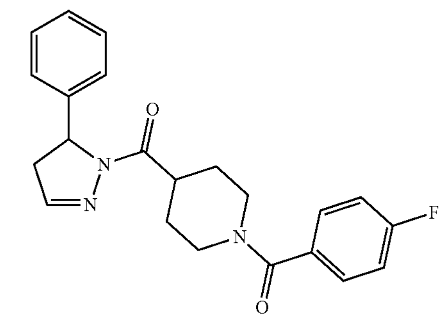 [SMILES: O=C(c1ccc(F)cc1)N1CCC(C(=O)N2N=CCC2c2ccccc2)CC1] | ¹H NMR (400 MHz, DMSO-d6) δ ppm 7.45 (m, 2H), 7.32 (dd, J = 7.6, 7.2 Hz, 2H), 7.25 (m, 4H), 7.11 (d, J = 7.2 Hz, 2H), 5.32 (dd, J = 12.0, 4.6 Hz, 1H), 4.44 (br s, 1H), 3.59 (br s, 1H), 3.49 (ddd, J = 18.8, 12.0, 1.3 Hz, 1H), 3.37 (m, 1H), 3.13 (br s, 1H), 2.92 (br s, 1H), 2.67 (m, 1H), 1.79 (m, 2H), 1.50 (m, 2H) LC Method 1: 2.38 min | 380 |
| 131 | (1-(2,4-difluorobenzoyl)piperidin-4-yl)(5-phenyl-4,5-dihydro-1H-pyrazol-1-yl)-methanone | 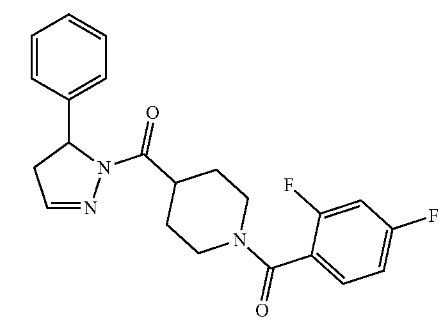 [SMILES: O=C(c1ccc(F)cc1F)N1CCC(C(=O)N2N=CCC2c2ccccc2)CC1] | ¹H NMR (400 MHz, DMSO-d6) δ ppm 7.47 (m, 1H), 7.37 (m, 1H), 7.32 (m, 2H), 7.24 (m, 2H), 7.17 (m, 1H), 7.10 (t, J = 7.5 Hz, 2H), 5.31 (m, 1H), 4.48 (m, 1H), 3.45 (m, 3H), 3.16 (m, 1H), 2.92 (m, 1H), 2.66 (m, 1H), 1.80 (m, 2H), 1.48 (m, 2H) LC Method 1: 2.44 min | 398 |
| 132 | 4-(4-(5-phenyl-4,5-dihydro-1H-pyrazole-1-carbonyl)piperidine-1-carbonyl)-benzonitrile | 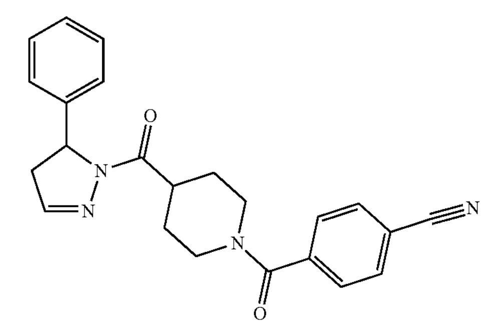 [SMILES: N#Cc1ccc(C(=O)N2CCC(C(=O)N3N=CCC3c3ccccc3)CC2)cc1] | ¹H NMR (400 MHz, DMSO-d6) δ ppm 7.91 (d, J = 8.4 Hz, 2H), 7.57 (d, J = 8.4 Hz, 2H), 7.32 (m, 2H), 7.24 (m, 2H), 7.11 br s, 2H), 5.31 (dd, J = 11.8, 4.6 Hz, 1H), 4.44 (br s, 1H), 3.49 (m, 2H), 3.37 (m, 1H), 3.15 (br s, 1H), 2.93 (m, 1H), 2.67 (m, 1H), 1.80 (m, 2H), 1.51 (m, 2H) LC Method 1: 2.28 min | 387 |
| 133 | (1-(1H-pyrazole-3-carbonyl)piperidin-4-yl)(5-phenyl-4,5-dihydro-1H-pyrazol-1-yl)methanone | 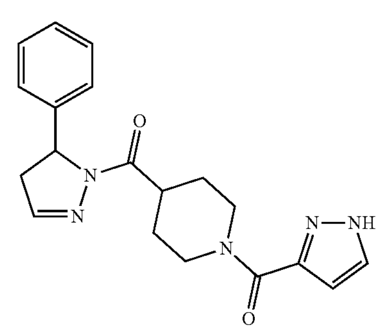 [SMILES: O=C(c1cc[nH]n1)N1CCC(C(=O)N2N=CCC2c2ccccc2)CC1] | ¹H NMR (400 MHz, DMSO-d6) δ ppm 13.13 (s, 1H), 7.79 (s, 1H), 7.32 (t, J = 7.4 Hz, 2H), 7.24 (m, 2H), 7.11 (d, J = 7.4 Hz, 2H), 6.53 (d, J = 2.3 Hz, 1H), 5.32 (dd, J = 12.0, 4.6 Hz, 1H), 4.62 (br s, 1H), 4.48 (m, 1H), 3.49 (ddd, J = 18.8, 11.8, 1.2 Hz, 1H), 3.39 (tt, J = 11.4, 3.8 Hz, 1H), 3.20 (br s, 1H), 2.86 (br s, 1H), 2.67 (ddd, J = 18.9, 4.5, 1.5 Hz, 1H), 1.82 (m, 2H), 1.50 (m, 2H) LC Method 1: 1.84 min | 352 |

-continued

| Ex | Name | Structure | ¹H NMR LC: retention time (min) | MS (M + H)⁺ |
|---|---|---|---|---|
| 134 | 3-oxo-3-(4-(5-phenyl-4,5-dihydro-1H-pyrazole-1-carbonyl)piperidin-1-yl)propanenitrile | 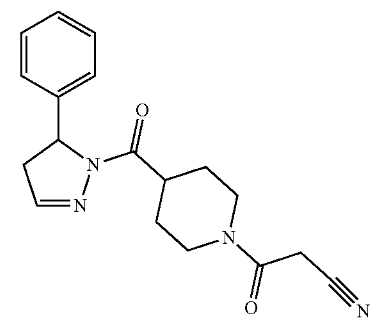 [SMILES: N#CCC(=O)N1CCC(C(=O)N2N=CCC2c2ccccc2)CC1] | ¹H NMR (400 MHz, DMSO-d6) δ ppm 7.32 (dd, J = 7.4, 7.2 Hz, 2H), 7.24 (m, 2H), 7.11 (m, 2H), 5.31 (dd, J = 11.9, 4.6 Hz, 1H), 4.29 (m, 1H), 4.04 (Syst AB, J = 18.9, 2H), 3.66 (d, J = 12.1 Hz, 1H), 3.49 (dd, J = 18.9, 12.1 Hz, 1H), 3.32 (m, 1H), 3.11 (m, 1H), 2.7 (m, 2H), 1.84 (t, J = 14.4 Hz, 1H), 1.73 (m, 1H), 1.57 (m, 1H), 1.37 (m, 1H) LC Method 1: 1.86 min | 325 |
| 135 | (2,4-dimethyl-thiazol-5-yl)(4-(5-phenyl-4,5-dihydro-1H-pyrazole-1-carbonyl)piperidin-1-yl)methanone | 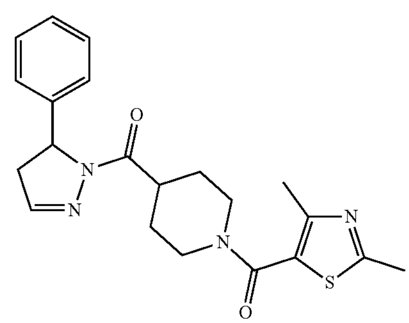 [SMILES: Cc1nc(C)c(C(=O)N2CCC(C(=O)N3N=CCC3c3ccccc3)CC2)s1] | ¹H NMR (400 MHz, DMSO-d6) δ ppm 7.32 (dd, J = 7.6, 7.2 Hz, 2H), 7.24 (m, 2H), 7.02 (d, J = 7.0 Hz, 2H), 5.31 (dd, J = 11.9, 4.6 Hz, 1H), 4.02 (br s, 2H), 3.49 (ddd, J = 18.9, 12.0, 1.5 Hz, 1H), 3.38 (tt, J = 11.4, 3.8 Hz, 1H), 3.07 (br s, 2H), 2.68 (ddd, J = 18.9, 4.7, 1.7 Hz, 1H), 2.61 (s, 3H), 2.26 (s, 3H), 1.88 (d, J = 11.6 Hz, 1H), 1.76 (d, J = 12.7 Hz, 1H), 1.45 (m, 2H) LC Method 1: 2.09 min | 397 |
| 136 | (1-(3,5-difluoro-benzoyl)piperidin-4-yl)(5-phenyl-4,5-dihydro-1H-pyrazol-1-yl)methanone | 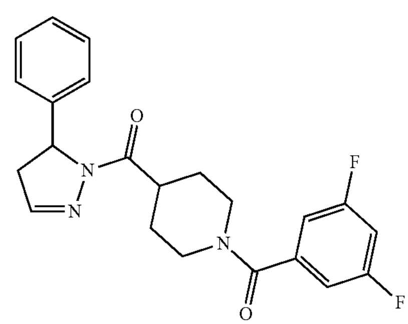 [SMILES: O=C(c1cc(F)cc(F)c1)N1CCC(C(=O)N2N=CCC2c2ccccc2)CC1] | ¹H NMR (400 MHz, DMSO-d6) δ ppm 7.34 (m, 3H), 7.24 (m, 2H), 7.15 (m, 2H), 7.11 (d, J = 7.21 Hz, 2H), 5.31 (dd, J = 12.0, 4.6 Hz, 1H), 4.42 (m, 1H), 3.51 (m, 1H), 3.49 (dd, J = 18.9, 11.9 Hz, 1H), 3.35 (m, 1H), 3.15 (m, 1H), 2.92 (m, 1H), 2.67 (m, 1H), 1.79 (m, 2H), 1.53 (m, 2H) LC Method 1: 2.49 min | 398 |
| 137 | (1-(1H-1,2,3-triazole-4-carbonyl)piperidin-4-yl)(5-phenyl-4,5-dihydro-1H-pyrazol-1-yl)methanone | 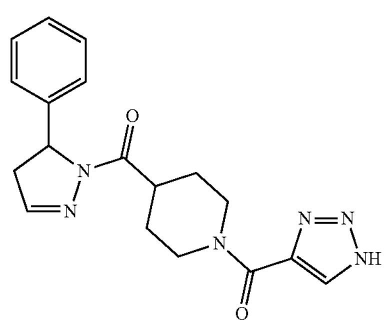 | ¹H NMR (400 MHz, DMSO-d6) δ ppm 8.26 (s, 1H), 7.32 (dd, J = 7.4, 7.2 Hz, 2H), 7.24 (m, 2H), 7.11 (d, J = 7.4 Hz, 2H), 5.32 (dd, J = 11.9, 4.6 Hz, 1H), 4.56 (m, 1H), 4.48 (d, J = 13.1 Hz, 1H), 3.49 (ddd, J = 18.8, 11.8, 1.2 Hz, 1H), 3.41 (tt, J = 11.5, 3.8 Hz, 1H), 3.27 (m, 1H), 2.91 (m, 1H), 2.68 (ddd, 18.9, 4.6, 1.8 Hz, 1H), 1.80 (m, 2H), 1.51 (m, 2H) LC Method 1: 1.85 min | 353 |

-continued

| Ex | Name | Structure | ¹H NMR LC: retention time (min) | MS (M + H)⁺ |
|---|---|---|---|---|
| 138 | (1-(1,2,3-thiadiazole-5-carbonyl)piperidin-4-yl)(5-phenyl-4,5-dihydro-1H-pyrazol-1-yl)-methanone | 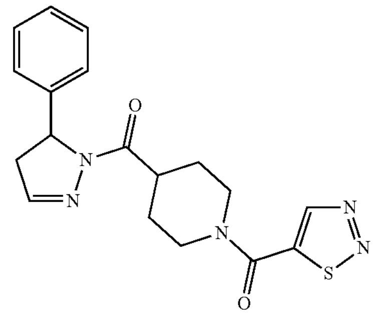 [SMILES: O=C(c1cnns1)N1CCC(C(=O)N2N=CCC2c2ccccc2)CC1] | ¹H NMR (400 MHz, DMSO-d6) δ ppm 9.21 (s, 1H), 7.31 (m, 2H), 7.24 (m, 2H), 7.11 (m, 2H), 5.32 (dd, J = 11.9, 4.6 Hz, 1H), 4.44 (dd, J = 12.0 Hz*2, 1H), 3.58 (br s, 1H), 18.8, 12.0, 1.1 Hz, 1H), 3.38 (tt, J = 11.2, 3.8 Hz, 1H), 3.23 (dd, J = 111.3 Hz*2, 1H), 3.00 (m, 1H), 2.68 (m, 1H), 1.82 (m, 2H), 1.58 (m, 2H) LC Method 1: 2.11 min | 370 |
| 139 | beno[d]thiazol-2-yl(4-(5-phenyl-4,5-dihydro-1H-pyrazole-1-carbonyl)piperidin-1-yl)methanone | 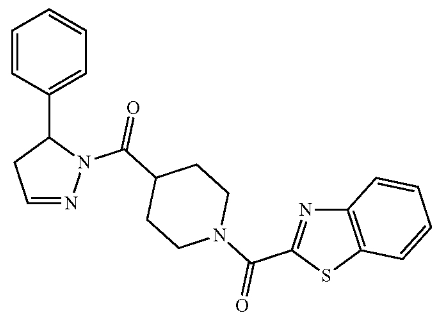 [SMILES: O=C(c1nc2ccccc2s1)N1CCC(C(=O)N2N=CCC2c2ccccc2)CC1] | ¹H NMR (400 MHz, CDCl3) δ ppm 8.1 (d, J = 7.8 Hz, 1H), 7.97 (d, J = 7.8 Hz, 1H), 7.52 (dtd, J = 21.3, 6.6 and 0.6 Hz, 2H), 7.33 (m, 2H), 7.28 (m, 2H), 7.17 (m, 2H), 7.01 (s, 1H), 5.40 (dd, J = 12.0, 4.7 Hz, 1H), 5.32 (d, J = 13.5 Hz, 1H), 4.7 (m, 1H), 3.48 (m, 2H), 3.12 (m, 1H), 2.85 (ddd, J = 18.8, 4.9, 1.7 Hz, 1H), 1.75-2.15 (m, 4H) LC Method 1: 2.68 min | 419 |
| 140 | (1-(1H-indazole-3-carbonyl)piperidin-4-yl)(5-phenyl-4,5-dihydro-1H-pyrazol-1-yl)methanone | 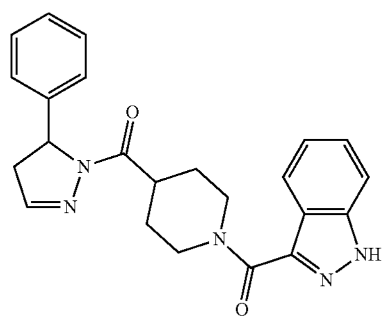 [SMILES: O=C(c1n[nH]c2ccccc12)N1CCC(C(=O)N2N=CCC2c2ccccc2)CC1] | ¹H NMR (400 MHz, DMSO-d6) δ ppm 13.47 (s, 1H), 7.92 (d, J = 8.2 Hz, 1H), 7.60 (d, J = 8.4 Hz, 1H), 7.41 (m, 1H), 7.32 (m, 2H), 7.25 (m, 2H), 7.20 (m, 1H), 7.11 (d, J = 6.8 Hz, 2H), 5.32 (dd, J = 11.8, 4.6 Hz, 1H), 4.61 (m, 2H), 3.45 (m, 2H), 3.28 (m, 1H), 2.96 (m, 1H), 2.68 (ddd, J = 18.8, 4.4, 1.3 Hz, 1H), 1.86 (m, 2H), 1.56 (m, 2H) LC Method 1: 2.23 min | 402 |
| 141 | (1-phenyl-1H-imidazol-4-yl)(4-(5-phenyl-1-4,5-dihydro-1H-pyrazole-1-carbonyl)piperidin-1-yl)methanone | 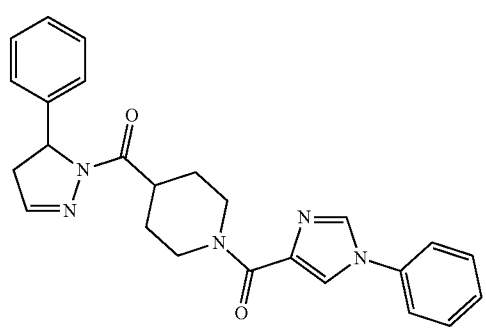 [SMILES: O=C(c1cn(-c2ccccc2)cn1)N1CCC(C(=O)N2N=CCC2c2ccccc2)CC1] | ¹H NMR (400 MHz, DMSO-d6) δ ppm 8.33 (d, J = 1.3 Hz, 1H), 8.19 (d, J = 1.5 Hz, 1H), 7.73 (d, J = 7.6 Hz, 2H), 7.55 (dd, J = 8.4, 7.6 Hz, 2H), 7.41 (m, 1H), 7.33 (dd, J = 7.6, 7.2 Hz, 2H), 7.24 (m, 2H), 7.11 (d, J = 7.2 Hz, 2H), 5.32 (dd, J = 12.0, 4.6 Hz, 1H), 5.08 (br s, 1H) 4.48 (br s, 1H), 3.50 (ddd, J = 18.8, 12.0, 1.5 Hz, 1H), 3.41 (tt, J = 11.5, 3.8 Hz, 1H), 3.23 (br s, 1H), 2.87 (br s, 1H), 2.68 (ddd, J = 18.8, 4.7, 1.7 Hz, 1H), 1.90 (m, 1H), 1.77 (m, 1H), 1.52 (m, 2H) LC Method 1: 2.23 min | 428 |

| Ex | Name | Structure | ¹H NMR LC: retention time (min) | MS (M + H)⁺ |
|---|---|---|---|---|
| 142 | (1(1H-beno[d][1,2,3]triazole-6-carbonyl)-piperidin-4-yl)(5-phenyl-4,5-dihydro-1H-pyrazol-1-yl)-methanone | 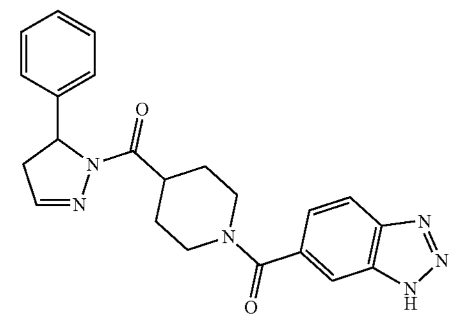 [SMILES: O=C(c1ccc2nn[nH]c2c1)N1CCC(C(=O)N2N=CCC2c2ccccc2)CC1] | ¹H NMR (400 MHz, DMSO-d6) δ ppm 7.94 (s, 2H), 7.43 (d, J = 8.2 Hz, 1H), 7.32 (m, 2H), 7.23 (m, 2H), 7.11 (d, J = 7.4 Hz, 2H), 5.32 (dd, J = 12.0, 4.6 Hz, 1H), 4.48 (br s, 1H), 3.62 (br s, 1H), 3.44 (m, 3H), 3.16 (br s, 1H), 2.97 (br s, 1H), 2.67 (ddd, J = 18.8, 4.7, 1.7 Hz, 1H), 1.45-1.95 (m, 4H) LC Method 1: 1.96 min | 403 |
| 143 | (1-(1H-indazole-6-carbonyl)piperidin-4-yl)(5-phenyl-4,5-dihydro-1H-pyrazol-1-yl)methanone | 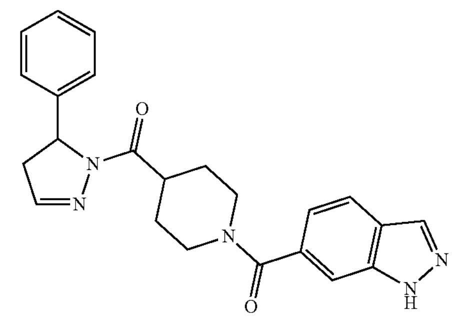 [SMILES: O=C(c1ccc2cn[nH]c2c1)N1CCC(C(=O)N2N=CCC2c2ccccc2)CC1] | ¹H NMR (400 MHz, DMSO-d6) δ ppm 13.23 (s, 1H), 8.14 (s, 1H), 7.82 (s, 1H) 7.58 (d, J = 8.5 Hz, 1H), 7.36 (dd, J = 8.5, 1.4 Hz, 1H), 7.32 (dd, J = 8.9, 7.6 Hz, 2H), 7.24 (m, 2H), 7.11 (d, J = 7.2 Hz, 2H), 5.32 (dd, J = 11.8, 4.6 Hz, 1H), 4.37 (br s, 1H), 3.83 (br s, 1H), 3.49 (ddd, J = 18.8, 11.8, 1.3 Hz, 1H), 3.38 (tt, J = 11.4, 3.7 Hz, 1H), 3.05 (br s, 2H), 2.67 (ddd, J = 18.8, 4.6, 1.5 Hz, 1H), 1.86 (br s, 1H), 1.73 (br s, 1H), 1.53 (m, 2H) LC Method 1: 2.03 min | 402 |
| 144 | imidazo[1,2-b]pyridazin-2-yl(4-(5-phenyl-4,5-dihydro-1H-pyrazole-1-carbonyl)piperidin-1-yl)methanone | 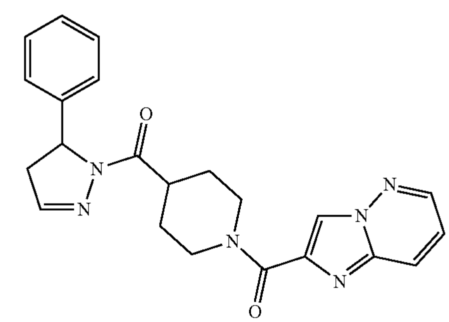 [SMILES: O=C(c1cn2ncccc2n1)N1CCC(C(=O)N2N=CCC2c2ccccc2)CC1] | ¹H NMR (400 MHz, DMSO-d6) δ ppm 8.59 (dd, J = 4.4, 1.5 Hz, 1H), 8.57 (s, 1H), 8.19 (m, 1H), 7.31 (m, 3H), 7.23 (m, 2H), 7.11 (d, J = 7.4 Hz, 2H), 5.32 (dd, J = 11.8. 4.6 Hz, 1H), 4.86 (br s, 1H), 4.51 (d, J = 10.8 Hz, 1H), 3.49 (dd, 18.8, 11.96 Hz, 1H), 3.42 (tt, J = 11.4, 3.8 Hz, 1H), 3.28 (br s, 1H), 2.92 (m, 1H), 2.68 (ddd, J = 18.9, 4.5, 1.5 Hz, 1H), 1.85 (m, 2H), 1.55 (m, 2H) LC Method 1: 1.98 min | 403 |
| 145 | 3-phenyl-1-(4-(5-phenyl-4,5-dihydro-1H-pyrazole-1-carbonyl)piperidin-1-yl)prop-2-yn-1-one | 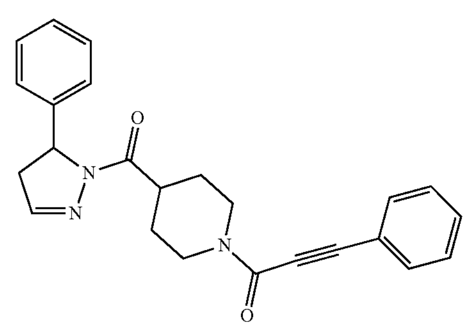 [SMILES: O=C(C#Cc1ccccc1)N1CCC(C(=O)N2N=CCC2c2ccccc2)CC1] | ¹H NMR (400 MHz, DMSO-d6) δ ppm 7.63 (d, J = 7 Hz, 2H), 7.51 (m, 3H), 7.32 (m, 2H), 7.11 (d, J = 7.4 Hz, 2H), 5.32 (dd, J = 11.9, 4.6 Hz, 1H), 4.35 (m, 2H), 3.50 (dd, J = 18.9, 12.0 Hz, 1H), 3.37 (m, 2H), 2.88 (m, 1H), 2.69 (ddd, J = 18.8, 4.6, 1.7 Hz, 1H), 1.88 (m, 2H), 1.47 (m, 2H) LC Method 1: 2.61 min | 386 |

| Ex | Name | Structure | $^1$H NMR LC: retention time (min) | MS (M + H)$^+$ |
|---|---|---|---|---|
| 146 | benzo[d]isoxazol-3-yl(4-(5-phenyl-4,5-dihydro-1H-pyrazole-1-carbonyl)piperidin-1-yl)methanone | 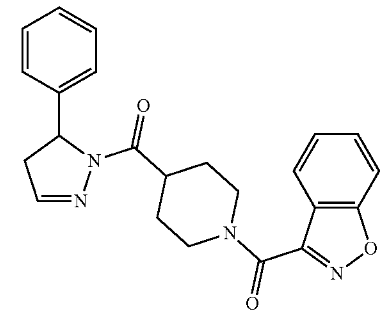 [SMILES: O=C(c1noc2ccccc12)N1CCC(C(=O)N2N=CCC2c2ccccc2)CC1] | $^1$H NMR (400 MHz, DMSO-d6) δ ppm 7.77 (d, J = 8.7 Hz, 1H), 7.75 d, J = 9.1 Hz, 1H), 7.49 (ddd, 9.11, 7.2, 0.8 Hz, 1H), 7.32 (m, 2H), 7.24 (m, 3H), 7.12 (d, J = 7.4 Hz, 2H), 5.33 (dd, J = 11.9, 4.6 Hz, 1H), 4.47 (m, 1H), 4.09 (m, 1H), 3.48 (m, 3H), 3.10 (m, 1H), 2.67 (ddd, J = 18.8, 4.7, 1.7 Hz, 1H), 1.91 (m, 2H), 1.60 (m, 2H) LC Method 1: 2.48 min | 403 |
| 147 | oxazol-5-yl(4-(5-phenyl-4,5-dihydro-1H-pyrazole-1-carbonyl)piperidin-1-yl)methanone | 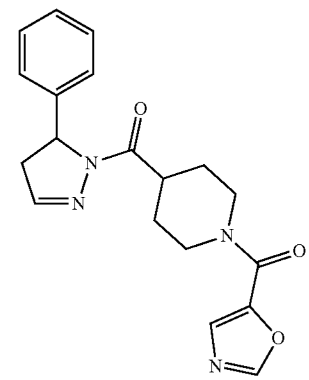 [SMILES: O=C(c1cnco1)N1CCC(C(=O)N2N=CCC2c2ccccc2)CC1] | $^1$H NMR (400 MHz, DMSOd6) δ ppm 8.53 (s, 1H), 7.68 (s, 1H), 7.32 (dd, J = 7.6, 7.2 Hz, 2H), 7.24 (m, 2H), 7.11 (d, J = 7.2 Hz, 2H), 5.32 (dd, J = 11.9, 4.5 Hz, 1H), 4.3 (m, 2H), 3.5 (ddd, J = 18.8, 11.8, 1.1, 1H), 3.4 (m, 1H) 3 (m, 1H), 2.70 (ddd, J = 18.8, 4.7, 1.7 Hz, 1H), 1.90 (d, J = 12.3 Hz, 1H), 1.80 (d, J = 12 Hz, 1H), 1.5 (m, 2H) LC Method 1: 1.90 min | 353 |
| 148 | oxazol-2-yl(4-(5-phenyl-4,5-dihydro-1H-pyrazole-1-carbonyl)piperidin-1-yl)methanone | 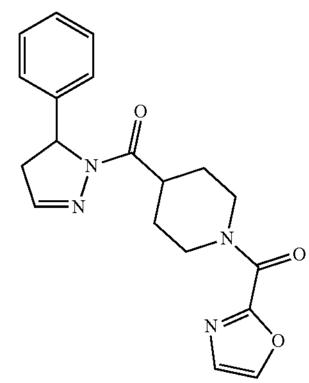 [SMILES: O=C(c1ncco1)N1CCC(C(=O)N2N=CCC2c2ccccc2)CC1] | $^1$H NMR (400 MHz, DMSO-d6) δ ppm 8.28 (s, 1H), 7.40 (s, 1H), 7.32 (m, 2H), 7.25 (s, 2H), 7.12 (d, J = 6.8 Hz, 2H), 5.32 (dd, J = 11.8, 4.2 Hz, 1H), 4.55 (d, J = 12 Hz, 1H), 4.42 (d, J = 11.4 Hz, 1H), 3.42 (m, 3H), 2.98 (m, 1H), 2.68 (d, J = 18 Hz, 1H), 1.90 (m, 2H), 1.50 (m, 2H) LC Method 1: 2.02 min | 353 |
| 149 | (3-methyl-1H-pyrazol-5-yl)(4-(5-phenyl-4,5-dihydro-1H-pyrazole-1-carbonyl)piperidin-1-yl)methanone | 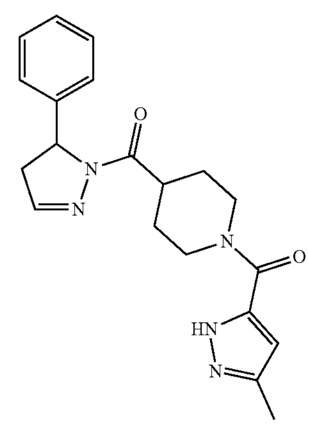 [SMILES: Cc1cc(C(=O)N2CCC(C(=O)N3N=CCC3c3ccccc3)CC2)[nH]n1] | $^1$H NMR (400 MHz, DMSO-d6) δ ppm 12.79 (s, 1H), 7.32 (dd, J = 7.4, 7.2 Hz, 2H), 7.23 (m, 2H), 7.10 (d, J = 7.2 Hz, 2H), 6.25 (s, 1H), 5.31 (dd, J = 11.8, 4.4 Hz, 1H), 4.66 (m, 1H), 4.45 (d, J = 9.5 Hz, 1H), 3.50 (dd, J = 18.6, 11.9 Hz, 1H), 3.38 (m, 1H), 3.17 (m, 1H), 2.83 (m, 1H), 2.67 (dd, J = 18.8, 3.23 Hz, 1H), 2.24 (s, 3H), 1.80 (m, 2H), 1.47 (m, 2H) LC Method 1: 1.95 min | 366 |

-continued

| Ex | Name | Structure | ¹H NMR LC: retention time (min) | MS (M + H)⁺ |
|---|---|---|---|---|
| 150 | (5-methylthiazol-2-yl)(4-(5-phenyl-4,5-dihydro-1H-pyrazole-1-carbonyl)piperidin-1-yl)methanone | 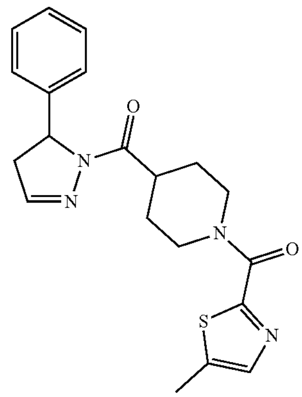 [SMILES: Cc1cnc(C(=O)N2CCC(C(=O)N3N=CCC3c3ccccc3)CC2)s1] | ¹H NMR (400 MHz, DMSO-d6) δ ppm 7.68 (s, 1H), 7.32 (dd, J = 7.6, 7.2 Hz, 2H), 7.25 (m, 2H), 7.11 (d, J = 7.2 Hz, 2H), 5.31 (dd, J = 12.0, 4.7 Hz, 1H), 5.22 (m, 1H), 4.42 (m, 1H), 3.50 (ddd, J = 18.8, 7.0, 1.5 Hz, 1H), 3.37 (m, 2H), 2.97 (m, 1H), 2.67 (ddd, J = 18.8, 4.7, 1.7 Hz, 1H), 2.49 (d, J = 1 Hz, 3H), 1.93 (m, 1H), 1.81 (m, 1H), 1.52 (m, 2H) LC Method 1: 2.36 min | 383 |
| 151 | isoxazol-5-yl(4-(5-phenyl-4,5-dihydro-1H-pyrazole-1-carbonyl)piperidin-1-yl)methanone | 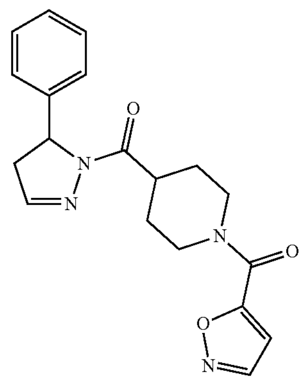 [SMILES: O=C(c1ccno1)N1CCC(C(=O)N2N=CCC2c2ccccc2)CC1] | ¹H NMR (400 MHz, DMSO-d6) δ ppm 8.73 (d, J = 1.9 Hz, 1H), 7.32 (m, 2H), 7.25 (m, 2H), 7.11 (d, J = 7 Hz, 2H), 6.91 (d, J = 1.7 Hz, 1H), 5.32 (dd, 11.8, 4.5 Hz, 1H), 4.39 (m, 1H), 3.79 (d, J = 12.34 Hz, 1H), 3.50 (dd, J = 12.1, 18.6 Hz, 1H), 3.40 (m, 1H), 3.29 (m, 1H), 3.00 (m, 1H), 2.68 (dd, J = 3.1, 17.5 Hz, 1H), 1.86 (m, 2H), 1.53 (m, 2H) LC Method 1: 2.06 min | 353 |
| 152 | (5-phenyl-4,5-dihydro-1H-pyrazol-1-yl)(1-(thiazole-5-carbonyl)piperidin-4-yl)methanone | 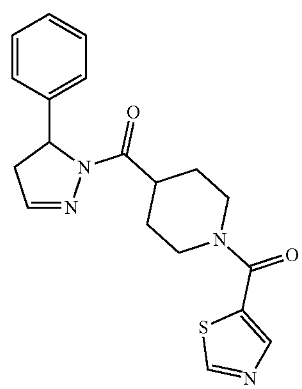 [SMILES: O=C(c1cncs1)N1CCC(C(=O)N2N=CCC2c2ccccc2)CC1] | ¹H NMR (400 MHz, DMSO-d6) δ ppm 9.22 (s, 1H), 8.16 (s, 1H), 7.32 (dd, J = 7.4, 7.2 Hz, 2H), 7.24 (m, 2H), 7.10 (d, J = 7.2 Hz, 2H), 5.32 (dd, J = 11.8, 4.4 Hz, 1H), 4.20 (m, 2H), 3.44 (m, 2H), 3.20 (m, 2H), 2.68 (dd, J = 18.9, 3.3 Hz, 1H), 1.91 (d, J = 11.2 Hz, 1H), 1.78 (d, J = 11.2 Hz, 1H), 1.55 (m, 2H) LC Method 1: 1.96 min | 369 |
| 153 | isoxazol-3-yl(4-(5-phenyl-4,5-dihydro-1H-pyrazole-1-carbonyl)piperidin-1-yl)methanone | 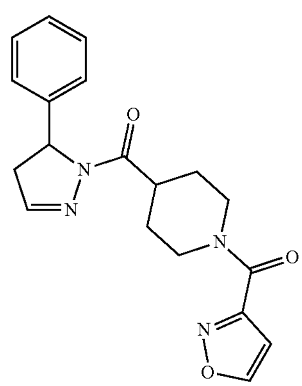 [SMILES: O=C(c1ccon1)N1CCC(C(=O)N2N=CCC2c2ccccc2)CC1] | ¹H NMR (400 MHz, DMSO-d6) δ ppm, 9.07 (s, 1H), 7.32 (m, 2H), 7.24 (brs, 2H), 7.11 (dd, J = 12.6, 5.7 Hz, 2H), 6.82 (s, 1H), 5.32 (dd, J = 11.6, 3.8 Hz, 1H), 4.46 (m, 1H), 3.86 (m, 1H), 3.45 (m, 2H), 3.25 (m, 1H), 2.98 (m, 1H), 2.67 (m, 1H), 1.97 (m, 1H), 1.84 (m, 1H), 1.50 (m, 2H) LC Method 1: 2.08 min | 353 |

-continued

| Ex | Name | Structure | ¹H NMR LC: retention time (min) | MS (M + H)⁺ |
|---|---|---|---|---|
| 154 | (5-phenyl-4,5-dihydro-1H-pyrazol-1-yl)(1-(thiazole-4-carbonyl)piperidin-4-yl)methanone | 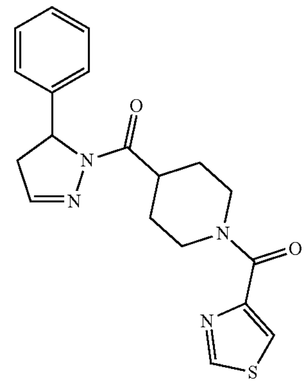 [SMILES: O=C(c1cscn1)N1CCC(C(=O)N2N=CCC2c2ccccc2)CC1] | ¹H NMR (400 MHz, DMSO-d6) δ ppm 9.16 (d, J = 1.9 Hz, 1H), 8.13 (d, J = 2,1 Hz, 1H), 7.32 (dd, J = 14.2, 7.0 Hz 2H), 7.24 (m, 2H), 7.11 (d, J = 7.4 Hz, 2H), 5.31 (dd, J = 11.8, 4.6 Hz, 1H), 4.46 (m, 1H), 4.11 (m, 1H), 3.49 (dd, J = 19, 12 Hz 1H), 3.39 (m, 1H), 3.19 (m, 1H), 2.91 (m, 1H), 2.67 (m, 1H), 1.80 (m, 1H), 1.52 (m, 2H) LC Method 1: 1.97 min | 369 |
| 155 | (1-(1,2,5-thiadiazole-3-carbonyl)piperidin-4-yl)(5-phenyl-4,5-dihydro-1H-pyrazol-1-yl)methanone | 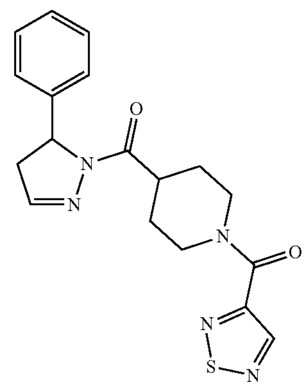 [SMILES: O=C(c1cnsn1)N1CCC(C(=O)N2N=CCC2c2ccccc2)CC1] | ¹H NMR (400 MHz, DMSO-d6) δ ppm 9.08 (s, 1H), 7.32 (m, 2H), 7.25 (m, 2H), 7.11 (dd, J = 13.6 6.8 Hz, 2H), 5.32 (dd, J = 11.7, 3.9 Hz, 1H), 4.46 (m, 1H), 3.86 (m, 1H), 3.45 (m, 2H), 3.25 (m, 1H), 2.98 (m, 1H), 2.67 (m, 1H), 1.97 (m, 1H), 1.84 (m, 1H), 1.50 (m, 2H) LC Method 1: 2.18 min | 370 |
| 156 | isothiazol-4-yl(4-(5-phenyl-4,5-dihydro-1H-pyrazole-1-carbonyl)piperidin-1-yl)methanone | 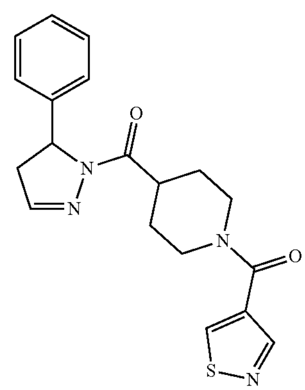 [SMILES: O=C(c1cnsc1)N1CCC(C(=O)N2N=CCC2c2ccccc2)CC1] | ¹H NMR (400 MHz, DMSO-d6) δ ppm 9.26 (s, 1H), 8.67 (s, 1H), 7.32 (dd, J = 14.8, 7.4 Hz, 2H), 7.24 (m, 2H), 7.11 (d, J = 7.2 Hz, 2H), 5.32 (dd, J = 12, 4.6 Hz, 1H), 4.46 (m, 1H), 3.7 (m, 1H), 3.55-3.35 (m, 2H), 3.22 (m, 1H), 2.94 (m, 1H), 2.68 (ddd, J = 19, 4.7, 1.7 Hz, 1H), 1.82 (m, 2H), 1.55 (m, 2H) LC Method 1: 2.02 min | 369 |
| 157 | (4-methylthiazol-2-yl)(4-(5-phenyl-4,5-dihydro-1H-pyrazole-1-carbonyl)piperidin-1-yl)methanone | 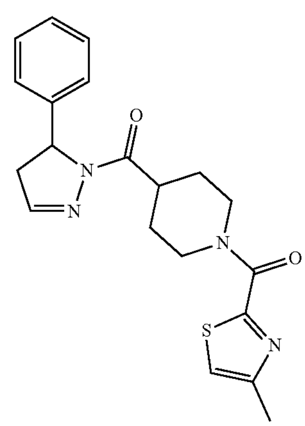 [SMILES: Cc1csc(C(=O)N2CCC(C(=O)N3N=CCC3c3ccccc3)CC2)n1] | H NMR (400 MHz, DMSO-d6) δ ppm 7.56 (s, 1H), 7.32 (dd, J = 14.8, 7.2 Hz, 2H), 7.25 (m, 2H), 7.11 (d, J = 7 Hz, 2H), 5.32 (dd, J = 11.8, 4.6 Hz, 1H), 5.19 (m, 1H), 4.43 (m, 1H), 3.49 (dd, J = 18.4, 11.6 Hz, 1H), 3.43 (m, 1H), 3.35 (m, 1H), 2.98 (m, 1H), 2.68 (ddd, J = 18.7, 4.5, 1.5 Hz, 1H), 2.42 (s, 3H), 2-1.75 (m, 2H), 1.53 (m 2H) LC Method 1: 2.35 min | 383 |

| Ex | Name | Structure | ¹H NMR LC: retention time (min) | MS (M + H)⁺ |
|---|---|---|---|---|
| 158 | (5-methyloxazol-4-yl)(4-(5-phenyl-4,5-dihydro-1H-pyrazole-1-carbonyl)piperidin-1-yl)methanone | 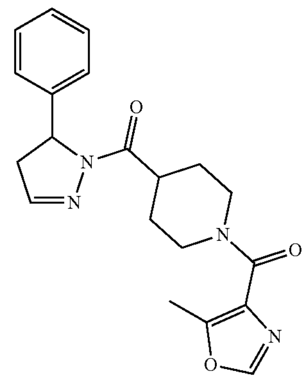 [SMILES: Cc1ocnc1C(=O)N1CCC(C(=O)N2N=CCC2c2ccccc2)CC1] | ¹H NMR (400 MHz, DMSO-d6) δ ppm 8.30 (s, 1H), 7.32 (dd, J = 14.8, 7.2 Hz, 2H), 7.24 (m, 2H), 7.1 (d, 7.4 Hz, 2H), 5.31 (dd, 11.9, 4.5 Hz, 1H), 4.41 (d, J = 12.1 Hz, 2H), 3.49 (m, 1H), 3.38 (m, 1H), 3.19 (m, 1H), 2.86 (m, 1H), 2.67 (dd, J = 18.8, 3.2 Hz, 1H), 2.43 (s, 3H), 1.88 (m, 1H), 1.75 (m, 1H), 1.49 (m, 2H) LC Method 1: 2.02 min | 367 |

Example 159

(1-(cyclopropanecarbonyl)piperidin-4-yl)(5-phenyl-4,5-dihydro-1H-pyrazol-1-yl)methanone

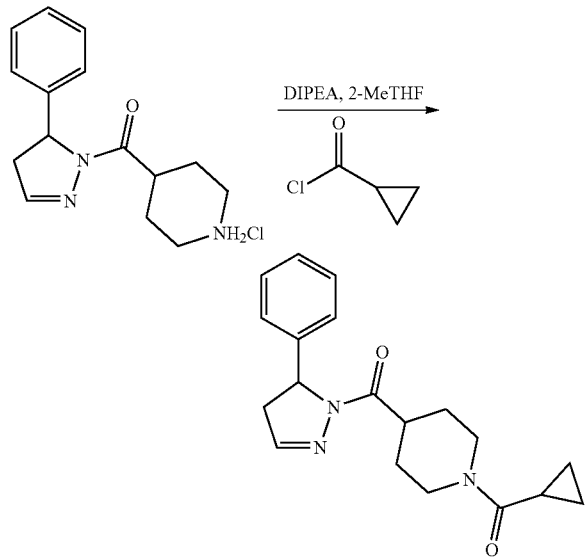

To a solution of (5-phenyl-4,5-dihydro-1H-pyrazol-1-yl)(piperidin-4-yl)methanone, hydrochloride (200 mg, 0.681 mmol) in 2-MeTHF (8 mL) stirred under nitrogen at rt was added neat DIPEA (0.357 mL, 2.042 mmol) followed by neat cyclopropanecarbonyl chloride (0.093 mL, 1.021 mmol). The reaction mixture was stirred at rt for 1 h. EtOAc (25 mL) were added and washed with 0.5M HCl (25 mL), NaHCO₃ (25 mL) and brine (25 mL), dried over sodium sulfate and evaporated in vacuo to give a colourless oil. This residue was purified by column chromatography (silica, EtOAc/CyH 0/100 to 100/0) to afford pure expected product as an oil. It was precipitated into diisopropyl ether to afford the title compound (142 mg, 0.436 mmol, 64.1, purity: >95% by LCMS, recovery: 64%) as a white solid. LCMS (m/z) 326 (M+H⁺), retention time: 2.09 min, Method 1 5V.

The following compounds were synthesized in an analogous manner. Acyl chloride was substituted for sulfonyl chloride for (5-phenyl-4,5-dihydro-1H-pyrazol-1-yl)(1-(phenylsulfonyl)piperidin-4-yl)methanone and for acetyl anhydride for 1-(4-methyl-4-(5-phenyl-4,5-dihydro-1H-pyrazole-1-carbonyl)piperidin-1-yl)ethanone.

| Ex Name | Structure | ¹H NMR LC: retention time (min) | MS (M + H)⁺ |
|---|---|---|---|
| 160 (5-phenyl-4,5-dihydro-1H-pyrazol-1-yl)(1-(phenylsulfonyl)piperidin-4-yl)methanone | | ¹H NMR (400 MHz, DMSO-d6) δ ppm 7.73 (m, 3H), 7.65 (dd, J = 7.6, 7.0 Hz, 2H), 7.31 (dd, J = 7.6, 7.2 Hz, 2H), 7.23 (m, 1H), 7.18 (s, 1H), 7.08 (m, 2H), 5.27 (dd, 1.11, 4.6 Hz, 1H), 3.62 (m, 2H), 3.45 (ddd, J = 18.9. 11.9, 1.4 Hz, 1H), 3.01 (m, 1H), 2.64 (ddd, J = 18.9, 4.7, 1.8 Hz, 1H), 2.39 (tdd, J = 11.6, 8.5, 2.7 Hz, 2H), 1.75-1.90 (m, 2H), 1.54 (m, 2H) LC Method 1: 2.57 min | 398 |

-continued

| Ex | Name | Structure | ¹H NMR<br>LC: retention time (min) | MS (M + H)⁺ |
|---|---|---|---|---|
| 161 | 2-methoxy-1-(4-(5-phenyl-4,5-dihydro-1H-pyrazole-1-carbonyl)piperidin-1-yl)ethanone | 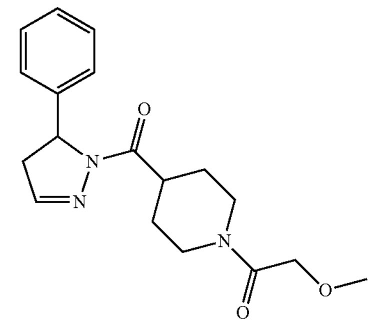 [SMILES: COCC(=O)N1CCC(C(=O)N2N=CCC2c2ccccc2)CC1] | ¹H NMR (400 MHz, DMSO-d6) δ ppm 7.32 (dd, J = 7.6, 7.2, 2H), 7.24 (m, 2H), 7.11 (d, J = 7.4Hz, 2H), 5.31 (dd, J = 11.8, 4.6 Hz, 1H), 4.31 (br s, 1H), 4.06 (dd, J = 16.3, 13.4 Hz, 2H), 3.78 (d, J = 13.3 Hz, 1H), 3.49 (dd, J = 18.4, 12.3 Hz, 1H), 3.32 (m, 1H), 3.27 (s, 3H), 3.07 (m, 1H), 2.67 (m, 2H), 1.77 (m, 2H), 1.42 (m, 2H)<br>LC Method 1: 1.87 min | 330 |
| 162 | (1-(cyclopentanecarbonyl))piperidin-4-yl)(5-phenyl-4,5-dihydro-1H-pyrazol-1-yl)methanone | 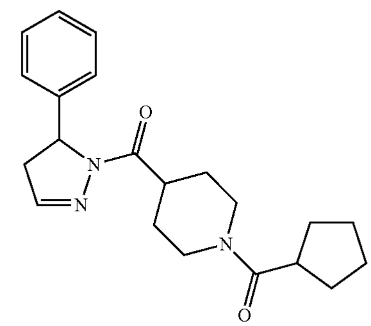 [SMILES: O=C(C1CCCC1)N1CCC(C(=O)N2N=CCC2c2ccccc2)CC1] | ¹H NMR (400 MHz, DMSO-d6) δ ppm 7.32 (dd, J = 7.6, 7.2 Hz, 2H), 7.23 (m, 2H), 7.10 (d, J = 7.6 Hz, 2H), 5.31 (dd, J = 11.8,44.6 Hz, 1H), 4.38 (br s, 1H), 3.99(d, J = 13.5 Hz, 1H), 3.49 (dd, 18.8, 11.9 Hz, 1H), 3.31 (m, 1H), 3.09 (m, 1H), 2.96 (m, 1H), 2.66 (m, 2H), 1.2-1.9 (m, 12H)<br>LC Method 1: 2.41 min | 354 |
| 163 | 1-(4-(5-phenyl-4,5-dihydro-1H-pyrazole-1-carbonyl)piperidin-1-yl)butan-1-one | 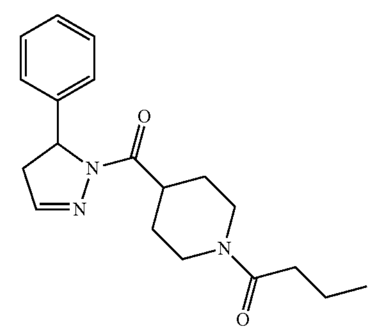 [SMILES: CCCC(=O)N1CCC(C(=O)N2N=CCC2c2ccccc2)CC1] | ¹H NMR (400 MHz, DMSO-d6) δ ppm 7.32 (dd, J = 7.6, 7.0 Hz, 2H), 7.24 (m, 2H), 7.1 (d, J = 7.6 Hz, 2H), 5.31 (dd, J = 11.9, 4.7 Hz, 1H), 4.37 (m, 1H), 3.88 (d, J = 13.5 Hz, 1H), 3.49 (dd, J = 18.8. 12.9 Hz, 1H), 3.29 (m, 1H), 3.08 (m, 1H), 2.66 (m, 2H), 2.26 (m, 2H), 1.8.3 (d, J = 12.5 Hz, 1H), 1.69 (m, 1H), 1.49 (q, J = 7.4 Hz, 2H), 1.35 (m, 2H), 0.87 (t, J = 7.4 Hz, 3H)<br>LC Method 1: 2.18 min | 328 |
| 164 | (1-benzoylpiperidin-4-yl)(5-phenyl-4,5-dihydro-1H-pyrazol-1-yl)methanone | 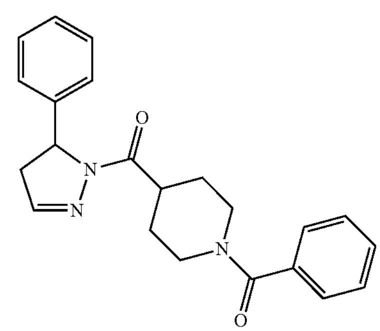 [SMILES: O=C(c1ccccc1)N1CCC(C(=O)N2N=CCC2c2ccccc2)CC1] | ¹H NMR (400 MHz, DMSO-d6) δ ppm 7.43 (m, 3H), 7.35 (m, 4H), 7.24 (m, 2H), 7.11 (d, J = 7.4 Hz, 2H), 5.31 (dd, J = 11.8, 4.6 Hz, 1H), 4.45 (br s, 1H), 3.6 (br s, 1H), 3.49 (ddd, 18.8. 11.9, 1.3 Hz, 1H), 3.36 (m, 1H), 3.13 (br s, 1H), 2.91 (br s, 1H), 2.67 (ddd, 18.8, 4.5, 1.7 Hz, 1H), 1.79 (m, 2H), 1.50 (m, 2H)<br>LC Method 1: 2.32 min | 362 |

| Ex | Name | Structure | ¹H NMR<br>LC: retention time (min) | MS<br>(M + H)⁺ |
|---|---|---|---|---|
| 165 | 2-cyclohexyl-1-(4-(5-phenyl-4,5-dihydro-1H-pyrazole-1-carbonyl)piperidin-1-yl)ethanone | 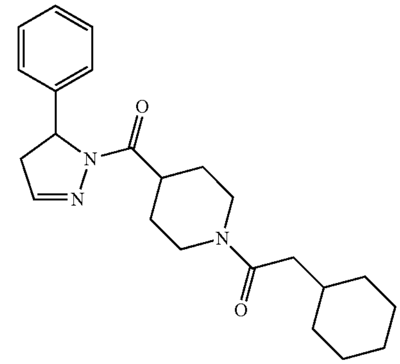 [SMILES: O=C(CC1CCCCC1)N1CCC(C(=O)N2N=CCC2c2ccccc2)CC1] | ¹H NMR (400 MHz, DMSO-d6) δ ppm 7.32 (dd, J = 7.6, 7.2 Hz, 2H), 7.24 (m, 2H), 7.10 (d, J = 7.6 Hz, 2H), 5.30 (dd, J = 11.8, 4.6 Hz, 1H), 4.40 (m, 1H), 3.90 (d, J = 13.8 Hz, 1H), 3.49 (dd, J = 18.8, 12.0 Hz, 1H), 3.31 (m, 1H), 3.08 (m, 1H), 2.66 (m, 2H), 2.16 (m, 2H), 1.81 (d, J = 13.2 Hz, 1H), 1.64 (m, 7H), 0.9-1.5 (m, 7H)<br>LC Method 1: 2.67 min | 382 |
| 166 | (1-benzoyl-4-methylpiperidin-4-yl)(5-phenyl-4,5-dihydro-1H-pyrazol-1-yl)methanone | 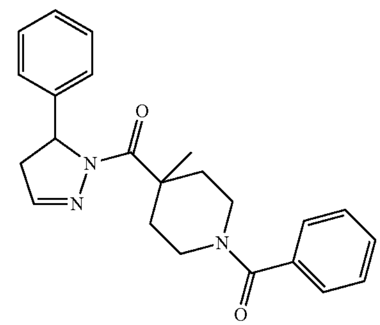 [SMILES: CC1(C(=O)N2N=CCC2c2ccccc2)CCN(C(=O)c2ccccc2)CC1] | ¹H NMR (400 MHz, DMSO-d6) δ ppm 7.43 (m, 3H), 7.34 (m, 4H), 7.24 (m, 2H), 7.12 (d, J = 7.2 Hz, 2H), 5.36 (dd, J = 11.8, 4.6 Hz, 1H), 3.95 (br s, 1H), 3.43 (m, 2H), 3.14 (m, 2H), 2.58 (ddd, J = 18.8, 6.3, 1.7 Hz, 1H), 2.26 (m, 2H), 1.52 (m, 2H), 1.36 (s, 3H)<br>LC Method 1: 2.57 min | 376 |
| 167 | 1-(4-methyl-4-(5-phenyl-4,5 dihydro-1H-pyrazole-1-carbonyl)piperidin-1-yl)ethanone | 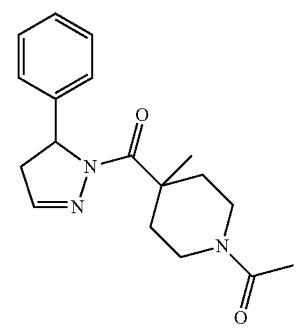 [SMILES: CC(=O)N1CCC(C)(C(=O)N2N=CCC2c2ccccc2)CC1] | ¹H NMR (400 MHz, DMSO-d6) δ ppm, 7.33 (dd, J = 7.6,7.4 Hz, 2H), 7.23 (m, 2H), 7.11 (d, J = 7.8 Hz, 2H), 5.36 (m, 1H), 3.78 (m, 1H), 3.52 (m, 1H), 3.40 (m, 1H), 3.16 (m, 1H), 2.92 (m, 1H), 2.59 (m, 1H), 2.31 (m, 1H), 2.17 (m, 1H), 1.95 (d, J = 7.4Hz, 3H), 1.44 (m, 2H), 1.33 (d, J = 2.7 Hz, 3H)<br>LC Method 1: 2.12 min | 314 |
| 168 | (1-(1H-indole-2-carbonyl)piperidin-4-yl)(5-phenyl-4,5-dihydro-1H-pyrazol-1-yl)methanone | 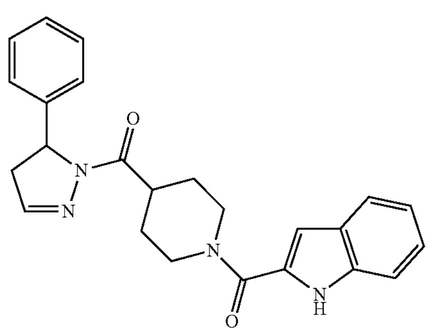 [SMILES: O=C(c1cc2ccccc2[nH]1)N1CCC(C(=O)N2N=CCC2c2ccccc2)CC1] | ¹H NMR (400 MHz, DMSO-d6) δ ppm 11.56 (s, 1H), 7.60 (d, J = 8 Hz, 1H), 7.41 (d, J = 8.2 Hz, 1H), 7.33 (m. 2H), 7.24 (m, 2H), 7.18 (m, 1H), 7.12 (d, J = 7.2 Hz, 2H), 7.04 (m, 1H), 6.76 (d, J = 1.5 Hz, 1H), 5.33 (dd, J = 11.8, 4.6 Hz, 1H), 4.45 (m, 2H), 3.51 (m, 1H), 3.41 (m, 2H), 3.15 (m, 1H), 2.68 (ddd, J = 19.0. 4.6, 1.5 Hz, 1H), 1.94 (d, J = 12Hz, 1H), 1.81 (d, J = 11.6 Hz, 1H), 1.56 (m, 2H)<br>LC Method 1: 2.48 min | 401 |

| Ex | Name | Structure | $^1$H NMR<br>LC: retention time (min) | MS<br>(M + H)$^+$ |
|---|---|---|---|---|
| 169 | (1-(1H-indole-3-carbonyl)piperidin-4-yl)(5-phenyl-4,5-dihydro-1H-pyrazol-1-yl)methanone | 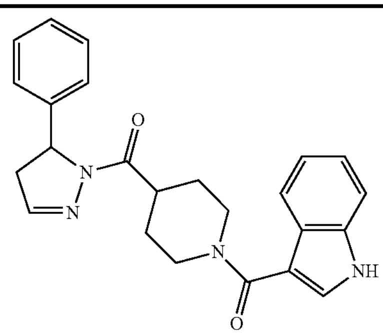 | $^1$H NMR (400 MHz, DMSO-d6) δ ppm 11.59 (s, 1H), 7.96 (s, 1H), 7.66 (d, J = 2.7 Hz, 1H), 7.62 (d, J = 7.8 Hz, 1H), 7.44 (d, J = 8 Hz, 1H), 7.32 (t, J = 7.4Hz, 2H), 7.24 (m, 2H), 7.11 (m, 4H), 5.32 (dd, J = 12.0, 4.6 Hz, 1H), 4.28 (d, J = 10.8 Hz, 2H), 3.49 (dd, J = 18.3, 12.4 Hz, 1H), 3.05 (m, 2H), 2.65 (m, 1H), 1.87 (m, 1H), 1.75 (m, 1H), 1.52 (m, 2H)<br>LC Method 1: 2.29 min | 401 |

Example 170

Benzyl ((2R)-1-oxo-1-(5-phenyl-4,5-dihydro-1H-pyrazol-1-yl)propan-2-yl)carbamate

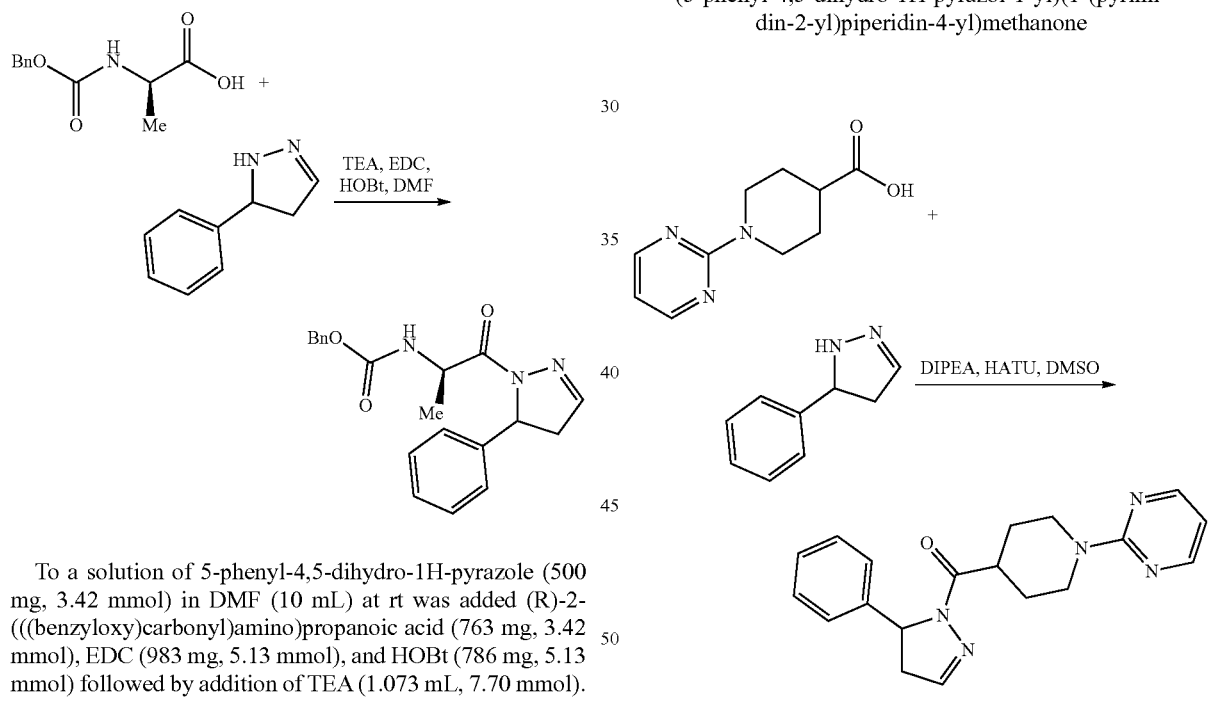

To a solution of 5-phenyl-4,5-dihydro-1H-pyrazole (500 mg, 3.42 mmol) in DMF (10 mL) at rt was added (R)-2-(((benzyloxy)carbonyl)amino)propanoic acid (763 mg, 3.42 mmol), EDC (983 mg, 5.13 mmol), and HOBt (786 mg, 5.13 mmol) followed by addition of TEA (1.073 mL, 7.70 mmol). The reaction was stirred at rt overnight. On completion of the reaction by TLC (using 5% of MeOH in DCM), the reaction mixture was diluted with cold water (20 mL) and extracted with DCM (2×20 mL). The combined organics were washed with water (10 mL) followed by brine and dried over anhydrous Na$_2$SO$_4$, filtered and concentrated under reduced pressure to afford crude material. The crude product was purified via silica gel (100-200 mesh) column and was eluted with Hex/EtOAc. Collected fractions: from 15-20% were concentrated under reduced pressure to afford the desired product benzyl ((2R)-1-oxo-1-(5-phenyl-4,5-dihydro-1H-pyrazol-1-yl)propan-2-yl)carbamate (43 mg, 0.119 mmol, 3.48% yield) as a yellow gum. MS (m/z) 352 (M+H$^+$). $^1$H NMR (DMSO-d$_6$) δ ppm 7.45 (d, J=8.08 Hz, 1H) 7.17-7.40 (m, 9H) 7.11 (d, J=7.07 Hz, 2H) 5.31 (dd, J=11.87, 4.80 Hz, 1H) 5.00 (s, 2H) 4.81 (t, J=7.58 Hz, 1H) 3.50 (ddd, J=18.95, 12.00, 1.39 Hz, 1H) 2.69 (ddd, J=18.95, 4.80, 1.52 Hz, 1H) 1.29 (d, J=7.33 Hz, 3H)

Example 171

(5-phenyl-4,5-dihydro-1H-pyrazol-1-yl)(1-(pyrimidin-2-yl)piperidin-4-yl)methanone In a vial a solution of 1-(pyrimidin-2-yl)piperidine-4-carboxylic acid (312 mg, 1.51 mmol) in DMSO (1 mL) was added DIPEA (0.478 mL, 2.74 mmol) followed by 5-phenyl-4,5-dihydro-1H-pyrazole (200 mg, 1.37 mmol) and then HATU (780 mg, 2.052 mmol) was added. The reaction was stirred overnight. The reaction was diluted with EtOAc and washed with water and brine. The organic layer was then dried over MgSO$_4$, filtered, and concentrated. The concentrated mixture was dissolved in DMSO and purified by prep HPLC. Pure fractions were isolated and concentrated to provide the title compound as the TFA salt (65 mg, 9.6%). The key to this reaction is to add the HATU last. MS (m/z) 336 (M+H$^+$). $^1$H NMR (400 MHz, DMSO-d$_6$) δ ppm 1.39-1.60 (m, 2H), 1.72-1.96 (m, 2H), 2.68 (ddd, J=19.0, 4.7, 1.6 Hz, 1H), 2.99-3.14 (m, 2H), 3.35-3.56 (m, 2H), 4.56-4.68 (m, 2H), 5.31 (dd, J=11.9, 4.6 Hz, 1H), 6.67 (t, J=4.8 Hz, 1H), 7.08-7.16 (m, 2H), 7.22-7.36 (m, 4H), 8.40 (d, J=4.8 Hz, 2H)

The following compounds were synthesized in an analogous manner. LiOH may be substituted for KOH in some cases. Some compounds underwent a chiral separation by reverse phase HPLC to isolate a single enantiomer. HATU was substituted by PyBROP for the example (5-(4-(difluoromethoxy)phenyl)-4,5-dihydro-1H-pyrazol-1-yl)(1-(5-fluoropyrimidin-2-yl)piperidin-4-yl)methanone. DMSO may be substituted by DCM, 2-MeTHF or DMF.

| Ex | Name | Structure | $^1$H NMR LC: retention time (min) | MS (M + H)$^+$ |
|---|---|---|---|---|
| 172 | (S)-(5-phenyl-4,5-dihydro-1H-pyrazol-1-yl)(1-(pyrimidin-2-yl)piperidin-4-yl)methanone | 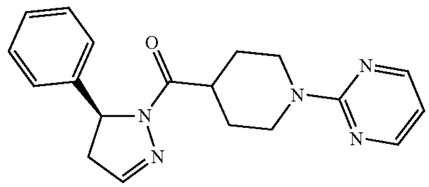 [SMILES: O=C(C1CCN(c2ncccn2)CC1)N1N=CC[C@H]1c1ccccc1] | $^1$H NMR (400 MHz, DMSO-d6) δ ppm 8.34 (d, J = 4.8 Hz, 2H), 7.29-7.35 (m, 2H), 7.20-7.26 (m, 2H), 7.07-7.13 (m, 2H), 6.59 (t, J = 4.8 Hz, 1H), 5.31 (dd, J = 11.9.4.5 Hz, 1H), 4.66 (d, J = 13.1 Hz, 2H), 3.49 (ddd, J = 18.9. 11.9. 1.5 Hz, 1H), 3.35-3.43 (m, 1H), 2.92-3.03 (m, 2H), 2.63-2.72 (m, 1H), 1.87 (d, J = 11.4Hz, 1H), 1.75 (d, J = 11.1 Hz, 1H), 1.35-1.54 (m, 2H) | 336 |
| 173 | 3-hydroxy-2,2-dimethyl-1-(5-phenyl-4,5-dihydro-1H-pyrazol-1-yl)propan-1-one 2,2,2-trifluoroacetate | 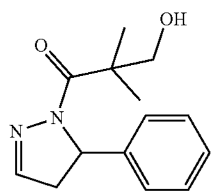 [SMILES: CC(C)(CO)C(=O)N1N=CCC1c1ccccc1] | $^1$H NMR (400 MHz, DMSO-d6) δ ppm 1.17 (s, 3H), 1.20 (s, 3H), 2.51-2.58 (m, 1H), 3.32-3.43 (m, 1H), 3.61-3.71 (m, 2H), 3.98- 4.03 (m, 1H), 5.32 (dd, J = 11.9, 4.6 Hz, 1H), 7.08-7.34 (m, 6H) | 247 |
| 174 | (5-phenyl-4,5-dihydro-1H-pyrazol-1-yl)(thiophen-2-yl)methanone 2,2,2-trifluoroacetate | 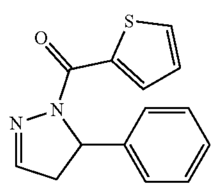 [SMILES: O=C(c1cccs1)N1N=CCC1c1ccccc1] | $^1$H NMR (400 MHz, DMSO-d6) δ ppm 2.77 (ddd, J = 19.0, 4.7, 1.6 Hz, 1H), 3.56 (ddd, J = 19.0, 11.8. 1.6 Hz, 1H), 5.52 (dd, J = 11.8, 4.7 Hz, 1H), 7.12-7.47 (m, 7 H), 7.87 (dd, J = 5.1, 1.3 Hz, 1H), 7.97 (dd, J = 3.8. 1.3 Hz, 1H) | 257 |
| 175 | (1-methyl-1H-pyrrol-2-yl)(4-(5-phenyl-4,5-dihydro-1H-pyrazole-1-carbonyl)piperidin-1-yl)methanone 2,2,2-trifluoroacetate | 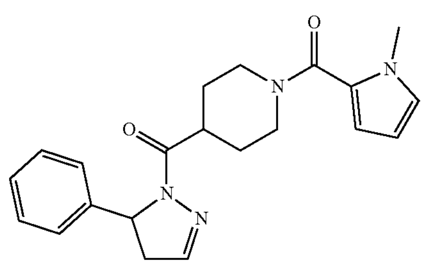 [SMILES: Cn1cccc1C(=O)N1CCC(C(=O)N2N=CCC2c2ccccc2)CC1] | $^1$H NMR (400 MHz, DMSO-d6) δ ppm 1.39-1.58 (m, 2H), 1.70-1.79 (m, 1H), 1.83-1.93 (m, 1H), 2.66 (ddd, J = 19.0, 4.6, 1.5 Hz, 1H), 2.93-3.12 (m, 2H), 3.31-3.41 (m, 1H), 3.48 (ddd, J = 18.9, 11.9, 1.3 Hz, 1H), 3.64 (s, 3H), 4.23-4.37 (m, 2H), 5.31 (dd, J = 11.9, 4.8 Hz, 1H), 6.01 (dd, J = 3.7, 2.7 Hz, 1H), 6.26 (dd, J = 3.7, 1.6 Hz, 1H), 6.84-6.89 (m, 1H), 7.07-7.16 (m, 2H), 7.19-7.36 (111, 4H) | 365 |
| 176 | (5-phenyl-4,5-dihydro-1H-pyrazol-1-yl)(1-(pyridin-2-yl)piperidin-4-yl)methanone 2,2,2-trifluoroacetate | 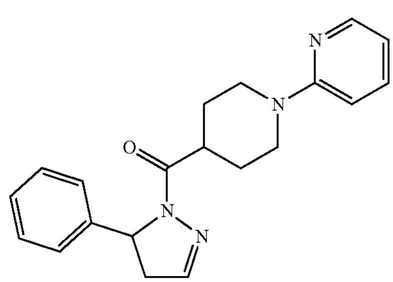 [SMILES: O=C(C1CCN(c2ccccn2)CC1)N1N=CCC1c1ccccc1] | $^1$H NMR (400 MHz, DMSO-d6) δ ppm 1.51-1.73 (m, 2H), 1.78-1.91 (m, 1H), 1.92-2.04 (m, 1H), 2.69 (ddd, J = 19.0, 4.6, 1.8 Hz, 1H), 3.19-3.34 (m, 2H), 3.39-3.57 (m, 2H), 4.14-4.27 (m, 2H), 5.31 (dd, J = 11.9, 4.6 Hz, 1H), 6.84-6.91 (m, 1H), 7.06-7.15 (m, 2H), 7.18-7.40 (m, 5H), 7.87-7.95 (m, 1H), 8.02 (dd, J = 5.9. 1.4Hz, 1H) | 335 |

| Ex | Name | Structure | ¹H NMR LC: retention time (min) | MS (M + H)⁺ |
|---|---|---|---|---|
| 177 | (S)-(5-phenyl-4,5-dihydro-1H-pyrazol-1-yl)(1-(pyridin-2-yl)piperidin-4-yl)methanone | 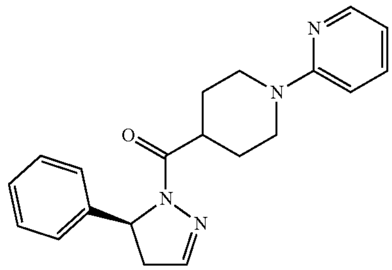 [SMILES: O=C(C1CCN(c2ccccn2)CC1)N1N=CC[C@H]1c1ccccc1] | ¹H NMR (400 MHz, DMSO-d6) δ ppm 1.51-1.73 (m, 2H), 1.78-1.91 (m, 1H), 1.92-2.04 (m, 1H), 2.69 (ddd, J = 19.0, 4.6, 1.8 Hz, 1H), 3.19-3.34 (m, 2H), 3.39-3.57 (m, 2H), 4.14-4.27 (m, 2H), 5.31 (dd, J = 11.9, 4.6 Hz, 1H), 6.84-6.91 (m, 1H), 7.06-7.15 (m, 2H), 7.18-7.40 (m, 5H), 7.87-7.95 (m, 1H), 8.02 (dd, J = 5.9, 1.4Hz, 1H) LC Method 3: 0.53 min | 335 |
| 178 | 2,2,2-trifluoro-1-(4-(5-phenyl-4,5-dihydro-1H-pyrazole-1-carbonyl)piperidin-1-yl)ethanone 2,2,2-trifluoroacetate | 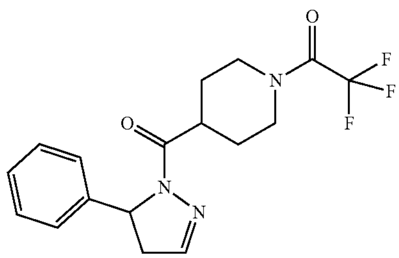 [SMILES: O=C(C1CCN(C(=O)C(F)(F)F)CC1)N1N=CCC1c1ccccc1] | ¹H NMR (400 MHz, DMSO-d6) δ ppm 1.37-1.63 (m, 2H), 1.78-2.05 (m, 2H), 2.68 (ddd, J = 19.0, 4.6, 1.3 Hz, 1H), 2.95-3.12 (m, 1H), 3.30-3.56 (m, 3H), 3.81-3.93 (m, 1H), 4.20-4.34 (m, 1H), 5.31 (dd, J = 11.9, 4.6 Hz, 1H), 7.07-7.16 (m, 2H), 7.19-7.40 (m, 4H) | 354 |
| 179 | (5-phenyl-4,5-dihydro-1H-pyrazol-1-yl)(1-(5-(trifluoromethyl)pyridin-2-yl)piperidin-4-yl)methanone 2,2,2-trifluoroacetate | 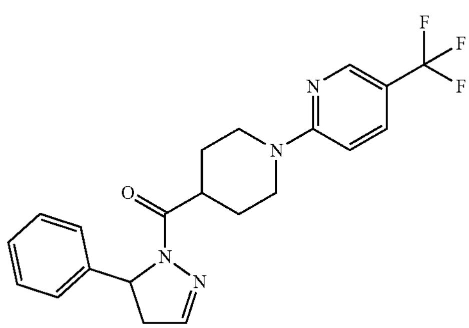 [SMILES: O=C(C1CCN(c2ccc(C(F)(F)F)cn2)CC1)N1N=CCC1c1ccccc1] | ¹H NMR (400 MHz, DMSO-d6) δ ppm 1.39-1.65 (m, 2H), 1.71-1.98 (m, 2H), 2.68 (ddd, J = 18.9, 4.6, 1.8 Hz, 1H), 2.97-3.15 (m, 2H), 3.35-3.59 (m, 2H), 4.36-4.49 (m, 2H), 5.31 (dd, J = 11.9, 4.6 Hz, 1H), 6.98 (d, J = 9.1 Hz, 1H), 7.06-7.16 (m, 2H), 7.18-7.40 (m, 4H), 7.77 (dd, J = 9.1, 2.5 Hz, 1H), 8.34-8.45 (m, 1H) | 403 |
| 180 | (1-(benzo[d]oxazol-2-yl)piperidin-4-yl)(5-phenyl-4,5-dihydro-1H-pyrazol-1-yl)methanone 2,2,2-trifluoroacetate | 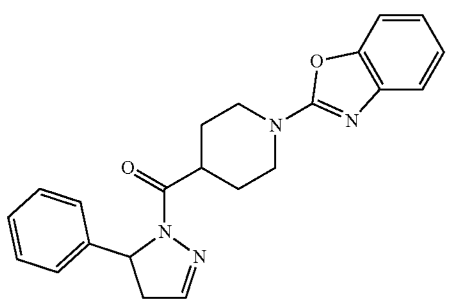 [SMILES: O=C(C1CCN(c2nc3ccccc3o2)CC1)N1N=CCC1c1ccccc1] | ¹H NMR (400 MHz, DMSO-d6) δ ppm 1.52-1.72 (m, 2H), 1.78-2.02 (m, 2H), 2.69 (ddd, J = 19.0, 4.8, 1.8 Hz, 1H), 3.19-3.44 (m, 3H), 3.50 (ddd, J = 19.0, 12.1, 1.5 Hz, 1H), 4.09-4.23 (m, 2H), 5.32 (dd, J = 11.9. 4.6 Hz, 1H), 6.99-7.37 (m, 9 H), 7.39-7.44 (m, 1H) | 375 |
| 181 | 1-(4-(5-phenyl-4,5-dihydro-1H-pyrazole-1-carbonyl)piperidin-1-yl)ethanone | 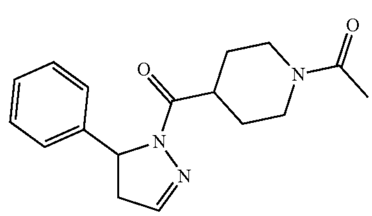 [SMILES: CC(=O)N1CCC(C(=O)N2N=CCC2c2ccccc2)CC1] | ¹H NMR (400 MHz, DMSO-d6) δ ppm 1.21-1.58 (m, 2H), 1.63-1.76 (m, 1H), 1.77-1.88 (m, 1H), 1.97 (s, 3H), 2.55-2.74 (m, 2H), 3.03-3.16 (m, 1H), 3.24-3.37 (m, 1H), 3.42-3.56 (m, 1H), 3.76-3.88 (m, 1H), 4.28-4.43 (m, 1H), 5.30 (dd, J = 11.9, 4.6 Hz, 1H), 7.06-7.16 (m, 2H), 7.20-7.37 (m, 4H) | 300 |

| Ex | Name | Structure | ¹H NMR<br>LC: retention time (min) | MS<br>(M + H)⁺ |
|---|---|---|---|---|
| 182 | 1-(4-(5-(2,3-dihydrobenzo-furan-5-yl)-4,5-dihydro-1H-pyrazole-1-carbonyl)piperidin-1-yl)ethanone | | ¹H NMR (400 MHz, DMSO-d6) δ ppm, 7.22 (s, 1H), 6.96 (br s, 1H), 6.82 (d, J = 8.2 Hz, 1H), 6.67 (d, J = 8.2 Hz, 1H), 5.22 (dd, J = 11.8, 4.6 Hz, 1H), 4.49 (t, J = 8.6 Hz, 2H), 4.34 (br s, 1H), 3.81 (d, J = 13.5 Hz, 1H), 3.44 (dd, J = 18.6, 12.0 Hz, 1H), 3.27 (tt, J = 11.4, 3.8 Hz, 1H), 3.13 (t, J = 8.6 Hz, 2H), 3.09 (m, 1H), 2.64 (m, 2H), 1.98 (s, 3H), 1.74 (m, 2H), 1.47 (m, 2H)<br>LC Method 1: 1.87 min | 342 |
| 183 | 1-(4-(5-(2,3-dihydro-1H-inden-5-yl)-4,5-dihydro-1H-pyrazole-1-carbonyl)piperidin-1-yl)ethanone | | ¹H NMR (400 MHz, CDCl3-d3) δ ppm 7.16 (d, J = 7.6 Hz, 1H), 7.0 (m, 2H), 6.91 (m, 1H), 5.33 (dd, J = 11.8, 4.9 Hz, 1H), 4.56 t (J = 13.5 Hz, 1H), 3.86 (d, J = 12.1 Hz, 1H), 3.38 (m, 2H), 3.16 (m, 1H), 2.87 (t. J = 7.4Hz, 4H), 2.81 (m, 2H), 2.09 (s, 3H), 2.06 (t, J = 7.4 Hz, 2H), 1.79 (m, 4H)<br>LC Method 1: 2.25 min | 340 |
| 184 | (5-(2.3-dihydro-1H-inden-5-yl)-4,5-dihydro-1H-pyrazol-1-yl)(1-(5-fluoropyrimidin-2-yl)piperidin-4-yl)methanone | | ¹H NMR (400 MHz, CDCl3-d3) δ ppm 8.20 (s, 2H), 7.17 (d, J = 7.8 Hz, 1H), 7.00 (m, 2H), 6.93 (d, J = 7.8 Hz, 1H), 5.35 (dd, J = 12.1, 5.1 Hz, 1H), 4.69 (m, 2H), 3.43 (ddd, J = 18.8, 12.1, 1.7 Hz, 1H), 3.40 (m, 1H), 3.05 (m, 2H), 2.87 (m,4H), 2.81 (ddd, J = 18.8, 4.9, 1.7 Hz, 1H), 2.06 (qt, J = 7.4 Hz, 2H), 1.99 (m, 1H), 1.88 (m, 1H), 1.76 (111, 2H)<br>LC Method 1: 2.98 min | 394 |
| 185 | (5-(4-(difluoromethoxy)phenyl)-4,5-dihydro-1H-pyrazol-1-yl)(1-(5-fluoropyrimidin-2-yl)piperidin-4-yl)methanone | | ¹H NMR (400 MHz, DMSO-d6) δ ppm 8.42 (s, 2H), 7.17 (m, 6H), 5.32 (dd, J = 11.8, 4.6 Hz, 1H), 4.56 (d, J = 12.9 Hz, 2H), 3.48 (dd, J = 18.6, 12.1 Hz, 1H), 3.36 (m, 1H), 3.0 (m, 2H), 2.68 (dd, J = 18.4, 3.8 Hz, 1H), 1.87 (d, J = 12.3 Hz, 1H), 1.75 (d, J = 12.1 Hz, 1H), 1.46 (m, 2H)<br>LC Method 1: 2.74 min | 420 |

| Ex | Name | Structure | $^1$H NMR<br>LC: retention time (min) | MS<br>$(M + H)^+$ |
|---|---|---|---|---|
| 186 | (5-(6-methylpyridin-3-yl)-4,5-dihydro-1H-pyrazol-1-yl)(1-(oxazole-5-carbonyl)piperidin-4-yl)methanone | 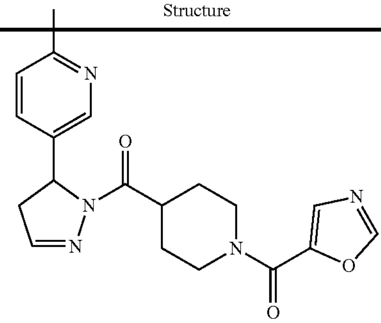 | $^1$H NMR (400 MHz, DMSO-d6) δ ppm 8.53 (s, 1H), 8.26 (s, 1H), 7.68 (s, 1H), 7.39 (d, J = 6.3 Hz, 1H), 7.28 (s, 1H), 7.20 (d, J = 8 Hz, 1H), 5.33 (dd, J = 11.8. 4.7 Hz, 1H), 4.33 (m, 1H), 4.15 (m, 1H), 3.50 (dd, J = 18.6, 12.1 Hz, 1H), 3.38 (m, 2H), 3.30 (m, 1H), 2.95 (m, 1H), 2.76 (dd, J = 18.8. 3.4 Hz, 1H), 2.43 (s, 3H), 1.88 (d, J = 11.4 Hz, 1H), 1.79 (d, J = 12.0 Hz, 1H), 1.51 (br s, 1H)<br>LC Method 1: 0.77 min | 368 |
| 187 | (1-(5-fluoropyrimidin-2-yl)piperidin-4-yl)(5-(6-methylpyridin-3-yl)-4,5-dihydro-1H-pyrazol-1-yl)methanone | 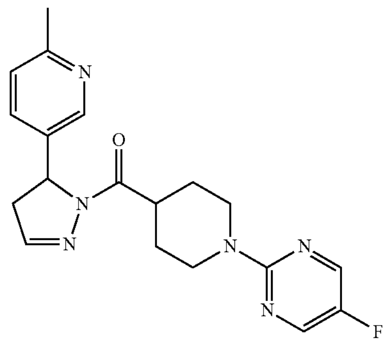 [SMILES: Cc1ccc(C2CC=NN2C(=O)C2CCN(c3ncc(F)cn3)CC2)cn1] | $^1$H NMR (400 MHz, DMSO-d6) δ ppm, 8.43 (s, 2H), 8.25 (d, J = 2.1 Hz, 1H), 7.38 (dd, J = 2.3 Hz, 1H), 7.27 (s, 1H), 7.2 (d, J = 8.2 Hz, 1H), 5.31 (dd, J = 11.9, 4.8 Hz, 1H), 4.55 (m, 2H), 3.50 (ddd, J = 18.9, 12.0, 1.3 Hz, 1H), 3.34 (m, 1H), 2.99 (m, 2H), 2.75 (ddd, J = 18.9, 4.9, 1.7 Hz, 1H), 2.42 (s, 3H), 1.84 (d, J = 11.2 Hz, 1H), 1.74 (d, J = 12.1 Hz, 1H), 1.44 (m, 2H)<br>LC Method 1: 1.49 min | 369 |
| 188 | 4-(1-(1-(5-fluoropyrimidin-2-yl)piperidine-4-carbonyl)-4,5-dihydro-1H-pyrazol-5-yl)benzonitrile | 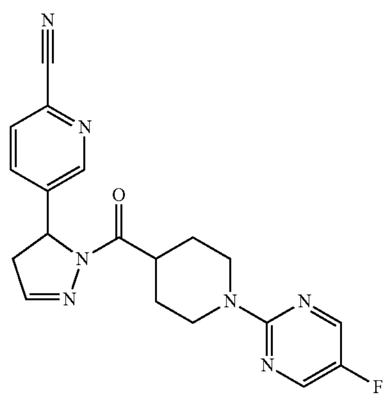 [SMILES: N#Cc1ccc(C2CC=NN2C(=O)C2CCN(c3ncc(F)cn3)CC2)cn1] | $^1$H NMR (400 MHz, DMSO-d6) δ ppm, 8.43 (s, 2H), 7.8 (d, J = 8.0 Hz, 2H), 7.31 (d, J = 8.2 Hz, 2H), 7.26 (s, 1H), 5.39 (dd, J = 12.0, 4.7 Hz, 1H), 4.56 (d, J = 13.1 Hz, 2H), 3.52 (dd, J = 18.7, 12.4 Hz, 1H), 3.36 (m, 1H), 3.00 (m, 2H), 2.72 (dd, J = 18.9.4.0 Hz, 1H), 1.89 (d, J = 12.1Hz, 1H), 1.75 (d, J = 11.6Hz, 1H), 1.46 (m, 2H).<br>LC Method 1: 2.50 min | 379 |

Example 189

(4-fluoro-1-(5-fluoropyrimidin-2-yl)piperidin-4-yl)(5-phenyl-4,5-dihydro-1H-pyrazol-1-yl)methanone

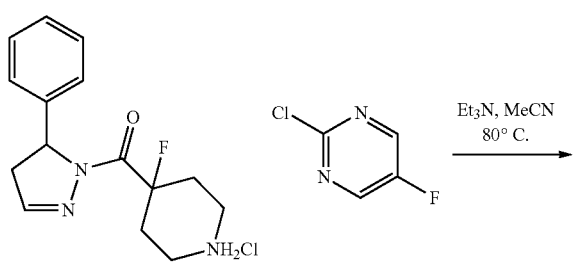

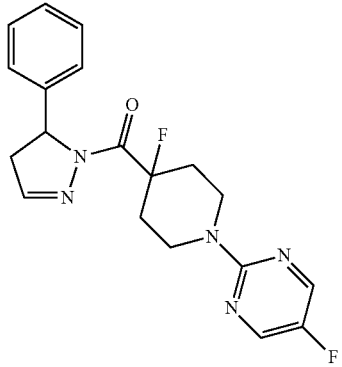

To a suspension of (4-fluoropiperidin-4-yl)(5-phenyl-4,5-dihydro-1H-pyrazol-1-yl)methanone, hydrochloride (250 mg, 0.802 mmol), 2-chloro-5-fluoropyrimidine (0.198 mL, 1.604 mmol) in acetonitrile (8 mL) stirred under nitrogen at rt was added neat Et₃N (0.447 mL, 3.21 mmol). The reaction mixture was stirred at 90° C. overnight. 0.5M HCl (20 mL) and EtOAc (25 mL) were added. After separation, the aqueous layer was extracted with EtOAc (2×20 mL). The combined organic layers were washed with saturated brine, dried over sodium sulphate and evaporated in vacuo to give a colourless oil. This residue was purified by column chromatography (silica EtOAc/CyH 0/100 to 50/50) to the title compound (198 mg, 0.533 mmol, purity: >95% by LCMS, recovery: 66%) as a white solid. LCMS (m/z) 372 (M+H⁺), retention time: 2.67 min, Method 1 5V.

The following compound were synthesized in an analogous manner. TEA was substituted for DIPEA.

isocyanate (0.108 mL, 1.362 mmol). The reaction mixture was stirred at rt overnight. 0.5M HCl (25 mL) and EtOAc (30 mL) were added. After separation, the aqueous layer was extracted with EtOAc (2×30 mL). The combined organic layers were washed with saturated brine, dried over sodium sulphate and evaporated in vacuo to give a colourless oil. This residue was purified by column chromatography [silica, (EtOH/EtOAc 1:4)/CyH 0/100 to 100/0] to afford the title compound as a foam which was precipitated into diethyl ether/diisopropyl ether to give as white solid (185 mg, 0.563 mmol, purity: >95% by LCMS, recovery: 83%) as a white solid. LCMS (m/z) 329 (M+H⁺), retention time: 1.92 min, Method 1 5V.

| Ex Name | Structure | ¹H NMR and LC: retention time (min) | MS (M + H)⁺ |
|---|---|---|---|
| 190 (1-(5-fluoropyrimidin-2-yl)-4-methylpiperidin-4-yl)(5-phenyl-4,5-dihydro-1H-pyrazol-1-yl)methanone | | ¹H NMR (400 MHz, DMSO-d6) δ ppm 8.41 (d, J = 0.8 Hz, 2H), 7.32 (dd, J = 7.6, 7.2 Hz, 2H), 7.22 (m, 2H), 7.12 (d, 7.0 Hz, 2H), 5.37 (dd, J = 11.9, 4.6 Hz, 1H), 3.99 (m, 2H), 3.4 (ddd, J = 18.8, 11.8. 1.3 Hz, 1H), 3.31 (m, 2H), 2.59 (ddd, J = 18.8.4.5. 1.7Hz, 1H), 2.33 (m, 1H), 2.22 (m, 1H), 1.50 (m, 2H), 1.36 (s, 3H) LC Method 1: 2.93 min | 368 |

Example 191

N-ethyl-4-(5-phenyl-4,5-dihydro-1H-pyrazole-1-carbonyl)piperidine-1-carboxamide

Example 192

1-(3-bromo-5-phenyl-4,5-dihydro-1H-pyrazol-1-yl)-2,2-dimethylpropan-1-one

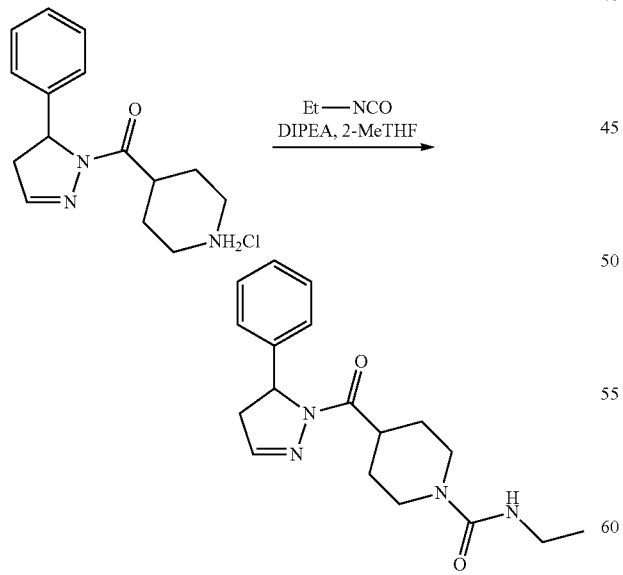

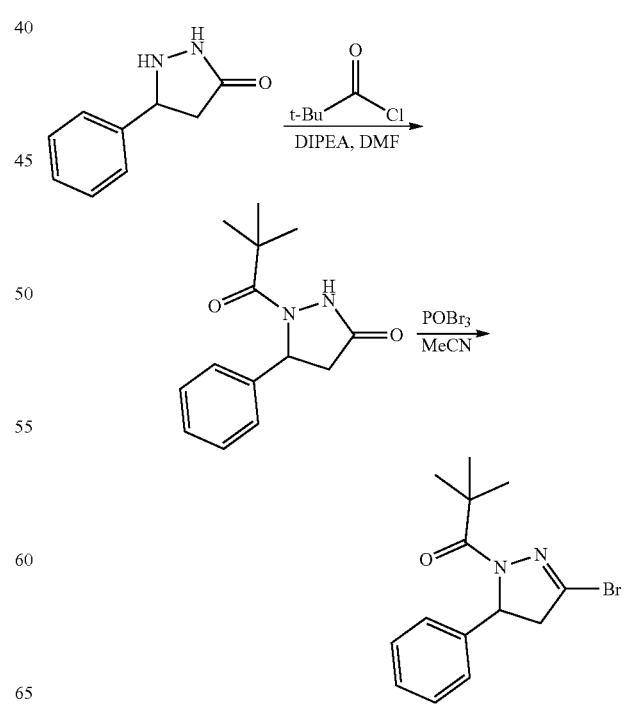

To a suspension of (5-phenyl-4,5-dihydro-1H-pyrazol-1-yl)(piperidin-4-yl)methanone, hydrochloride (200 mg, 0.681 mmol) and DIPEA (0.178 mL, 1.021 mmol) in 2-MeTHF (8 mL) stirred under nitrogen at rt was added neat ethyl 5-Phenylpyrazolidin-3-one (434 mg, 2.68 mmol) was dissolved in DMF (5 mL) and the reaction mixture cooled to 0° C. in an ice bath. To this was added DIPEA (0.935 mL, 5.35 mmol) followed by the dropwise addition of pivaloyl chloride (0.329 mL, 2.68 mmol). The reaction mixture was then stirred for 18 h, during which time the reaction mixture warmed to RT. The reaction mixture was then concentrated in vacuo partitioned between DCM (100 mL) and water (100 mL), the aq. phase was separated and washed with further DCM (100 mL). The combined organic fractions were then concentrated in vacuo to give an orange/brown oil. This was purified by silica chromatography, eluting with EtOAc:cyclohexane (0-60% EtOAc), the appropriate fractions were combined and concentrated in vacuo to give 5-phenyl-1-pivaloylpyrazolidin-3-one (84 mg, 13%), MS (m/z) 247 (M+H+). In addition N'-pivaloylcinnamohydrazide (32 mg, 5%) was isolated as a by-product.

Phosphorus oxybromide (54 mg, 0.188 mmol) was added to a solution of 5-phenyl-1-pivaloylpyrazolidin-3-one (72 mg, 0.292 mmol) in acetonitrile (2 mL) and the reaction mixture was heated at reflux (85° C.) under an atmosphere of nitrogen for 1 h 50 mins. LCMS indicated a major peak for the product and no starting material left. The reaction mixture was cooled to RT and evaporated under reduced pressure. The residue was partitioned between EtOAc (10 mL) and sat sodium bicarbonate solution (10 mL). The organic extract was dried (hydrophobic frit) and concentrated under reduced pressure. The residue was then subjected to purification by mass-directed automated preparative HP LC (Sunfire C18 column) to afford the title compound (12 mg, 0.039 mmol, 13% yield) as a white solid. MS (m/z) 310/312 (M+H+). $^1$H NMR (400 MHz, CDCl$_3$) δ ppm 7.32-7.41 (m, 2H) 7.23-7.32 (m, 1H) 7.13-7.23 (m, 2H) 5.52 (dd, J=12.0, 5.1 Hz, 1H) 3.61 (dd, J=18.2, 11.9 Hz, 1H) 2.93 (dd, J=18.2, 5.0 Hz, 1H) 1.34 (s, 9H).

Example 193

1-(4-(5-phenyl-4,5-dihydro-1H-pyrazole-1-carbonyl)piperidin-1-yl)ethanone

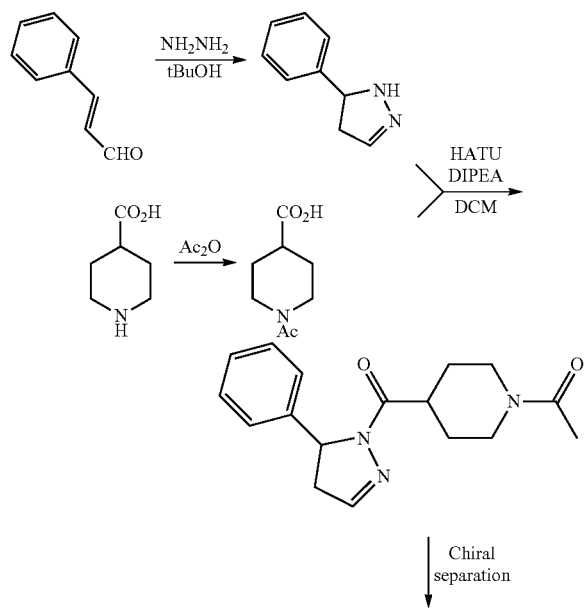

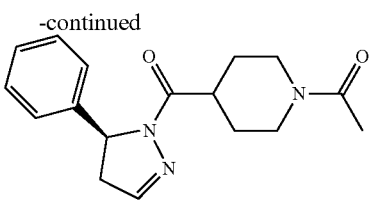

Neat hydrazine monohydrate (17.07 mL, 352 mmol) was heated to reflux. A solution of cinnamaldehyde (19.05 mL, 141 mmol) in tert-butanol (40 mL) was added dropwise, and the mixture was refluxed overnight. The reaction mixture was evaporated in vacuo to give a yellow oil. This residue was purified by column chromatography (AcOEt/CyH 0-50%) to afford 5-phenyl-4,5-dihydro-1H-pyrazole (11.645 g, 80 mmol, 56.6% yield) as a yellow oil. MS (m/z) 147 (M+H+).

A suspension of piperidine-4-carboxylic acid (5 g, 38.7 mmol) in acetic anhydride (36.5 ml, 387 mmol) was heated at 130° C. for 3 h (the reaction mixture became homogeneous). After 3 h, the reaction mixture was evaporated in vacuo to give a brown oil which crystallized during the night. The solid was triturated in iPr$_2$O and filtered to efford 1-acetylpiperidine-4-carboxylic acid (6.42 g, 30.8 mmol, 79% yield) as a cream solid. MS (m/z) 172 (M+H+).

To a solution of 5-phenyl-4,5-dihydro-1H-pyrazole (1 g, 6.84 mmol), 1-acetylpiperidine-4-carboxylic acid (1.757 g, 10.26 mmol) and DIPEA (2.389 mL, 13.68 mmol) in DCM (30 mL) stirred under nitrogen at room temp was added solid HATU (3.90 g, 10.26 mmol). The reaction mixture was stirred at RT overnight. To the reaction mixture 0.5 M HCl (100 mL) and EtOAc (100 mL) were added. After separation, the aqueous layer was extracted with EtOAc (2×100 mL). The combined organic phases were washed with saturated brine, dried over sodium sulphate and evaporated in vacuo to give a dark orange oil. Column chromatography [(EtOAc/EtOH 4:1)/CyH 0-100%] failed to afford the pure expected product. A second attempt of column chromatography (EtOH/DCM 0-5%) afforded pure 1-(4-(5-phenyl-4,5-dihydro-1H-pyrazole-1-carbonyl)piperidin-1-yl)ethanone (926 mg, 3.09 mmol, 45% yield) as a light yellow oil. MS (m/z) 300 (M+H+).

The enantiomers were separated via chiral chromatography on reverse phase HPLC (Chiralpak AD-H, 5 μm, 1 mL/min; C7/EtOH 50/50) to provide 125 mg (25%) of (S)-2,2-dimethyl-1-(5-phenyl-4,5-dihydro-1H-pyrazol-1-yl)propan-1-one (Rt=10.1 min) and 125 mg (25%) of (R)-2,2-dimethyl-1-(5-phenyl-4,5-dihydro-1H-pyrazol-1-yl)propan-1-one (Rt=16.3 min) as white solids. The absolute configuration of the active enantiomer was assigned as (S), based on the assignment of (S)-2,2-dimethyl-1-(5-phenyl-4,5-dihydro-1H-pyrazol-1-yl)propan-1-one as the active enantiomer as described earlier. MS (m/z) 300 (M+H+). $^1$HNMR (400 MHz, DMSO-d6) δ ppm 1.23-1.58 (m, 2H), 1.65-1.75 (m, 1H), 1.78-1.87 (m, 1H), 1.98 (s, 3H), 2.56-2.71 (m, 2H), 3.04-3.16 (m, 1H), 3.25-3.32 (m, 1H), 3.42-3.54 (m, 1H), 3.82 (d, J=13.7 Hz, 1H), 4.30-4.39 (m, 1H), 5.31 (dd, J=11.9, 4.7 Hz, 1H), 7.11 (d, J=7.40 Hz, 2H), 7.21-7.28 (m, 2H), 7.29-7.36 (m, 2H).

The following compounds were synthesized in an analogous manner using 2-(3H-[1,2,3]triazolo[4,5-b]pyridin-3-yl)-1,1,3,3-tetramethylisouronium hexafluorophosphate(V) (HATU) or bromotripyrrolidinophosphonium hexafluorophosphate (PyBroP) as the coupling agent and using DCM or DMF as solvent.

| Ex | Name | Structure | ¹H NMR LC: retention time (min) | MS (M + H)⁺ |
|---|---|---|---|---|
| 194 | 1-(4-(5-(4-(difluoromethoxy)phenyl)-4,5-dihydro-1H-pyrazole-1-carbonyl)piperidin-1-yl)ethanone | 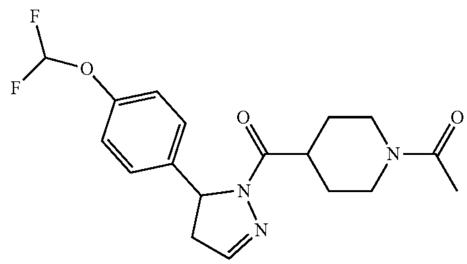 [SMILES: CC(=O)N1CCC(C(=O)N2N=CCC2c2ccc(OC(F)F)cc2)CC1] | ¹H NMR (400 MHz, DMSO-d6) δ ppm 7.31-7.05 (m, 5H), 8.32 (br d J = 8.5 Hz, 1H), 4.34 (br s, 1H), 3.80 (br d, J = 12 Hz, 1H), 3.48 (m, 1H), 3.39-3.22 (m, 1H), 3.17-2.99 (m, 1H), 2.75-2.56 (m, 2H), 1.98 (s, 3H), 1.89-1.64 (m, 2H), 1.58-1.23 (m, 2H). LC Method 1 2.93 min | 366 |
| 195 | 1-(4-(5-(2,3-dihydrobenzo[b][1,4]dioxin-6-yl)-4,5-dihydro-1H-pyrazole-1-carbonyl)piperidin-1-yl)ethanone | 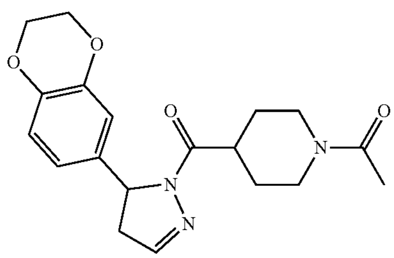 [SMILES: CC(=O)N1CCC(C(=O)N2N=CCC2c2ccc3c(c2)OCCO3)CC1] | ¹H NMR (400 MHz, DMSO-d6) δ ppm 7.20 (s, 1H), 6.79 (d, J = 8.7 Hz, 1H), 6.57 (m, 2H), 5.20(dd, J = 11.7, 4.3 Hz, 1H), 4.35 (m, 1H), 4.21 (s, 4H), 3.82 (m, 1H), 3.42 (dd, J = 18.7, 12.1 Hz, 1H), 3.28 (m, 1H), 3.09 (m, 1H), 2.63 (m, 2H), 1.98 (s, 3H), 1.81 (m, 1H), 1.69 (m, 1H), 1.47 (m, 2H) LC Method 1 1.85 min | 358 |

Example 196

(S)-1-(4-(5-(3-fluorophenyl)-4,5-dihydro-1H-pyrazole-1-carbonyl)piperidin-1-yl)ethanone

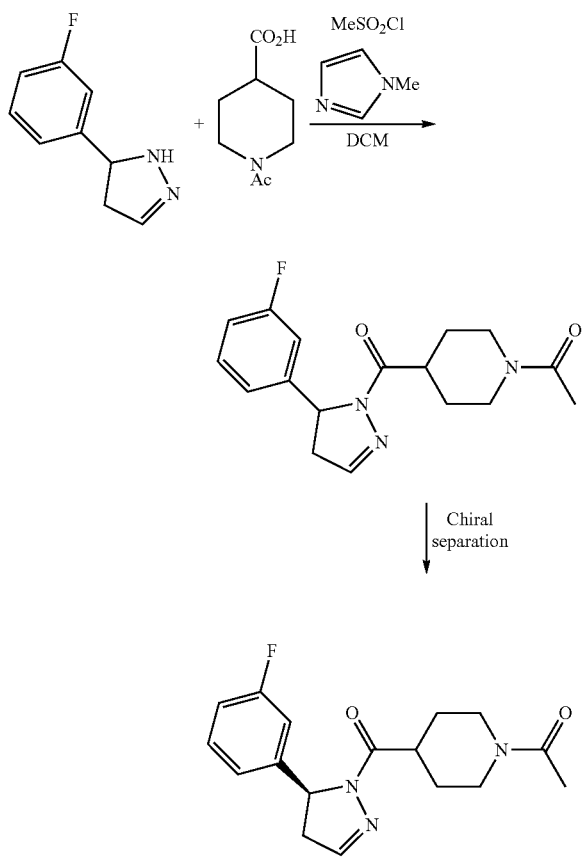

To a stirred solution of 1-methylimidazole (3.88 mL, 48.7 mmol) in DCM (15 mL) was added methanesulfonyl chloride (0.95 mL, 12.2 mmol) at 0° C. and the reaction mixture was stirred at 0° C. for 15 min and then 1-acetylpiperidine-4-carboxylic acid (2.1 g, 12.2 mmol) was added at 0° C., the resulting reaction mixture was stirred at rt for 1 h. Then added a solution 5-(3-fluorophenyl)-4,5-dihydro-1H-pyrazole (2 g, 12.18 mmol) in DCM (15.00 mL), then contents were stirred at rt for 16 hr. Then sodium bicarbonate solution (30 mL) was added and extracted with DCM (2×30 mL), the combined organics were dried over anh.Na2SO4, filtered and concentrated to get the crude product (2.5 g).

The crude product was purified by silicagel (100-200 mesh) column using 0.5-1% MeOH in DCM to afford 1.1 g of desired compound which was further purified by Prep. HPLC to afford 1-(4-(5-(3-fluorophenyl)-4,5-dihydro-1H-pyrazole-1-carbonyl)piperidin-1-yl)ethanone (800 mg, 2.5 mmol, 20% yield) as white solid. MS (m/z) 318 (M+H⁺). The racemate (714 mg) was separated into the two enantiomers via chiral chromatography on reverse phase HP LC (Chiralpak AD-H, 4.6×150 mm column, 60:40 EtOH: Heptane with 0.1% isopropylamine at 254 nm, 1 mL/min) to provide 316 mg (44%) of (S)-1-(4-(5-(3-fluorophenyl)-4,5-dihydro-1H-pyrazole-1-carbonyl)piperidin-1-yl)ethanone and 309 mg (43%) of (R)-1-(4-(5-(3-fluorophenyl)-4,5-dihydro-1H-pyrazole-1-carbonyl)piperidin-1-yl)ethanone as white solids. The absolute configuration of the active enantiomer was assigned as (S), based on the assignment of (S)-2,2-dimethyl-1-(5-phenyl-4,5-dihydro-1H-pyrazol-1-yl)propan-1-one as the active enantiomer as described earlier. MS (m/z) 318 (M+H⁺). 1H NMR (400 MHz, DMSO-d6) δ ppm 1.28-1.56 (m, 2H), 1.62-1.77 (m, 1H), 1.77-1.90 (m, 1H), 1.98 (s, 3H), 2.54-2.84 (m, 2H), 3.00-3.20 (m, 1H), 3.20-3.38 (m, 1H), 3.40-3.56 (m, 1H), 3.82 (d, J=12.4 Hz, 1H), 4.24-4.48 (m, 1H), 5.33 (dd, J=11.9, 4.8 Hz, 1H), 6.82-7.02 (m, 2H), 7.02-7.16 (m, 1H), 7.24 (s, 1H), 7.37 (td, J=8.0, 6.1 Hz, 1H).

The following compounds were synthesized in an analogous manner.

| Ex | Name | Structure | ¹H NMR<br>LC, chiral HPLC or chiral SFC<br>retention time (min) | MS<br>(M + H)⁺ |
|---|---|---|---|---|
| 197 | 1-(4-(5-(3,5-difluorophenyl)-4,5-dihydro-1H-pyrazole-1-carbonyl)piperidin-1-yl)ethanone | 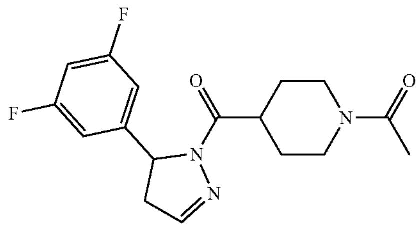 [SMILES: CC(=O)N1CCC(C(=O)N2N=CCC2c2cc(F)cc(F)c2)CC1] | ¹H NMR (400 MHz, DMSO-d₆) δ ppm 7.24 (s, 1H), 7.12 (t, J = 9.3 Hz, 1H), 6.83 (d, J = 8.2 Hz, 2H), 5.34 (dd, J = 12.0, 5.1 Hz, 1H), 4.26-4.48 (m, 1H), 3.69-3.97 (m, 1H), 3.48 (dd, J = 18.6, 12.5 Hz, 1H), 3.20-3.31 (m, 1H), 2.97-3.20 (m, 1H), 2.54-2.84 (m, 2H), 1.98 (s, 3H), 1.84 (d, J = 13.1 Hz, 1H), 1.61-1.77 (m, 1H), 1.41-1.61 (m, 1H), 1.17- 1.41 (m, 1H). Chiral SFC 4.31 and 4.86 mm | 336 |
| 198 | 1-(4-(5-(2-fluorophenyl)-4,5-dihydro-1H-pyrazole-1-carbonyl)piperidin-1-yl)ethanone | 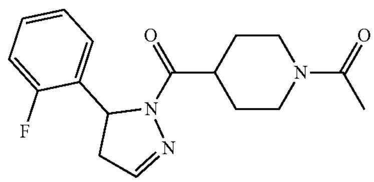 [SMILES: CC(=O)N1CCC(C(=O)N2N=CCC2c2ccccc2F)CC1] | ¹H NMR (400 MHz, DMSO-d₆) δ ppm 7.24-7.35 (m, 2H), 7.10-7.21 (m, 2H), 6.98-7.08 (m, 1H), 5.44 (dd, J = 12.1, 5.0 Hz, 1H), 4.25-4.40 (m, 1H), 3.81 (br d, J = 13.4Hz, 1H), 3.51 (ddd, J = 18.8,12.1, 1.3 Hz, 1H), 3.23-3.29 (m, 1H), 3.01-3.16 (m, 1H), 2.55-2.77 (m, 2H), 1.97 (s, 3H), 1.75-1.88 (m, 1H), 1.70 (br t, J = 11.4Hz, 1H), 1.26- 1.56 (m, 2H). Chiral SFC 5.8 and 8.13 min | 318 |
| 199 | (S)-1-(4-(5-(2-fluorophenyl)-4,5-dihydro-1H-pyrazole-1-carbonyl)piperidin-1-yl)ethanone | 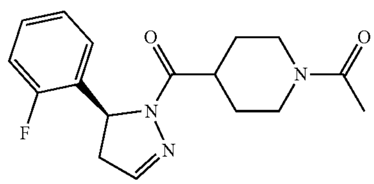 [SMILES: CC(=O)N1CCC(C(=O)N2N=CC[C@H]2c2ccccc2F)CC1] | ¹H NMR (400 MHz, DMSO-d6) δ ppm 7.23-7.39 (m, 2H), 7.09-7.23 (m, 2H), 6.95-7.09 (m, 1H), 5.45 (dd, J = 12.1,5.1 Hz, 1H), 4.24-4.43 (m, 1H), 3.81 (d, J = 12.6 Hz, 1H), 3.51 (ddd, J = 9.0, 12.1, 1.5 Hz, 1H), 3.22-3.31 (m, 1H), 3.00-3.20 (m, 1H), 2.55-2.83 (m, 2H), 1.98 (s, 3H), 1.82 (d, J = 13.4Hz, 1H), 1.63-1.76 (m, 1H), 1.24-1.53 (in, 2H). Chiral HP: LC 5.85 min | 318 |
| 200 | 1-(4-(5-(4-fluorophenyl)-4,5-dihydro-1H-pyrazole-1-carbonyl)piperidin-1-yl)ethanone | 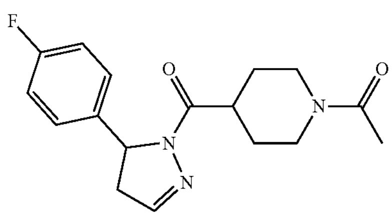 [SMILES: CC(=O)N1CCC(C(=O)N2N=CCC2c2ccc(F)cc2)CC1] | ¹H NMR (400 MHz, DMSO-d₆) δ ppm 7.22 (s, 1H), 7.14 (d, J = 7.9 Hz, 4H), 5.31 (dd, J = 11.8. 4.60 Hz, 1H), 3.80 (br d, J = 12.9 Hz, 1H), 3.40-3.59 (m, 1H), 3.29 (s, 1H), 2.97-3.13 (m, 1H), 2.56-2.77 (m, 2H), 1.97 (s, 3H), 1.80 (br d, J = 12.5 Hz, 1H), 1.69 (br t, J = 11.2 Hz, 1H), 1.22-1.54 (m, 2H). Chiral SFC 3.37 and 5.01 min | 318 |
| 201 | (S)-1-(4-(5-(4-fluorophenyl)-4,5-dihydro-1H-pyrazole-1-carbonyl)piperidin-1-yl)ethanone | 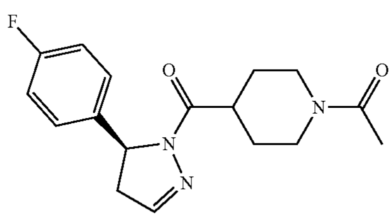 [SMILES: CC(=O)N1CCC(C(=O)N2N=CC[C@H]2c2ccc(F)cc2)CC1] | ¹H NMR (400 MHz, DMSO-d6) δ ppm 7.23 (s, 1H), 7.07-7.20 (in, 4H), 5.32 (dd, J = 11.9, 4.8 Hz, 1H), 4.34 (td. J = 8.0, 4.6 Hz, 1H), 3.81 (d, J = 12.6 Hz, 1H), 3.48 (dd, J = 18.4, 12.4 Hz, 1H), 3.21-3.31 (m, 1H), 3.00-3.20 (m, 1H), 2.54-2.76 (m, 2H), 1.98 (s, 3H), 1.80 (d, J = 12.6 Hz, 1H), 1.70 (t, J = 10.9 Hz, 1H), 1.39-1.60 (m, 1H), 1.18-1.39 (m, 1H). LC Method 1. Chiral HP: 7.80 min | 318 |
| 202 | ((1-methyl-cyclopropyl)(5-phenyl-4,5-dihydro-1H-pyrazol-1-yl)methanone | 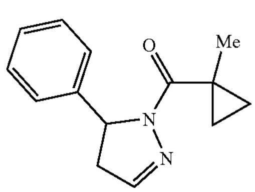 [SMILES: CC1(C(=O)N2N=CCC2c2ccccc2)CC1] | ¹H NMR (400 MHz, DMSO-d₆) δ ppm 7.28-7.36 (m, 2H), 7.15-7.26 (m, 2 H), 7.01-7.12 (m, 2H), 5.27 (dd, J = 11.95,4.93 Hz, 1H), 3.41 (ddd, J = 18.80. 11.89. 1.53 Hz, 1H), 2.60 (ddd, J = 18.74, 4.93, 1.75 Hz, 1H), 1.38 (s, 3H), 1.01 (ddd, J = 9.54, 5.92, 3.62 Hz, 1H), 0.83-0.92 (m, 1H), 0.41-0.62 (m, 2H). Chiral SFC: 2.50 and 3.13 min | 229 |

Example 203

(S)-1-(4-(5-(3,5-difluorophenyl)-4,5-dihydro-1H-pyrazole-1-carbonyl)piperidin-1-yl)ethanone

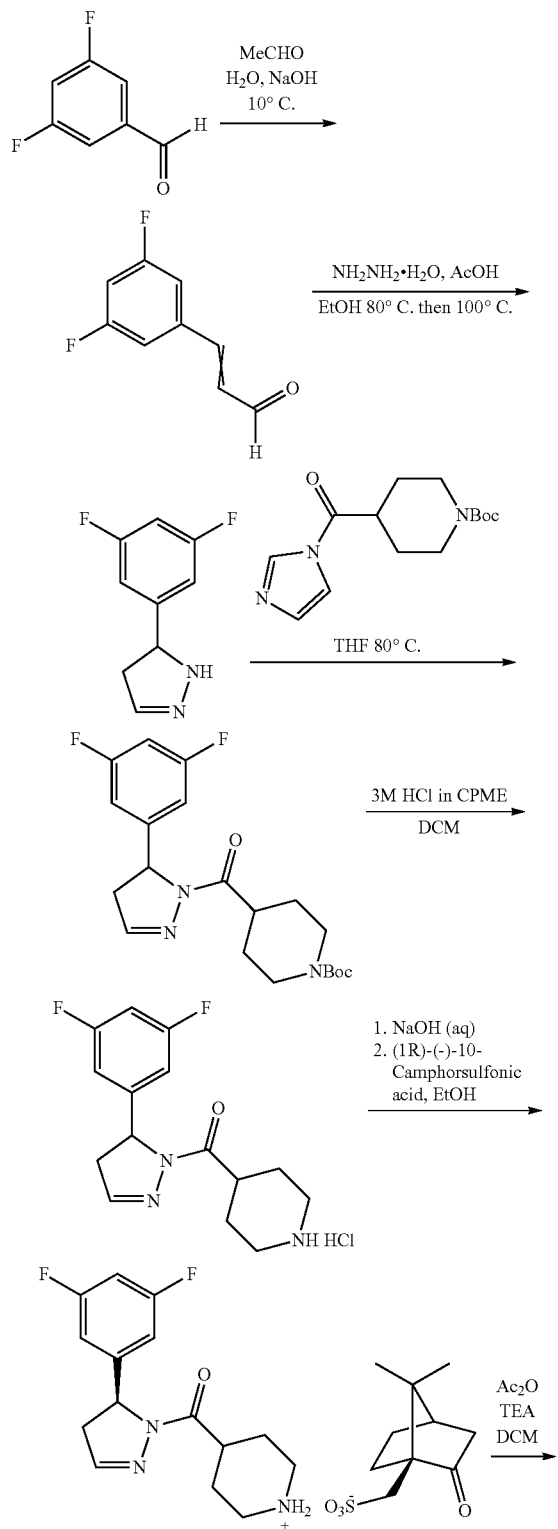

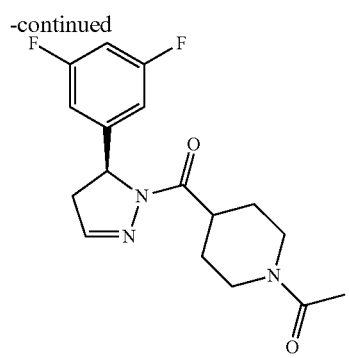

Step 1: To a suspension of 3,5-difluorobenzaldehyde (200 g, 1.407 mol) in H$_2$O (1.6 L) stirred at 10° C. with a mechanical stirrer was added neat acetaldehyde (87 mL, 1.548 mol). A 1 M solution NaOH (1548 mL, 1.548 mol) is added dropwise over 50 min. The reaction mixture was stirred at rt for 24 h. The reaction mixture was extracted with DCM (3×450 mL). The combined organic layer was dried over Na$_2$SO$_4$, filtered and evaporated to give a orange oil which solidified. A trituration in iPr$_2$O afforded 3-(3,5-difluorophenyl)acrylaldehyde (58 g, 345 mmol, purity: 95%, recovery: 24.5%) as a light yellow powder. LCMS (m/z) 169 (M+H$^+$), retention time: 2.31 min, Method 1 20 V. $^1$H NMR (400 MHz, DMSO-d6) δ ppm: 9.69 (d, J=7.8 Hz, 1H), 7.70 (d, J=15.9 Hz, 1H), 7.56 (m, 2H), 7.36 (tt, J=9.3 and 2.3 Hz, 1H), 6.99 (dd, J=15.9 and 7.6 Hz, 1H).

Step 2: To a solution of hydrazine monohydrate (118 mL, 2427 mmol in EtOH (2.2 L) stirred at 0° C. was added neat acetic acid (150 mL, 2.629 mol). After the end of addition, solid 3-(3,5-difluorophenyl)acrylaldehyde (340 g, 2.022 mol) was added portionwise. The reaction mixture was stirred at 100° C. for 21 h. The reaction mixture was evaporated in vacuo to afford 5-(3,5-difluorophenyl)-4,5-dihydro-1H-pyrazole (365 g, 2.004 mol, purity: 51%, recovery: 99%) as an orange oil. This oil was used in next reaction without further purification. LCMS (m/z) 183 (M+H$^+$), retention time: 1.93 min, Method 1 20 V.

Step 3A: Synthesis of tert-butyl 4-(1H-imidazole-1 carbonyl)piperidine-1-carboxylate:

1-(tert-butoxycarbonyl)piperidine-4-carboxylic acid (512 g, 2233 mmol) is dissolved in DCM (2 L) at 0° C. 1,1′-Carbonyldiimidazole (380 g, 2345 mmol) was added portionwise and the reaction mixture was stirred at rt for 2 h. H$_2$O (1.5 L) and DCM was added. After separation, The organic phase was washed with water (2×800 mL) and then dried over Na$_2$SO$_4$, filtered and concentrated in vacuo. The residue was triturated into iPr$_2$O; the solid was filtered and washed with iPr$_2$O (2×800 mL) to afford tert-butyl 4-(1H-imidazole-1 carbonyl)piperidine-1-carboxylate (621 g, 2223 mmol, purity: >95%, recovery: 100%) as a white powder. LCMS (m/z) 228 (M−H$^-$) corresponding to the acid coming from the hydrolysis of the imidazolyl amide on the LC column, retention time: 2.07 min, Method 1 20 V. $^1$H NMR (400 MHz, DMSO-d6) δ ppm: 8.53 (s, 1H), 7.76 (s, 1H), 7.10 (s, 1H), 3.98 (d, J=11.9 and 2.0 Hz, 2H), 3.46 (tt, J=11.2 and 3.4 Hz, 1H), 2.90 (br s, 2H), 1.87 (d, J=12.7 Hz, 2H), 1.58-1.45 (m, 2H), 1.41 (s, 9H).

Step 3B: To a solution of 5-(3,5-difluorophenyl)-4,5-dihydro-1H-pyrazole (365 g, 2.004 mol) in THF (1.5 L) stirred at rt was added solid tert-butyl 4-(1H-imidazole-1carbonyl)piperidine-1-carboxylate (560 g, 2.004 mol) portionwise. The reaction mixture was stirred at rt for 1 h and heat at 80° C. for 4 h. The reaction mixture was evaporated in vacuo. DCM (1.5 L) was added and washed with H$_2$O (2×1 L). The combined organic layer was dried over Na$_2$SO$_4$ and evaporated in vacuo to afford tert-butyl 4-(5-(3,5-difluorophenyl)-4,5-dihydro-1H-pyrazole-1-carbonyl)piperidine-1-carboxylate (858 g, 2.181 mol, purity: 82%, recovery: 109%) as a orange oil. This oil was used in next reaction without further purification. LCMS (m/z) 394 (M+H+), retention time: 2.75 min, Method 1 20 V. Step 4: To a solution of tert-butyl 4-(5-(3,5-difluorophenyl)-4,5-dihydro-1H-pyrazole-1-carbonyl)piperidine-1-carboxylate (858 g, 2.181 mol) in DCM (1.5 L) stirred at rt was added a 3M solution of HCl in CPME (1.454 L, 4.362 mol) portionwise. The reaction mixture was stirred at rt for 30 h. The solid was filtered, washed with iPr$_2$O (2×1 L), followed by Et$_2$O (2×1 L) to afford (5-(3,5-difluorophenyl)-4,5-dihydro-1H-pyrazol-1-yl)(piperidin-4-yl)methanone, Hydrochloride as a yellow powder (460 g, 1.395 mol, purity: 68%, recovery: 64.0%). This powder was used in next reaction without further purification. LCMS (m/z) 294 (M+H+), retention time: 1.19 min, Method 1 20 V. $^1$H NMR (400 MHz, DMSO-d6) δ ppm: 7.27 (s, 1H), 7.14 (tt, J=9.3 and 2.2 Hz, 1H), 6.84 (d, J=6.5 Hz, 2H), 5.34 (dd, J=12.0 and 4.9 Hz, 1H), 3.48 (dd, J=19.1 and 12.0, 1H), 3.29 (m, 3H), 2.95 (m, 2H), 2.75 (ddd, J=19.1 and 5.0 and 1.4 Hz, 1H), 1.85 (m, 5H)

Step 5: To a solution of (5-(3,5-difluorophenyl)-4,5-dihydro-1H-pyrazol-1-yl)(piperidin-4-yl)methanone, Hydrochloride (460 g, 1.395 mol) in H$_2$O (1 L) was added a 1 M solution of NaOH (2.092 L, 2.092 mol). The solution was stirred at rt for 1 h. The reaction mixture was extracted with DCM (3×850 mL). The combined organic layer was dried over Na$_2$SO$_4$, filtered and evaporated in vacuo to give the free base as a pale brown oil (400 g). The free base was dissolved in EtOH (800 mL) at rt and this solution was separated in two equal batches. Solid (1R)-(−)-10-camphorsulfonic (39.5 g, 170 mmol for each batch) was added and the suspensions were heated at 80° C. for 30 min. The resulting solutions were then evaporated in vacuo to give dark brown oily solids. A minimum of EtOH was added in both batches to suspend the solids, then heated at reflux and EtOH (3.55 L for each batch in total) was added until complete solubilization of the solids. The resulting mixtures were combined (total 7.9 L) and allowed to cooled to rt. The resulting solid was filtered and washed with cold ethanol (300 mL) and iPr$_2$O (2×400 mL) to afford (S)-(5-(3,5-difluorophenyl)-4,5-dihydro-1H-pyrazol-1-yl)(piperidin-4-yl)methanone, 1R-(−)-Camphor-10-sulphonic acid salt (182 g, 346 mmol, purity: >95%, recovery: 24.8%) as a white powder. LCMS (m/z) 294.2 (M+H+), retention time: 1.21 min, Method 1 20 V. Chiral HPLC method 1: 2.60 and 3.32 min, ee=98.5%. $^1$H NMR (400 MHz, DMSO-d6) δ ppm: 8.62 (br s, 1H), 8.29 (s, 1H), 7.27 (s, 1H), 7.13 (t, J=9.3 Hz, 1H), 6.85 (d, J=6.3 Hz, 2H), 5.34 (dd, J=11.8 and 5.0 Hz, 1H), 3.49 (dd, J=18.9 and 12.1 Hz, 1H), 3.32 (m, 3H), 2.99 (m, 2H), 2.90 (d, J=14.8 Hz, 1H), 2.76 (ddd, J=19.0, 4.7 and 1.1 Hz, 1H), 2.67 (m, 1H), 2.40 (d, J=14.6 Hz, 1H), 2.24 (dt, J=18.0 and 3.7 Hz, 1H), 2.01 (d, J=13.2 Hz, 1H), 1.94 (t, J=4.4 Hz, 1H), 1.78 (m, 5H), 1.29 (m, 2H), 1.04 (s, 3H), 0.74 (s, 3H).

Step 6: To a suspension of (S)-(5-(3,5-difluorophenyl)-4,5-dihydro-1H-pyrazol-1-yl)(piperidin-4-yl)methanone, 1R-(−)-Camphor-10-sulphonic acid salt (182 g, 346 mmol) in DCM (1.3 L) at 0° C. was added TEA (121 mL, 866 mmol) dropwise. Neat Ac$_2$O (32.7 mL, 346 mmol) was added dropwise and the mixture was stirred at rt for 25 min. H$_2$O was added and the pH adjusted to 8 with NaHCO$_3$. The organic layer was washed with 0.5 M HCl solution (2×1.2 L), dried over Na$_2$SO$_4$ and filtered. This solution was treated with vegetable charcoal (25 g). The solution was heated at reflux for 25 min, filtered on celite and concentrated in vacuo. The residue was triturated in hot Et$_2$O (1.2 L) for 1 h; the resulting mixture was cooled to rt and filtered to afford (S)-1-(4-(5-(3,5-difluorophenyl)-4,5-dihydro-1H-pyrazole-1-carbonyl)piperidin-1-yl)ethanone (111 g, 331 mmol, purity: 100%, recovery: 96%) as a white powder. This product was dried under high vacuum for 6 h. LCMS (m/z) 336.1 (M+H+), retention time: 2.00 min, Method 1 20 V. Chiral HPLC method 1: 6.04 and 3.32 min, ee=99.9%. $^1$H NMR (400 MHz, DMSO-d6) δ ppm: 7.24 (s, 1H), 7.12 (tt, J=9.3 and 1.9 Hz, 1H), 6.84 (m, 2H), 5.34 (dd, J==12.0 and 4.9 Hz, 1H), 4.35 (m, 1H), 3.82 (m, 1H), 3.48 (ddd, J=19.0, 12.1 and 1.0 Hz, 1H), 3.31 (m, 1H), 3.10 (m, 1H), 2.74 (ddd, J=19.1, 5.0 and 1.5 Hz, 1H), 2.62 (qd, J=12.8 and 2.5 Hz, 1H), 1.99 (s, 3H), 1.84 (m, 1H), 1.71 (t, J=11.5 Hz, 1H), 1.49 (m, 1H), 1.33 (m, 1H).

The PXRD pattern of FIG. 5 was obtained from a sample of (S)-1-(4-(5-(3,5-difluorophenyl)-4,5-dihydro-1H-pyrazole-1-carbonyl)piperidin-1-yl)ethanone prepared by trituration in hot diethyl ether, followed by cooling to room temperature and filtering, using a Rigaku Miniflex II Desktop X-ray Diffractometer as follows. Material was loaded on a zero background slide sample holder and scanned according to the parameters:
Start angle=2 Stop angle=40
Step width=0.02
Count time=1.0
kV=30 mA=15
Scan Axis=2 theta/theta.

Example 204

1-(4-(5-(4-chlorophenyl)-4,5-dihydro-1H-pyrazole-1-carbonyl)piperidin-1-yl)ethanone

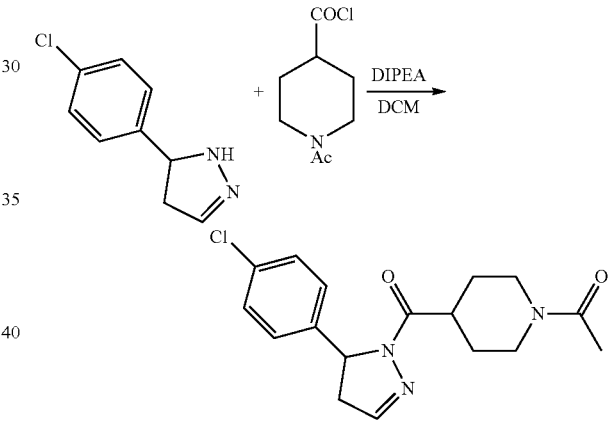

To a solution of 1-acetylpiperidine-4-carbonyl chloride (1.05 g, 5.54 mmol) in DCM (20 mL) stirred under nitrogen at 0° C. was added DIPEA (2.4 mL, 13.8 mmol), followed by 5-(4-chlorophenyl)-4,5-dihydro-1H-pyrazole (0.5 g, 2.77 mmol) portionwise during 1 min. The reaction mixture was stirred at rt for about 16 hour. The reaction was monitored by TLC. TLC Mobile Phase: 40% EtOAc in Hexane, Rf Value: 0.2. The reaction mixture was diluted with water (10 mL) and extracted with DCM (3×30 mL), and separated organic layers washed with sat. bicarbonate solution (25 ml) and brine solution (25 mL) and dried over anhydrous Na2SO4, filtered and concentrated under reduced pressure to afford crude compound. The crude compound was purified by silica gel column chromatography (100-200 mesh) eluting with 10-30% EtOAc in Hexane. The collected fractions was concentrated under reduced pressure to afford the title compound (292 mg, 0.83 mmol, 30% yield). LC Method 4 retension time 8.81 min. MS (m/z) 334/336 (M+H+). $^1$H NMR (400 MHz, DMSO-d$_6$) δ ppm 7.29-7.43 (m, 2H), 7.23 (s, 1H), 7.13 (dd, J=8.6, 2.9 Hz, 2H), 5.30 (dd, J=11.8, 4.8 Hz, 1H), 4.33 (br.s, 1H), 3.72-3.88 (m, 1H), 3.40-3.56 (m, 1H), 3.22-3.29 (m, 1H), 3.01-3.16 (m, 1H), 2.52-2.74 (m, 2H), 1.97 (s, 3H), 1.80 (br. d., J=11.6 Hz, 1H), 1.69 (br. t., J=11.2 Hz, 1H), 1.21-1.55 (m, 2H).

The following compounds were synthesized in an analogous manner using either DIPEA or TEA as the base.

| Ex | Name | Structure | $^1$H NMR Chiral SFC retention time (min) | MS (M + H)$^+$ |
|---|---|---|---|---|
| 205 | (1-(4-(5-(4-chloro-3-fluorophenyl)-4,5-dihydro-1H-pyrazole-1-carbonyl)piperidin-1-yl)ethanone | 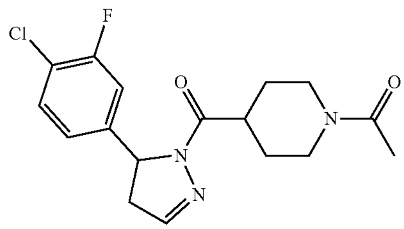 [SMILES: CC(=O)N1CCC(C(=O)N2N=CCC2c2ccc(Cl)c(F)c2)CC1] | $^1$H NMR (400 MHz, DMSO-d$_6$) δ ppm 1.18-1.54 (m, 2H), 1.63-1.72 (m, 1H), 1.81 (br d, J = 12.72 Hz, 1H), 1.97 (S, 3H), 2.55-2.83 (m, 2H), 3.00-3.14 (m, 1H), 3.29 (s, 1H), 3.39-3.55 (m, 1H), 3.81 (br d, J = 13.59 Hz, 1H), 4.33 (br d, J = 9.21 Hz, 1H), 5.32 (dd, J = 11.95, 4.93 Hz, 1H), 6.98 (br t, J = 6.47 Hz, 1H), 7.15 (br d, J = 10.30 Hz, 1H), 7.23 (s, 1H), 7.46-7.59 (m, 1H) Chiral SFC: 3.77 and 4.29 min | 352/ 354 |
| 206 | 1-(5-phenyl-4,5-dihydro-1H-pyrazole-1-carbonyl)cyclopropane carbonitrile | 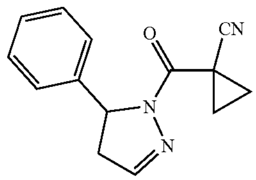 [SMILES: N#CC1(C(=O)N2N=CCC2c2ccccc2)CC1] | H NMR (400 MHz, DMSO-d$_6$) δ ppm 0.41-0.62 (m, 2H), 0.83-0.92 (m, 1H), 1.01 (ddd, J = 9.54, 5.92, 3.62 Hz, 1H), 1.38 (s, 3H), 2.60 (ddd, J = 18.74, 4.93, 1.75 Hz, 1H), 3.41 (ddd, J = 18.80, 11.89, 1.53 Hz, 1H), 5.27 (dd, J = 11.95, 4.93 Hz, 1H), 7.01-7.12 (m, 2H), 7.15-7.26 (m, 2H), 7.28-7.36 (m, 2H) Chiral SFC: 2.80 and 2.99 min | 240 |

Example 207

(5-phenyl-4,5-dihydro-1H-pyrazol-1-yl)(1-(thiazol-2-yl)piperidin-4-yl)methanone

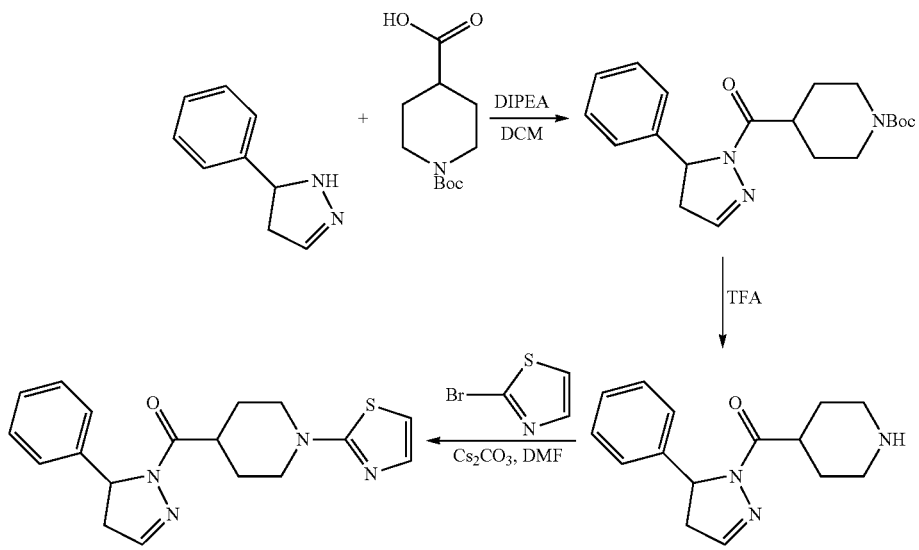

To a solution of tert-butyl 4-(chlorocarbonyl)piperidine-1-carboxylate (10.2 g, 41 mmol) in DCM (100 mL) was added 5-phenyl-4,5-dihydro-1H-pyrazole (15 g, 103 mmol) and DIPEA (54 mL, 308 mmol) at 0° C. and the reaction was stirred at rt for 3 h. Water (100 mL) was added and extracted with DCM (2×100 mL), the organic layer was separated and dried over anh.Na$_2$SO$_4$, filtered and concentrated to afford crude tert-butyl 4-(5-phenyl-4,5-dihydro-1H-pyrazole-1-carbonyl)piperidine-1-carboxylate (2.7 g, 7.5 mmol, 7% yield) as yellow semi-solid. MS (m/z) 380 (M+Na$^+$).

To a solution of tert-butyl 4-(5-phenyl-4,5-dihydro-1H-pyrazole-1-carbonyl)piperidine-1-carboxylate (2.7 g, 7.55 mmol) in DCM (40 mL) was added TFA (2.9 mL, 37.8 mmol) at 0° C. and the reaction was stirred at rt for 4 h. After completion of the reaction remove the solvent under reduced pressure to afford crude product. The obtained crude product was dissolved in MeOH (50 mL) and added amberlyst A-21 ion exchange resin up to PH~8, the resin filtered and the filtrate was concentrated and dried under high vacuum to afford (5-phenyl-4,5-dihydro-1H-pyrazol-1-yl)(piperidin-4-yl)methanone (1.5 g, 5.78 mmol, 76% yield) as white solid. MS (m/z) 258 (M+H$^+$).

To a solution of (5-phenyl-4,5-dihydro-1H-pyrazol-1-yl)(piperidin-4-yl)methanone (1 g, 3.89 mmol) and 2-bromothiazole (0.765 g, 4.66 mmol) in dry DMF (10 mL) was added Cs$_2$CO$_3$ (1.9 g, 5.83 mmol). The reaction mixture was stirred at 100° C. for 16 hr and then cooled to rt. The reaction mixture was diluted with EtOAc (30 mL), washed with water (50 mL), the organic layer separated and the aqueous layer was further extracted with EtOAc (30 mL), the combined organics were washed with water (50 mL), separated organic layer was dried over anh.Na$_2$SO$_4$, filtered and concentrated to afford crude product. The crude product was dissolved in DCM (10 mL) and was pre-adsorbed onto silica gel and purified by normal phase chromatography using silica gel (100-200 mesh) column and was eluted with Hexane/EtOAc (60/40). Collected fractions were concentrated under reduced pressure to afford the title compound (130 mg, 0.363 mmol, 9% yield) as an orange color gum. MS (m/z) 341 (M+H$^+$). $^1$H NMR (400 MHz, DMSO-d6) δ ppm, 7.27-7.38 (m, 2H), 7.18-7.26 (m, 2H), 7.03-7.18 (m, 3H), 6.80 (d, J=3.7 Hz, 1H), 5.31 (dd, J=11.8, 4.6 Hz, 1H), 3.83-3.95 (m, 2H), 3.49 (ddd, J=19.0, 12.0, 1.5 Hz, 1H), 3.30-3.38 (m, 1H), 3.02-3.16 (m, 2H), 2.59-2.74 (m, 1H), 1.90 (br. d., J=11.4 Hz, 1H), 1.78 (br. d., J=11.4 Hz, 1H), 1.50-1.70 (m, 2H).

Also prepared by the method of Example 90:

| Ex | Name | Structure | $^1$H NMR | MS (M + H)$^+$ |
|---|---|---|---|---|
| 208 | 1-(5-(1H-indol-5-yl)-4,5-dihydro-1H-pyrazol-1-yl)-2,2-dimethylpropan-1-one | 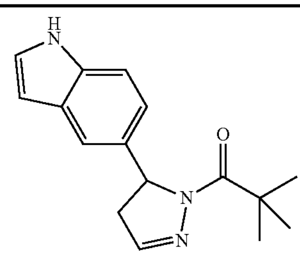 | $^1$H NMR (400 MHz, DMSO-d6) δ ppm 11.03 (br. s., 1H), 7.29-7.34 (m, 2H), 7.25 (s, 1H), 7.19 (t, J = 1.6 Hz, 1H), 6.82 (dd, J = 8.3, 1.8 Hz, 1H), 6.36 (ddd, J = 3.0, 2.1, 0.8 Hz, 1H), 5.37 (dd, J = 11.7, 4.4Hz, 1H), 3.39 (ddd, J = 18.8, 11.8, 1.5 Hz, 1H), 2.60 (ddd, J = 18.8, 4.4, 1.9 Hz, 1H), 1.25 (s, 9H) | 270 |

Also prepared by the method of Example 171:

| Ex | Name | Structure | $^1$H NMR | MS (M + H)$^+$ |
|---|---|---|---|---|
| 209 | (5-phenyl-4,5-dihydro-1H-pyrazol-1-yl)(pyridin-3-yl)methanone trifluoroacelate | 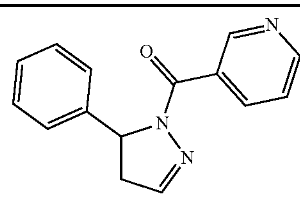 | $^1$H NMR (400 MHz, DMSO-d6) δ ppm 2.73-2.99 (m, 1H), 3.58 (ddd, J = 19.01, 11.68, 1.39 Hz, 1H), 5.56 (dd, J = 11.75, 4.93 Hz, 1H), 7.57-7.85 (m, 1H) 7.22-7.51 (m, 7H), 8.37 (d, J = 6.82 Hz, 1H), 8.80 (br. s., 1H), 9.06 (br. s., 1H) | 252 |

Pharmaceutical Compositions

Example A

An ointment is prepared by combining 20% (w/w) of the compound of Example 8, and 80% (w/w) of petrolatum. The mixture is passed through a roller mill until a uniform consistency is obtained.

Example B

Aerosol Spray: A solution is prepared from the following components: [Ingredient (Amount (w/w))]: Compound 8 (1.00), propylene glycol (5.00), golysorbate 80 (1.00), ethanol (78.00), purified water (15.00). The solution is placed in a conventional aerosol container, a valve mechanism is attached, and the container is charged with nitrogen to 100 psig.

Example C

Tablets are prepared using conventional methods and are formulated as follows: [Ingredient (Amount per tablet)]: Compound (5 mg), microcrystalline cellulose (100 mg), lactose (100 mg), sodium starch glycollate (30 mg), magnesium stearate (2 mg).

Example D

Capsules are prepared using conventional methods and are formulated as follows: [Ingredient (Amount per tablet)]: Compound (15 mg), dried starch (178 mg), magnesium stearate (2 mg).

BIOLOGICAL ASSAYS

Biological In Vitro Assay
A fluorescent polarization based binding assay was used to asses the activity of the compounds of this invention, the details of which are disclosed in International Patent Appln. No. PCT/IB2014/059004, now, International Patent Appln. Pub. No. WO2014/125444.

The pIC$_{50}$s are averaged to determine a mean value, for a minimum of 2 experiments.

As determined using the above method, the compounds of Examples 1-209 exhibited a pIC$_{50}$ between approximately 5.0 and 9.0.

For example, the compounds of Examples 1, 2, 4-6, 9, 11, 13, 14, 15, 18, 20-22, 25, 27-50, 53-63, 65-69, 71-77, 80, 81, 90-94, 170-173, 175, 176, 178-181 and 208 exhibited a pIC$_{50}$ between approximately 6.0 and 9.0.

The compounds of Examples 2, 3, 5-7, 9, 10, 13-16, 18, 19, 21, 22, 26, 29, 32, 33, 36-38, 40, 43, 44, 53, 54, 56, 58, 62, 65-68, 70, 75, 76, 79, 80, 83, 85, 87, 93, 95, 102, 105, 109, 112-114, 116, 122-125, 130, 131, 133, 136-140, 143, 145-149, 151-159, 164, 168, 169, 171, 172, 175-180, 183-

185, 187-190, 193, 196-199, 203, 205 and 207 exhibited a $pIC_{50}$ between approximately 7.0 and 9.0. In addition, the compounds of Examples 3, 7, 68 and 189 exhibited a $pIC_{50}$ between approximately 8.0 and 9.0.

For instance, the compounds of Examples 2, 13, 15, 32, 40, 42, 44, 48, 50, 56, 62, 66, 68, 91, 93 and 172 inhibited RIP1 kinase in the above method with a mean $pIC_{50}$ of approximately 7.4, 7.7, 7.1, 7.5, 7.3, 6.7, 7.8, 6.4, 6.2, 7.2, 7.1, 7.5, 8.1, 6.6, 7.0 and 7.8 respectively. In addition, the compounds of Examples 11, 12, 17, 55, 70, 81, 203 and 209 inhibited RIP1 kinase in the above method with a mean $pIC_{50}$ of approximately 7.5, 6.3, 6.9, 6.6, 6.4, 6.5, 7.5, and 5.6 respectively.

Biological In Vivo Assay

The efficacy of RIP1 inhibitors can be tested in mice in vivo using a TNF-driven systemic inflammatory response syndrome model (Duprez, L., et al. 2011. Immunity 35(6): 908-918) using TNF plus the caspase inhibitor zVAD. The model is terminated at ~3 hrs (under IACUC guidelines for temperature loss). TNF (or TNF/zVAD) induced manifestations include temperature loss, the production of numerous cytokines (including IL-6, IL-1b, MIP1β and MIP2) in the periphery, liver and intestinal inflammation and an increase of markers of cellular (LDH and CK) and liver damage (AST and ALT) in the serum. Inhibition of these TNF/zVAD induced manifestations can be shown by IP pre-dosing with selected compounds. For example, mice (8 mice per group) were pre-dosed IP with vehicle or compound 15 minutes before i.v. administration of mouse TNF (30 µg/mouse) and zVAD (0.4 mg/mouse) simultaneously. Temperature loss in the mice was measured by rectal probe. The study was terminated when the control group lost 7 degrees, per our IACUC protocol. All data are shown as means±standard error of the mean. Representative data for the compounds of Examples 13, 193, and 2013, expressed over time and at the 2.5, 3 and 2.5 hour time points, respectively, are provided in FIGS. 1A-3B. Data for the compounds of Examples 13, 48, 66, 155, 158, 193 and 203 tested in this model are provided in Table 1.

TABLE 1

| Example No. | Dose (mg/kg) | % Inhibition | Route |
|---|---|---|---|
| 13 | 20 | 80 | IP |
| 48 | 0.5 | 17 | IP |
| 48 | 5 | 52 | IP |
| 48 | 50 | 91 | IP |
| 66 | 0.1 | 52 | IP |
| 155 | 10 | 49 | PO |
| 158 | 10 | 77 | PO |
| 193 | 140 | 94 | PO |
| 203 | 1 | 9% | PO |
| 203 | 10 | 46% | PO |
| 203 | 100 | 88% | PO |

Figure 4A:
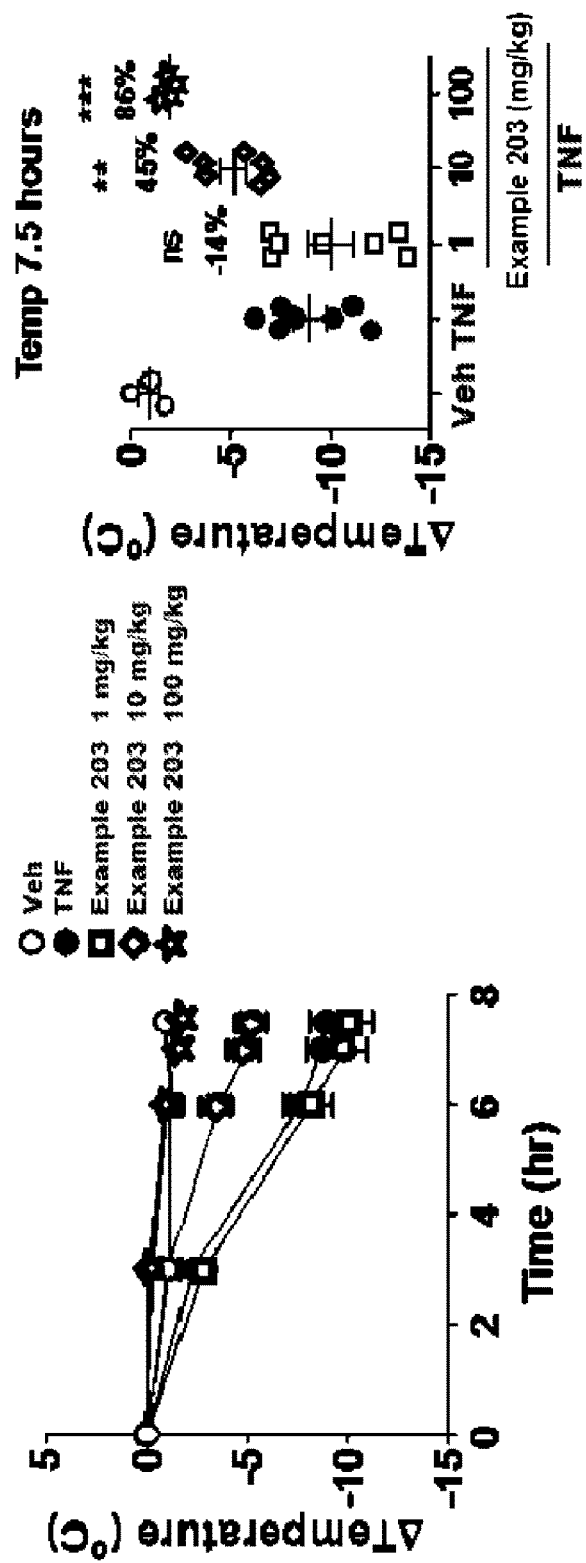
FIG. 4A shows the temperature loss over time in mice after oral pre-dosing with the compound of Example 203 or vehicle followed by i.v. administration of mouse TNF.
Figure 4B:
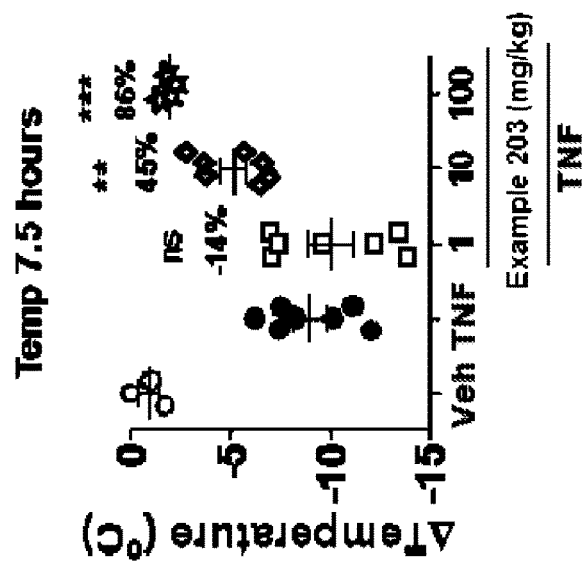
FIG. 4B shows the temperature loss in mice 7.5 hours after oral pre-dosing with the compound of Example 203 or vehicle followed by i.v. administration of mouse TNF.

The model can be run in a long modality (using TNF alone i.v.) which results in the termination of the study in ~8 hrs (under IACUC guidelines for temperature loss). For the TNF (alone) version of the model, mice (8 mice per group) were orally pre-dosed with vehicle or test compound at 100 mg/kg 15 minutes before i.v. administration of mouse TNF (30 µg/mouse). All data are shown as means±standard error of the mean. Data for compounds tested in this model are provided in Table 2. Representative data for Example 203, expressed over time and at the 7.5 hour time point, respectively, is provided in FIGS. 4A and 4B.

TABLE 2

| Example No. | Dose (mg/kg) | % Inhibition |
|---|---|---|
| 203 | 1 | -14 |
| 203 | 10 | 45 |
| 203 | 100 | 86 |

Biological In Vitro Cell Assay

The efficacy of RIP1 inhibitors can be tested in mice in vitro using a human monocytic leukemia U937 or mouse L929 fibrosarcoma cells in a necroptosis assay. As determined using the method described in He, S. et al. 2009. Cell 137(6):1100-1111 and International Patent Appln. No. PCT/IB2014/059004, now, International Patent Appln. Pub. No. WO2014/125444, the compounds of Examples 1-209 exhibited a $pIC_{50}$ between approximately 5.0 and 9.0.

For instance, the compounds of Examples 2, 3, 6, 7, 9, 10, 13-16, 18, 19, 22, 40, 43, 44, 53, 54, 56, 58, 62, 65-68, 76, 79, 80, 87, 105, 108, 112, 114, 122, 124, 125, 130, 131, 139, 140, 146-148, 151, 153-155, 158, 164, 171, 172, 175-177, 179, 180, 184, 185, 187-190 inhibited necrosis in U937 cells in the above method with a mean $pIC_{50}$ between approximately 7.0 and 9.0.

For instance, the compounds of Examples 3, 7, 13, 15, 40, 44, 50, 53, 56, 60, 65, 66, 68, 76, 79, 93, and 190 inhibited necrosis in U937 cells in the above method with a mean $pIC_{50}$ between approximately 7.0 and 9.0.

For instance, the compounds of Examples 2, 13, 15, 32, 40, 42, 44, 48, 50, 56, 62, 66, 68, 91, 93 and 172 inhibited necrosis in U937 cells in the above method with a mean $pIC_{50}$ of approximately 7.8, 8.3, 7.2, 6.8, 7.5, 6.6, 7.8, 6.4, 6.8, 7.5, 7.2, 8.0, 8.6, 7.0, 7.0 and 8.0 respectively.

In addition, the compounds of Examples 16, 17, 23, 64, 81, 174 and 209 inhibited necrosis in U937 cells in the above method with a mean $pIC_{50}$ of approximately 7.9, 6.2, 6.3, 6.5, 6.2, 6.3 and 5.7 respectively.

For instance, the compounds of Examples 2, 13, 15, 40, 44, 48, 50, 56, 66, 68, 91, 93 and 172 inhibited necrosis in L929 cells in the above method with a mean $pIC_{50}$ of approximately 6.7, 8.3, 7.7, 7.8, 7.4, 6.7, 7.7, 7.3, 11.8, 8.3, 6.6, 7.1 and 6.2, respectively. Viability was measured by quantitating cellular levels of ATP using the Cell Titer-Glo kit. All data are means±standard deviation of the mean.

References: WO2010075561A; EP295695 (U.S. Pat. Nos. 4,839,376; 4,990,529); EP322691 (U.S. Pat. No. 4,895,947); WO2009086303 (US20090163545); Postovskii, I. Y.; Vereshchagina, N. N., *Doklady Akademii Nauk SSSR*, 110, 802-804 (1956); Liu, X.-H., *Hecheng Huaxue*, 15 (2), 212-215 (2007); Santos, J. M.; Lopez, Y.; Aparicio, D.; Palacios, F., *J. Org. Chem.*, 73(2), 550-557 (2008); Liu, X.-H.; Zhu, J.; Pan, C.-X.; Song, B.-A., *Yingyong Huaxue*, 24 (10), 1162-1166 (2007).

What is claimed is:
1. A compound according to Formula (I):

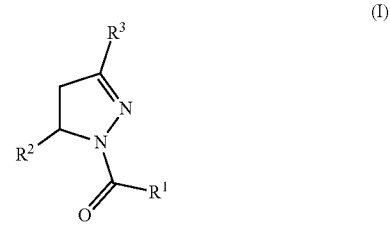

(I)

wherein:
$R^1$ is $(C_1-C_4)$alkoxy-$CH_2$—, phenyl$(C_1-C_4)$alkoxy-$CH_2$—, or a substituted or unsubstituted $(C_2-C_4)$alkynyl, $(C_3-C_6)$cycloalkyl, $(C_3-C_6)$cycloalkyl-$(C_1-C_4)$alkyl-group, or a substituted or unsubstituted 5-6 membered heterocycloalkyl group further optionally substituted by halogen or $(C_1-C_4)$alkyl,
wherein said substituted $(C_3-C_6)$cycloalkyl, $(C_3-C_6)$cycloalkyl-alkyl-, or 5-6 membered heterocycloalkyl group is substituted by 1, 2 or 3 substituents independently selected from hydroxyl, (benzyloxy)carbonyl)amino, cyano, halogen, $(C_1-C_4)$alkyl, halo$(C_1-C_4)$alkyl, $(C_1-C_4)$alkoxy, $(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkoxy-CO—, $(C_1-C_4)$alkylN-HCO—, $((C_1-C_4)$alkyl$)((C_1-C_4)$alkyl$)$NCO—, halo$(C_1-C_4)$alkyl-CO—, optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-$SO_2$—, optionally substituted phenyl$(C_1-C_4)$alkyl-CO—, optionally substituted 5-6 membered heteroaryl-CO—, and optionally substituted 9-10 membered heteroaryl-CO—,
wherein said optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-$SO_2$-, optionally substituted phenyl$(C_1-C_4)$alkyl-CO—, optionally substituted 5-6 membered heteroaryl-CO—, or optionally substituted 9-10 membered heteroaryl-CO— is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$cycloalkyl and 5-6 membered heterocycloalkyl; or
said substituted $(C_2-C_4)$alkynyl, $(C_3-C_6)$cycloalkyl or 5-6 membered heterocycloalkyl group is substituted by an optionally substituted phenyl, 5-6 membered heteroaryl or 9-membered heteroaryl group,
wherein said phenyl, 5-6 membered heteroaryl or 9-membered heteroaryl group is optionally substituted by 1 or 2 substituents independently selected from halogen, $(C_1-C_4)$alkyl, $(C_1-C_4)$alkyl-CO—, halo$(C_1-C_4)$alkyl, and halo$(C_1-C_4)$alkyl-CO—;
$R^2$ is a substituted or unsubstituted phenyl, $(C_3-C_6)$cycloalkyl, 5-6 membered oxygen-containing heterocycloalkyl, 5-6 membered heteroaryl, 9-membered heteroaryl, 9-10 membered carbocyclic-aryl, or 9-10 membered heterocyclic-aryl group,
wherein said substituted phenyl, $(C_3-C_6)$cycloalkyl, 5-6 membered heterocycloalkyl, 5-6 membered heteroaryl, 9-membered heteroaryl, 9-10 membered carbocyclic-aryl, or 9-10 membered heterocyclic-aryl group is substituted by 1, 2 or 3 substituents independently selected from halogen, $(C_1-C_4)$alkyl, halo$(C_1-C_4)$alkyl, $(C_1-C_4)$alkoxy, halo$(C_1-C_4)$alkoxy, and cyano;
$R^3$ is H or halogen;
or a salt thereof,
provided the compound is not:
cyclohexyl(5-phenyl-4,5-dihydro-1H-pyrazol-1-yl)methanone.

2. The compound, or salt thereof, according to claim 1, wherein:
$R^1$ is a substituted or unsubstituted $(C_4-C_6)$cycloalkyl, $(C_4-C_6)$cycloalkyl-alkyl-, or 5-6 membered heterocycloalkyl group,
wherein said substituted $(C_4-C_6)$cycloalkyl, $(C_4-C_6)$cycloalkyl-alkyl-, or 5-6 membered heterocycloalkyl group is substituted by 1, 2 or 3 substituents independently selected from hydroxyl, (benzyloxy)carbonyl)amino, halogen, $(C_1-C_4)$alkyl, halo$(C_1-C_4)$alkyl, $(C_1-C_4)$alkyl-CO—, halo$(C_1-C_4)$alkyl-CO—, and an optionally substituted 5-6 membered heteroaryl-CO—, wherein said optionally substituted 5-6 membered heteroaryl-CO— is optionally substituted by 1 or 2 substituents independently selected from $(C_1-C_4)$alkyl, $(C_1-C_4)$alkyl-CO—, halo$(C_1-C_4)$alkyl, and halo$(C_1-C_4)$alkyl-CO—, or
said substituted $(C_4-C_6)$cycloalkyl or 5-6 membered heterocycloalkyl group is substituted by an optionally substituted phenyl, 5-6 membered heteroaryl or 9-membered heteroaryl optional substituted by 1 or 2 substituents independently selected from halogen, $(C_1-C_4)$alkyl, $(C_1-C_4)$alkyl-CO—, halo$(C_1-C_4)$alkyl, and halo$(C_1-C_4)$alkyl-CO—;
$R^2$ is a substituted or unsubstituted phenyl, $(C_3-C_6)$cycloalkyl, 5-membered oxygen-containing heterocycloalkyl, 5-6 membered heteroaryl or 9-membered heteroaryl group,
wherein said substituted phenyl, $(C_3-C_6)$cycloalkyl, 5-membered heterocycloalkyl, 5-6 membered heteroaryl or 9-membered heteroaryl group is substituted by 1, 2 or 3 substituents independently selected from halo, $(C_1-C_4)$alkyl, halo$(C_1-C_4)$alkyl, $(C_1-C_4)$alkoxy, and cyano; and
$R^3$ is H.

3. The compound, or salt thereof, according to claim 1, wherein:
$R^1$ is a substituted or unsubstituted $(C_4-C_6)$cycloalkyl, $(C_4-C_6)$cycloalkyl-alkyl-, or 5-6 membered heterocycloalkyl group,
wherein said substituted $(C_4-C_6)$cycloalkyl, $(C_4-C_6)$cycloalkyl-alkyl-, or 5-6 membered heterocycloalkyl group is substituted by 1, 2 or 3 substituents independently selected from hydroxyl, (benzyloxy)carbonyl)amino, halogen, $(C_1-C_4)$alkyl, halo$(C_1-C_4)$alkyl, $(C_1-C_4)$alkyl-CO—, halo$(C_1-C_4)$alkyl-CO—, and an optionally substituted 5-6 membered heteroaryl-CO—, wherein said optionally substituted 5-6 membered heteroaryl-CO— is optionally substituted by 1 or 2 substituents independently selected from $(C_1-C_4)$alkyl, $(C_1-C_4)$alkyl-CO—, halo$(C_1-C_4)$alkyl, and halo$(C_1-C_4)$alkyl-CO—, or
said substituted $(C_4-C_6)$cycloalkyl or 5-6 membered heterocycloalkyl group is substituted by an optionally substituted phenyl, 5-6 membered heteroaryl or 9-membered heteroaryl optional substituted by 1 or 2 substituents independently selected from halogen, $(C_1-C_4)$alkyl, $(C_1-C_4)$alkyl-CO—, halo$(C_1-C_4)$alkyl, and halo$(C_1-C_4)$alkyl-CO—;
$R^2$ is a substituted or unsubstituted phenyl, 5-6 membered oxygen-containing heterocycloalkyl, wherein said substituted 5-6 membered heterocycloalkyl is substituted by 1, 2 or 3 substituents independently selected from halo, $(C_1-C_4)$alkyl, halo$(C_1-C_4)$alkyl, $(C_1-C_4)$alkoxy, and cyano; and $R^3$ is H.

4. The compound, or salt thereof, according to claim 1, having Formula (II):

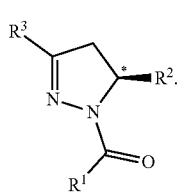

(II)

5. The compound, or salt thereof, according to claim 4, wherein $R^1$ is a substituted or unsubstituted 5-6 membered heterocycloalkyl group.

6. The compound, or salt thereof, according to claim 4, wherein $R^1$ is a substituted or unsubstituted 5-6 membered heterocycloalkyl group further optionally substituted by halogen or $(C_1-C_4)$alkyl.

7. The compound, or salt thereof, according to claim 4, wherein $R^1$ is a substituted piperidinyl group, wherein the substituted piperidinyl group is substituted by a substituent selected from $(C_1-C_4)$alkyl-CO—, halo$(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkylNHCO—, optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-SO$_2$—, optionally substituted phenyl$(C_1-C_4)$alkyl-CO—, optionally substituted 5-6 membered heteroaryl-CO—, and optionally substituted 9-10 membered heteroaryl-CO—, wherein said optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-SO$_2$—, optionally substituted phenyl$(C_1-C_4)$alkyl-CO—, optionally substituted 5-6 membered heteroaryl-CO—, or optionally substituted 9-10 membered heteroaryl-CO—, is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$cycloalkyl and 5-6 membered heterocycloalkyl.

8. The compound, or salt thereof, according to claim 4, wherein $R^1$ is a substituted piperidinyl group, further optionally substituted by halogen or $(C_1-C_4)$alkyl, wherein the substituted piperidinyl group is substituted by a substituent selected from $(C_1-C_4)$alkyl-CO—, halo$(C_1-C_4)$alkyl-CO—, cyano$(C_1-C_4)$alkyl-CO—, $(C_1-C_4)$alkoxy-$(C_1-C_4)$alkyl-CO—, $(C_1-C_4)$alkylNHCO—, optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-SO$_2$—, optionally substituted phenyl$(C_1-C_4)$alkyl-CO—, optionally substituted 5-6 membered heteroaryl-CO—, and optionally substituted 9-10 membered heteroaryl-CO—, wherein said optionally substituted $(C_3-C_6)$cycloalkyl-CO—, optionally substituted $(C_3-C_6)$cycloalkyl-$(C_1-C_4)$alkyl-CO—, optionally substituted phenyl-CO—, optionally substituted phenyl-SO$_2$—, optionally substituted phenyl$(C_1-C_4)$alkyl-CO—, optionally substituted 5-6 membered heteroaryl-CO—, or optionally substituted 9-10 membered heteroaryl-CO— is optionally substituted by 1 or 2 substituents independently selected from halogen, cyano, $(C_1-C_4)$alkyl, $(C_1-C_4)$alkoxy, $(C_1-C_4)$alkyl-CO—, halo$(C_1-C_4)$alkyl, halo$(C_1-C_4)$alkyl-CO—, $(C_3-C_6)$cycloalkyl and 5-6 membered heterocycloalkyl.

9. The compound, or salt thereof, according to claim 4, wherein $R^1$ is a substituted piperidin-4-yl group substituted by CH$_3$CO—, CF$_3$CO—, or 1-methyl-1H-pyrrol-2-yl-CO—.

10. The compound, or salt thereof, according to claim 4, wherein $R^1$ is a substituted piperidinyl group, wherein the substituted piperidinyl group is optionally substituted by a halogen or $(C_1-C_4)$alkyl substituent and is further substituted by an optionally substituted phenyl, 5-6 membered heteroaryl or 9-membered heteroaryl, wherein the optionally substituted phenyl, 6-membered heteroaryl or 9-membered heteroaryl group is optionally substituted by 1 or 2 substituents independently selected from halogen, $(C_1-C_4)$alkyl, $(C_1-C_4)$alkyl-CO—, halo$(C_1-C_3)$alkyl, and halo$(C_1-C_3)$alkyl-CO—.

11. The compound, or salt thereof, according to claim 4, wherein $R^2$ is a substituted or unsubstituted phenyl, $(C_3-C_6)$cycloalkyl, 5-6 membered oxygen-containing heterocycloalkyl, 5-6 membered heteroaryl, 9-membered heteroaryl, 9-10 membered carbocyclic-aryl, or 9-10 membered heterocyclic-aryl group, wherein said substituted phenyl, $(C_3-C_6)$cycloalkyl, 5-6 membered heterocycloalkyl, 5-6 membered heteroaryl, 9-membered heteroaryl, 9-10 membered carbocyclic-aryl, or 9-10 membered heterocyclic-aryl group is substituted by 1, 2 or 3 substituents independently selected from halogen, $(C_1-C_4)$alkyl, halo$(C_1-C_4)$alkyl, $(C_1-C_4)$alkoxy, halo$(C_1-C_4)$alkoxy, and cyano.

12. The compound, or salt thereof, according to claim 4, wherein $R^2$ is unsubstituted phenyl.

13. The compound, or salt thereof, according to claim 4, wherein $R^2$ is phenyl substituted by 1 or 2 substituents independently selected from halo, $(C_1-C_4)$alkyl, halo$(C_1-C_4)$alkyl, $(C_1-C_4)$alkoxy, halo$(C_1-C_4)$alkoxy, and cyano.

14. The compound, or salt thereof, according to claim 4, wherein $R^2$ is an optionally substituted 6-membered heteroaryl containing 1 or 2 nitrogen heteroatoms, wherein the heteroaryl is optionally substituted by 1 or 2 substituents independently selected from halo, $(C_1-C_4)$alkyl, halo$(C_1-C_4)$alkyl, and $(C_1-C_4)$alkoxy.

15. The compound, or salt thereof, according claim 4, wherein $R^3$ is H.

16. The compound, or salt thereof, according to claim 4, wherein the salt is a pharmaceutically acceptable salt.

17. A compound of Formula (II) which is (S)-1-(4-(5-(3,5-difluorophenyl)-4,5-dihydro-1H-pyrazole-1-carbonyl)piperidin-1-yl)ethanone

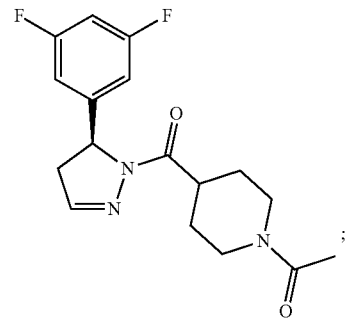

or a pharmaceutically acceptable salt thereof.

18. A compound of Formula (II) which is (S)-1-(4-(5-(3,5-difluorophenyl)-4,5-dihydro-1H-pyrazole-1-carbonyl)piperidin-1-yl)ethanone

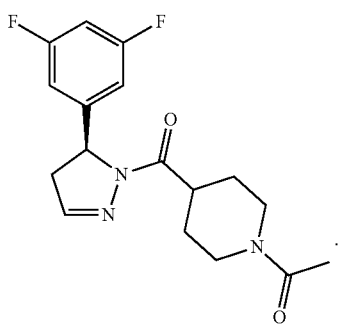 [SMILES: CC(=O)N1CCC(C(=O)N2N=CC[C@H]2c2cc(F)cc(F)c2)CC1]

19. The compound according to claim 18, providing a PXRD pattern substantially in accordance with FIG. 5.

20. A pharmaceutical composition comprising the compound, or pharmaceutically acceptable salt thereof, according to claim 4, and one or more pharmaceutically acceptable excipients.

21. The pharmaceutical composition according to claim 20, which further comprises at least one other therapeutically active agent.

22. A pharmaceutical composition comprising the compound, or pharmaceutically acceptable salt thereof, according to claim 17, and one or more pharmaceutically acceptable excipients.

23. The pharmaceutical composition according to claim 22, which further comprises at least one other therapeutically active agent.

24. A pharmaceutical composition comprising the compound, or pharmaceutically acceptable salt thereof, according to claim 18, and one or more pharmaceutically acceptable excipients.

25. The pharmaceutical composition according to claim 24, which further comprises at least one other therapeutically active agent.

26. A pharmaceutical composition comprising the compound, or pharmaceutically acceptable salt thereof, according to claim 19, and one or more pharmaceutically acceptable excipients.

27. The pharmaceutical composition according to claim 26, which further comprises at least one other therapeutically active agent.

28. A method of alleviating or mitigating a RIP1 kinase-mediated disease or disorder in a human in need thereof comprising administering to the human a therapeutically effective amount of the compound or pharmaceutically acceptable salt thereof according to claim 4.

29. A method of alleviating or mitigating a RIP1 kinase-mediated disease or disorder in a human in need thereof comprising administering to the human a therapeutically effective amount of the compound or pharmaceutically acceptable salt thereof according to claim 17.

30. The method according to claim 28, wherein the disease or disorder is amyotrophic lateral sclerosis.

31. The method according to claim 29, wherein the disease or disorder is amyotrophic lateral sclerosis.

\* \* \* \* \*